(12) United States Patent
Orengo et al.

(10) Patent No.: US 12,624,114 B2
(45) Date of Patent: May 12, 2026

(54) METHOD OF REDUCING SERUM AMYLOID A (SAA) PROTEIN LEVELS IN A PATIENT BY ADMINISTERING AN INTERLEUKIN-33 (IL-33) ANTIBODY

(71) Applicant: Regeneron Pharmaceuticals, Inc., Tarrytown, NY (US)

(72) Inventors: Jamie M. Orengo, Cortlandt Manor, NY (US); Jeanne Allinne, Paris (FR); Andrew J. Murphy, Croton-on-Hudson, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/523,048

(22) Filed: Nov. 29, 2023

(65) Prior Publication Data

US 2024/0209102 A1 Jun. 27, 2024

Related U.S. Application Data

(63) Continuation of application No. 17/028,011, filed on Sep. 22, 2020, now Pat. No. 11,866,503, which is a (Continued)

(51) Int. Cl.

| | |
|---|---|
| *C07K 16/28* | (2006.01) |
| *A61K 38/17* | (2006.01) |
| *A61K 39/00* | (2006.01) |
| *A61K 39/395* | (2006.01) |
| *A61K 45/06* | (2006.01) |
| *A61P 1/00* | (2006.01) |
| *A61P 1/04* | (2006.01) |
| *A61P 9/14* | (2006.01) |
| *A61P 11/00* | (2006.01) |
| *A61P 11/02* | (2006.01) |
| *A61P 11/06* | (2006.01) |
| *A61P 17/00* | (2006.01) |
| *A61P 17/06* | (2006.01) |
| *A61P 25/00* | (2006.01) |
| *A61P 29/00* | (2006.01) |
| *A61P 37/00* | (2006.01) |

(Continued)

(52) U.S. Cl.
CPC ...... *C07K 16/2866* (2013.01); *A61K 38/1793* (2013.01); *A61K 39/3955* (2013.01); *A61K 45/06* (2013.01); *A61P 1/00* (2018.01); *A61P 1/04* (2018.01); *A61P 9/14* (2018.01); *A61P 11/00* (2018.01); *A61P 11/02* (2018.01); *A61P 11/06* (2018.01); *A61P 17/00* (2018.01); *A61P 17/06* (2018.01); *A61P 25/00* (2018.01); *A61P 29/00* (2018.01); *A61P 37/00* (2018.01); *A61P 37/08* (2018.01); *C07K 14/7155* (2013.01); *C07K 16/244* (2013.01); *A61K 2039/507* (2013.01); *C07K 2317/21* (2013.01); *C07K 2317/34* (2013.01); *C07K 2317/56* (2013.01); *C07K 2317/565* (2013.01); *C07K 2317/76* (2013.01); *C07K 2319/00* (2013.01)

(58) Field of Classification Search
CPC .............. C07K 16/2866; C07K 16/244; C07K 14/7155; C07K 2317/21; C07K 2317/34; C07K 2317/56; C07K 2317/565; C07K 2317/76; C07K 2319/00; A61K 38/1793; A61K 39/3955; A61K 45/06; A61K 2039/507; A61K 2039/505; A61K 2039/54; A61K 2039/545; A61P 1/00; A61P 1/04; A61P 9/14; A61P 11/00; A61P 11/02; A61P 11/06; A61P 17/00; A61P 17/06; A61P 25/00; A61P 29/00; A61P 37/00; A61P 37/08; A61P 19/02
See application file for complete search history.

(56) References Cited

U.S. PATENT DOCUMENTS

| | | |
|---|---|---|
| 5,500,362 A | 3/1996 | Robinson et al. |
| 5,576,191 A | 11/1996 | Gayle et al. |

(Continued)

FOREIGN PATENT DOCUMENTS

| | | |
|---|---|---|
| EP | 0604693 A1 | 7/1994 |
| EP | 0367566 A1 | 5/1997 |

(Continued)

OTHER PUBLICATIONS

Bozinovski S, et al. (Jan. 17, 2012) PNAS. 109(3):935-940. (https://doi.org/10.1073/pnas.1109382109).*

(Continued)

*Primary Examiner* — Robert S Landsman
(74) *Attorney, Agent, or Firm* — Schwabe, Williamson & Wyatt PC; Eileen Woo

(57) ABSTRACT

The present invention provides methods for treating inflammatory diseases, or conditions associated with, or resulting in part from, elevated levels of IL-33 and IL-4, in particular inflammatory lung disorders. The methods of the present invention comprise administering to a subject in need thereof one or more therapeutically effective doses of an IL-33 antagonist alone or in combination with one or more therapeutically effective doses of an IL-4R antagonist. In certain embodiments, the methods of the present invention include use of the antagonists to treat any inflammatory disease or condition mediated in part by enhanced IL-33-mediated signaling and IL-4-mediated signaling.

17 Claims, 11 Drawing Sheets

Specification includes a Sequence Listing.

Related U.S. Application Data continuation of application No. 15/827,357, filed on Nov. 30, 2017, now Pat. No. 10,815,305.

(60) Provisional application No. 62/567,318, filed on Oct. 3, 2017, provisional application No. 62/473,738, filed on Mar. 20, 2017, provisional application No. 62/428,634, filed on Dec. 1, 2016.

(51) Int. Cl.

| | | |
|---|---|---|
| *A61P 37/08* | (2006.01) | |
| *C07K 14/715* | (2006.01) | |
| *C07K 16/24* | (2006.01) | |

(56) References Cited

U.S. PATENT DOCUMENTS

| | | | |
|---|---|---|---|
| 5,599,905 A | 2/1997 | Mosley et al. |
| 5,714,146 A | 2/1998 | Lewis et al. |
| 5,717,072 A | 2/1998 | Mosley et al. |
| 5,821,337 A | 10/1998 | Carter et al. |
| 5,856,296 A | 1/1999 | Mosley et al. |
| 5,985,280 A | 11/1999 | Ritter et al. |
| 6,156,877 A | 12/2000 | Ritter et al. |
| 6,391,581 B1 | 5/2002 | Mosley et al. |
| 6,548,655 B1 | 4/2003 | Mosley et al. |
| 6,716,587 B2 | 4/2004 | Mosley et al. |
| 7,141,653 B2 | 11/2006 | Greenfeder et al. |
| 7,186,809 B2 | 3/2007 | Pluenneke et al. |
| 7,317,090 B2 | 1/2008 | Mosley et al. |
| 7,422,742 B2 | 9/2008 | Greenfeder et al. |
| 7,465,450 B2 | 12/2008 | Pluenneke et al. |
| 7,531,169 B2 | 5/2009 | Singh et al. |
| 7,605,237 B2 | 10/2009 | Stevens et al. |
| 7,608,693 B2 | 10/2009 | Martin et al. |
| 7,794,717 B2 | 9/2010 | Stevens et al. |
| 7,872,113 B2 | 1/2011 | Carter et al. |
| 8,030,003 B2 | 10/2011 | Rothenberg et al. |
| 8,075,887 B2 | 12/2011 | Martin et al. |
| 8,075,897 B2 | 12/2011 | Spertini et al. |
| 8,092,802 B2 | 1/2012 | Stevens et al. |
| 8,119,771 B2 | 2/2012 | Martin |
| 8,187,596 B1 | 5/2012 | Chackerian et al. |
| 8,252,284 B2 | 8/2012 | Singh et al. |
| 8,324,192 B2 | 12/2012 | Dohil et al. |
| 8,337,839 B2 | 12/2012 | Martin et al. |
| 8,338,135 B2 | 12/2012 | Stevens et al. |
| 8,497,528 B2 | 7/2013 | Lee et al. |
| 8,604,171 B2 | 12/2013 | Singh et al. |
| 8,637,239 B2 | 1/2014 | Furuta et al. |
| 8,735,095 B2 | 5/2014 | Martin et al. |
| 9,453,072 B2 | 9/2016 | Murphy et al. |
| 9,637,535 B2 | 5/2017 | Murphy et al. |
| 10,000,564 B2 | 6/2018 | Murphy et al. |
| 10,815,305 B2 | 10/2020 | Orengo et al. |
| 11,866,503 B2 | 1/2024 | Orengo et al. |
| 2003/0103938 A1 | 6/2003 | Jinguan et al. |
| 2003/0124121 A1 | 7/2003 | Pluenneke et al. |
| 2005/0031609 A1 | 2/2005 | Hultsch et al. |
| 2005/0074462 A1 | 4/2005 | Holmgren et al. |
| 2005/0118176 A1 | 6/2005 | Mosley et al. |
| 2005/0255532 A1 | 11/2005 | Ruben et al. |
| 2005/0282181 A1 | 12/2005 | Yan et al. |
| 2006/0013811 A1 | 1/2006 | Dina et al. |
| 2007/0041976 A1 | 2/2007 | Pluenneke et al. |
| 2007/0042978 A1 | 2/2007 | Girard et al. |
| 2007/0087411 A1 | 4/2007 | Sharma et al. |
| 2007/0274996 A1 | 11/2007 | Carter et al. |
| 2008/0054606 A1 | 3/2008 | Mitsuo et al. |
| 2009/0041718 A1 | 2/2009 | Schmitz et al. |
| 2009/0074793 A1 | 3/2009 | Martin et al. |
| 2009/0098142 A1 | 4/2009 | Kasaian et al. |
| 2009/0264392 A1 | 10/2009 | Warndahl et al. |
| 2009/0304699 A1 | 12/2009 | Amatucci et al. |
| 2010/0260705 A1 | 10/2010 | Martin |
| 2010/0260770 A1 | 10/2010 | Coyle |
| 2011/0195500 A1 | 8/2011 | Rothenberg et al. |
| 2012/0004205 A1 | 1/2012 | Rothenberg et al. |
| 2012/0052072 A1 | 3/2012 | Martin et al. |
| 2012/0164080 A1 | 6/2012 | Hill et al. |
| 2012/0207752 A1 | 8/2012 | Chackerian et al. |
| 2012/0207815 A1 | 8/2012 | Benhamou et al. |
| 2012/0263709 A1 | 10/2012 | Rankin et al. |
| 2013/0078675 A1 | 3/2013 | Martin et al. |
| 2013/0287777 A1 | 10/2013 | Duffy et al. |
| 2013/0324435 A1 | 12/2013 | Rothenberg et al. |
| 2013/0336980 A1 | 12/2013 | Duffy et al. |
| 2014/0004107 A1 | 1/2014 | Smith et al. |
| 2014/0072583 A1 | 3/2014 | Ardeleanu et al. |
| 2014/0140954 A1 | 5/2014 | Schmitz et al. |
| 2014/0187523 A1 | 7/2014 | Dohil et al. |
| 2014/0271642 A1 | 9/2014 | Murphy et al. |
| 2014/0271658 A1 | 9/2014 | Murphy et al. |
| 2014/0356372 A1 | 12/2014 | Stahl et al. |
| 2015/0017182 A1 | 1/2015 | Mannent et al. |
| 2015/0246973 A1 | 9/2015 | Graham et al. |
| 2016/0152718 A1 | 6/2016 | Kostic et al. |
| 2016/0289322 A1 | 10/2016 | Fujino et al. |
| 2016/0362487 A1 | 12/2016 | Murphy et al. |

FOREIGN PATENT DOCUMENTS

| | | | |
|---|---|---|---|
| EP | 1113818 B1 | 5/2006 |
| EP | 2022507 A1 | 2/2009 |
| EP | 2069784 A1 | 6/2009 |
| EP | 1527100 A1 | 7/2009 |
| EP | 2152740 A1 | 2/2010 |
| EP | 1725261 B1 | 1/2011 |
| EP | 2283860 A2 | 2/2011 |
| EP | 2475388 A1 | 7/2012 |
| EP | 3027015 A1 | 6/2016 |
| RU | 2162711 | 2/2001 |
| WO | 92/19259 A1 | 11/1992 |
| WO | 94/14975 A1 | 7/1994 |
| WO | 01/092340 A2 | 12/2001 |
| WO | 05/047331 A2 | 5/2005 |
| WO | 05/079844 A2 | 9/2005 |
| WO | 05/085284 A1 | 9/2005 |
| WO | 06/003407 A2 | 1/2006 |
| WO | 06/072564 A1 | 7/2006 |
| WO | 06/083390 A2 | 8/2006 |
| WO | 08/054606 | 5/2008 |
| WO | 08/132709 A1 | 11/2008 |
| WO | 08/144610 A1 | 11/2008 |
| WO | 09/053098 A1 | 4/2009 |
| WO | 09/124954 A1 | 10/2009 |
| WO | 10/053751 A1 | 5/2010 |
| WO | 10/065557 A2 | 6/2010 |
| WO | 11/026966 A2 | 3/2011 |
| WO | 11/031600 A1 | 3/2011 |
| WO | 12/047954 A1 | 4/2012 |
| WO | 12/094643 | 7/2012 |
| WO | 12/177945 A2 | 12/2012 |
| WO | 13/051928 A1 | 4/2013 |
| WO | 13/155010 A1 | 10/2013 |
| WO | 14/031610 A1 | 2/2014 |
| WO | 14/039461 A1 | 3/2014 |
| WO | 14/059178 A1 | 4/2014 |
| WO | 14/152195 A1 | 9/2014 |
| WO | 14/164959 A2 | 10/2014 |
| WO | 15/099175 A1 | 7/2015 |
| WO | 15/106080 A2 | 7/2015 |
| WO | 15/127229 A1 | 8/2015 |
| WO | 15/171861 A1 | 11/2015 |

OTHER PUBLICATIONS

Homer et al., "Modern Concepts on the Role of Inflammation in Pulmonary Fibrosis," Arch Pathol Lab Med, vol. 135: pp. 780-788, (Jun. 2011).

U.S. Appl. No. 62/428,634, filed Dec. 1, 2016.

U.S. Appl. No. 62/473,738, filed Mar. 20, 2017.

U.S. Appl. No. 62/567,318, filed Oct. 30, 2017.

(56)          References Cited

OTHER PUBLICATIONS

PCT/US2017/064041, Nov. 30, 2017.
U.S. Appl. No. 15/827,357, filed Nov. 30, 2017, U.S. Pat. No. 10,815,305.
U.S. Appl. No. 17/028,011, filed Sep. 22, 2020, U.S. Pat. No. 11,866,503.
"AnaptysBio Announces Development of Novel Anti-IL33 Therapeutic Antibody," AnaptysBio, Inc., 1 page, (2014). [Retrieved from the Internet Juy. 3, 2014: <URL: http://www.anaptysbio.com/anti-1133/>]. (Author Unknown).
Abonia, et al., 2013, Journal of Allergy Clin Immunol, "High prevalence of eosinophilic esophagitis in patients with inherited connective tissue disorders".
Aceves et al., "Remodeling and fibrosis in chronic eosinophil inflammation," HHS Public Access; 32(0): 15-21. doi:10.1159/000357004. (2014).
Aceves, et al., 2009, Immunol Allergy Clin N Am 29 p. 197-211, "Relationships Between Eosinophilic Inflammation, Tissue Remodeling, and Fibrosis in Eosinophilic Esophagitis".
Ali et al., "Caspase 3 inactivates biologically active full length interleukin-33 as a classical cytokine but does not prohibit nuclear translocation," Biochemical and Biophysical Research Communications, 391(3):1512-1516, (2010).
Ali, "Characterization of Interleukin-33 and the IL-33 Receptor Complex," Dissertation, pp. 1-126, (2009).
Alignment between Human IL-33 and Cynomolgus Monkey IL-33 with 93.704% identity. 26; Sep. 2017.
Anonymous, "Evaluation of SAR440340 and as Combination Therapy with Dupilumab in Moderate-to-Severe Asthma Patients," U.S. National Library of Medicine, ClinicalTrials.gov, Identifier: NCT03387852; Jan. 1, 2018.
Arron et al. "Peripheral Biomarkers of an IL-13 Induced Bronchial Epithelial Gene Signature in Asthma," Am. J. Respir. Crit. Care Med. Online Abstracts Issue. 2009, B21 Airway Inflammation: New Information about Mediators and Biomarkers/Poster Discussion/ Monday, May 18, 2009, 1 page.
Assa'ad, et al., 2011, Gastroenterology 141:1593-1604, "An Antibody Against IL-5 Reduces Numbers of Esophageal Intraepithelial Eosinophils in Children with Eosinophilic Esophagitis".
Bachert et al. (2005) Drugs, 65(11): 1537-1552. "Pharmacological management of nasal polyposis".
Balint and Larrick, (1993) Gene 137:109-118, "Antibody engineering by parsimonious mutagenesis".
Barnes, 2008, The Journal of Clinical Investigation 118(11):3546-3556, "The cytokine network in asthma and chronic obstructive pulmonary disease".
Bateman et al. (2004) Am. J. Respir. Crit. Care Med. 170:836-844. "Can guideline-defined asthma control be achieved?"
Beyer, et al., 2002, Journal of Allergy Clin Immunol 109(4):707-713, "Human milk-specific mucosal lymphocytes of the gastrointestinal tract display a T H2 cytokine profile".
Bhardwaj and Ghaffari, 2012, Ann Allergy Asthma Immunol 109:155-159, "Biomarkers for eosinophilic esophagitis: a review".
Blanchard and Rothenberg, 2009, Immunol Allergy Clin N Am 29, p. 141-148, "Chemotactic Factors Associated with Eosinophilic Gastrointestinal Diseases".
Blanchard, et al., 2005, Clin Exp Allergy 35:1096-1103, "Inhibition of human interleukin-13-induced respiratory and esophageal inflammation by anti-human-interleukin-13 antibody (CAT-354)".
Blanchard, et al., 2006, The Journal of Clinical Investigation 116(2), "Eotaxin-3 and a uniquely conserved gene-expression profile in eosinophilic esophagitis".
Blanchard, et al., 2007, Journal of Allergy Clin Immunol 120(6), "IL-13 involvement in eosinophilic esophagitis: Transcriptome analysis and reversibility with glucocorticoids".
Blanchard, et al., 2010, The Journal of Immunology, "Coordinate Interaction between IL-13 and Epithelial Differentiation Cluster Genes in Eosinophilic Esophagitis".

Blanchard, et al., 2011, J Allergy Clin Immunol, 127(1):208-217, "A striking local esophageal cytokine expression profile in eosinophilic esophagitis".
Brown-Whitehorn and Spergel (2010) Expert Rev Clin Immunol. 6:1: 101-115, "The link between allergies and eosinophilic esophagitis: implications for management strategies".
Burmeister-Getz et al. (2009) J. Clin. Pharmacol. 49:1025-1036, "Human pharmacokinetics/pharmacodynamics of an interleukin-4 and interleukin-13 dual antagonist in asthma".
Caldas et al. (Mol. Immunol. May 2003; 39 (15): 941-952).
Carter (2006) The Journal of Immunology 6:343-357, "Potent Antibody Therapeutics by Design".
Casset, et al., "A peptide mimetic of an anti-CD4 monoclonal antibody by rational design" Biochemical and Biophysical Research Communications 307 (2003) 198-205.
Chehade and Sampson, 2009, Immunol Allergy Clin N Am 29, p. 149-158, "The Role of Lymphocytes in Eosinophilic Gastrointestinal Disorders".
Cheng et al. (2012) Am J Physiol Gastrointest Liver Physiol 303:G 1175-G 1187, "Tissue remodeling in eosinophilic esophagitis".
Chien et al., "Significant structural and functional change of an antigen-binding site by a distant amino acid substitution: Proposal of a structural mechanism" (Proc. Natl. Acad. Sci. USA. Jul. 1989; 86 (14): 5532-5536).
Corren et al. (2010) American Journal of Respiratory and Critical Care Medicine 181 (8): 788-796, "A Randomized, Controlled, Phase 2 Study of AMG 317, an IL-4R Antagonist, in Patients with Asthma".
Davies et al., 1996, "Affinity improvement of single antibody VH domains: residues in all three hypervariable regions affect antigen binding" Immunitechnol. 2:169-179 (Elsevier, Netherlands).
Davis (2004) Seminars in Immunology 16: 239-243, "The evolutionary and structural 'logic' of antigen receptor diversity".
De Pascalis et al. "Graftin of 'Abbreviated' Complementarity-Determining Regions Containing Specificity- Determining Residues Essential for Ligand Contact to Engineer a Less Immunogenic Humanized Monoclonal Antibody", J. Immunol. 2002; 169 (6): 3076-3084.
Dellon, "The Pathogenesis of Eosinophilic Esophagitis: Beyond the Eosinophil", Dig. Dis. Sci. (2013) 58:1445-1448.
Desreumaux, et al., "Interleukin 3, Granulocyte-Macrophage Colony-Stimulating Factor, and Interleukin 5 in Eosinophilic Gastroenteritis" (1996), Gastroenterology 110:7 68-77 4.
Dong Li et al., "IL-33 promotes ST2-dependent lung fibrosis by the induction of alternatively activated macrophages and innate lymphoid cells in mice," Journal of Allergy and Clinical Immunology, vol. 134 (No. 6), 1422-1432, e11, (2014). doi:10.1016/j.jaci.2014. 05.011.
Edwards et al., "The remarkable flexibility of the human antibody repertoire; isolation of over one thousand different antibodies to a single protein, BLyS," JMB, vol. 334: 103-118, (2003). Doi.10. 1016/j.mb.2003.09.054.
European Search Report dated Dec. 18, 2014 for corresponding European application No. 14162081.5.
Fillon, et al., "Epithelial Function in Eosinophilic Gastrointestinal Diseases" (2009), Immunol Allergy Clin N Am 29, pp. 171-178.
Foote et al., "Antibody Framework Residues Affecting the Conformation of the Hypervariable Loops" (1992) J. Mol. Biol. 224:487-499.
Foroughi, et al., "Anti-IgE Treatment of Eosinophil Associated Gastrointestinal Disorders" (2007), J. Allergy Clin Immunol 120(3):594-601.
Franciosi et al., "Eosinophilic Esophagitis" (2009), Immunol Allergy Clin N Am 29, pp. 19-27.
Gavett, et al. "Interleukin-4 receptor blockade prevents airway responses induced by antigen challenge in mice" (1997) The American Physiological Society 272:L253-L261.
Gadani et al., "Interleukin-4: A Cytokine to Remember," J Immunol. Nov. 1, 2012; 189(9): 4213-4219. doi:10.4049/jimmunol.1202246.
GenBank: Accession No. AEP47229, "Sequence 67 from patent U.S. Pat. No. 8,008,076," Sep. 30, 2011. [Retrieved from the Internet Mar. 28, 2017: <URL: http://www.ncbi.nlm.nih.gov/protein/AEP47229>].

(56) References Cited

OTHER PUBLICATIONS

GenBank: Accession No. AEP47235, "Sequence 111 from patent U.S. Pat. No. 8,008,076," Sep. 30, 2011. [Retrieved from the Internet Mar. 28, 2017: <URL: http://www.ncbi.nlm.nih.gov/protein/AEP47235>].
GenBank: Accession No. AFD49488, "Sequence 28 from patent U.S. Pat. No. 8,129,503," Mar. 14, 2012. [Retrieved from the Internet Mar. 28, 2017: <URL: http://www.ncbi.nlm.nih.gov/protein/AFD49488>].
GenBank: Accession No. BAC05421, "unnamed protein product [Homo sapiens]," Sep. 14, 2016. [Retrieved from the Internet Mar. 28, 2017: <URL: http://www.ncbi.nlm.nih.gov/protein/BAC05421>].
Gevaert et al., "Nasal IL-5 levels determine the response to anti-IL-5 treatment in patients with nasal polyps" (2006) Journal of Allergy and Clinical Immunology. 118(5):1133-1141.
Giusti et al. Somatic diversification of S107 from an antiphosphocholine to an anti-DNA autoantibody is due to a single base change in its heavy chain variable region (Proc. Natl. Acad. Sci. USA. May 1987; 84 (9): 2926-2930).
Goel et al., "Plasticity within the Antigen-Combining site may manifest as molecular mimicry in the humoral immune response," The Journal of Immunology, vol. 173: 7358-7367 (2004).
Groves, et al. (2007) AERODERM in AD Poster at St. John's Institute of Dermatology, "Inhibition of IL-4 and IL-13 with an IL-4 mutein (Aeroderm) protects against flares in atopic eczema".
Grunewald, et al., "An Antagonistic IL-4 Mutant Prevents Type I Allergy in the Mouse: Inhibition of the IL-4/IL-I 3 Receptor System completely Abrogates Humoral Immune Response to Allergen and Development of Allergic Symptoms in Vivo" (1998) The Journal of Immunology 160(8):4004-4009.
Gussow et al. "Humanization of Monoclonal Antibodies" Methods in Enzymology. (1991); 203: 99-121.
Hayakawa et al., "Soluble ST2 Blocks Interleukin-33 Signaling in Allergic Airway Inflammatioel," Journal of Biological Chemistry, 282(36):26369-26380, (2007).
Hijnen, et al. (2004) J. Allergy Clin. Immunology 113(2): 334-340, "Serum thymus and activation-egulated chemokine (TARC) and cutaneous T Cell-attracting chemokine (CT ACK) levels in allergic diseases: TARC and CT ACK are disease-specific markers for atopic dermatitis".
Holm et al. "Functional mapping and single chain construction of the anti-cytokeratin 8 monoclonal antibody TS1" (Mol. Immunol. Feb. 2007; 44 (6): 1075-1084).
Holt et al., "Domain antibodies: Proteins for Therapy," Trends Biotechnol. (2003) 21:484-490 (Cell Press, Cambridge, GB).
Hong et al., "The inhibitory function of Fc-ST2 depends on cell type; IL-1RAcP and ST2 are necessary but insufficient for IL-33 activity," Immunol Res, 56:122-130 , (2013).
Hopkins et al. (2007) Otolaryngology-Head and Neck Surgery. 2007, 137(4):555-561. "The Lund-Mackay staging system for chronic rhinosinusitis: How is it used and what does it predict?"
Hueber et al., "IL-33 induces skin inflammation with mast cell and neutrophil activation," Eur. J. Immunol, 41: 2229-2237, doi: 10.1002/eji.201041360, (2011).
International Preliminary Report on Patentability corresponding to International Patent Application No. PCT/US2013/055747, issued Feb. 24, 2015.
International Search Report and Written Opinion corresponding to International Patent Application No. PCT/US2014/043440, dated Oct. 6, 2014.
International Search Report corresponding to International Patent Application No. PCT/US2013/055747, mailed Feb. 13, 2014.
International Search Report and Written Opinion for International Application No. PCT/US2015/020564 mailed Jun. 12, 2015.
International Search Report and Written Opinion for International Patent Application No. PCT/US2015/017834 dated May 20, 2015.
Jahnz-Rozyk, et al. "Serum thymus and activation-regulated chemokine, macrophage-derived chemokine and eotaxin as marker of severity of atopic dermatitis" (2005) Allergy 60: 685-688.

Jiang et al., "IL-33 attenuates EAE by suppressing IL-17 and IFN-γ production and inducing alternatively activated macrophages," EJI Journal, vol. 42: 1804-1814, (2012).
Junttila, et al., "Tuning sensitivity to IL-4 and IL-13: differential expression of IL-4Ra, IL-I 3Ral, and Ye regulates relative cytokine sensitivity" (2008) J. Exp. Med. 205(11): 2595-2608.
Jyonouchi, et al., Jan. 2014, Clin. Exp. Allergy, 44(1): 58-68, "Invariant Natural Killer T cells in children with Eosinophilic Esophagitis".
Kagami, et al., "Significant elevation of serum levels of eotaxin-3/CCL26, but not of eotaxin-2/CCL24, in patients with atopic dermatitis: serum eotaxin-3/CCL26 levels reflect the disease activity of atopic dermatitis" (2003) Clin. Exp. Immunology 134: 309-313.
Kakinuma, et al., "Serum macrophage-derived chemokine (MDC) levels are closely related with the disease activity of atopic dermatitis" (2002) Clin. Exp. Immunol 127:270-273.
Kakinuma, et al., "Thymus and activation-regulated chemokine in atopic dermatitis: Serum thymus and activation-regulated chemokine level is closely related with disease activity" (2001) J. Allergy Clin. Immunol. 107(3):535-541.
Kakkar, et al., "Population PK and IgE Pharmacodynamic Analysis of a Fully Human Momoclonal Antibody Against IL4 Receptor" (2011) Pharmaceutical Research, Kluwer Academic Publishers-Plenum Publishers 28(10):2530-2542.
Kamekura et al., "The role of IL-33 and its receptor ST2 I human nasal epithelium with allergic rhinitis," Clinical & Experimental Allergy, vol. 42:218-228, (2012).
Katial, "Biomarkers for Nononcologic Gastrointestinal Disease" (2009), Immunol Allergy Clin N Am 29, pp. 119-127.
Kelly et al., "Poster 1013: IL-4R alpha antibody inhibits IgE production and airway remodeling in mouse model of house dust mite-induced eosinophilic asthma" (2014) World Allergy Organization Journal 7(1):P8.
Kim et al., "Beneficial effect of anti-interleukin-33 on the murine model of allergic inflammation of the lower airway," J Asthma., 49(7):738-743, doi: 10.3109/02770903.2012.702841, (2012).
Kim et al., "Anti-IL-33 antibody has a therapeutic effect in a murine model of allergic rhinitis," Allergy, 8 pages, doi: 10.1111/j.1398-9995.2011.02735.x., (2011).
Kim, et al., "Rebound eosinophilia after treatment of nypere-osinophilic syndrome and eosinophilic gastroenteritis with monoclonal anti-IL-5 antibody SCH55700" (2004), J Allergy Clin Immunol 114(6):1449-1455.
Konikoff, et al., "A Randomized, Double-Blind, Placebo-Controlled Trial of Fluticasone Propionate for Pediatric Eosinophilic Esophagitis" 2006, Gastroenterology 131:1381-1391.
Kopf, et al., "Disruption of the murine IL-4 gene blocks Th2 cytokine responses" (1993) Letters to Nature 362: 245-248.
Kostic et al., "A Fully Human IL4Ra Antibody for Inhibition of IL-4/IL-13-driven TH2 Responses in Allergic Disease" (2010) Clinical Immunology 135:SI05-SI06.
Kottyan, et al., "Genome-wide association analysis of eosinophilic esophagitis provides insight into the tissue specificity of this allergic disease" (Aug. 2014) Nature Genetics vol. 46, No. 8: 895-902.
Kulis, et al., "Single-tree nut immunotherapy attenuates allergic reactions in mice with hypersensitivity to multiple tree nuts" (2011) J. Allergy Clin Immunol 127: 81-88.
Leung, et al., "Effect of Anti-IgE Therapy in Patients with Peanut Allergy" (2003) The New England Journal of Medicine 348:986-993.
Leung, et al., "New insights into atopic dermatitis" (2004) The Journal of Clinical Investigation 113(5): 651-657.
Lezcano-Meza et al., "Interleukin (IL)-4 and to a lesser extent either IL-13 or interferon-gamma regulate the production of eotaxin-2/CCL24 in nasal polyps" (2003) Allergy. 58(10): 1011-1017.
Li et al., "IL-33 blockade suppresses the development of experimental autoimmune encephalomyelitis in C57BL/6 mice," Journal of Neuroimmunology, 247: 25-31, (2012).
Liacouras, et al., "Eosinophilic esophagitis: Updated consensus recommendations for children and adults" (Jul. 2011) J. Allergy Clin Immunol 128(1).

(56) References Cited

OTHER PUBLICATIONS

Liew et al., "Disease-associated functions: of IL-33: the new kid in the IL-1 family," Nature Reviews, Immunology, 10(2):103-110, (2010).

Liew et al., "Interleukin-33 in Health and Disease," Nature Reviews—Immunology, vol. 16; Nov. 2016; pp. 676-689. [Retrieved from the Internet at <www.nature.com/nri>].

Liu et al., "Anti-Il-33 antibody treatment inhibits airway inflammation in a murine model of allergic asthma," Biomedical and Biophysical Research Communications, vol. 386: (2009) pp. 181-185.

Liu, et al., "Hydrodynamics-based transfection in animals by systemic administration of plasmid DNA" (1999) Gene Therapy, 6:1258-1266.

Lloyd et al., "Modelling the human immune response: performance of a human antibody repertoire against a broad panel of therapeutically relevant antigens," Protein Engineering, Design & Selection, vol. 22 (3):159-168, (2009).

Lohning et al., "T1/ST2 is preferentially expressed on murine Th2 cells, independent of interleukin 4, interleukin 5, and interleukin 10, and important for Th2 effector function," Proc. Natl. Acad. Sci. USA, 95(12):6930-6935, (1998).

Lucendo et al., "Adult versus pediatric eosinophilic esophagitis: important differences and similarities for the clinician to understand" (2012) Expert Rev. Clin. Immunol. 8(8):733-745.

Ludmila et al., "Poster 1013: IL-4R alpha antibody inhibits IgE production and airway remodeling in the mouse of house dust mite-induced eosinophilic asthma" (2014) World Allergy Organization Journal. 7(1):P8.

Lwin, et al., "Eosinophilic gastritis: histopathological characterization and quantification of the normal gastric eosinophil content" (2011) Modern Pathology 24:556-563.

MacCallum et al., "Antibody-antigen Interactions: Contact Analysis and Binding Site Topography", J. Mol. Biol. Oct. 11, 1996; 262 (5): 732-745.

Maliszewski et al., "In Vivo Biological Effects of Recombinant Soluble Interleukin-4 Receptor." Jul. 1994, Proc. Soc. Exp. Biol. Med. 206:233-7 (Blackwell Science, USA).

Mannon et al., "Interleukin 13 and its role in gut defense and inflammation" (2012) GUT 61(12):1765-1773.

Mariuzza et al., "The Structural Basis of Antigen-Antibody Recognition", Annu. Rev. Biophys. Biophys. Chem. 1987; 16: 139-159.

Masterson, et al., "Update on clinical and immunological features of eosinophilic gastrointestinal diseases" (2011) Curr. Opin. Gastroenterol. 27(6): 515-522.

Miller, "Role of IL-33 in inflammation and disease," Journal of Inflammation, vol. 8:22, (2011). Available on the Internet at <http://journal-inflammation.com/content/8/1/22>.

Mishra et al., "Intratracheal IL-13 Induces Eosinophilic Esophagitis by an IL-5, Eotaxin-1, and STAT6-Dependent Mechanism" (2003) Gastroenterology 125:1419-1427.

Mishra, et al., "An etiological role for aeroallergens and eosinophils in experimental esophagitis" (2001) J. Clin. Invest. 107:83-90.

Mishra, et al., "IL-5 Promotes Eosinophil Trafficking to the Esophagus" (2002) The Journal of Immunology 168:2464-2469.

Molfino et al., "Molecular and clinical rationale for therapeutic targeting of interleukin-5 and its receptor" (2012) Clinical & Experimental Allergy. 42(5):712-737.

Morioka et al., "IL-4/IL-13 antagonist DNA vaccination successfully suppresses Th2 type chronic dermatitis", Br. J. Dermatol. Jun. 2009; 160 (6): 1172-9.

Nadeau, et al., Letters to the Editor, "Rapid oral desensitization in combination with omalizumab therapy in patients with cow's milk allergy" (2011) J. Allergy Clin. Immunol 127(6).

Nguyen et al., "Immune modulation for treatment of allergic disease" (2011) Immunological Reviews 242(1):258-271.

Niederberger, "Allergen-specific immunotherapy" (2009) Immunology Letters 122: 131-133.

Niranjan, et al., "Pathogenesis of allergen-induced eosinophilic esophagi tis is independent of interleukin (IL)-13" (2013) Immunology and Cell Biology, pp. 1-8.

Noel, et al., "Eosinophilic Esophagitis" (2004) The New England Journal of Medicine 351:940-941.

Novartis, 2013, QAX576 "A double blinded, randomized, placebo-controlled trial of intravenous QAX576 in the treatment of eosinophilic esophagitis".

Oh, et al., "Investigational therapeutics targeting the IL-4/IL-13/ST AT-6 pathway for the treatment of asthma" (2010) Eur. Respir. Rev. 19(115):46-54.

Ohno, et al. "Antigen-binding specificities of antibodies are primarily determined by seven residues of V $_H$" (1985) Proc. Natl. Acad. Sci. USA 82: 2945-2949.

Ong, "Editorial update on emerging treatments of atopic dermatitis" (2012) Expert Opinion on Emerging Drugs 17:2: 129-133.

Oshikawa et al., "Acute eosinophilic pneumonia with increased soluble ST2 in serum and bronchoalveolar lavage fluid," Respiratory Medicine, 95:532-533, (2001).

Oshikawa et al., "Elevated Soluble ST2 Protein Levels in Sera of Patients with Asthma with an Acute Exacerbation," Am J Respir Crit Care Med, 164:277-281, (2001).

Otani et al., "Anti-IL-5 therapy educes mast cell and IL-9 cell numbers in pediatric patients with eosinophilic esophagitits" (2013) Journal of Allergy and Clinical Immunology 131(6):1576-1582.

Otulana et al. (2011) Am. J. Respir. Crit. Care Med. Vol. 183. pp. A6179. "A Phase 2b Study of inhaled Pitrakinra, An IL-4R/IL-13 Antagonist, Successfully Identified Responder Subpopulations of Patients with Uncontrolled Asthma".

Oyoshi, et al. (2005) Advances in Immunology 102: 135-226, "Cellular and Molecular Mechanisms in Atopic Dermatitis".

Palmer et al., "Interleukin-33 biology with potential insights into human diseases," Nature Reviews, Rheumatology, 7(No):321-329, (2011).

Palmer et al., "The IL-1 receptor accessory protein (AcP) is required for IL-33 signaling and soluble AcP enhances the ability of soluble ST2 to inhibit IL-33," Cytokine, 42(3):358-364, (2008).

Pastorelli et al., "Epithelial-derived IL-33 and its receptor ST2 are dysregulated in ulcerative colitis and in experimental Th1/Th2 driven enteritis," PNAS, 107(17):8017-8022, doi: 10.1073/pnas. 0912678107, (2010).

Peserico, et al. (2008) British Journal of Dermatology 158: 801-807, "Reduction of relapses of atopic dermatitis with methylprednisolone aceptonate cream twice weekly in addition to maintenance treatment with emollient: a multicentre, randomized, double-blind, controlled study".

Prieto et al., 2013, Curr Gastroenterol Rep 15:324, "Eosinophilic Esophagitis in Adults: an Update on Medical Management".

Prussin, et al., 2009, J Allergy Clin Immunol. 124(6): 1326-1332, "Eosinophilic gastrointestinal disease and peanut allergy are alternatively associated with IL-5+ and IL-5-TH2 responses".

Rafi, et al. (2010) Allergy and Asthma Proceedings 31(1): 76-83, "Effects of omalizumab in patients with food allergy".

Rayapudi, et al., 2010, Journal of Leukocyte Biology 88, "Indoor insect allergens are potent inducers of experimental eosinophilic esophagitis in mice".

Receptos, Inc. 2013 Annual Report.

Results of "Manual search of homology for sequence SEQ ID No. 158" by Russian Examiner (from corresponding Russian application No. 2011120194) dated Oct. 16, 2013.

Results of "Search of homology by means of the Internet search shell NCBI Blast®" by Russian Examiner (from corresponding Russian application No. 2011120194) dated Oct. 16, 2013 "for: a) sequence SEQ ID No. 150 . . . b) sequence SEQ ID No. 148 . . . c) sequence SEQ ID No. 156 . . . sequence SEQ ID No. 160".

Ring, et al., J. Eur. Acad. Dermatol. Venereal. (2012) 26(8) 1045-1060, "Guidelines for treatment of a topic eczema (atopic dermatitis) Part 1".

Roitt, et al. (2001) Mosby—Harcourt Publishers Limited, "Immunology—Sixth Edition" pp. 110-111.

Roll, et al. (2006) J. Invest Allergol Clin Immunol 16(2): 79-85, "Safety of specific immunotherapy using a four-hour ultra-rush induction scheme in bee and wasp allergy".

(56)     References Cited

OTHER PUBLICATIONS

Rothenberg, 2009, Gastroenterology 137:1238-1249, "Biology and Treatment of Eosinophilic Esophagitis".

Rothenberg, Jan. 2004, J Allergy Clin Immunol, "Eosinophilic gastrointestinal disorders (EGID)", pp. 11-28.

Rudikoff et al. "Single amino acid substitution altering antigen-binding specificity", Proc. Natl. Acad. Sci. USA. 1982; 79: 1979-1983.

Sampson, et al. (May 2011) J. Allergy Clin Immunol. 127(5):1309-1311, Letters to the Editor, "A phase II, randomized, double-blind, parallel-group, placebo-controlled oral food challenge trial of Xolair (omalizumab) in peanut allergy".

Sanofi and Regeneron Report Positive Proof-of-Concept Data for Dupilumab, an IL-4R alpha Antibody, in Atopic Dermatitis 71st Annual Meeting of the American Academy of Dermatology (2013) http://files.shareholder.com/downloads/REGN/26892 I 20 I 2x0x64053 I/794a7 e54-6904-4 I 6b-ba38-a4cccl726852/REGN News Mar. 2, 2013 General Releases.pdf.

Sanofi with Regeneron Pharmaceuticals. "An Evaluation of Dupilumab in Patients with Nasal Polyposis and Chronic Symptoms of Sinusitis," Trial in Progress, Jun. 2014. Clinical Trials.gov Identifier: NCT01920893. Retrieved from the Internet URL: http://c linica ltrials. govishow/NCT01920893 Accessed on Sep. 29, 2014: 9 pages.

Sato et al., 1993, "Recombinant Soluble Murine IL-4 Receptor Can Inhibit or Enhance IgE Responses in Vivo." J Immunol 150:2717-23 (American Association of Immunologists, USA).

Scavuzzo et al. (2005) Biomedicine & pharmacotherapy. 59(6):323-9. "Inflammatory mediators and eosinophilia in atopic and non-atopic patients with nasal polyposis".

Schmidt-Weber (2012) Chem Immunol Allergy 96: 120-125, "Anti-IL-4 as a New Strategy in Allergy".

Schmitt, et al. (2007) J. of Allergy and Clinical Immunology 120(6): 1389-1398, "What are the best outcome measurements for atopic eczema? A systematic review".

Schmitz et al., "IL-33, an Interleukin-1-like Cytokine that Signals via the IL-1 Receptor-Related Protein ST2 and Induces T Helper Type 2-Associated Cytokines," Immunity, 23:479-490, (2005).

Schneider, et al. (2013) J. Allergy Clin Immunol 132(6): 1368-1374, "A pilot study of omalizumab to facilitate rapid oral desensitization in high-risk peanut-allergic patients".

Sekiya et al. (2002) Allergy. 57:173-177. "Increased levels of a TH2-type CC chemokine thymus and activation-regulated chemokine (TARC) in serum and induced sputum of asthmatics".

Slager et al. (2012) Journal of Allergy, Asthma and Immunology. 130(2):516-522. "IL-4 Receptor Polymorphisms Predict Reduction in Asthma Exacerbations During Response to an Anti IL-4 Receptor Antagonist".

Spirin (1986) Vysshaya shkola, Moscow, pp. 17-23, "Molecular Biology Ribosome structure and protein biosynthesis", original Russian article and English language translation of same provided by foreign associate handling local prosecution of Russian application No. 2011120194.

Stein, et al., 2006, J Allergy Clin Immunol 118(6):1312-1319, "Anti-IL-5 (mepolizumab) therapy for eosinophilic esophagitis".

Stevenson et al., "Moving towards a new generation of animal models for asthma and COPD with improved clinical relevance," Pharmacol Ther., 130(2):93-105, Abstract Only, doi: 10.1016/j.pharmthera.2010.10.008, (2011). Epub Nov. 11, 2010.

Stolarski et al., "IL-33 Exacerbates Eosinophil-Mediated Airway Inflammation," J Immunol, 185:3472-3480, doi: 10.4049/jimmunol.1000730, (2010).

Stone et al., (2008) Clinical & Experimental Allergy 38(12):1858-1865, "Immunomodulatory therapy of eosinophil-associated gastrointestinal diseases".

Strauman, 2009, Immunol Allergy Clin N Am 29, pp. 11-18, "Clinical Evaluation of the Adult who has Eosinophilic Esophagitis".

Straumann, 2005, J Allergy Clin Immunol 115(2):418-419, "Eosinophilic esophagi tis: Escalating epidemiology?"

Straumann, et al., 2001, J Allergy Clin Immunol 108(6):954-961, "Idiopathic eosinophilic esophagitis is associated with a T H2-type allergic inflammatory response".

Straumann, et al., 2009 Gut, "Anti-interleukin-5 antibody treatment (mepolizumab) in active eosinophilic eosophagitis: a randomized, placebo-controlled, double-blind trial".

Tajima et al., "The Increase in Serum Soluble ST2 Protein Upon Acute Exacerbation of Idiopathic Pulmonary Fibrosis," Chest, 124:1206-1214, (2003).

Tazawa, et al. (2004) Arch Dermatol Res 295:459-464, "Relative importance of IL-4 and IL-13 in lesional skin of atopic dermatitis".

Tomkinson et al. (2001) J. Immunol 166: 5792-5800, "A Murine IL-4 Receptor Antagonist that Inhibits IL-4- and IL-13-induced Responses Prevents Antigen-Induced Airway Eosinophilia and Airway Hyperresponsiveness".

Uniprot: "Alignment human and cynomolgus monkey IL-33", Aug. 3, 2017 (Aug. 3, 2017), XP055396027, retrieved from the Internet: <http://www.uniprot.org/align/A20170803AAFB7E4D2F1D05654627429E83DA5CCEC7E4343> [retrieved on Aug. 3, 2017].

U.S. Appl. No. 14/210,599, Requirement for Restriction/Election mailed Jun. 29, 2015.

U.S. Appl. No. 14/210,599, Non-Final Office Action mailed Sep. 25, 2015.

U.S. Appl. No. 14/205,512, Requirement for Restriction/Election mailed Mar. 15, 2016.

U.S. Appl. No. 14/210,599, Non-Final Office Action mailed May 23, 2016.

U.S. Appl. No. 14/205,512, Notice of Allowance mailed May 27, 2016.

U.S. Appl. No. 14/210,599, Notice of Allowance mailed Dec. 19, 2016.

U.S. Appl. No. 15/248,348, Requirement for Restriction/Election mailed Sep. 14, 2017.

U.S. Appl. No. 15/248,348, Notice of Allowance mailed Jan. 17, 2018.

U.S. Appl. No. 15/463,910, Notice of Allowance mailed Feb. 26, 2018.

U.S. Appl. No. 15/827,357, Requirement for Restriction/Election mailed Apr. 1, 2019.

U.S. Appl. No. 15/827,357, Non-Final Office Action mailed Aug. 20, 2019.

U.S. Appl. No. 15/827,357, Non-Final Office Action mailed Jan. 22, 2020.

U.S. Appl. No. 15/827,357, Notice of Allowance mailed Jun. 23, 2020.

U.S. Appl. No. 17/028,011, Non-Final Office Action mailed Feb. 23, 2023.

U.S. Appl. No. 17/028,011, Notice of Allowance mailed Aug. 30, 2023.

Vajdos et al. "Comprehensive Functional Maps of the Antigen-binding Site of an Anti-ErbB2 Antibody Obtained with Shotgun Scanning Mutagenesis" J. Mol. Biol. (Jul. 5, 2002); 320 (2): 415-428.

Veerappan, et al., 2009, Clinical Gastroenterology and Hepatology 7:420-426, "Prevalence of Eosinophilic Esophagitis in an Adult Population Undergoing Upper Endoscopy: A Prospective Study".

Vestergaard, et al. (2000) The Journal of Investigative Dermatology 115(4): 640-646, "A Th2 Chemokine, TARC, Produced by Keratinocytes May Recruit CLA +CCR4+ Lymphocytes into Lesional Atopic Dermatitis Skin".

Virchow et al. (1994) Lung. 172:313-334. "Cellular and immunological markers of allergic and intrinsic bronchial asthma".

Waddell et al., "IL-33 signaling protects from murine oxazolone colities by supporting intestinal epithelial function," HHS Public Access; Inflamm Bowel Author Manuscript, vol. 21(12): 2737-2746, 1-20 (2015). Doi:10.1097/MIB.0000000000000532.

Walder et al. (2009) The Journal of Pain pp. 1-9 "ASICl and ASIC3 Play Different Roles in the Development of Hyperalgesia After Inflammatory Muscle Injury".

Waldmann et al. (1997) Nature 386: 173-177 "A proton-gated cation channel involved in acid-sensing".

(56) References Cited

OTHER PUBLICATIONS

Walker, et al. (1993) Clinical and Experimental Allergy 23:145-153, "Atopic dermatitis: correlation of peripheral blood T cell activation, eosinophilia and serum factors with clinical severity".

Wang et al., 2008, Current Opinion in Immunology 20:697-702, "The IL-17 cytokine family and their ole in allergic inflammation".

Wark, et al. (2006) Advanced Drug Delivery Reviews 58:657-670, "Latest technologies for enhancement of antibody affinity".

Weihrauch, et al. (2005) Cancer Research 65:5516-5519, "Elevated Serum Levels of CC Thymus and Activation-Related Chemokine (T ARC) in Primary Hodgkin's Disease: Potential for a Prognostic Factor".

Weinbrand-Goichberg, et al., 2013, Immunol Res, "Eosinophilic esophagitis: an immune-mediated esophageal disease".

Wenzel et al., (2013) New England Journal of Medicine 368(26):2455-2466, "Dupilumab in Persistent Asthma with Elevated Eosinophil Levels".

Wershil, 2009, Immunol Allergy Clin N Am 29, pp. 189-195. "Exploring the Role of Mast Cells in Eosinophilic Esopha_gitis".

Whalley, et al. (2004) British Journal of Dermatology 150: 274-283, "A new instrument for assessing quality of life in atopic dermatitis: international development of the Quality of Life Index for Atopic Dermatitis (QoLIAD)".

Wilhelm et al., 2011, Frontiers in Immunology 2(68), "Innate lymphoid cells and type 2 (Th2) mediated immune responses-pathogenic or beneficial?"

Wills-Karp et al., 2008, Science Signaling 1(51), "Untangling the Complex Web of IL-4 and IL-13 Mediated Signaling Pathways".

Winkler et al. "Changing the Antigen Binding Specificity by Single Point Mutations of an Anti-p24 (HIV-1) Antibody" J. Immunol. Oct. 15, 2000; 165 (8): 4505-4514.

Winter et al., (1993) Immunology Today 14(6):243-246, "Humanized Antibodies".

WIPO Application No. PCT/US2017/064041, PCT International Search Report and Written Opinion of the International Searching Authority mailed Feb. 9, 2018.

WIPO Application No. PCT/US2014/023930, PCT International Search Report and Written Opinion of the International Searching Authority mailed Dec. 12, 2014.

WIPO Application No. PCT/US2014/027058, PCT International Search Report and Written Opinion of the International Searching Authority mailed Jun. 26, 2014.

WIPO Application No. PCT/US2014/023930, PCT International Preliminary Report on Patentability mailed 09- 24-2015.

WIPO Application No. PCT/US2014/027058, PCT International Preliminary Report on Patentability mailed 09- 24-2015.

Wu et al., "Humanization of a Murine Monoclonal Antibody by Simultaneous Optimization of Framework and CDR Residues" J. Mol. Biol. Nov. 19, 1999; 294 (1): 151-162.

Xiao et al., "Interleukin-33 deficiency exacerbated experimental autoimmune encephalomyelitis with an influence on immune cells and glia cells," Molecular Immunology, vol. 101:550-563, (2018).

Yamanaka et al., "The Role of Cytokines/Chemokines in the Pathogenesis of Atopic Dermatitis" Curr. Probl. Dermatol. 2011; 41: 80-92.

Yan et al., (2006) Work J Gastroenterol 12(15):2328-2334 "Eosinophilic esophagitis: A newly established cause of dysphagia".

Zuo, et al., 2010, Journal of Immunology 185:660-669, "IL-13 Induces Esophageal Remodeling and Gene Expression by an Eosinophil-Independent, IL-13 R {alpha} 2-Inhibited Pathway".

Zurawski, SM et al. 1995 "The primary binding subunit of the human Interleukin-4 receptor is also a component of the Interleukin-13 receptor" J. of Biol. Chem. Am. Society of Biolochemical Biologists. 270(23): 13869-13878.

* cited by examiner

A

B

C

D

SEQUENCE LISTING

```
Sequence total quantity: 356
SEQ ID NO: 1               moltype = DNA  length = 366
FEATURE                    Location/Qualifiers
misc_feature               1..366
                           note = Synthetic
source                     1..366
                           mol_type = other DNA
                           organism = synthetic construct
SEQUENCE: 1
caggtgcagc tggtggagtc tggggggaggc gtggtccagc ctgggaggtc cctgagactc   60
tcctgtgcag cgtctggatt caccttcagt agttatggca tgcattgggt ccgccaggct  120
ccaggcaagg ggctggagtg ggtggcagtt atatggtatg atggaagaaa taaatactat  180
acagactccg tgaagggccg attcaccatc tccagagaca attccaagaa cacgctgtat  240
ctgcaaatgg acagcctgag agccgaggac acggctgtgt attactgtgc gagagagagg  300
tatatcagca gctattatgg ggggttcgac ccctggggcc agggagccct ggtcaccgtc  360
tcctca                                                             366

SEQ ID NO: 2               moltype = AA  length = 122
FEATURE                    Location/Qualifiers
REGION                     1..122
                           note = Synthetic
source                     1..122
                           mol_type = protein
                           organism = synthetic construct
SEQUENCE: 2
QVQLVESGGG VVQPGRSLRL SCAASGFTFS SYGMHWVRQA PGKGLEWVAV IWYDGRNKYY   60
TDSVKGRFTI SRDNSKNTLY LQMDSLRAED TAVYYCARER YISSYYGGFD PWGQGALVTV  120
SS                                                                  122

SEQ ID NO: 3               moltype = DNA  length = 24
FEATURE                    Location/Qualifiers
misc_feature               1..24
                           note = Synthetic
source                     1..24
                           mol_type = other DNA
                           organism = synthetic construct
SEQUENCE: 3
ggattcacct tcagtagtta tggc                                          24

SEQ ID NO: 4               moltype = AA  length = 8
FEATURE                    Location/Qualifiers
REGION                     1..8
                           note = Synthetic
source                     1..8
                           mol_type = protein
                           organism = synthetic construct
SEQUENCE: 4
GFTFSSYG                                                             8

SEQ ID NO: 5               moltype = DNA  length = 24
FEATURE                    Location/Qualifiers
misc_feature               1..24
                           note = Synthetic
source                     1..24
                           mol_type = other DNA
                           organism = synthetic construct
SEQUENCE: 5
atatggtatg atggaagaaa taaa                                          24

SEQ ID NO: 6               moltype = AA  length = 8
FEATURE                    Location/Qualifiers
REGION                     1..8
                           note = Synthetic
source                     1..8
                           mol_type = protein
```

```
                        organism = synthetic construct
SEQUENCE: 6
IWYDGRNK                                                              8

SEQ ID NO: 7           moltype = DNA  length = 45
FEATURE                Location/Qualifiers
misc_feature           1..45
                       note = Synthetic
source                 1..45
                       mol_type = other DNA
                       organism = synthetic construct
SEQUENCE: 7
gcgagagaga ggtatatcag cagctattat gggggttcg acccc                     45

SEQ ID NO: 8           moltype = AA  length = 15
FEATURE                Location/Qualifiers
REGION                 1..15
                       note = Synthetic
source                 1..15
                       mol_type = protein
                       organism = synthetic construct
SEQUENCE: 8
ARERYISSYY GGFDP                                                      15

SEQ ID NO: 9           moltype = DNA  length = 321
FEATURE                Location/Qualifiers
misc_feature           1..321
                       note = Synthetic
source                 1..321
                       mol_type = other DNA
                       organism = synthetic construct
SEQUENCE: 9
gacatccaga tgacccagtc tccatcctcc gtgtctgcat ctgtaggaga cagagtcacc    60
atcacttgtc gggcgagtca gggtattagt agttggttag cctggtatca gcagaaacca    120
gggaaagccc ctaaggtcct gatctatgct gcatccagtt tgcaaagtgg ggtcccatca    180
aggttcagcg gcagtggatc tgggacagat ttcactctca ccatcagcag cctgcagcct    240
gaagattttg caacttacta ttgtcaacag gctaacagtt tcccattcac tttcggccct    300
gggaccaaac tggatatcaa g                                              321

SEQ ID NO: 10          moltype = AA  length = 107
FEATURE                Location/Qualifiers
REGION                 1..107
                       note = Synthetic
source                 1..107
                       mol_type = protein
                       organism = synthetic construct
SEQUENCE: 10
DIQMTQSPSS VSASVGDRVT ITCRASQGIS SWLAWYQQKP GKAPKVLIYA ASSLQSGVPS    60
RFSGSGSGTD FTLTISSLQP EDFATYYCQQ ANSFPFTFGP GTKLDIK                  107

SEQ ID NO: 11          moltype = DNA  length = 18
FEATURE                Location/Qualifiers
misc_feature           1..18
                       note = Synthetic
source                 1..18
                       mol_type = other DNA
                       organism = synthetic construct
SEQUENCE: 11
cagggtatta gtagttgg                                                  18

SEQ ID NO: 12          moltype = AA  length = 6
FEATURE                Location/Qualifiers
REGION                 1..6
                       note = Synthetic
source                 1..6
                       mol_type = protein
                       organism = synthetic construct
SEQUENCE: 12
QGISSW                                                                6

SEQ ID NO: 13          moltype =   length =
SEQUENCE: 13
000

SEQ ID NO: 14          moltype =   length =
SEQUENCE: 14
000

SEQ ID NO: 15          moltype = DNA  length = 27
```

-continued

```
FEATURE                Location/Qualifiers
misc_feature           1..27
                       note = Synthetic
source                 1..27
                       mol_type = other DNA
                       organism = synthetic construct
SEQUENCE: 15
caacaggcta acagtttccc attcact                                    27

SEQ ID NO: 16          moltype = AA  length = 9
FEATURE                Location/Qualifiers
REGION                 1..9
                       note = Synthetic
source                 1..9
                       mol_type = protein
                       organism = synthetic construct
SEQUENCE: 16
QQANSFPFT                                                        9

SEQ ID NO: 17          moltype = DNA  length = 357
FEATURE                Location/Qualifiers
misc_feature           1..357
                       note = Synthetic
source                 1..357
                       mol_type = other DNA
                       organism = synthetic construct
SEQUENCE: 17
gaggtgcagc tgttggagtc tggggggagac ttggtacagc ctggggggtc cctgagactc  60
tcctgtgcag cctctggatt caccttcagc agctatgcca tgagctgggt ccgccaggct  120
ccagggaagg ggctggagtg ggtctcagtt attagtggta gtggaagtag cacagactac  180
gcagactccg tgaagggccg gttcaccatt tccagagaca attccaggga cacgctgcat  240
ctgcaaatga acagcctgag agccgaggac acggccgtat attactgtgc gaaaacgttc  300
tactacttct acggtttgga cgtctggggc caagggacca cggtcaccgt ctcctca      357

SEQ ID NO: 18          moltype = AA  length = 119
FEATURE                Location/Qualifiers
REGION                 1..119
                       note = Synthetic
source                 1..119
                       mol_type = protein
                       organism = synthetic construct
SEQUENCE: 18
EVQLLESGGD LVQPGGSLRL SCAASGFTFS SYAMSWVRQA PGKGLEWVSV ISGSGSSTDY  60
ADSVKGRFTI SRDNSRDTLH LQMNSLRAED TAVYYCAKTF YYFYGLDVWG QGTTVTVSS   119

SEQ ID NO: 19          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 19
ggattcacct tcagcagcta tgcc                                       24

SEQ ID NO: 20          moltype = AA  length = 8
FEATURE                Location/Qualifiers
REGION                 1..8
                       note = Synthetic
source                 1..8
                       mol_type = protein
                       organism = synthetic construct
SEQUENCE: 20
GFTFSSYA                                                         8

SEQ ID NO: 21          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 21
attagtggta gtggaagtag caca                                       24

SEQ ID NO: 22          moltype = AA  length = 8
FEATURE                Location/Qualifiers
REGION                 1..8
                       note = Synthetic
```

```
source                    1..8
                          mol_type = protein
                          organism = synthetic construct
SEQUENCE: 22
ISGSGSST                                                                          8

SEQ ID NO: 23             moltype = DNA   length = 36
FEATURE                   Location/Qualifiers
misc_feature              1..36
                          note = Synthetic
source                    1..36
                          mol_type = other DNA
                          organism = synthetic construct
SEQUENCE: 23
gcgaaaacgt tctactactt ctacggtttg gacgtc                                          36

SEQ ID NO: 24             moltype = AA   length = 12
FEATURE                   Location/Qualifiers
REGION                    1..12
                          note = Synthetic
source                    1..12
                          mol_type = protein
                          organism = synthetic construct
SEQUENCE: 24
AKTFYYFYGL DV                                                                     12

SEQ ID NO: 25             moltype = DNA   length = 321
FEATURE                   Location/Qualifiers
misc_feature              1..321
                          note = Synthetic
source                    1..321
                          mol_type = other DNA
                          organism = synthetic construct
SEQUENCE: 25
gacatccaga tgacccagtc tccatcctcc ctgtctgcat ctttaagaga cagagtcacc  60
atcacttgcc gggcgagtca gggcattagc aattatttag cctggtatca gcagaaacca  120
gggaaagttc ctaaggtcct aatctatgct gcatccactt tgcaatcagg ggtcccatct  180
cggttcagtg gcagtggatc tgggacagtt ttcactctca ccatcagcag cctgcagact  240
gaagatgttg caacttatta ctgtcaaaag tatagcagtc ccccattcac tttcggccct  300
gggaccaaag tggatatcaa a                                            321

SEQ ID NO: 26             moltype = AA   length = 107
FEATURE                   Location/Qualifiers
REGION                    1..107
                          note = Synthetic
source                    1..107
                          mol_type = protein
                          organism = synthetic construct
SEQUENCE: 26
DIQMTQSPSS LSASLRDRVT ITCRASQGIS NYLAWYQQKP GKVPKVLIYA ASTLQSGVPS  60
RFSGSGSGTV FTLTISSLQT EDVATYYCQK YSSAPFTFGP GTKVDIK               107

SEQ ID NO: 27             moltype = DNA   length = 18
FEATURE                   Location/Qualifiers
misc_feature              1..18
                          note = Synthetic
source                    1..18
                          mol_type = other DNA
                          organism = synthetic construct
SEQUENCE: 27
cagggcatta gcaattat                                                              18

SEQ ID NO: 28             moltype = AA   length = 6
FEATURE                   Location/Qualifiers
REGION                    1..6
                          note = Synthetic
source                    1..6
                          mol_type = protein
                          organism = synthetic construct
SEQUENCE: 28
QGISNY                                                                            6

SEQ ID NO: 29             moltype =   length =
SEQUENCE: 29
000

SEQ ID NO: 30             moltype =   length =
SEQUENCE: 30
000
```

-continued

```
SEQ ID NO: 31          moltype = DNA  length = 27
FEATURE                Location/Qualifiers
misc_feature           1..27
                       note = Synthetic
source                 1..27
                       mol_type = other DNA
                       organism = synthetic construct
SEQUENCE: 31
caaaagtata gcagtgcccc attcact                                              27

SEQ ID NO: 32          moltype = AA  length = 9
FEATURE                Location/Qualifiers
REGION                 1..9
                       note = Synthetic
source                 1..9
                       mol_type = protein
                       organism = synthetic construct
SEQUENCE: 32
QKYSSAPFT                                                                  9

SEQ ID NO: 33          moltype = DNA  length = 351
FEATURE                Location/Qualifiers
misc_feature           1..351
                       note = Synthetic
source                 1..351
                       mol_type = other DNA
                       organism = synthetic construct
SEQUENCE: 33
caggtgcttc tggtacagtc tggggctgag gtgaagaagc ctggggccac agtgaaggtc  60
tcctgcaagg cttctggatc cactttcacc ggctactata tgcactgggt gcgacaggcc  120
cctggacaag ggcttgagtg gatgggatgg atcaacccta acaatggtgg cacaaactat  180
gcacagaagt tcagggcag ggtcaccatg accagggaca cgtccatcag cacagcctac  240
atggaattga gcaggctgag atctgacgac acggccgtat attactgtgc gagagagttg  300
cggtataact ggaagtcctg gggccaggga accctggtca ccgtctcctc a           351

SEQ ID NO: 34          moltype = AA  length = 117
FEATURE                Location/Qualifiers
REGION                 1..117
                       note = Synthetic
source                 1..117
                       mol_type = protein
                       organism = synthetic construct
SEQUENCE: 34
QVLLVQSGAE VKKPGATVKV SCKASGSTFT GYYMHWVRQA PGQGLEWMGW INPNNGGTNY  60
AQKFQGRVTM TRDTSISTAY MELSRLRSDD TAVYYCAREL RYNWKSWGQG TLVTVSS      117

SEQ ID NO: 35          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 35
ggatccactt tcaccggcta ctat                                                 24

SEQ ID NO: 36          moltype = AA  length = 8
FEATURE                Location/Qualifiers
REGION                 1..8
                       note = Synthetic
source                 1..8
                       mol_type = protein
                       organism = synthetic construct
SEQUENCE: 36
GSTFTGYY                                                                   8

SEQ ID NO: 37          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 37
atcaacccta acaatggtgg caca                                                 24

SEQ ID NO: 38          moltype = AA  length = 8
FEATURE                Location/Qualifiers
```

-continued

```
REGION                  1..8
                        note = Synthetic
source                  1..8
                        mol_type = protein
                        organism = synthetic construct
SEQUENCE: 38
INPNNGGT                                                              8

SEQ ID NO: 39           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 39
gcgagagagt tgcggtataa ctggaagtcc                                     30

SEQ ID NO: 40           moltype = AA  length = 10
FEATURE                 Location/Qualifiers
REGION                  1..10
                        note = Synthetic
source                  1..10
                        mol_type = protein
                        organism = synthetic construct
SEQUENCE: 40
ARELRYNWKS                                                            10

SEQ ID NO: 41           moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 41
gaaattgtgt tgacgcagtc tccaggcacc ctgtctttgt ctccagggga aagagtcacc   60
ctctcctgca gggccagtca gagtgttggc aggccctact tagcctggta ccaacagata   120
cctggccagg ctcccaggct cctcatctat ggtgcatcca gcagggccac tgacatccca   180
gacaggttca gtggcaatgg gtctgggaca gacttcactc tcaccatcag tagactggag   240
cctgaagatt ttgcagtgta ttactgtcag cagtatgata attcccctta tacttttggc   300
caggggacca ggctggagat caaa                                          324

SEQ ID NO: 42           moltype = AA  length = 108
FEATURE                 Location/Qualifiers
REGION                  1..108
                        note = Synthetic
source                  1..108
                        mol_type = protein
                        organism = synthetic construct
SEQUENCE: 42
EIVLTQSPGT LSLSPGERVT LSCRASQSVG RPYLAWYQQI PGQAPRLLIY GASSRATDIP   60
DRFSGNGSGT DFTLTISRLE PEDFAVYYCQ QYDNSPYTFG QGTRLEIK              108

SEQ ID NO: 43           moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 43
cagagtgttg gcaggcccta c                                              21

SEQ ID NO: 44           moltype = AA  length = 7
FEATURE                 Location/Qualifiers
REGION                  1..7
                        note = Synthetic
source                  1..7
                        mol_type = protein
                        organism = synthetic construct
SEQUENCE: 44
QSVGRPY                                                               7

SEQ ID NO: 45           moltype =    length =
SEQUENCE: 45
000

SEQ ID NO: 46           moltype =    length =
```

-continued

```
SEQUENCE: 46
000

SEQ ID NO: 47          moltype = DNA   length = 27
FEATURE                Location/Qualifiers
misc_feature           1..27
                       note = Synthetic
source                 1..27
                       mol_type = other DNA
                       organism = synthetic construct
SEQUENCE: 47
cagcagtatg ataattcccc ttatact                                    27

SEQ ID NO: 48          moltype = AA   length = 9
FEATURE                Location/Qualifiers
REGION                 1..9
                       note = Synthetic
source                 1..9
                       mol_type = protein
                       organism = synthetic construct
SEQUENCE: 48
QQYDNSPYT                                                        9

SEQ ID NO: 49          moltype = DNA   length = 366
FEATURE                Location/Qualifiers
misc_feature           1..366
                       note = Synthetic
source                 1..366
                       mol_type = other DNA
                       organism = synthetic construct
SEQUENCE: 49
gaggtgcagc tggtggagtc tggggggaggc ttggtacaac ctggggggtc cctgagactc   60
tcctgtgcag cctctggatt caccttttaga agctttgcca tgagctgggt ccgccaggct  120
ccagggaagg ggctggaatt ggtctcagat ctcaggacta gtggtggtag tacatactac  180
gcagactccg tgaagggccg gctcaccatc tccagagaca attccaagaa cacgctgtat  240
ctgcaaatga acagcctgag agccgaggac acggccgtat attactgtgc gaaaagccac  300
tatagcacca gctggttcgg gggctttgac tactggggcc agggaaccct ggtcactgtc  360
tcctca                                                          366

SEQ ID NO: 50          moltype = AA   length = 122
FEATURE                Location/Qualifiers
REGION                 1..122
                       note = Synthetic
source                 1..122
                       mol_type = protein
                       organism = synthetic construct
SEQUENCE: 50
EVQLVESGGG LVQPGGSLRL SCAASGFTFR SFAMSWVRQA PGKGLELVSD LRTSGGSTYY   60
ADSVKGRLTI SRDNSKNTLY LQMNSLRAED TAVYYCAKSH YSTSWFGGFD YWGQGTLVTV  120
SS                                                              122

SEQ ID NO: 51          moltype = DNA   length = 24
FEATURE                Location/Qualifiers
misc_feature           1..24
                       note = Synthetic
source                 1..24
                       mol_type = other DNA
                       organism = synthetic construct
SEQUENCE: 51
ggattcacct ttagaagctt tgcc                                       24

SEQ ID NO: 52          moltype = AA   length = 8
FEATURE                Location/Qualifiers
REGION                 1..8
                       note = Synthetic
source                 1..8
                       mol_type = protein
                       organism = synthetic construct
SEQUENCE: 52
GFTFRSFA                                                         8

SEQ ID NO: 53          moltype = DNA   length = 24
FEATURE                Location/Qualifiers
misc_feature           1..24
                       note = Synthetic
source                 1..24
                       mol_type = other DNA
                       organism = synthetic construct
SEQUENCE: 53
```

```
ctcaggacta gtggtggtag taca                                              24

SEQ ID NO: 54          moltype = AA   length = 8
FEATURE                Location/Qualifiers
REGION                 1..8
                       note = Synthetic
source                 1..8
                       mol_type = protein
                       organism = synthetic construct
SEQUENCE: 54
LRTSGGST                                                                8

SEQ ID NO: 55          moltype = DNA   length = 45
FEATURE                Location/Qualifiers
misc_feature           1..45
                       note = Synthetic
source                 1..45
                       mol_type = other DNA
                       organism = synthetic construct
SEQUENCE: 55
gcgaaaagcc actatagcac cagctggttc gggggctttg actac                      45

SEQ ID NO: 56          moltype = AA   length = 15
FEATURE                Location/Qualifiers
REGION                 1..15
                       note = Synthetic
source                 1..15
                       mol_type = protein
                       organism = synthetic construct
SEQUENCE: 56
AKSHYSTSWF GGFDY                                                        15

SEQ ID NO: 57          moltype = DNA   length = 321
FEATURE                Location/Qualifiers
misc_feature           1..321
                       note = Synthetic
source                 1..321
                       mol_type = other DNA
                       organism = synthetic construct
SEQUENCE: 57
gacatccaga tgacccagtc tccatcttcc gtgtctgctt ctgtaggaga cagagtcacc      60
atcacttgtc gggcgagtca gggttttagc agctggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcaccaa cctgcagcct     240
gaagattttg caacttacta ttgtcaacag gctaacagtt tccctctcac tttcggcgga     300
gggaccaagg tggagatcaa a                                               321

SEQ ID NO: 58          moltype = AA   length = 107
FEATURE                Location/Qualifiers
REGION                 1..107
                       note = Synthetic
source                 1..107
                       mol_type = protein
                       organism = synthetic construct
SEQUENCE: 58
DIQMTQSPSS VSASVGDRVT ITCRASQGFS SWLAWYQQKP GKAPKLLIYA ASSLQSGVPS      60
RFSGSGSGTD FTLTITNLQP EDFATYYCQQ ANSFPLTFGG GTKVEIK                   107

SEQ ID NO: 59          moltype = DNA   length = 18
FEATURE                Location/Qualifiers
misc_feature           1..18
                       note = Synthetic
source                 1..18
                       mol_type = other DNA
                       organism = synthetic construct
SEQUENCE: 59
cagggtttta gcagctgg                                                    18

SEQ ID NO: 60          moltype = AA   length = 6
FEATURE                Location/Qualifiers
REGION                 1..6
                       note = Synthetic
source                 1..6
                       mol_type = protein
                       organism = synthetic construct
SEQUENCE: 60
QGFSSW                                                                  6

SEQ ID NO: 61          moltype =    length =
```

```
SEQUENCE: 61
000

SEQ ID NO: 62          moltype =    length =
SEQUENCE: 62
000

SEQ ID NO: 63          moltype = DNA   length = 27
FEATURE                Location/Qualifiers
misc_feature           1..27
                       note = Synthetic
source                 1..27
                       mol_type = other DNA
                       organism = synthetic construct
SEQUENCE: 63
caacaggcta acagtttccc tctcact                                            27

SEQ ID NO: 64          moltype = AA   length = 9
FEATURE                Location/Qualifiers
REGION                 1..9
                       note = Synthetic
source                 1..9
                       mol_type = protein
                       organism = synthetic construct
SEQUENCE: 64
QQANSFPLT                                                                9

SEQ ID NO: 65          moltype = DNA   length = 366
FEATURE                Location/Qualifiers
misc_feature           1..366
                       note = Synthetic
source                 1..366
                       mol_type = other DNA
                       organism = synthetic construct
SEQUENCE: 65
gaggtgcagc tggtggagtc tggggggaggc ttggtacagc ctggggggtc cctgagactc      60
tcctgtgcag cctctggatt cacgtttagc agctatgtca tgagctgggt ccgccaggct      120
ccagggaagg ggctggagtg ggtctcaagt attagtggta atggtggtag cacaaactac      180
gcagactccg tgaagggccg gttcaccatc tccagagaca attccaagaa cacgctgttt      240
ctggaaatga acagcctgag agccgaggac acggccgtat attactgtgc gaaatcactg      300
ggaactacca cgactttttt ggggtttgac tattggggc agggaaccct ggtcaccgtc      360
tcctca                                                                 366

SEQ ID NO: 66          moltype = AA   length = 122
FEATURE                Location/Qualifiers
REGION                 1..122
                       note = Synthetic
source                 1..122
                       mol_type = protein
                       organism = synthetic construct
SEQUENCE: 66
EVQLVESGGG LVQPGGSLRL SCAASGFTFS SYVMSWVRQA PGKGLEWVSS ISGNGGSTNY      60
ADSVKGRFTI SRDNSKNTLF LEMNSLRAED TAVYYCAKSL GTTTTFLGFD YWGQGTLVTV      120
SS                                                                     122

SEQ ID NO: 67          moltype = DNA   length = 24
FEATURE                Location/Qualifiers
misc_feature           1..24
                       note = Synthetic
source                 1..24
                       mol_type = other DNA
                       organism = synthetic construct
SEQUENCE: 67
ggattcacgt ttagcagcta tgtc                                              24

SEQ ID NO: 68          moltype = AA   length = 8
FEATURE                Location/Qualifiers
REGION                 1..8
                       note = Synthetic
source                 1..8
                       mol_type = protein
                       organism = synthetic construct
SEQUENCE: 68
GFTFSSYV                                                                8

SEQ ID NO: 69          moltype = DNA   length = 24
FEATURE                Location/Qualifiers
misc_feature           1..24
                       note = Synthetic
```

```
source                    1..24
                          mol_type = other DNA
                          organism = synthetic construct
SEQUENCE: 69
attagtggta atggtggtag caca                                              24

SEQ ID NO: 70             moltype = AA  length = 8
FEATURE                   Location/Qualifiers
REGION                    1..8
                          note = Synthetic
source                    1..8
                          mol_type = protein
                          organism = synthetic construct
SEQUENCE: 70
ISGNGGST                                                                8

SEQ ID NO: 71             moltype = DNA  length = 45
FEATURE                   Location/Qualifiers
misc_feature              1..45
                          note = Synthetic
source                    1..45
                          mol_type = other DNA
                          organism = synthetic construct
SEQUENCE: 71
gcgaaatcac tgggaactac cacgactttt ttggggtttg actat                       45

SEQ ID NO: 72             moltype = AA  length = 15
FEATURE                   Location/Qualifiers
REGION                    1..15
                          note = Synthetic
source                    1..15
                          mol_type = protein
                          organism = synthetic construct
SEQUENCE: 72
AKSLGTTTTF LGFDY                                                        15

SEQ ID NO: 73             moltype = DNA  length = 321
FEATURE                   Location/Qualifiers
misc_feature              1..321
                          note = Synthetic
source                    1..321
                          mol_type = other DNA
                          organism = synthetic construct
SEQUENCE: 73
gacatccaga tgacccagtc tccatcttcc gtgtctgcat ctgtaggaga cagagtcacc       60
atcacttgtc gggcgagtca gggtattagc agctggttag cctggtatca gcagaaacca      120
gggaaagccc ctaaactcct gatctatgct gcatccagtt tgcaaagtgg ggtcccatca      180
aggttcagcg gcagtggatc tgggacatat ttcactctca ccatcagcag cctgcagcct      240
gaagattttg caacttacta ttgtcaacag gctaacagtt ccctctcac tttcggcgga       300
gggaccaagg tggagatcaa a                                                321

SEQ ID NO: 74             moltype = AA  length = 107
FEATURE                   Location/Qualifiers
REGION                    1..107
                          note = Synthetic
source                    1..107
                          mol_type = protein
                          organism = synthetic construct
SEQUENCE: 74
DIQMTQSPSS VSASVGDRVT ITCRASQGIS SWLAWYQQKP GKAPKLLIYA ASSLQSGVPS       60
RFSGSGSGTY FTLTISSLQP EDFATYYCQQ ANSFPLTFGG GTKVEIK                    107

SEQ ID NO: 75             moltype = DNA  length = 18
FEATURE                   Location/Qualifiers
misc_feature              1..18
                          note = Synthetic
source                    1..18
                          mol_type = other DNA
                          organism = synthetic construct
SEQUENCE: 75
cagggtatta gcagctgg                                                     18

SEQ ID NO: 76             moltype = AA  length = 6
FEATURE                   Location/Qualifiers
REGION                    1..6
                          note = Synthetic
source                    1..6
                          mol_type = protein
                          organism = synthetic construct
```

```
SEQUENCE: 76
QGISSW                                                                             6

SEQ ID NO: 77          moltype =    length =
SEQUENCE: 77
000

SEQ ID NO: 78          moltype =    length =
SEQUENCE: 78
000

SEQ ID NO: 79          moltype = DNA   length = 27
FEATURE                Location/Qualifiers
misc_feature           1..27
                       note = Synthetic
source                 1..27
                       mol_type = other DNA
                       organism = synthetic construct
SEQUENCE: 79
caacaggcta acagtttccc tctcact                                                      27

SEQ ID NO: 80          moltype = AA   length = 9
FEATURE                Location/Qualifiers
REGION                 1..9
                       note = Synthetic
source                 1..9
                       mol_type = protein
                       organism = synthetic construct
SEQUENCE: 80
QQANSFPLT                                                                          9

SEQ ID NO: 81          moltype = DNA   length = 363
FEATURE                Location/Qualifiers
misc_feature           1..363
                       note = Synthetic
source                 1..363
                       mol_type = other DNA
                       organism = synthetic construct
SEQUENCE: 81
caggtgcagc tgcaggagtc gggcccagga ctggtgaagc cttcggagac cctgtccctc     60
acctgcactg tctctggtgg ctccatcagt agttattact ggagctggat ccggcagccc     120
ccagggaagg gactggagtt gattgggtat atttattaca gtgggagcac caattataac     180
ccctccctca agagtcgagt caccatatct gtagacacg gccgtatatt actgtgcgag     240
                                     ... (line continues)
aagctgagct ctgtgaccgc tgcggacacg gccgtatatt actgtgcgag atcccagtat     300
accagtagtt ggtacggttc ttttgatatc tggggccaag ggacaatggt caccgtctct     360
tca                                                                               363

SEQ ID NO: 82          moltype = AA   length = 121
FEATURE                Location/Qualifiers
REGION                 1..121
                       note = Synthetic
source                 1..121
                       mol_type = protein
                       organism = synthetic construct
SEQUENCE: 82
QVQLQESGPG LVKPSETLSL TCTVSGGSIS SYYWSWIRQP PGKGLELIGY IYYSGSTNYN     60
PSLKSRVTIS VDTSKNHFSL KLSSVTAADT AVYYCARSQY TSSWYGSFDI WGQGTMVTVS     120
S                                                                                 121

SEQ ID NO: 83          moltype = DNA   length = 24
FEATURE                Location/Qualifiers
misc_feature           1..24
                       note = Synthetic
source                 1..24
                       mol_type = other DNA
                       organism = synthetic construct
SEQUENCE: 83
ggtggctcca tcagtagtta ttac                                                        24

SEQ ID NO: 84          moltype = AA   length = 8
FEATURE                Location/Qualifiers
REGION                 1..8
                       note = Synthetic
source                 1..8
                       mol_type = protein
                       organism = synthetic construct
SEQUENCE: 84
GGSISSYY                                                                          8
```

-continued

```
SEQ ID NO: 85         moltype = DNA   length = 21
FEATURE               Location/Qualifiers
misc_feature          1..21
                      note = Synthetic
source                1..21
                      mol_type = other DNA
                      organism = synthetic construct
SEQUENCE: 85
atttattaca gtgggagcac c                                              21

SEQ ID NO: 86         moltype = AA   length = 7
FEATURE               Location/Qualifiers
REGION                1..7
                      note = Synthetic
source                1..7
                      mol_type = protein
                      organism = synthetic construct
SEQUENCE: 86
IYYSGST                                                              7

SEQ ID NO: 87         moltype = DNA   length = 45
FEATURE               Location/Qualifiers
misc_feature          1..45
                      note = Synthetic
source                1..45
                      mol_type = other DNA
                      organism = synthetic construct
SEQUENCE: 87
gcgagatccc agtataccag tagttggtac ggttcttttg atatc                    45

SEQ ID NO: 88         moltype = AA   length = 15
FEATURE               Location/Qualifiers
REGION                1..15
                      note = Synthetic
source                1..15
                      mol_type = protein
                      organism = synthetic construct
SEQUENCE: 88
ARSQYTSSWY GSFDI                                                     15

SEQ ID NO: 89         moltype = DNA   length = 321
FEATURE               Location/Qualifiers
misc_feature          1..321
                      note = Synthetic
source                1..321
                      mol_type = other DNA
                      organism = synthetic construct
SEQUENCE: 89
gacatccaga tgacccagtc tccatcttcc gtgtctgcat ctgtaggaga cagagtcacc   60
atcacttgtc gggcgagtca gggtattagc acctggttag cctggtttca gcagaaacca   120
gggaaagccc ctaagctcct gatctatgct gcatccactt tacaaggtgg ggtcccatca   180
aggttcagcg gcagtggatc tgggccagaa ttcactctca ccatcagcag cctgcagcct   240
gaagattttg caacttacta ttgtcaacag gctaacagtt tcccgtggac gttcggccaa   300
gggaccaagg tggaaatcaa a                                              321

SEQ ID NO: 90         moltype = AA   length = 107
FEATURE               Location/Qualifiers
REGION                1..107
                      note = Synthetic
source                1..107
                      mol_type = protein
                      organism = synthetic construct
SEQUENCE: 90
DIQMTQSPSS VSASVGDRVT ITCRASQGIS TWLAWFQQKP GKAPKLLIYA ASTLQGGVPS   60
RFSGSGSGPE FTLTISSLQP EDFATYYCQQ ANSFPWTFGQ GTKVEIK                  107

SEQ ID NO: 91         moltype = DNA   length = 18
FEATURE               Location/Qualifiers
misc_feature          1..18
                      note = Synthetic
source                1..18
                      mol_type = other DNA
                      organism = synthetic construct
SEQUENCE: 91
cagggtatta gcacctgg                                                  18

SEQ ID NO: 92         moltype = AA   length = 6
FEATURE               Location/Qualifiers
REGION                1..6
```

```
                              note = Synthetic
source                        1..6
                              mol_type = protein
                              organism = synthetic construct
SEQUENCE: 92
QGISTW                                                                        6

SEQ ID NO: 93         moltype =    length =
SEQUENCE: 93
000

SEQ ID NO: 94         moltype =    length =
SEQUENCE: 94
000

SEQ ID NO: 95         moltype = DNA   length = 27
FEATURE               Location/Qualifiers
misc_feature          1..27
                      note = Synthetic
source                1..27
                      mol_type = other DNA
                      organism = synthetic construct
SEQUENCE: 95
caacaggcta acagtttccc gtggacg                                                 27

SEQ ID NO: 96         moltype = AA   length = 9
FEATURE               Location/Qualifiers
REGION                1..9
                      note = Synthetic
source                1..9
                      mol_type = protein
                      organism = synthetic construct
SEQUENCE: 96
QQANSFPWT                                                                     9

SEQ ID NO: 97         moltype = DNA   length = 366
FEATURE               Location/Qualifiers
misc_feature          1..366
                      note = Synthetic
source                1..366
                      mol_type = other DNA
                      organism = synthetic construct
SEQUENCE: 97
caggttcagc tggtgcagtc tggagctgag gtgaagaagc ctggggcctc agtgaaggtc   60
tcctgcaagg cctctggtta cacctttaac agctatggta tcagctgggt gcgacaggcc   120
cctggacaag ggcttgagtg gatgggatgg atcagctccc acaatggtaa cagtcactat   180
gtacagaagt tccagggcag agtctccatg accacagaca catccacgag tacagcctac   240
atggaactga ggagccttag atctgacgac acggccgtgt attactgtgc gagacactcg   300
tataccacca gctggtacgg gggttttgac tattgggggcc agggaaccct ggtcaccgtc   360
tcctca                                                                       366

SEQ ID NO: 98         moltype = AA   length = 122
FEATURE               Location/Qualifiers
REGION                1..122
                      note = Synthetic
source                1..122
                      mol_type = protein
                      organism = synthetic construct
SEQUENCE: 98
QVQLVQSGAE VKKPGASVKV SCKASGYTFN SYGISWVRQA PGQGLEWMGW ISSHNGNSHY   60
VQKFQGRVSM TTDTSTSTAY MELRSLRSDD TAVYYCARHS YTTSWYGGFD YWGQGTLVTV   120
SS                                                                           122

SEQ ID NO: 99         moltype = DNA   length = 24
FEATURE               Location/Qualifiers
misc_feature          1..24
                      note = Synthetic
source                1..24
                      mol_type = other DNA
                      organism = synthetic construct
SEQUENCE: 99
ggttacacct ttaacagcta tggt                                                   24

SEQ ID NO: 100        moltype = AA   length = 8
FEATURE               Location/Qualifiers
REGION                1..8
                      note = Synthetic
source                1..8
                      mol_type = protein
```

-continued

```
                          organism = synthetic construct
SEQUENCE: 100
GYTFNSYG                                                            8

SEQ ID NO: 101            moltype = DNA   length = 24
FEATURE                   Location/Qualifiers
misc_feature              1..24
                          note = Synthetic
source                    1..24
                          mol_type = other DNA
                          organism = synthetic construct
SEQUENCE: 101
atcagctccc acaatggtaa cagt                                          24

SEQ ID NO: 102            moltype = AA   length = 8
FEATURE                   Location/Qualifiers
REGION                    1..8
                          note = Synthetic
source                    1..8
                          mol_type = protein
                          organism = synthetic construct
SEQUENCE: 102
ISSHNGNS                                                            8

SEQ ID NO: 103            moltype = DNA   length = 45
FEATURE                   Location/Qualifiers
misc_feature              1..45
                          note = Synthetic
source                    1..45
                          mol_type = other DNA
                          organism = synthetic construct
SEQUENCE: 103
gcgagacact cgtataccac cagctggtac gggggttttg actat                   45

SEQ ID NO: 104            moltype = AA   length = 15
FEATURE                   Location/Qualifiers
REGION                    1..15
                          note = Synthetic
source                    1..15
                          mol_type = protein
                          organism = synthetic construct
SEQUENCE: 104
ARHSYTTSWY GGFDY                                                    15

SEQ ID NO: 105            moltype = DNA   length = 321
FEATURE                   Location/Qualifiers
misc_feature              1..321
                          note = Synthetic
source                    1..321
                          mol_type = other DNA
                          organism = synthetic construct
SEQUENCE: 105
gacatccaga tgacccagtc tccatcttcc gtgtctgcat ctgtaggaga cagagtcacc   60
atcacttgtc gggcgagtca gggttttagc agctggttag cctggtatca gcagaaacca   120
gggaaagccc ctcagctcct gatctatgct gcatccagtt tgcaaagtgg ggtcccatca   180
aggttcagcg gcagtggatc tgggtcagat ttcactctca ccatcagcag cctgcagcct   240
gaagattttg caacttacta ttgtcaacag gctaacagtt tccctctcac tttcggcgga   300
gggaccaagg tggagatcaa a                                             321

SEQ ID NO: 106            moltype = AA   length = 107
FEATURE                   Location/Qualifiers
REGION                    1..107
                          note = Synthetic
source                    1..107
                          mol_type = protein
                          organism = synthetic construct
SEQUENCE: 106
DIQMTQSPSS VSASVGDRVT ITCRASQGFS SWLAWYQQKP GKAPQLLIYA ASSLQSGVPS   60
RFSGSGSGSD FTLTISSLQP EDFATYYCQQ ANSFPLTFGG GTKVEIK                 107

SEQ ID NO: 107            moltype = DNA   length = 18
FEATURE                   Location/Qualifiers
misc_feature              1..18
                          note = Synthetic
source                    1..18
                          mol_type = other DNA
                          organism = synthetic construct
SEQUENCE: 107
cagggtttta gcagctgg                                                 18
```

-continued

```
SEQ ID NO: 108          moltype = AA   length = 6
FEATURE                 Location/Qualifiers
REGION                  1..6
                        note = Synthetic
source                  1..6
                        mol_type = protein
                        organism = synthetic construct
SEQUENCE: 108
QGFSSW                                                                    6

SEQ ID NO: 109          moltype =   length =
SEQUENCE: 109
000

SEQ ID NO: 110          moltype =   length =
SEQUENCE: 110
000

SEQ ID NO: 111          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 111
caacaggcta acagtttccc tctcact                                             27

SEQ ID NO: 112          moltype = AA   length = 9
FEATURE                 Location/Qualifiers
REGION                  1..9
                        note = Synthetic
source                  1..9
                        mol_type = protein
                        organism = synthetic construct
SEQUENCE: 112
QQANSFPLT                                                                 9

SEQ ID NO: 113          moltype = DNA   length = 366
FEATURE                 Location/Qualifiers
misc_feature            1..366
                        note = Synthetic
source                  1..366
                        mol_type = other DNA
                        organism = synthetic construct
SEQUENCE: 113
gaggtgcagc tggtggagtc cggggggaggc ttggttcagc cggggggggtc cctgagactc     60
tcctgtgcag cctctggaat caccttgagc agctatggca tgagctgggt ccgccaggct       120
ccagggaagg gactggagtg ggtcgcatcc atttttggta gtggtggtgg cccatactac       180
gcagactccg tgaagggccg gttcaccatg tccagagaca attccaagaa cacgctgtat       240
ttgcaaatga acagcctgag agccgaggac acggccgtat attattgtgc gaaagatcga       300
tacagtggga gctactacgg aggttttgac tactggggcc ggggaaccct ggtcaccgtc       360
tcctca                                                                   366

SEQ ID NO: 114          moltype = AA   length = 122
FEATURE                 Location/Qualifiers
REGION                  1..122
                        note = Synthetic
source                  1..122
                        mol_type = protein
                        organism = synthetic construct
SEQUENCE: 114
EVQLVESGGG LVQPGGSLRL SCAASGITLS SYGMSWVRQA PGKGLEWVAS IFGSGGGPYY        60
ADSVKGRFTM SRDNSKNTLY LQMNSLRAED TAVYYCAKDR YSGSYYGGFD YWGRGTLVTV       120
SS                                                                       122

SEQ ID NO: 115          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 115
ggaatcacct tgagcagcta tggc                                               24

SEQ ID NO: 116          moltype = AA   length = 8
FEATURE                 Location/Qualifiers
```

-continued

```
REGION                  1..8
                        note = Synthetic
source                  1..8
                        mol_type = protein
                        organism = synthetic construct
SEQUENCE: 116
GITLSSYG                                                            8

SEQ ID NO: 117          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 117
attttttggta gtggtggtgg ccca                                        24

SEQ ID NO: 118          moltype = AA   length = 8
FEATURE                 Location/Qualifiers
REGION                  1..8
                        note = Synthetic
source                  1..8
                        mol_type = protein
                        organism = synthetic construct
SEQUENCE: 118
IFGSGGGP                                                            8

SEQ ID NO: 119          moltype = DNA   length = 45
FEATURE                 Location/Qualifiers
misc_feature            1..45
                        note = Synthetic
source                  1..45
                        mol_type = other DNA
                        organism = synthetic construct
SEQUENCE: 119
gcgaaagatc gatacagtgg gagctactac ggaggttttg actac              45

SEQ ID NO: 120          moltype = AA   length = 15
FEATURE                 Location/Qualifiers
REGION                  1..15
                        note = Synthetic
source                  1..15
                        mol_type = protein
                        organism = synthetic construct
SEQUENCE: 120
AKDRYSGSYY GGFDY                                                    15

SEQ ID NO: 121          moltype = DNA   length = 321
FEATURE                 Location/Qualifiers
misc_feature            1..321
                        note = Synthetic
source                  1..321
                        mol_type = other DNA
                        organism = synthetic construct
SEQUENCE: 121
gacatccaga tgacccagtc tccatcttcc gtgtctgcat ctgtaggaga cagagtcacc  60
atcacttgtc gggcgagtca gggtattacc agctggttag cctggtatca gcagaaacca  120
gggaaagccc ctacactcct gatctatgct gcatccagtt tgcaaactgg ggtcccatca  180
aggttcagcg gcagtggatc tgggacagat ttcactctca ccatcagcag cctgcagcct  240
gaacattttg caacttacta ttgtcaacag gctaacagtt ccctcctac tttcggcgga  300
gggaccaagg tggagatcaa a                                            321

SEQ ID NO: 122          moltype = AA   length = 107
FEATURE                 Location/Qualifiers
REGION                  1..107
                        note = Synthetic
source                  1..107
                        mol_type = protein
                        organism = synthetic construct
SEQUENCE: 122
DIQMTQSPSS VSASVGDRVT ITCRASQGIT SWLAWYQQKP GKAPTLLIYA ASSLQTGVPS  60
RFSGSGSGTD FTLTISSLQP EHFATYYCQQ ANSFPPTFGG GTKVEIK               107

SEQ ID NO: 123          moltype = DNA   length = 18
FEATURE                 Location/Qualifiers
misc_feature            1..18
                        note = Synthetic
source                  1..18
```

```
                          mol_type = other DNA
                          organism = synthetic construct
SEQUENCE: 123
cagggtatta ccagctgg                                             18

SEQ ID NO: 124            moltype = AA   length = 6
FEATURE                   Location/Qualifiers
REGION                    1..6
                          note = Synthetic
source                    1..6
                          mol_type = protein
                          organism = synthetic construct
SEQUENCE: 124
QGITSW                                                          6

SEQ ID NO: 125            moltype =   length =
SEQUENCE: 125
000

SEQ ID NO: 126            moltype =   length =
SEQUENCE: 126
000

SEQ ID NO: 127            moltype = DNA   length = 27
FEATURE                   Location/Qualifiers
misc_feature              1..27
                          note = Synthetic
source                    1..27
                          mol_type = other DNA
                          organism = synthetic construct
SEQUENCE: 127
caacaggcta acagtttccc tcctact                                   27

SEQ ID NO: 128            moltype = AA   length = 9
FEATURE                   Location/Qualifiers
REGION                    1..9
                          note = Synthetic
source                    1..9
                          mol_type = protein
                          organism = synthetic construct
SEQUENCE: 128
QQANSFPPT                                                       9

SEQ ID NO: 129            moltype = DNA   length = 366
FEATURE                   Location/Qualifiers
misc_feature              1..366
                          note = Synthetic
source                    1..366
                          mol_type = other DNA
                          organism = synthetic construct
SEQUENCE: 129
gaggtgcagc tggtggagtc tggggggaggc ttggtacagc ctggggggtc cctaagactc   60
tcctgtgcag cctctggatt cacctttagc agttatgcct tgacctgggt ccgccaggct   120
ccagggaagg ggctggagtg ggtctctttt attagtggta gtggtggtag gccattctac   180
gcagactccg tgaagggccg gttcaccatc tccagagaca attccaagaa catgctgtat   240
ctgcaaatga acagcctgag agccgaggac acggccatat attactgtgc gaagtccctg   300
tataccacca gctggtacgg ggggttcgac tcctggggcc agggaaccct ggtcaccgtc   360
tcctca                                                          366

SEQ ID NO: 130            moltype = AA   length = 122
FEATURE                   Location/Qualifiers
REGION                    1..122
                          note = Synthetic
source                    1..122
                          mol_type = protein
                          organism = synthetic construct
SEQUENCE: 130
EVQLVESGGG LVQPGGSLRL SCAASGFTFS SYALTWVRQA PGKGLEWVSF ISGSGGRPFY   60
ADSVKGRFTI SRDNSKNMLY LQMNSLRAED TAIYYCAKSL YTTSWYGGFD SWGQGTLVTV   120
SS                                                              122

SEQ ID NO: 131            moltype = DNA   length = 24
FEATURE                   Location/Qualifiers
misc_feature              1..24
                          note = Synthetic
source                    1..24
                          mol_type = other DNA
                          organism = synthetic construct
SEQUENCE: 131
```

-continued

```
ggattcacct ttagcagtta tgcc                                          24

SEQ ID NO: 132        moltype = AA  length = 8
FEATURE               Location/Qualifiers
REGION                1..8
                      note = Synthetic
source                1..8
                      mol_type = protein
                      organism = synthetic construct
SEQUENCE: 132
GFTFSSYA                                                            8

SEQ ID NO: 133        moltype = DNA  length = 24
FEATURE               Location/Qualifiers
misc_feature          1..24
                      note = Synthetic
source                1..24
                      mol_type = other DNA
                      organism = synthetic construct
SEQUENCE: 133
attagtggta gtggtggtag gcca                                          24

SEQ ID NO: 134        moltype = AA  length = 8
FEATURE               Location/Qualifiers
REGION                1..8
                      note = Synthetic
source                1..8
                      mol_type = protein
                      organism = synthetic construct
SEQUENCE: 134
ISGSGGRP                                                            8

SEQ ID NO: 135        moltype = DNA  length = 45
FEATURE               Location/Qualifiers
misc_feature          1..45
                      note = Synthetic
source                1..45
                      mol_type = other DNA
                      organism = synthetic construct
SEQUENCE: 135
gcgaagtccc tgtataccac cagctggtac ggggggttcg actcc                   45

SEQ ID NO: 136        moltype = AA  length = 15
FEATURE               Location/Qualifiers
REGION                1..15
                      note = Synthetic
source                1..15
                      mol_type = protein
                      organism = synthetic construct
SEQUENCE: 136
AKSLYTTSWY GGFDS                                                    15

SEQ ID NO: 137        moltype = DNA  length = 321
FEATURE               Location/Qualifiers
misc_feature          1..321
                      note = Synthetic
source                1..321
                      mol_type = other DNA
                      organism = synthetic construct
SEQUENCE: 137
gacatccaga tgacccagtc tccatcttcc gtgtctgcat ctgtaggaga cagagtcacc  60
atcacttgtc gggcgagtca gggtgtcgtc agctggttag cctggtatca gcagaaacca  120
gggaaagccc ctaagctcct gatctatgct gcatccagtt tgcaaagtgg ggtcccatca  180
aggttcagcg gcagtggatc tgggacagat ttcactctca ccatcagcag cctgcagcct  240
gaagattttg caacttatta ttgtcaacag tctaacagtt tccctttcac tctcggccct  300
gggaccaaag tggatatcaa a                                             321

SEQ ID NO: 138        moltype = AA  length = 107
FEATURE               Location/Qualifiers
REGION                1..107
                      note = Synthetic
source                1..107
                      mol_type = protein
                      organism = synthetic construct
SEQUENCE: 138
DIQMTQSPSS VSASVGDRVT ITCRASQGVV SWLAWYQQKP GKAPKLLIYA ASSLQSGVPS  60
RFSGSGSGTD FTLTISSLQP EDFATYYCQQ SNSFPFTLGP GTKVDIK                107

SEQ ID NO: 139        moltype = DNA  length = 18
```

-continued

```
FEATURE              Location/Qualifiers
misc_feature         1..18
                     note = Synthetic
source               1..18
                     mol_type = other DNA
                     organism = synthetic construct
SEQUENCE: 139
cagggtgtcg tcagctgg                                        18

SEQ ID NO: 140       moltype = AA   length = 6
FEATURE              Location/Qualifiers
REGION               1..6
                     note = Synthetic
source               1..6
                     mol_type = protein
                     organism = synthetic construct
SEQUENCE: 140
QGVVSW                                                     6

SEQ ID NO: 141       moltype =   length =
SEQUENCE: 141
000

SEQ ID NO: 142       moltype =   length =
SEQUENCE: 142
000

SEQ ID NO: 143       moltype = DNA   length = 24
FEATURE              Location/Qualifiers
misc_feature         1..24
                     note = Synthetic
source               1..24
                     mol_type = other DNA
                     organism = synthetic construct
SEQUENCE: 143
caacagtcta acagtttccc tttc                                 24

SEQ ID NO: 144       moltype = AA   length = 8
FEATURE              Location/Qualifiers
REGION               1..8
                     note = Synthetic
source               1..8
                     mol_type = protein
                     organism = synthetic construct
SEQUENCE: 144
QQSNSFPF                                                   8

SEQ ID NO: 145       moltype = DNA   length = 366
FEATURE              Location/Qualifiers
misc_feature         1..366
                     note = Synthetic
source               1..366
                     mol_type = other DNA
                     organism = synthetic construct
SEQUENCE: 145
caggtgcagc tggtgcagtc tgggggctgaa gtgaagaagc ctggggcctc agtgaaggtc   60
tcctgcaagg cttctggata caccttcacc ggccactata tgtactggat gcgacaggcc  120
cctggacaag ggcttgagtg gatgggatgg atcaacccta acagtggtgg cacaaactat  180
gcacagaagt ttcaggacag ggtcaccatg accagggaca cgtccatcag cacagcctac  240
atggagctga gcaggctgag atctgacgac acggccgtgt attactgtgc gagagggaga  300
tatggcagta gctggtacgg ggggtttgag tactggggcc agggaacccct ggtcaccgtc  360
tcctca                                                             366

SEQ ID NO: 146       moltype = AA   length = 122
FEATURE              Location/Qualifiers
REGION               1..122
                     note = Synthetic
source               1..122
                     mol_type = protein
                     organism = synthetic construct
SEQUENCE: 146
QVQLVQSGAE VKKPGASVKV SCKASGYTFT GHYMYWMRQA PGQGLEWMGW INPNSGGTNY   60
AQKFQDRVTM TRDTSISTAY MELSRLRSDD TAVYYCARGR YGSSWYGGFE YWGQGTLVTV  120
SS                                                                 122

SEQ ID NO: 147       moltype = DNA   length = 24
FEATURE              Location/Qualifiers
misc_feature         1..24
                     note = Synthetic
```

-continued

```
source                    1..24
                          mol_type = other DNA
                          organism = synthetic construct
SEQUENCE: 147
ggatacacct tcaccggcca ctat                                        24

SEQ ID NO: 148           moltype = AA   length = 8
FEATURE                  Location/Qualifiers
REGION                   1..8
                          note = Synthetic
source                    1..8
                          mol_type = protein
                          organism = synthetic construct
SEQUENCE: 148
GYTFTGHY                                                           8

SEQ ID NO: 149           moltype = DNA   length = 24
FEATURE                  Location/Qualifiers
misc_feature             1..24
                          note = Synthetic
source                    1..24
                          mol_type = other DNA
                          organism = synthetic construct
SEQUENCE: 149
atcaacccta acagtggtgg caca                                        24

SEQ ID NO: 150           moltype = AA   length = 8
FEATURE                  Location/Qualifiers
REGION                   1..8
                          note = Synthetic
source                    1..8
                          mol_type = protein
                          organism = synthetic construct
SEQUENCE: 150
INPNSGGT                                                           8

SEQ ID NO: 151           moltype = DNA   length = 45
FEATURE                  Location/Qualifiers
misc_feature             1..45
                          note = Synthetic
source                    1..45
                          mol_type = other DNA
                          organism = synthetic construct
SEQUENCE: 151
gcgagaggga gatatggcag tagctggtac ggggggtttg agtac                 45

SEQ ID NO: 152           moltype = AA   length = 15
FEATURE                  Location/Qualifiers
REGION                   1..15
                          note = Synthetic
source                    1..15
                          mol_type = protein
                          organism = synthetic construct
SEQUENCE: 152
ARGRYGSSWY GGFEY                                                   15

SEQ ID NO: 153           moltype = DNA   length = 321
FEATURE                  Location/Qualifiers
misc_feature             1..321
                          note = Synthetic
source                    1..321
                          mol_type = other DNA
                          organism = synthetic construct
SEQUENCE: 153
gacatccaga tgacccagtc tccatcttcc gtgtctgcat ctgttggaga cagagtcacc 60
atcacttgtc gggcgagtca gggtattacc agctggttag cctggtatca gcagaaacca 120
gggaaagccc ctaacctcct gatctatgct gcagccagtt tacaaagtgg ggtcccatca 180
aggttcagcg gcagtggatc tgggacggat ttcactctca ccatcagcag cctgcagcct 240
gaagacttta caacttacta ttgtcaacag gcttacagtc tccctctcac tttcggcgga 300
gggaccaagg tggagatcaa a                                           321

SEQ ID NO: 154           moltype = AA   length = 107
FEATURE                  Location/Qualifiers
REGION                   1..107
                          note = Synthetic
source                    1..107
                          mol_type = protein
                          organism = synthetic construct
SEQUENCE: 154
```

```
DIQMTQSPSS VSASVGDRVT ITCRASQGIT SWLAWYQQKP GKAPNLLIYA AASLQSGVPS   60
RFSGSGSGTD FTLTISSLQP EDFTTYYCQQ AYSLPLTFGG GTKVEIK                 107

SEQ ID NO: 155          moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 155
cagggtatta ccagctgg                                                18

SEQ ID NO: 156          moltype = AA   length = 6
FEATURE                 Location/Qualifiers
REGION                  1..6
                        note = Synthetic
source                  1..6
                        mol_type = protein
                        organism = synthetic construct
SEQUENCE: 156
QGITSW                                                             6

SEQ ID NO: 157          moltype =    length =
SEQUENCE: 157
000

SEQ ID NO: 158          moltype =    length =
SEQUENCE: 158
000

SEQ ID NO: 159          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 159
caacaggctt acagtctccc tctcact                                      27

SEQ ID NO: 160          moltype = AA   length = 9
FEATURE                 Location/Qualifiers
REGION                  1..9
                        note = Synthetic
source                  1..9
                        mol_type = protein
                        organism = synthetic construct
SEQUENCE: 160
QQAYSLPLT                                                          9

SEQ ID NO: 161          moltype = DNA   length = 366
FEATURE                 Location/Qualifiers
misc_feature            1..366
                        note = Synthetic
source                  1..366
                        mol_type = other DNA
                        organism = synthetic construct
SEQUENCE: 161
caggtgcagc tggtggagtc tgggggaggc gtggtccagc ctgggaggtc cctgagactc   60
tcctgtgcag cctctggatt caccttcagt agctatggct tgcactgggt ccgccagtct  120
ccaggcaagg ggctggaatg ggtggcactt atatcatatg acggaagtaa taaatactat  180
gcagactccg tgaagggccg attcaccatc tccagagaca attccaagaa cacgctgtat  240
ctgcaaatga acagcctgag acctgaggac acggctggat atttctgtgc gaaatcccta  300
tatacaacca gctggtacgg gggctttgac tattggggcc agggaaccct ggtcaccgtc  360
tcctca                                                            366

SEQ ID NO: 162          moltype = AA   length = 122
FEATURE                 Location/Qualifiers
REGION                  1..122
                        note = Synthetic
source                  1..122
                        mol_type = protein
                        organism = synthetic construct
SEQUENCE: 162
QVQLVESGGG VVQPGRSLRL SCAASGFTFS SYGLHWVRQS PGKGLEWVAL ISYDGSNKYY   60
ADSVKGRFTI SRDNSKNTLY LQMNSLRPED TAGYFCAKSL YTTSWYGGFD YWGQGTLVTV  120
SS                                                                122
```

-continued

```
SEQ ID NO: 163           moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 163
ggattcacct tcagtagcta tggc                                     24

SEQ ID NO: 164           moltype = AA  length = 8
FEATURE                  Location/Qualifiers
REGION                   1..8
                         note = Synthetic
source                   1..8
                         mol_type = protein
                         organism = synthetic construct
SEQUENCE: 164
GFTFSSYG                                                       8

SEQ ID NO: 165           moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 165
atatcatatg acggaagtaa taaa                                     24

SEQ ID NO: 166           moltype = AA  length = 8
FEATURE                  Location/Qualifiers
REGION                   1..8
                         note = Synthetic
source                   1..8
                         mol_type = protein
                         organism = synthetic construct
SEQUENCE: 166
ISYDGSNK                                                       8

SEQ ID NO: 167           moltype = DNA  length = 45
FEATURE                  Location/Qualifiers
misc_feature             1..45
                         note = Synthetic
source                   1..45
                         mol_type = other DNA
                         organism = synthetic construct
SEQUENCE: 167
gcgaaatccc tatatacaac cagctggtac gggggctttg actat             45

SEQ ID NO: 168           moltype = AA  length = 15
FEATURE                  Location/Qualifiers
REGION                   1..15
                         note = Synthetic
source                   1..15
                         mol_type = protein
                         organism = synthetic construct
SEQUENCE: 168
AKSLYTTSWY GGFDY                                               15

SEQ ID NO: 169           moltype = DNA  length = 321
FEATURE                  Location/Qualifiers
misc_feature             1..321
                         note = Synthetic
source                   1..321
                         mol_type = other DNA
                         organism = synthetic construct
SEQUENCE: 169
gacatccaga tgacccagtc tccatcttcc gtgtctgcat ctgtaggaga cagagtcacc  60
atcacttgtc gggcgagtca gggtattaga agctggttag cctggtatca gcaaaaacca  120
gggaaagccc ctaacctcct gatctatgct gcgtccagtt tgcaaagtgg ggtcccatca  180
aggttcagcg gcagtggatc tgggacagat ttcactctca ccatcagcag cctgcagcct  240
gaagattttg caacttacta ttgtcaacag gctaacagtt ccctcccac tttcggccct  300
gggaccaaag tggatatcaa a                                           321

SEQ ID NO: 170           moltype = AA  length = 107
FEATURE                  Location/Qualifiers
REGION                   1..107
                         note = Synthetic
```

-continued

```
source                     1..107
                           mol_type = protein
                           organism = synthetic construct
SEQUENCE: 170
DIQMTQSPSS VSASVGDRVT ITCRASQGIR SWLAWYQQKP GKAPNLLIYA ASSLQSGVPS    60
RFSGSGSGTD FTLTISSLQP EDFATYYCQQ ANSFPPTFGP GTKVDIK                 107

SEQ ID NO: 171             moltype = DNA   length = 18
FEATURE                    Location/Qualifiers
misc_feature               1..18
                           note = Synthetic
source                     1..18
                           mol_type = other DNA
                           organism = synthetic construct
SEQUENCE: 171
cagggtatta gaagctgg                                                  18

SEQ ID NO: 172             moltype = AA   length = 6
FEATURE                    Location/Qualifiers
REGION                     1..6
                           note = Synthetic
source                     1..6
                           mol_type = protein
                           organism = synthetic construct
SEQUENCE: 172
QGIRSW                                                                6

SEQ ID NO: 173             moltype =   length =
SEQUENCE: 173
000

SEQ ID NO: 174             moltype =   length =
SEQUENCE: 174
000

SEQ ID NO: 175             moltype = DNA   length = 27
FEATURE                    Location/Qualifiers
misc_feature               1..27
                           note = Synthetic
source                     1..27
                           mol_type = other DNA
                           organism = synthetic construct
SEQUENCE: 175
caacaggcta acagtttccc tcccact                                        27

SEQ ID NO: 176             moltype = AA   length = 9
FEATURE                    Location/Qualifiers
REGION                     1..9
                           note = Synthetic
source                     1..9
                           mol_type = protein
                           organism = synthetic construct
SEQUENCE: 176
QQANSFPPT                                                             9

SEQ ID NO: 177             moltype = DNA   length = 366
FEATURE                    Location/Qualifiers
misc_feature               1..366
                           note = Synthetic
source                     1..366
                           mol_type = other DNA
                           organism = synthetic construct
SEQUENCE: 177
gaggtgcagc tggtggagtc tggggggagc ttggtacagc ctgggggggtc cctgagactc   60
tcctgtgcag cctctgggtt caccttcagc aactatgcca tgacctgggt ccgccaggct  120
ccagggaagg ggctggagtg ggtctcaact atcagtggca gtggtgataa cacatactac  180
gcagactccg tgcagggccg gttcaccatc tccagaggcc attccaagaa cacgctgtat  240
ctgcaaatga acagcctgag agccgaggac acggccgtat attactgtgc gaaacctacg  300
tatagcagaa gctggtacgg tgcttttgat ttctggggcc aagggacaat ggtcaccgtc  360
tcttca                                                             366

SEQ ID NO: 178             moltype = AA   length = 122
FEATURE                    Location/Qualifiers
REGION                     1..122
                           note = Synthetic
source                     1..122
                           mol_type = protein
                           organism = synthetic construct
SEQUENCE: 178
```

```
EVQLVESGGG LVQPGGSLRL SCAASGFTFS NYAMTWVRQA PGKGLEWVST ISGSGDNTYY    60
ADSVQGRFTI SRGHSKNTLY LQMNSLRAED TAVYYCAKPT YSRSWYGAFD FWGQGTMVTV   120
SS                                                                 122

SEQ ID NO: 179          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 179
gggttcacct tcagcaacta tgcc                                          24

SEQ ID NO: 180          moltype = AA   length = 8
FEATURE                 Location/Qualifiers
REGION                  1..8
                        note = Synthetic
source                  1..8
                        mol_type = protein
                        organism = synthetic construct
SEQUENCE: 180
GFTFSNYA                                                             8

SEQ ID NO: 181          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 181
atcagtggca gtggtgataa caca                                          24

SEQ ID NO: 182          moltype = AA   length = 8
FEATURE                 Location/Qualifiers
REGION                  1..8
                        note = Synthetic
source                  1..8
                        mol_type = protein
                        organism = synthetic construct
SEQUENCE: 182
ISGSGDNT                                                             8

SEQ ID NO: 183          moltype = DNA   length = 45
FEATURE                 Location/Qualifiers
misc_feature            1..45
                        note = Synthetic
source                  1..45
                        mol_type = other DNA
                        organism = synthetic construct
SEQUENCE: 183
gcgaaaccta cgtatagcag aagctggtac ggtgcttttg atttc                   45

SEQ ID NO: 184          moltype = AA   length = 15
FEATURE                 Location/Qualifiers
REGION                  1..15
                        note = Synthetic
source                  1..15
                        mol_type = protein
                        organism = synthetic construct
SEQUENCE: 184
AKPTYSRSWY GAFDF                                                     15

SEQ ID NO: 185          moltype = DNA   length = 321
FEATURE                 Location/Qualifiers
misc_feature            1..321
                        note = Synthetic
source                  1..321
                        mol_type = other DNA
                        organism = synthetic construct
SEQUENCE: 185
gacatccaga tgacccagtc tccatcctcc gtgtctgcat ctgtaggaga cagagtcacc    60
atcacttgtc gggcgagtca gggtattagc agctggttag cctggtatca gcagaaaccg   120
gggaaagccc ctcaactcct gatctatgct gcatccagat tgcaaagtgg ggtcccatca   180
aggttctggg gcagtggatc tgggacagat ttcactctca ccatcagcag cctgcagcct   240
gaagattttg caacttacta ttgtcaacag gctaacaatt cccattcac ttcggccct    300
gggaccaaag tggatatcaa a                                             321
```

-continued

```
SEQ ID NO: 186          moltype = AA   length = 107
FEATURE                 Location/Qualifiers
REGION                  1..107
                        note = Synthetic
source                  1..107
                        mol_type = protein
                        organism = synthetic construct
SEQUENCE: 186
DIQMTQSPSS VSASVGDRVT ITCRASQGIS SWLAWYQQKP GKAPQLLIYA ASRLQSGVPS  60
RFWGSGSGTD FTLTISSLQP EDFATYYCQQ ANNFPFTFGP GTKVDIK              107

SEQ ID NO: 187          moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 187
cagggtatta gcagctgg                                              18

SEQ ID NO: 188          moltype = AA   length = 6
FEATURE                 Location/Qualifiers
REGION                  1..6
                        note = Synthetic
source                  1..6
                        mol_type = protein
                        organism = synthetic construct
SEQUENCE: 188
QGISSW                                                           6

SEQ ID NO: 189          moltype =    length =
SEQUENCE: 189
000

SEQ ID NO: 190          moltype =    length =
SEQUENCE: 190
000

SEQ ID NO: 191          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 191
caacaggcta acaatttccc attcact                                    27

SEQ ID NO: 192          moltype = AA   length = 9
FEATURE                 Location/Qualifiers
REGION                  1..9
                        note = Synthetic
source                  1..9
                        mol_type = protein
                        organism = synthetic construct
SEQUENCE: 192
QQANNFPFT                                                        9

SEQ ID NO: 193          moltype = DNA   length = 366
FEATURE                 Location/Qualifiers
misc_feature            1..366
                        note = Synthetic
source                  1..366
                        mol_type = other DNA
                        organism = synthetic construct
SEQUENCE: 193
caggttcagc tggtgcagtc tggagctgag gtgaagaagc ctggggcctc agtgaaggtc  60
tcctgcaagg cttctggtta cacctttacc agttatggta tcagctgggt gcgacaggcc 120
cctggacaag gccttgagtg gatgggatgg atccgcgctt acaatggtta cacaaactat 180
gcacagaagt tcagggcag agtcaccatg accacagaca catccacgaa caccgcctac 240
atggagctga ggaccctgaa ttctgacgat acggccgttt attactgtgc gagagatcga 300
tatagtggga gcttccacgg taactttgac tactggggcc agggaaccct ggtcaccgtc 360
tcctca                                                         366

SEQ ID NO: 194          moltype = AA   length = 122
FEATURE                 Location/Qualifiers
REGION                  1..122
                        note = Synthetic
```

-continued

```
source                  1..122
                        mol_type = protein
                        organism = synthetic construct
SEQUENCE: 194
QVQLVQSGAE VKKPGASVKV SCKASGYTFT SYGISWVRQA PGQGLEWMGW IRAYNGYTNY  60
AQKFQGRVTM TTDTSTNTAY MELRTLNSDD TAVYYCARDR YSGSFHGNFD YWGQGTLVTV  120
SS                                                                122

SEQ ID NO: 195         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 195
ggttacacct ttaccagtta tggt                                        24

SEQ ID NO: 196         moltype = AA  length = 8
FEATURE                Location/Qualifiers
REGION                 1..8
                       note = Synthetic
source                 1..8
                       mol_type = protein
                       organism = synthetic construct
SEQUENCE: 196
GYTFTSYG                                                           8

SEQ ID NO: 197         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 197
atccgcgctt acaatggtta caca                                        24

SEQ ID NO: 198         moltype = AA  length = 8
FEATURE                Location/Qualifiers
REGION                 1..8
                       note = Synthetic
source                 1..8
                       mol_type = protein
                       organism = synthetic construct
SEQUENCE: 198
IRAYNGYT                                                           8

SEQ ID NO: 199         moltype = DNA  length = 45
FEATURE                Location/Qualifiers
misc_feature           1..45
                       note = Synthetic
source                 1..45
                       mol_type = other DNA
                       organism = synthetic construct
SEQUENCE: 199
gcgagagatc gatatagtgg gagcttccac ggtaactttg actac              45

SEQ ID NO: 200         moltype = AA  length = 15
FEATURE                Location/Qualifiers
REGION                 1..15
                       note = Synthetic
source                 1..15
                       mol_type = protein
                       organism = synthetic construct
SEQUENCE: 200
ARDRYSGSFH GNFDY                                                   15

SEQ ID NO: 201         moltype = DNA  length = 321
FEATURE                Location/Qualifiers
misc_feature           1..321
                       note = Synthetic
source                 1..321
                       mol_type = other DNA
                       organism = synthetic construct
SEQUENCE: 201
gacatccaga tgacccagtc tccatcttcc gtgtctgcgt ctgtaggaga cagagtgacc  60
atcacttgtc gggcgagtca gggtattttc agctggttag cctggtatca gcagaaacca  120
gggaaagccc ctaaggtcct aatctatgct gcatccaatt tggaaagtgg ggtcccatca  180
```

-continued

```
aggttcagcg gcagtggatc tgggacagat ttcactctca ccatcagcag cctgcagcct   240
gaagattttg caacttacta ttgtcaacag gctaacagtt taccgctcac tttcggcgga   300
gggaccaagg tggagatcaa a                                             321

SEQ ID NO: 202          moltype = AA   length = 107
FEATURE                 Location/Qualifiers
REGION                  1..107
                        note = Synthetic
source                  1..107
                        mol_type = protein
                        organism = synthetic construct
SEQUENCE: 202
DIQMTQSPSS VSASVGDRVT ITCRASQGIF SWLAWYQQKP GKAPKVLIYA ASNLESGVPS   60
RFSGSGSGTD FTLTISSLQP EDFATYYCQQ ANSLPLTFGG GTKVEIK                 107

SEQ ID NO: 203          moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 203
cagggtattt tcagctgg                                                 18

SEQ ID NO: 204          moltype = AA   length = 6
FEATURE                 Location/Qualifiers
REGION                  1..6
                        note = Synthetic
source                  1..6
                        mol_type = protein
                        organism = synthetic construct
SEQUENCE: 204
QGIFSW                                                              6

SEQ ID NO: 205          moltype =    length =
SEQUENCE: 205
000

SEQ ID NO: 206          moltype =    length =
SEQUENCE: 206
000

SEQ ID NO: 207          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 207
caacaggcta acagtttacc gctcact                                       27

SEQ ID NO: 208          moltype = AA   length = 9
FEATURE                 Location/Qualifiers
REGION                  1..9
                        note = Synthetic
source                  1..9
                        mol_type = protein
                        organism = synthetic construct
SEQUENCE: 208
QQANSLPLT                                                           9

SEQ ID NO: 209          moltype = DNA   length = 366
FEATURE                 Location/Qualifiers
misc_feature            1..366
                        note = Synthetic
source                  1..366
                        mol_type = other DNA
                        organism = synthetic construct
SEQUENCE: 209
gaggtgcagc tggtggagtc tgggggaggc ttggtccagc ctggggggtc cctgagactc   60
tcctgtgcag cctctggatt caccttcagt acctattcta tgcactgggt ccgccaggct   120
ccagggaagg gactggaata tgtttcaact attaataata tggggatac cacatattat   180
gcagactctg tgaagggcag attcaccatc tccagagaca attccaagaa cacgctgtat   240
cttcaactgg gcagcctgag acctgaggac atggctgtgt attactgtgc gagacagacg   300
tataccagca gctggtacgg ggggttcgac tcctggggcc agggaaccct ggtcaccgtc   360
tcctca                                                             366
```

```
SEQ ID NO: 210          moltype = AA   length = 122
FEATURE                 Location/Qualifiers
REGION                  1..122
                        note = Synthetic
source                  1..122
                        mol_type = protein
                        organism = synthetic construct
SEQUENCE: 210
EVQLVESGGG LVQPGGSLRL SCAASGFTFS TYSMHWVRQA PGKGLEYVST INNNGDTTYY  60
ADSVKGRFTI SRDNSKNTLY LQLGSLRPED MAVYYCARQT YTSSWYGGFD SWGQGTLVTV  120
SS                                                                122

SEQ ID NO: 211          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 211
ggattcacct tcagtaccta ttct                                        24

SEQ ID NO: 212          moltype = AA   length = 8
FEATURE                 Location/Qualifiers
REGION                  1..8
                        note = Synthetic
source                  1..8
                        mol_type = protein
                        organism = synthetic construct
SEQUENCE: 212
GFTFSTYS                                                          8

SEQ ID NO: 213          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 213
attaataata atggggatac caca                                        24

SEQ ID NO: 214          moltype = AA   length = 8
FEATURE                 Location/Qualifiers
REGION                  1..8
                        note = Synthetic
source                  1..8
                        mol_type = protein
                        organism = synthetic construct
SEQUENCE: 214
INNNGDTT                                                          8

SEQ ID NO: 215          moltype = DNA   length = 45
FEATURE                 Location/Qualifiers
misc_feature            1..45
                        note = Synthetic
source                  1..45
                        mol_type = other DNA
                        organism = synthetic construct
SEQUENCE: 215
gcgagacaga cgtataccag cagctggtac gggggggttcg actcc                45

SEQ ID NO: 216          moltype = AA   length = 15
FEATURE                 Location/Qualifiers
REGION                  1..15
                        note = Synthetic
source                  1..15
                        mol_type = protein
                        organism = synthetic construct
SEQUENCE: 216
ARQTYTSSWY GGFDS                                                  15

SEQ ID NO: 217          moltype = DNA   length = 321
FEATURE                 Location/Qualifiers
misc_feature            1..321
                        note = Synthetic
source                  1..321
                        mol_type = other DNA
                        organism = synthetic construct
```

-continued

```
SEQUENCE: 217
gacatccaga tgacccagtc tccatcttcc gtgtctgcat ctgtaggcga cagagtcacc      60
atcacttgtc gggcgagtca gggtattacc agctggttag cctggtatca gcagaaacca     120
gggaaagccc ctaaactcct gatctatgct gcatccaatt tgcaaagtgg ggtcccatca     180
aggttcagcg gcagtggatc tgggacagat ttcactctca ccatcaccag cctgcagcct     240
gaggattttg caacttacta ttgtcaacag gctaacagtc tcccattcac tttcggccct     300
gggaccaaag tggatatcaa a                                              321

SEQ ID NO: 218        moltype = AA  length = 107
FEATURE               Location/Qualifiers
REGION                1..107
                      note = Synthetic
source                1..107
                      mol_type = protein
                      organism = synthetic construct
SEQUENCE: 218
DIQMTQSPSS VSASVGDRVT ITCRASQGIT SWLAWYQQKP GKAPKLLIYA ASNLQSGVPS      60
RFSGSGSGTD FTLTITSLQP EDFATYYCQQ ANSLPFTFGP GTKVDIK                   107

SEQ ID NO: 219        moltype = DNA  length = 18
FEATURE               Location/Qualifiers
misc_feature          1..18
                      note = Synthetic
source                1..18
                      mol_type = other DNA
                      organism = synthetic construct
SEQUENCE: 219
cagggtatta ccagctgg                                                   18

SEQ ID NO: 220        moltype = AA  length = 6
FEATURE               Location/Qualifiers
REGION                1..6
                      note = Synthetic
source                1..6
                      mol_type = protein
                      organism = synthetic construct
SEQUENCE: 220
QGITSW                                                                6

SEQ ID NO: 221        moltype =   length =
SEQUENCE: 221
000

SEQ ID NO: 222        moltype =   length =
SEQUENCE: 222
000

SEQ ID NO: 223        moltype = DNA  length = 27
FEATURE               Location/Qualifiers
misc_feature          1..27
                      note = Synthetic
source                1..27
                      mol_type = other DNA
                      organism = synthetic construct
SEQUENCE: 223
caacaggcta acagtctccc attcact                                         27

SEQ ID NO: 224        moltype = AA  length = 9
FEATURE               Location/Qualifiers
REGION                1..9
                      note = Synthetic
source                1..9
                      mol_type = protein
                      organism = synthetic construct
SEQUENCE: 224
QQANSLPFT                                                             9

SEQ ID NO: 225        moltype = DNA  length = 366
FEATURE               Location/Qualifiers
misc_feature          1..366
                      note = Synthetic
source                1..366
                      mol_type = other DNA
                      organism = synthetic construct
SEQUENCE: 225
gaggtgcagc tggtggagtc tggggggaggc ttggtacagc ctggggggtc cctgagactc     60
tcctgtgcag cctctggatt caccctttagc agctatgcca tgagctgggt ccgccaggct    120
ccagggaagg ggctggagtg ggtctcagct attagtggta gtggtggcag cacatactac    180
gcagactccg tgaagggccg gttcaccatc tccagagaca attccaagaa ctcgctgtat    240
```

-continued

```
ctgcaattga acagcctgag agccgaggac acggccgtat attactgtgc gaagacgctg  300
tatactacca gctggtacgg gggcttccag cactggggcc agggcaccct ggtcactgtc  360
tcctca                                                            366

SEQ ID NO: 226              moltype = AA   length = 122
FEATURE                     Location/Qualifiers
REGION                      1..122
                            note = Synthetic
source                      1..122
                            mol_type = protein
                            organism = synthetic construct
SEQUENCE: 226
EVQLVESGGG LVQPGGSLRL SCAASGFTLS SYAMSWVRQA PGKGLEWVSA ISGSGGSTYY   60
ADSVKGRFTI SRDNSKNSLY LQLNSLRAED TAVYYCAKTL YTTSWYGGFQ HWGQGTLVTV  120
SS                                                                 122

SEQ ID NO: 227              moltype = DNA   length = 24
FEATURE                     Location/Qualifiers
misc_feature               1..24
                            note = Synthetic
source                      1..24
                            mol_type = other DNA
                            organism = synthetic construct
SEQUENCE: 227
ggattcaccc ttagcagcta tgcc                                          24

SEQ ID NO: 228              moltype = AA   length = 8
FEATURE                     Location/Qualifiers
REGION                      1..8
                            note = Synthetic
source                      1..8
                            mol_type = protein
                            organism = synthetic construct
SEQUENCE: 228
GFTLSSYA                                                             8

SEQ ID NO: 229              moltype = DNA   length = 24
FEATURE                     Location/Qualifiers
misc_feature               1..24
                            note = Synthetic
source                      1..24
                            mol_type = other DNA
                            organism = synthetic construct
SEQUENCE: 229
attagtggta gtggtggcag caca                                          24

SEQ ID NO: 230              moltype = AA   length = 8
FEATURE                     Location/Qualifiers
REGION                      1..8
                            note = Synthetic
source                      1..8
                            mol_type = protein
                            organism = synthetic construct
SEQUENCE: 230
ISGSGGST                                                             8

SEQ ID NO: 231              moltype = DNA   length = 45
FEATURE                     Location/Qualifiers
misc_feature               1..45
                            note = Synthetic
source                      1..45
                            mol_type = other DNA
                            organism = synthetic construct
SEQUENCE: 231
gcgaagacgc tgtatactac cagctggtac gggggcttcc agcac                   45

SEQ ID NO: 232              moltype = AA   length = 15
FEATURE                     Location/Qualifiers
REGION                      1..15
                            note = Synthetic
source                      1..15
                            mol_type = protein
                            organism = synthetic construct
SEQUENCE: 232
AKTLYTTSWY GGFQH                                                    15

SEQ ID NO: 233              moltype = DNA   length = 321
FEATURE                     Location/Qualifiers
misc_feature               1..321
```

-continued

```
                             note = Synthetic
source                       1..321
                             mol_type = other DNA
                             organism = synthetic construct
SEQUENCE: 233
gacatccaga tgacccagtc tccatcttcc gtgtctgcat ctataggaga cagagtcacc    60
atcacttgtc gggcgagtca gggaatcagc agttggttag cctggtatca gcagaaacca   120
gggaaagtcc ctaagctcct gatctatgct gcgtcctctt tgcaaagtgg gttcccatca   180
aggttcagcg gcagtggatc tgggacagat ttcactctca ccatcagtag cctgcagccc   240
gaagattttg caacttacta ttgtcaacag actcacagtt tcccgtggac ggtcggccaa   300
gggaccaagg tggaaatcaa a                                             321

SEQ ID NO: 234              moltype = AA  length = 107
FEATURE                     Location/Qualifiers
REGION                      1..107
                             note = Synthetic
source                       1..107
                             mol_type = protein
                             organism = synthetic construct
SEQUENCE: 234
DIQMTQSPSS VSASIGDRVT ITCRASQGIS SWLAWYQQKP GKVPKLLIYA ASSLQSGFPS    60
RFSGSGSGTD FTLTISSLQP EDFATYYCQQ THSFPWTVGQ GTKVEIK                 107

SEQ ID NO: 235             moltype = DNA  length = 18
FEATURE                     Location/Qualifiers
misc_feature                1..18
                             note = Synthetic
source                       1..18
                             mol_type = other DNA
                             organism = synthetic construct
SEQUENCE: 235
cagggaatca gcagttgg                                                  18

SEQ ID NO: 236             moltype = AA  length = 6
FEATURE                     Location/Qualifiers
REGION                      1..6
                             note = Synthetic
source                       1..6
                             mol_type = protein
                             organism = synthetic construct
SEQUENCE: 236
QGISSW                                                                6

SEQ ID NO: 237             moltype =    length =
SEQUENCE: 237
000

SEQ ID NO: 238             moltype =    length =
SEQUENCE: 238
000

SEQ ID NO: 239             moltype = DNA  length = 24
FEATURE                     Location/Qualifiers
misc_feature                1..24
                             note = Synthetic
source                       1..24
                             mol_type = other DNA
                             organism = synthetic construct
SEQUENCE: 239
caacagactc acagtttccc gtgg                                           24

SEQ ID NO: 240             moltype = AA  length = 8
FEATURE                     Location/Qualifiers
REGION                      1..8
                             note = Synthetic
source                       1..8
                             mol_type = protein
                             organism = synthetic construct
SEQUENCE: 240
QQTHSFPW                                                              8

SEQ ID NO: 241             moltype = DNA  length = 366
FEATURE                     Location/Qualifiers
misc_feature                1..366
                             note = Synthetic
source                       1..366
                             mol_type = other DNA
                             organism = synthetic construct
SEQUENCE: 241
```

-continued

```
gaggtgcagc tggtggagtc tggggggaggc ttggtacagc ctggggggtc cctgagactc   60
tcctgtgcag cctctggatt caccccttagg agctatttca tgacctgggt ccgccaggtt  120
ccagggaagg ggctggaggg ggtctcagct attagtggca ttagtggtgg cacatactac  180
acagactccg ttaagggccg gttcaccatc tccagagaca attccaagaa cacgctgttt  240
ctgcaaatga acagcctgag agccgaggac acggccgtat atttctgtgc gagaacggtg  300
tatagtagta gttactacgg gggcttccag cactggggc agggcaccct ggtcaccgtc  360
tcctca                                                              366

SEQ ID NO: 242              moltype = AA  length = 122
FEATURE                     Location/Qualifiers
REGION                      1..122
                            note = Synthetic
source                      1..122
                            mol_type = protein
                            organism = synthetic construct
SEQUENCE: 242
EVQLVESGGG LVQPGGSLRL SCAASGFTLR SYFMTWVRQV PGKGLEGVSA ISGISGGTYY   60
TDSVKGRFTI SRDNSKNTLF LQMNSLRAED TAVYFCARTV YSSSYYGGFQ HWGQGTLVTV  120
SS                                                                  122

SEQ ID NO: 243              moltype = DNA  length = 24
FEATURE                     Location/Qualifiers
misc_feature               1..24
                            note = Synthetic
source                      1..24
                            mol_type = other DNA
                            organism = synthetic construct
SEQUENCE: 243
ggattcaccc ttaggagcta tttc                                          24

SEQ ID NO: 244              moltype = AA  length = 8
FEATURE                     Location/Qualifiers
REGION                      1..8
                            note = Synthetic
source                      1..8
                            mol_type = protein
                            organism = synthetic construct
SEQUENCE: 244
GFTLRSYF                                                            8

SEQ ID NO: 245              moltype = DNA  length = 24
FEATURE                     Location/Qualifiers
misc_feature               1..24
                            note = Synthetic
source                      1..24
                            mol_type = other DNA
                            organism = synthetic construct
SEQUENCE: 245
attagtggca ttagtggtgg caca                                          24

SEQ ID NO: 246              moltype = AA  length = 8
FEATURE                     Location/Qualifiers
REGION                      1..8
                            note = Synthetic
source                      1..8
                            mol_type = protein
                            organism = synthetic construct
SEQUENCE: 246
ISGISGGT                                                            8

SEQ ID NO: 247              moltype = DNA  length = 45
FEATURE                     Location/Qualifiers
misc_feature               1..45
                            note = Synthetic
source                      1..45
                            mol_type = other DNA
                            organism = synthetic construct
SEQUENCE: 247
gcgagaacgg tgtatagtag tagttactac gggggcttcc agcac                   45

SEQ ID NO: 248              moltype = AA  length = 15
FEATURE                     Location/Qualifiers
REGION                      1..15
                            note = Synthetic
source                      1..15
                            mol_type = protein
                            organism = synthetic construct
SEQUENCE: 248
ARTVYSSSYY GGFQH                                                    15
```

-continued

```
SEQ ID NO: 249            moltype = DNA  length = 321
FEATURE                   Location/Qualifiers
misc_feature              1..321
                          note = Synthetic
source                    1..321
                          mol_type = other DNA
                          organism = synthetic construct
SEQUENCE: 249
gacatccaga tgacccagtc tccatcttcc gtgtctgtat ctgtaggaga cagagtcacc   60
atcacttgtc gggcgagtca gggtattagc agttggttag cctggtatca gcagaaacca   120
gggaaagccc ctaagctcct gatctatgtt gcatccagtt tacaaagtgg ggtcccatca   180
aggttcagcg gcagtggatc tgggacagat ttcactctca ccatcagcag cctgcagcct   240
gaagattttg caacttacta ttgtcaacag actaacagtt tccctctcac tttcggcgga   300
gggaccaagg tggagatcaa a                                             321

SEQ ID NO: 250            moltype = AA  length = 107
FEATURE                   Location/Qualifiers
REGION                    1..107
                          note = Synthetic
source                    1..107
                          mol_type = protein
                          organism = synthetic construct
SEQUENCE: 250
DIQMTQSPSS VSVSVGDRVT ITCRASQGIS SWLAWYQQKP GKAPKLLIYV ASSLQSGVPS   60
RFSGSGSGTD FTLTISSLQP EDFATYYCQQ TNSFPLTFGG GTKVEIK                 107

SEQ ID NO: 251            moltype = DNA  length = 18
FEATURE                   Location/Qualifiers
misc_feature              1..18
                          note = Synthetic
source                    1..18
                          mol_type = other DNA
                          organism = synthetic construct
SEQUENCE: 251
cagggtatta gcagttgg                                                 18

SEQ ID NO: 252            moltype = AA  length = 6
FEATURE                   Location/Qualifiers
REGION                    1..6
                          note = Synthetic
source                    1..6
                          mol_type = protein
                          organism = synthetic construct
SEQUENCE: 252
QGISSW                                                              6

SEQ ID NO: 253            moltype =    length =
SEQUENCE: 253
000

SEQ ID NO: 254            moltype =    length =
SEQUENCE: 254
000

SEQ ID NO: 255            moltype = DNA  length = 27
FEATURE                   Location/Qualifiers
misc_feature              1..27
                          note = Synthetic
source                    1..27
                          mol_type = other DNA
                          organism = synthetic construct
SEQUENCE: 255
caacagacta acagtttccc tctcact                                       27

SEQ ID NO: 256            moltype = AA  length = 9
FEATURE                   Location/Qualifiers
REGION                    1..9
                          note = Synthetic
source                    1..9
                          mol_type = protein
                          organism = synthetic construct
SEQUENCE: 256
QQTNSFPLT                                                           9

SEQ ID NO: 257            moltype = DNA  length = 366
FEATURE                   Location/Qualifiers
misc_feature              1..366
                          note = Synthetic
```

-continued

```
source                    1..366
                          mol_type = other DNA
                          organism = synthetic construct
SEQUENCE: 257
gaggtgcagc tggtggagtc tggggggaggc ttggtacagc ctggggggtc cctgagactc    60
tcctgtgcag cctctggatt caccccttagg agttatgtca tgtactgggt ccgccaggt    120
ccagggaagg ggctggaggg ggtctcaggt attagtggca gtagtggtgg cacatactac   180
acagactccg tgaagggccg gttcaccatc tccagagaca attccaagaa cacgctgttt    240
ctgcaaatga acagcctgag agccgaggac acggccgtat atttctgtgc gagatcggtg    300
tatagtacca cctggtacgg gggcttccag cactggggc agggcaccct ggtcaccgtc    360
tcctca                                                                366

SEQ ID NO: 258            moltype = AA  length = 122
FEATURE                   Location/Qualifiers
REGION                    1..122
                          note = Synthetic
source                    1..122
                          mol_type = protein
                          organism = synthetic construct
SEQUENCE: 258
EVQLVESGGG LVQPGGSLRL SCAASGFTLR SYVMYWVRQG PGKGLEGVSG ISGSSGGTYY     60
TDSVKGRFTI SRDNSKNTLF LQMNSLRAED TAVYFCARSV YSTTWYGGFQ HWGQGTLVTV    120
SS                                                                    122

SEQ ID NO: 259            moltype = DNA  length = 24
FEATURE                   Location/Qualifiers
misc_feature              1..24
                          note = Synthetic
source                    1..24
                          mol_type = other DNA
                          organism = synthetic construct
SEQUENCE: 259
ggattcaccc ttaggagtta tgtc                                            24

SEQ ID NO: 260            moltype = AA  length = 8
FEATURE                   Location/Qualifiers
REGION                    1..8
                          note = Synthetic
source                    1..8
                          mol_type = protein
                          organism = synthetic construct
SEQUENCE: 260
GFTLRSYV                                                               8

SEQ ID NO: 261            moltype = DNA  length = 24
FEATURE                   Location/Qualifiers
misc_feature              1..24
                          note = Synthetic
source                    1..24
                          mol_type = other DNA
                          organism = synthetic construct
SEQUENCE: 261
attagtggca gtagtggtgg caca                                            24

SEQ ID NO: 262            moltype = AA  length = 8
FEATURE                   Location/Qualifiers
REGION                    1..8
                          note = Synthetic
source                    1..8
                          mol_type = protein
                          organism = synthetic construct
SEQUENCE: 262
ISGSSGGT                                                               8

SEQ ID NO: 263            moltype = DNA  length = 45
FEATURE                   Location/Qualifiers
misc_feature              1..45
                          note = Synthetic
source                    1..45
                          mol_type = other DNA
                          organism = synthetic construct
SEQUENCE: 263
gcgagatcgg tgtatagtac cacctggtac gggggcttcc agcac                     45

SEQ ID NO: 264            moltype = AA  length = 15
FEATURE                   Location/Qualifiers
REGION                    1..15
                          note = Synthetic
source                    1..15
```

-continued

```
                              mol_type = protein
                              organism = synthetic construct
SEQUENCE: 264
ARSVYSTTWY GGFQH                                                    15

SEQ ID NO: 265        moltype = DNA   length = 321
FEATURE               Location/Qualifiers
misc_feature          1..321
                      note = Synthetic
source                1..321
                      mol_type = other DNA
                      organism = synthetic construct
SEQUENCE: 265
gacatccaga tgacccagtc tccatcttcc gtgtctgtat ctgtgggaga cagagtcacc  60
atcacttgtc gggcgagtca ggttattagc agttggttag cctggtatca gctgaaacca  120
gggaaagccc ctaaactcct gatctatgct gcatccagtt tacaaagtgg ggtcccatca  180
aggttcagcg gcagtggatc tgggacagat ttcactctca ccatcagcgg cctgcagcct  240
gaagattttg cagtttacta ttgtcaacag actaacagtt tccctctcac tttcggcgga  300
gggaccaagg tggagatcaa a                                             321

SEQ ID NO: 266        moltype = AA   length = 107
FEATURE               Location/Qualifiers
REGION                1..107
                      note = Synthetic
source                1..107
                      mol_type = protein
                      organism = synthetic construct
SEQUENCE: 266
DIQMTQSPSS VSVSVGDRVT ITCRASQVIS SWLAWYQLKP GKAPKLLIYA ASSLQSGVPS  60
RFSGSGSGTD FTLTISGLQP EDFAVYYCQQ TNSFPLTFGG GTKVEIK               107

SEQ ID NO: 267        moltype = DNA   length = 18
FEATURE               Location/Qualifiers
misc_feature          1..18
                      note = Synthetic
source                1..18
                      mol_type = other DNA
                      organism = synthetic construct
SEQUENCE: 267
caggttatta gcagttgg                                                 18

SEQ ID NO: 268        moltype = AA   length = 6
FEATURE               Location/Qualifiers
REGION                1..6
                      note = Synthetic
source                1..6
                      mol_type = protein
                      organism = synthetic construct
SEQUENCE: 268
QVISSW                                                              6

SEQ ID NO: 269        moltype =    length =
SEQUENCE: 269
000

SEQ ID NO: 270        moltype =    length =
SEQUENCE: 270
000

SEQ ID NO: 271        moltype = DNA   length = 27
FEATURE               Location/Qualifiers
misc_feature          1..27
                      note = Synthetic
source                1..27
                      mol_type = other DNA
                      organism = synthetic construct
SEQUENCE: 271
caacagacta acagtttccc tctcact                                       27

SEQ ID NO: 272        moltype = AA   length = 9
FEATURE               Location/Qualifiers
REGION                1..9
                      note = Synthetic
source                1..9
                      mol_type = protein
                      organism = synthetic construct
SEQUENCE: 272
QQTNSFPLT                                                           9
```

-continued

```
SEQ ID NO: 273         moltype = DNA   length = 366
FEATURE                Location/Qualifiers
misc_feature           1..366
                       note = Synthetic
source                 1..366
                       mol_type = other DNA
                       organism = synthetic construct
SEQUENCE: 273
gaggtgcagc tggtggagtc tggggggaaac ttggaacagc ctggggggtc ccttagactc   60
tcctgtacag cctctggatt caccttttagc agatctgcca tgaactgggt ccgccgggct  120
ccagggaagg ggctggagtg ggtctcagga attagtggta gtggtggtcg aacatactac  180
gcagactccg tgaagggccg gttcaccatc tccagagaca attccaagaa tacgctatat  240
ctgcaaatga acagcctgag cgccgaggac acggccgcat attactgtgc gaaagattcg  300
tatactacca gttggtacgg aggtatggac gtctggggcc acgggaccac ggtcaccgtc  360
tcctca                                                              366

SEQ ID NO: 274         moltype = AA   length = 122
FEATURE                Location/Qualifiers
REGION                 1..122
                       note = Synthetic
source                 1..122
                       mol_type = protein
                       organism = synthetic construct
SEQUENCE: 274
EVQLVESGGN LEQPGGSLRL SCTASGFTFS RSAMNWVRRA PGKGLEWVSG ISGSGGRTYY   60
ADSVKGRFTI SRDNSKNTLY LQMNSLSAED TAAYYCAKDS YTTSWYGGMD VWGHGTTVTV  120
SS                                                                  122

SEQ ID NO: 275         moltype = DNA   length = 24
FEATURE                Location/Qualifiers
misc_feature           1..24
                       note = Synthetic
source                 1..24
                       mol_type = other DNA
                       organism = synthetic construct
SEQUENCE: 275
ggattcacct ttagcagatc tgcc                                           24

SEQ ID NO: 276         moltype = AA   length = 8
FEATURE                Location/Qualifiers
REGION                 1..8
                       note = Synthetic
source                 1..8
                       mol_type = protein
                       organism = synthetic construct
SEQUENCE: 276
GFTFSRSA                                                              8

SEQ ID NO: 277         moltype = DNA   length = 24
FEATURE                Location/Qualifiers
misc_feature           1..24
                       note = Synthetic
source                 1..24
                       mol_type = other DNA
                       organism = synthetic construct
SEQUENCE: 277
attagtggta gtggtggtcg aaca                                           24

SEQ ID NO: 278         moltype = AA   length = 8
FEATURE                Location/Qualifiers
REGION                 1..8
                       note = Synthetic
source                 1..8
                       mol_type = protein
                       organism = synthetic construct
SEQUENCE: 278
ISGSGGRT                                                              8

SEQ ID NO: 279         moltype = DNA   length = 45
FEATURE                Location/Qualifiers
misc_feature           1..45
                       note = Synthetic
source                 1..45
                       mol_type = other DNA
                       organism = synthetic construct
SEQUENCE: 279
gcgaaagatt cgtatactac cagttggtac ggaggtatgg acgtc                    45

SEQ ID NO: 280         moltype = AA   length = 15
```

```
FEATURE               Location/Qualifiers
REGION                1..15
                      note = Synthetic
source                1..15
                      mol_type = protein
                      organism = synthetic construct
SEQUENCE: 280
AKDSYTTSWY GGMDV                                                    15

SEQ ID NO: 281        moltype = DNA   length = 321
FEATURE               Location/Qualifiers
misc_feature          1..321
                      note = Synthetic
source                1..321
                      mol_type = other DNA
                      organism = synthetic construct
SEQUENCE: 281
gacatccaga tgacccagtc tccatcttcc gtgtctgcat ctgtaggaga cagagtcacc  60
atcacttgtc gggcgagtca gggtattttc agctggttag cctggtatca gcagaaacca  120
ggaaaagccc ctaagctcct gatctatgct gcttccagtt tacaaagtgg ggtcccatca  180
agattcagcg gcagtggatc tgggacagat ttcactctca ccatcagcag cctgcagcct  240
gaggattttg caatttacta ttgtcaacag gctaacagtg tcccgatcac cttcggccaa  300
gggacacgac tggagattaa a                                            321

SEQ ID NO: 282        moltype = AA   length = 107
FEATURE               Location/Qualifiers
REGION                1..107
                      note = Synthetic
source                1..107
                      mol_type = protein
                      organism = synthetic construct
SEQUENCE: 282
DIQMTQSPSS VSASVGDRVT ITCRASQGIF SWLAWYQQKP GKAPKLLIYA ASSLQSGVPS  60
RFSGSGSGTD FTLTISSLQP EDFAIYYCQQ ANSVPITFGQ GTRLEIK               107

SEQ ID NO: 283        moltype = DNA   length = 18
FEATURE               Location/Qualifiers
misc_feature          1..18
                      note = Synthetic
source                1..18
                      mol_type = other DNA
                      organism = synthetic construct
SEQUENCE: 283
cagggtattt tcagctgg                                                 18

SEQ ID NO: 284        moltype = AA   length = 6
FEATURE               Location/Qualifiers
REGION                1..6
                      note = Synthetic
source                1..6
                      mol_type = protein
                      organism = synthetic construct
SEQUENCE: 284
QGIFSW                                                              6

SEQ ID NO: 285        moltype =    length =
SEQUENCE: 285
000

SEQ ID NO: 286        moltype =    length =
SEQUENCE: 286
000

SEQ ID NO: 287        moltype = DNA   length = 27
FEATURE               Location/Qualifiers
misc_feature          1..27
                      note = Synthetic
source                1..27
                      mol_type = other DNA
                      organism = synthetic construct
SEQUENCE: 287
caacaggcta acagtgtccc gatcacc                                       27

SEQ ID NO: 288        moltype = AA   length = 9
FEATURE               Location/Qualifiers
REGION                1..9
                      note = Synthetic
source                1..9
                      mol_type = protein
```

-continued

```
                         organism = synthetic construct
SEQUENCE: 288
QQANSVPIT                                                     9

SEQ ID NO: 289          moltype = DNA  length = 366
FEATURE                 Location/Qualifiers
misc_feature            1..366
                        note = Synthetic
source                  1..366
                        mol_type = other DNA
                        organism = synthetic construct
SEQUENCE: 289
gaggtgcagc tggtggagtc tggggggaggc ttggtacagc ctggggggtc cctgagactc   60
tcctgttcag cctctggatt caccttagc agctatgcca tgaactgggt ccgccaggct  120
ccagggaagg ggctggagtg ggtcaccgct attagtggca gtggtggtgg cacatactac  180
gcagactccg tgaagggccg gttcaccatc tccagagaca attccaagaa ctcgctgttt  240
ctgcaattga acagcctgag agccgaggac acggccgtgt attactgtgc gaaacaaacg  300
tataccagca gctggtacgg tggctttgat atctggggcc agggggacaat ggtcaccgtc  360
tcttca                                                       366

SEQ ID NO: 290          moltype = AA  length = 122
FEATURE                 Location/Qualifiers
REGION                  1..122
                        note = Synthetic
source                  1..122
                        mol_type = protein
                        organism = synthetic construct
SEQUENCE: 290
EVQLVESGGG LVQPGGSLRL SCSASGFTFS SYAMNWVRQA PGKGLEWVTA ISGSGGGTYY   60
ADSVKGRFTI SRDNSKNSLF LQLNSLRAED TAVYYCAKQT YTSSWYGGFD IWGQGTMVTV  120
SS                                                          122

SEQ ID NO: 291          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 291
ggattcacct ttagcagcta tgcc                                    24

SEQ ID NO: 292          moltype = AA  length = 8
FEATURE                 Location/Qualifiers
REGION                  1..8
                        note = Synthetic
source                  1..8
                        mol_type = protein
                        organism = synthetic construct
SEQUENCE: 292
GFTFSSYA                                                       8

SEQ ID NO: 293          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 293
attagtggca gtggtggtgg caca                                    24

SEQ ID NO: 294          moltype = AA  length = 8
FEATURE                 Location/Qualifiers
REGION                  1..8
                        note = Synthetic
source                  1..8
                        mol_type = protein
                        organism = synthetic construct
SEQUENCE: 294
ISGSGGGT                                                       8

SEQ ID NO: 295          moltype = DNA  length = 45
FEATURE                 Location/Qualifiers
misc_feature            1..45
                        note = Synthetic
source                  1..45
                        mol_type = other DNA
                        organism = synthetic construct
```

-continued

```
SEQUENCE: 295
gcgaaacaaa cgtataccag cagctggtac ggtggctttg atatc              45

SEQ ID NO: 296          moltype = AA  length = 15
FEATURE                 Location/Qualifiers
REGION                  1..15
                        note = Synthetic
source                  1..15
                        mol_type = protein
                        organism = synthetic construct
SEQUENCE: 296
AKQTYTSSWY GGFDI                                               15

SEQ ID NO: 297          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 297
gacatccaga tgacccagtc gccatcttcc gtgtccgcgt ctgtaggaga cagagtcacc  60
atcacttgtc gggcgagtca gggttttagt tcctggttag cctggtatca gcagatacca  120
gggaaagccc ccaagctcct gatctatgct gcatcaaggt tgcaaagtgg ggtcccatcc  180
aggttccgcg gcagtggatc tgggacagat ttcactctca ccatcagcag cctgcagcct  240
gaggattttg caacttacta ttgtcaacag gctaacagtt cccgctcac tttcggcgga  300
gggaccaagg tggagatcaa a                                        321

SEQ ID NO: 298          moltype = AA  length = 107
FEATURE                 Location/Qualifiers
REGION                  1..107
                        note = Synthetic
source                  1..107
                        mol_type = protein
                        organism = synthetic construct
SEQUENCE: 298
DIQMTQSPSS VSASVGDRVT ITCRASQGFS SWLAWYQQIP GKAPKLLIYA ASRLQSGVPS  60
RFRGSGSGTD FTLTISSLQP EDFATYYCQQ ANSFPLTFGG GTKVEIK             107

SEQ ID NO: 299          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 299
cagggtttta gttcctgg                                            18

SEQ ID NO: 300          moltype = AA  length = 6
FEATURE                 Location/Qualifiers
REGION                  1..6
                        note = Synthetic
source                  1..6
                        mol_type = protein
                        organism = synthetic construct
SEQUENCE: 300
QGFSSW                                                         6

SEQ ID NO: 301          moltype =    length =
SEQUENCE: 301
000

SEQ ID NO: 302          moltype =    length =
SEQUENCE: 302
000

SEQ ID NO: 303          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 303
caacaggcta acagtttccc gctcact                                  27

SEQ ID NO: 304          moltype = AA  length = 9
FEATURE                 Location/Qualifiers
```

-continued

```
REGION                    1..9
                          note = Synthetic
source                    1..9
                          mol_type = protein
                          organism = synthetic construct
SEQUENCE: 304
QQANSFPLT                                                                        9

SEQ ID NO: 305            moltype = AA   length = 167
FEATURE                   Location/Qualifiers
REGION                    1..167
                          note = Synthetic
source                    1..167
                          mol_type = protein
                          organism = synthetic construct
SEQUENCE: 305
SITGISPITE SLASLSTYND QSITFALEDE SYEIYVEDLK KDKKKDKVLL SYYESQHPSS  60
ESGDGVDGKM LMVTLSPTKD FWLQANNKEH SVELHKCEKP LPDQAFFVLH NRSFNCVSFE  120
CKTDPGVFIG VKDNHLALIK VDYSENLGSE NILFKLSEIL EHHHHHH                167

SEQ ID NO: 306            moltype = AA   length = 167
FEATURE                   Location/Qualifiers
REGION                    1..167
                          note = Synthetic
source                    1..167
                          mol_type = protein
                          organism = synthetic construct
SEQUENCE: 306
SITGISPITE SLASLSTYND QSITFALEDE SYEIYVEDLK KDKKKDKVLL SYYESQHPSS  60
ESGDGVDGKM LMVTLSPTKD FWLQANNKEH SVELHKCEKP LPDQAFFVLH NRSFNCVSFE  120
CKTDPGVFIG VKDNHLALIK VDYSENLGSE NILFKLSEIL EHHHHHH                167

SEQ ID NO: 307            moltype = DNA   length = 354
FEATURE                   Location/Qualifiers
misc_feature              1..354
                          note = Synthetic
source                    1..354
                          mol_type = other DNA
                          organism = synthetic construct
SEQUENCE: 307
caggtcacct tgaaggagtc tggtcctgtg ctggtgaaac ccacagagag cctcacgctg  60
acctgctccg tctctggatt ctcactcagt aatgttagaa tgggtgtgag ctggatccgt  120
cagtccccag ggaaggccct ggagtggctt gcacacattt tttcgaatga cgaaaaatcc  180
tacaccacat ctctgaagac caggctcacc atctccaagg acacctcag aagccaggtg  240
gtccttacca tgaccgacat ggaccctggg gacacagcca catattactg tgcacggata  300
cggaatttgg cctttaatta ctggggccag ggaaccctgg tcaccgtctc ctca         354

SEQ ID NO: 308            moltype = AA   length = 118
FEATURE                   Location/Qualifiers
REGION                    1..118
                          note = Synthetic
source                    1..118
                          mol_type = protein
                          organism = synthetic construct
SEQUENCE: 308
QVTLKESGPV LVKPTESLTL TCSVSGFSLS NVRMGVSWIR QSPGKALEWL AHIFSNDEKS  60
YTTSLKTRLT ISKDTSRSQV VLTMTDMDPG DTATYYCARI RNLAFNYWGQ GTLVTVSS    118

SEQ ID NO: 309            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 309
ggattctcac tcagtaatgt tagaatgggt                                    30

SEQ ID NO: 310            moltype = AA   length = 10
FEATURE                   Location/Qualifiers
REGION                    1..10
                          note = Synthetic
source                    1..10
                          mol_type = protein
                          organism = synthetic construct
SEQUENCE: 310
GFSLSNVRMG                                                          10

SEQ ID NO: 311            moltype = DNA   length = 21
```

-continued

```
FEATURE           Location/Qualifiers
misc_feature      1..21
                  note = Synthetic
source            1..21
                  mol_type = other DNA
                  organism = synthetic construct
SEQUENCE: 311
attttttcga atgacgaaaa a                                        21

SEQ ID NO: 312    moltype = AA  length = 7
FEATURE           Location/Qualifiers
REGION            1..7
                  note = Synthetic
source            1..7
                  mol_type = protein
                  organism = synthetic construct
SEQUENCE: 312
IFSNDEK                                                         7

SEQ ID NO: 313    moltype = DNA  length = 30
FEATURE           Location/Qualifiers
misc_feature      1..30
                  note = Synthetic
source            1..30
                  mol_type = other DNA
                  organism = synthetic construct
SEQUENCE: 313
gcacggatac ggaatttggc ctttaattac                               30

SEQ ID NO: 314    moltype = AA  length = 10
FEATURE           Location/Qualifiers
REGION            1..10
                  note = Synthetic
source            1..10
                  mol_type = protein
                  organism = synthetic construct
SEQUENCE: 314
ARIRNLAFNY                                                      10

SEQ ID NO: 315    moltype = DNA  length = 339
FEATURE           Location/Qualifiers
misc_feature      1..339
                  note = Synthetic
source            1..339
                  mol_type = other DNA
                  organism = synthetic construct
SEQUENCE: 315
gacttcgtga tgacccagtc tccagactcc ctggctgtgt ctctgggcga gagggccacc  60
atcaactgca agtccagcca gagtgtgtta cacaggtcca gcaataagaa ctacttagct 120
tggtatcagc agaagccagg acagcctcct aacctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcaata ttatggtact 300
ctatttactt tcggccctgg gaccaaagtg gatatcaaa                        339

SEQ ID NO: 316    moltype = AA  length = 113
FEATURE           Location/Qualifiers
REGION            1..113
                  note = Synthetic
source            1..113
                  mol_type = protein
                  organism = synthetic construct
SEQUENCE: 316
DFVMTQSPDS LAVSLGERAT INCKSSQSVL HRSSNKNYLA WYQQKPGQPP NLLIYWASTR  60
ESGVPDRFSG SGSGTDFTLT ISSLQAEDVA VYYCQQYYGT LFTFGPGTKV DIK        113

SEQ ID NO: 317    moltype = DNA  length = 36
FEATURE           Location/Qualifiers
misc_feature      1..36
                  note = Synthetic
source            1..36
                  mol_type = other DNA
                  organism = synthetic construct
SEQUENCE: 317
cagagtgtgt tacacaggtc cagcaataag aactac                        36

SEQ ID NO: 318    moltype = AA  length = 12
FEATURE           Location/Qualifiers
REGION            1..12
                  note = Synthetic
```

```
source                          1..12
                                mol_type = protein
                                organism = synthetic construct
SEQUENCE: 318
QSVLHRSSNK NY                                                                    12

SEQ ID NO: 319                  moltype =    length =
SEQUENCE: 319
000

SEQ ID NO: 320                  moltype =    length =
SEQUENCE: 320
000

SEQ ID NO: 321                  moltype = DNA   length = 27
FEATURE                         Location/Qualifiers
misc_feature                    1..27
                                note = Synthetic
source                          1..27
                                mol_type = other DNA
                                organism = synthetic construct
SEQUENCE: 321
cagcaatatt atggtactct atttact                                                    27

SEQ ID NO: 322                  moltype = AA   length = 9
FEATURE                         Location/Qualifiers
REGION                          1..9
                                note = Synthetic
source                          1..9
                                mol_type = protein
                                organism = synthetic construct
SEQUENCE: 322
QQYYGTLFT                                                                        9

SEQ ID NO: 323                  moltype = AA   length = 537
FEATURE                         Location/Qualifiers
REGION                          1..537
                                note = hST2-hFc
source                          1..537
                                mol_type = protein
                                organism = synthetic construct
SEQUENCE: 323
KFSKQSWGLE NEALIVRCPR QGKPSYTVDW YYSQTNKSIP TQERNRVFAS GQLLKFLPAA  60
VADSGIYTCI VRSPTFNRTG YANVTIYKKQ SDCNVPDYLM YSTVSGSEKN SKIYCPTIDL  120
YNWTAPLEWF KNCQALQGSR YRAHKSFLVI DNVMTEDAGD YTCKFIHNEN GANYSVTATR  180
SFTVKDEQGF SLFPVIGAPA QNEIKEVEIG KNANLTCSAC FGKGTQFLAA VLWQLNGTKI  240
TDFGEPRIQQ EEGQNQSFSN GLACLDMVLR IADVKEEDLL LQYDCLALNL HGLRRHTVRL  300
SRKNPIDHHS DKTHTCPPCP APELLGGPSV FLFPPKPKDT LMISRTPEVT CVVVDVSHED  360
PEVKFNWYVD GVEVHNAKTK PREEQYNSTY RVVSVLTVLH QDWLNGKEYK CKVSNKALPA  420
PIEKTISKAK GQPREPQVYT LPPSRDELTK NQVSLTCLVK GFYPSDIAVE WESNGQPENN  480
YKTTPPVLDS DGSFFLYSKL TVDKSRWQQG NVFSCSVMHE ALHNHYTQKS LSLSPGK     537

SEQ ID NO: 324                  moltype = AA   length = 543
FEATURE                         Location/Qualifiers
REGION                          1..543
                                note = hST2-mFc
source                          1..543
                                mol_type = protein
                                organism = synthetic construct
SEQUENCE: 324
KFSKQSWGLE NEALIVRCPR QGKPSYTVDW YYSQTNKSIP TQERNRVFAS GQLLKFLPAA  60
VADSGIYTCI VRSPTFNRTG YANVTIYKKQ SDCNVPDYLM YSTVSGSEKN SKIYCPTIDL  120
YNWTAPLEWF KNCQALQGSR YRAHKSFLVI DNVMTEDAGD YTCKFIHNEN GANYSVTATR  180
SFTVKDEQGF SLFPVIGAPA QNEIKEVEIG KNANLTCSAC FGKGTQFLAA VLWQLNGTKI  240
TDFGEPRIQQ EEGQNQSFSN GLACLDMVLR IADVKEEDLL LQYDCLALNL HGLRRHTVRL  300
SRKNPIDHHS EPRGPTIKPC PPCKCPAPNL LGGPSVFIFP PKIKDVLMIS LSPIVTCVVV  360
DVSEDDPDVQ ISWFVNNVEV HTAQTQTHRE DYNSTLRVVS ALPIQHQDWM SGKEFKCKVN  420
NKDLPAPIER TISKPKGSVR APQVYVLPPP EEEMTKKQVT LTCMVTDFMP EDIYVEWTNN  480
GKTELNYKNT EPVLDSDGSY FMYSKLRVEK KNWVERNSYS CSVVHEGLHN HHTTKSFSRT  540
PGK                                                                             543

SEQ ID NO: 325                  moltype = AA   length = 884
FEATURE                         Location/Qualifiers
REGION                          1..884
                                note = hST2-hIL1RAcP-mFc
source                          1..884
                                mol_type = protein
                                organism = synthetic construct
SEQUENCE: 325
```

```
KFSKQSWGLE NEALIVRCPR QGKPSYTVDW YYSQTNKSIP TQERNRVFAS GQLLKFLPAA    60
VADSGIYTCI VRSPTFNRTG YANVTIYKKQ SDCNVPDYLM YSTVSGSEKN SKIYCPTIDL   120
YNWTAPLEWF KNCQALQGSR YRAHKSFLVI DNVMTEDAGD YTCKFIHNEN GANYSVTATR   180
SFTVKDEQGF SLFPVIGAPA QNEIKEVEIG KNANLTCSAC FGKGTQFLAA VLWQLNGTKI   240
TDFGEPRIQQ EEGQNQSFSN GLACLDMVLR IADVKEEDLL LQYDCLALNL HGLRRHTVRL   300
SRKNPIDHHS SERCDDWGLD TMRQIQVFED EPARIKCPLF EHFLKFNYST AHSAGLTLIW   360
YWTRQDRDLE EPINFRLPEN RISKEKDVLW FRPTLLNDTG NYTCMLRNTT YCSKVAFPLE   420
VVQKDSCFNS PMKLPVHKLY IEYGIQRITC PNVDGYFPSS VKPTITWYMG CYKIQNFNNV   480
IPEGMNLSFL IALISNNGNY TCVVTYPENG RTFHLTRTLT VKVVGSPKNA VPPVIHSPND   540
HVVYEKEPGE ELLIPCTVYF SFLMDSRNEV WWTIDGKKPD DITIDVTINE SISHSRTEDE   600
TRTQILSIKK VTSEDLKRSY VCHARSAKGE VAKAAKVKQK VPAPRYTVES GEPRGPTIKP   660
CPPCKCPAPN LLGGPSVFIF PPKIKDVLMI SLSPIVTCVV VDVSEDDPDV QISWFVNNVE   720
VHTAQTQTHR EDYNSTLRVV SALPIQHQDW MSGKEFKCKV NNKDLPAPIE RTISKPKGSV   780
RAPQVYVLPP PEEEMTKKQV TLTCMVTDFM PEDIYVEWTN NGKTELNYKN TEPVLDSDGS   840
YFMYSKLRVE KKNWVERNSY SCSVVHEGLH NHHTTKSFSR TPGK                    884

SEQ ID NO: 326          moltype = AA  length = 880
FEATURE                 Location/Qualifiers
REGION                  1..880
                        note = mST2-mIL1RAcP-mFc
source                  1..880
                        mol_type = protein
                        organism = synthetic construct
SEQUENCE: 326
SKSSWGLENE ALIVRCPQRG RSTYPVEWYY SDTNESIPTQ KRNRIFVSRD RLKFLPARVE    60
DSGIYACVIR SPNLNKTGYL NVTIHKKPPS CNIPDYLMYS TVRGSDKNFK ITCPTIDLYN   120
WTAPVQWFKN CKALQEPRFR AHRSYLFIDN VTHDDEGDYT CQFTHAENGT NYIVTATRSF   180
TVEEKGFSMF PVITNPPYNH TMEVEIGKPA SIACSACFGK GSHFLADVLW QINKTVVGNF   240
GEARIQEEEG RNESSSNDMD CLTSVLRITG VTEKDLSLEY DCLALNLHGM IRHTIRLRRK   300
QPIDHRSERC DDWGLDTMRQ IQVFEDEPAR IKCPLFEHPL KYNYSTAHSS GLTLIWYWTR   360
QDRDLEEPIN FRLPENRISK EKDVLWFRPT LLNDTGNYTC MLRNTTYCSK VAFPLEVVQK   420
DSCFNSAMRF PVHKMYIEHG IHKITCPNVD GYFPSSVKPS VTWYKGCTEI VDFHNVLPEG   480
MNLSFFIPLV SNNGNYTCVV TYPENGRLFH LTRTVTVKVV GSPKDALPPQ IYSPNDRVVY   540
EKEPGEELVI PCKVYFSFIM DSHNEVWWTI DGKKPDDVTV DITINESVSY SSTEDETRTQ   600
ILSIKKVTPE DLRRNYVCHA RNTKGEAEQA AKVKQKVIPP RYTVESGEPR GPTIKPCPPC   660
KCPAPNLLGG PSVFIFPPKI KDVLMISLSP IVTCVVVDVS EDDPDVQISW FVNNVEVHTA   720
QTQTHREDYN STLRVVSALP IQHQDWMSGK EFKCKVNNKD LPAPIERTIS KPKGSVRAPQ   780
VYVLPPPEEE MTKKQVTLTC MVTDFMPEDI YVEWTNNGKT ELNYKNTEPV LDSDGSYFMY   840
SKLRVEKKNW VERNSYSCSV VHEGLHNHHT TKSFSRTPGK                         880

SEQ ID NO: 327          moltype = AA  length = 876
FEATURE                 Location/Qualifiers
REGION                  1..876
                        note = hST2-hL1RAcP-hFc
source                  1..876
                        mol_type = protein
                        organism = synthetic construct
SEQUENCE: 327
KFSKQSWGLE NEALIVRCPR QGKPSYTVDW YYSQTNKSIP TQERNRVFAS GQLLKFLPAA    60
VADSGIYTCI VRSPTFNRTG YANVTIYKKQ SDCNVPDYLM YSTVSGSEKN SKIYCPTIDL   120
YNWTAPLEWF KNCQALQGSR YRAHKSFLVI DNVMTEDAGD YTCKFIHNEN GANYSVTATR   180
SFTVKDEQGF SLFPVIGAPA QNEIKEVEIG KNANLTCSAC FGKGTQFLAA VLWQLNGTKI   240
TDFGEPRIQQ EEGQNQSFSN GLACLDMVLR IADVKEEDLL LQYDCLALNL HGLRRHTVRL   300
SRKNPIDHHS SERCDDWGLD TMRQIQVFED EPARIKCPLF EHFLKFNYST AHSAGLTLIW   360
YWTRQDRDLE EPINFRLPEN RISKEKDVLW FRPTLLNDTG NYTCMLRNTT YCSKVAFPLE   420
VVQKDSCFNS PMKLPVHKLY IEYGIQRITC PNVDGYFPSS VKPTITWYMG CYKIQNFNNV   480
IPEGMNLSFL IALISNNGNY TCVVTYPENG RTFHLTRTLT VKVVGSPKNA VPPVIHSPND   540
HVVYEKEPGE ELLIPCTVYF SFLMDSRNEV WWTIDGKKPD DITIDVTINE SISHSRTEDE   600
TRTQILSIKK VTSEDLKRSY VCHARSAKGE VAKAAKVKQK VPAPRYTVED KTHTCPPCPA   660
PELLGGPSVF LFPPKPKDTL MISRTPEVTC VVVDVSHEDP EVKFNWYVDG VEVHNAKTKP   720
REEQYNSTYR VVSVLTVLHQ DWLNGKEYKC KVSNKALPAP IEKTISKAKG QPREPQVYTL   780
PPSRDELTKN QVSLTCLVKG FYPSDIAVEW ESNGQPENNY KTTPPVLDSD GSFFLYSKLT   840
VDKSRWQQGN VFSCSVMHEA LHNHYTQKSL SLSPGK                            876

SEQ ID NO: 328          moltype = AA  length = 310
FEATURE                 Location/Qualifiers
REGION                  1..310
                        note = human ST2 extracellular domain
source                  1..310
                        mol_type = protein
                        organism = synthetic construct
SEQUENCE: 328
KFSKQSWGLE NEALIVRCPR QGKPSYTVDW YYSQTNKSIP TQERNRVFAS GQLLKFLPAA    60
VADSGIYTCI VRSPTFNRTG YANVTIYKKQ SDCNVPDYLM YSTVSGSEKN SKIYCPTIDL   120
YNWTAPLEWF KNCQALQGSR YRAHKSFLVI DNVMTEDAGD YTCKFIHNEN GANYSVTATR   180
SFTVKDEQGF SLFPVIGAPA QNEIKEVEIG KNANLTCSAC FGKGTQFLAA VLWQLNGTKI   240
TDFGEPRIQQ EEGQNQSFSN GLACLDMVLR IADVKEEDLL LQYDCLALNL HGLRRHTVRL   300
SRKNPIDHHS                                                          310
```

-continued

```
SEQ ID NO: 329          moltype = AA   length = 306
FEATURE                 Location/Qualifiers
REGION                  1..306
                        note = mouse ST2 extracellular domain
source                  1..306
                        mol_type = protein
                        organism = synthetic construct
SEQUENCE: 329
SKSSWGLENE ALIVRCPQRG RSTYPVEWYY SDTNESIPTQ KRNRIFVSRD RLKFLPARVE  60
DSGIYACVIR SPNLNKTGYL NVTIHKKPPS CNIPDYLMYS TVRGSDKNFK ITCPTIDLYN  120
WTAPVQWFKN CKALQEPRFR AHRSYLFIDN VTHDDEGDYT CQFTHAENGT NYIVTATRSF  180
TVEEKGFSMF PVITNPPYNH TMEVEIGKPA SIACSACFGK GSHFLADVLW QINKTVVGNF  240
GEARIQEEEG RNESSSNDMD CLTSVLRITG VTEKDLSLEY DCLALNLHGM IRHTIRLRRK  300
QPIDHR                                                             306

SEQ ID NO: 330          moltype = AA   length = 339
FEATURE                 Location/Qualifiers
REGION                  1..339
                        note = human IL1RAcP extracellular domain
source                  1..339
                        mol_type = protein
                        organism = synthetic construct
SEQUENCE: 330
SERCDDWGLD TMRQIQVFED EPARIKCPLF EHFLKFNYST AHSAGLTLIW YWTRQDRDLE  60
EPINFRLPEN RISKEKDVLW FRPTLLNDTG NYTCMLRNTT YCSKVAFPLE VVQKDSCFNS  120
PMKLPVHKLY IEYGIQRITC PNVDGYFPSS VKPTITWYMG CYKIQNFNNV IPEGMNLSFL  180
IALISNNGNY TCVVTYPENG RTFHLTRTLT VKVVGSPKNA VPPVIHSPND HVVYEKEPGE  240
ELLIPCTVYF SFLMDSRNEV WWTIDGKKPD DITIDVTINE SISHSRTEDE TRTQILSIKK  300
VTSEDLKRSY VCHARSAKGE VAKAAKVKQK VPAPRYTVE                         339

SEQ ID NO: 331          moltype = AA   length = 339
FEATURE                 Location/Qualifiers
REGION                  1..339
                        note = mouse IL1RAcP extracellular domain
source                  1..339
                        mol_type = protein
                        organism = synthetic construct
SEQUENCE: 331
SERCDDWGLD TMRQIQVFED EPARIKCPLF EHFLKYNYST AHSSGLTLIW YWTRQDRDLE  60
EPINFRLPEN RISKEKDVLW FRPTLLNDTG NYTCMLRNTT YCSKVAFPLE VVQKDSCFNS  120
AMRFPVHKMY IEHGIHKITC PNVDGYFPSS VKPSVTWYKG CTEIVDFHNV LPEGMNLSFF  180
IPLVSNNGNY TCVVTYPENG RLFHLTRTVT VKVVGSPKDA LPPQIYSPND RVVYEKEPGE  240
ELVIPCKVYF SFIMDSHNEV WWTIDGKKPD DVTVDITINE SVSYSSTEDE TRTQILSIKK  300
VTPEDLRRNY VCHARNTKGE AEQAAKVKQK VIPPRYTVE                         339

SEQ ID NO: 332          moltype = AA   length = 227
FEATURE                 Location/Qualifiers
REGION                  1..227
                        note = human IgG1 Fc
source                  1..227
                        mol_type = protein
                        organism = synthetic construct
SEQUENCE: 332
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK              227

SEQ ID NO: 333          moltype = AA   length = 233
FEATURE                 Location/Qualifiers
REGION                  1..233
                        note = mouse IgG2a Fc
source                  1..233
                        mol_type = protein
                        organism = synthetic construct
SEQUENCE: 333
EPRGPTIKPC PPCKCPAPNL LGGPSVFIFP PKIKDVLMIS LSPIVTCVVV DVSEDDPDVQ  60
ISWFVNNVEV HTAQTQTHRE DYNSTLRVVS ALPIQHQDWM SGKEFKCKVN NKDLPAPIER  120
TISKPKGSVR APQVYVLPPP EEEMTKKQVT LTCMVTDFMP EDIYVEWTNN GKTELNYKNT  180
EPVLDSDGSY FMYSKLRVEK KNWVERNSYS CSVVHEGLHN HHTTKSFSRT PGK        233

SEQ ID NO: 334          moltype = AA   length = 167
FEATURE                 Location/Qualifiers
REGION                  1..167
                        note = M.fascicularis IL-33-6His
source                  1..167
                        mol_type = protein
                        organism = synthetic construct
SEQUENCE: 334
```

```
SITGISPITE SLASLSTYND QSITFALEDE SYEIYVEDLK KDKKKDKVLL SYYESQHPSS    60
ESGDGVDGKM LMVTLSPTKD FWLQANNKEH SVELHKCEKP LPDQAFFVLH NRSFNCVSFE   120
CKTDPGVFIG VKDNHLALIK VDYSENLGSE NILFKLSEIL EHHHHHH                 167

SEQ ID NO: 335              moltype = AA   length = 117
FEATURE                    Location/Qualifiers
REGION                     1..117
                           note = HCVR-mouse surrogate IL-4R Ab
source                     1..117
                           mol_type = protein
                           organism = synthetic construct
SEQUENCE: 335
EVQLQQSGPE LVKPGASVRM SCKASGYTFT DYNIHWVKQS HGKSLEWIGY IYPNNGDNGY    60
NQKFRGKATL TVDKSSSTAY MELRSLTSDD SAVYYCARGR LRYFDVWGTG TTVTVSS      117

SEQ ID NO: 336              moltype = AA   length = 111
FEATURE                    Location/Qualifiers
REGION                     1..111
                           note = LCVR-mouse surrogate IL-4R Ab
source                     1..111
                           mol_type = protein
                           organism = synthetic construct
SEQUENCE: 336
NIVLTQSPAS LAVSLGQRAT ISCRASESVD NYGHSFMHWY QQKPGQPPKL LIYLASNLES    60
GVPARFSGSG SRTDFTLTLD PVEADDAATY YCQQYNEDPP TFGSGTKLEI K            111

SEQ ID NO: 337              moltype = AA   length = 124
FEATURE                    Location/Qualifiers
REGION                     1..124
                           note = Dupilumab HCVR
source                     1..124
                           mol_type = protein
                           organism = synthetic construct
SEQUENCE: 337
EVQLVESGGG LEQPGGSLRL SCAGSGFTFR DYAMTWVRQA PGKGLEWVSS ISGSGGNTYY    60
ADSVKGRFTI SRDNSKNTLY LQMNSLRAED TAVYYCAKDR LSITIRPRYY GLDVWGQGTT   120
VTVS                                                               124

SEQ ID NO: 338              moltype = AA   length = 112
FEATURE                    Location/Qualifiers
REGION                     1..112
                           note = Dupilumab LCVR
source                     1..112
                           mol_type = protein
                           organism = synthetic construct
SEQUENCE: 338
DIVMTQSPLS LPVTPGEPAS ISCRSSQSLL YSIGYNYLDW YLQKSGQSPQ LLIYLGSNRA    60
SGVPDRFSGS GSGTDFTLKI SRVEAEDVGF YYCMQALQTP YTFGQGTKLE IK           112

SEQ ID NO: 339              moltype = AA   length = 8
FEATURE                    Location/Qualifiers
REGION                     1..8
                           note = Dupilumab HCDR1
source                     1..8
                           mol_type = protein
                           organism = synthetic construct
SEQUENCE: 339
GFTFRDYA                                                             8

SEQ ID NO: 340              moltype = AA   length = 8
FEATURE                    Location/Qualifiers
REGION                     1..8
                           note = Dupilumab HCDR2
source                     1..8
                           mol_type = protein
                           organism = synthetic construct
SEQUENCE: 340
ISGSGGNT                                                             8

SEQ ID NO: 341              moltype = AA   length = 18
FEATURE                    Location/Qualifiers
REGION                     1..18
                           note = Dupilumab HCDR3
source                     1..18
                           mol_type = protein
                           organism = synthetic construct
SEQUENCE: 341
AKDRLSITIR PRYYGLDV                                                 18
```

-continued

```
SEQ ID NO: 342          moltype = AA   length = 11
FEATURE                 Location/Qualifiers
REGION                  1..11
                        note = Dupilumab LCDR1
source                  1..11
                        mol_type = protein
                        organism = synthetic construct
SEQUENCE: 342
QSLLYSIGYN Y                                                   11

SEQ ID NO: 343          moltype =   length =
SEQUENCE: 343
000

SEQ ID NO: 344          moltype = AA   length = 9
FEATURE                 Location/Qualifiers
REGION                  1..9
                        note = Dupilumab LCDR3
source                  1..9
                        mol_type = protein
                        organism = synthetic construct
SEQUENCE: 344
MQALQTPYT                                                      9

SEQ ID NO: 345          moltype = AA   length = 451
FEATURE                 Location/Qualifiers
REGION                  1..451
                        note = Dupilumab heavy chain
source                  1..451
                        mol_type = protein
                        organism = synthetic construct
SEQUENCE: 345
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLMISR TPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL G                             451

SEQ ID NO: 346          moltype = AA   length = 219
FEATURE                 Location/Qualifiers
REGION                  1..219
                        note = Dupilumab light chain
source                  1..219
                        mol_type = protein
                        organism = synthetic construct
SEQUENCE: 346
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                     219

SEQ ID NO: 347          moltype = AA   length = 207
FEATURE                 Location/Qualifiers
REGION                  1..207
                        note = human IL-4Ralpha
source                  1..207
                        mol_type = protein
                        organism = synthetic construct
SEQUENCE: 347
MKVLQEPTCV SDYMSISTCE WKMNGPTNCS TELRLLYQLV FLLSEAHTCI PENNGGAGCV  60
CHLLMDDVVS ADNYTLDLWA GQQLLWKGSF KPSEHVKPRA PGNLTVHTNV SDTLLLTWSN  120
PYPPDNYLYN HLTYAVNIWS ENDPADFRIY NVTYLEPSLR IAASTLKSGI SYRARVRAWA  180
QCYNTTWSEW SPSTKWHNSY REPFEQH                                  207

SEQ ID NO: 348          moltype = AA   length = 270
FEATURE                 Location/Qualifiers
REGION                  1..270
                        note = hIL33_095760 (prior to proteolytic processing)
source                  1..270
                        mol_type = protein
                        organism = synthetic construct
SEQUENCE: 348
MKPKMKYSTN KISTAKWKNT ASKALCFKLG KSQQKAKEVC PMYFMKLRSG LMIKKEACYF  60
RRETTKRPSL KTGRKHKRHL VLAACQQQST VECFAFGISG VQKYTRALHD SSITGISPIT  120
EYLASLSTYN DQSITFALED ESYEIYVEDL KKDEKKDKVL LSYYESQHPS NESGDGVDGK  180
MLMVTLSPTK DFWLHANNKE HSVELHKCEK PLPDQAFFVL HNMHSNCVSF ECKTDPGVFI  240
```

-continued

```
GVKDNHLALI KVDSSENLCT ENILFKLSET                                        270

SEQ ID NO: 349          moltype = AA   length = 159
FEATURE                 Location/Qualifiers
REGION                  1..159
                        note = hIL33_mature_PEPTIDE (after proteolytic processing)
source                  1..159
                        mol_type = protein
                        organism = synthetic construct
SEQUENCE: 349
SITGISPITE YLASLSTYND QSITFALEDE SYEIYVEDLK KDEKKDKVLL SYYESQHPSN  60
ESGDGVDGKM LMVTLSPTKD FWLHANNKEH SVELHKCEKP LPDQAFFVLH NMHSNCVSFE  120
CKTDPGVFIG VKDNHLALIK VDSSENLCTE NILFKLSET                          159

SEQ ID NO: 350          moltype = AA   length = 12
FEATURE                 Location/Qualifiers
REGION                  1..12
                        note = Amino Acid residues 1-12 of SEQ ID NO: 349; also
                         corresponds to residues 112-123 of SEQ ID NO: 348 (Uniprot
                         O95760)
source                  1..12
                        mol_type = protein
                        organism = synthetic construct
SEQUENCE: 350
SITGISPITE YL                                                          12

SEQ ID NO: 351          moltype = AA   length = 87
FEATURE                 Location/Qualifiers
REGION                  1..87
                        note = Amino Acid residues 50-94 of SEQ ID NO: 349; also
                         corresponds to residues 161-205 of SEQ ID NO: 348 (Uniprot
                         O95760)
source                  1..87
                        mol_type = protein
                        organism = synthetic construct
SEQUENCE: 351
ITEYLASLST YNDQSITFAL EDESYEIYVE DLKKDEKKDK VLLSYYESQH PSNESGDGVD  60
GKMLMVTLSP TKDFWLHANN KEHSVEL                                       87

SEQ ID NO: 352          moltype = AA   length = 556
FEATURE                 Location/Qualifiers
REGION                  1..556
                        note = Human ST2 (See GenBank accession number NP_057316)
source                  1..556
                        mol_type = protein
                        organism = synthetic construct
SEQUENCE: 352
MGFWILAILT ILMYSTAAKF SKQSWGLENE ALIVRCPRQG KPSYTVDWYY SQTNKSIPTQ  60
ERNRVFASGQ LLKFLPAAVA DSGIYTCIVR SPTFNRTGYA NVTIYKKQSD CNVPDYLMYS  120
TVSGSEKNSK IYCPTIDLYN WTAPLEWFKN CQALQGSRYR AHKSFLVIDN VMTEDAGDYT  180
CKFIHNENGA NYSVTATRSF TVKDEQGFSL FPVIGAPAQN EIKEVEIGKN ANLTCSACFG  240
KGTQFLAAVL WQLNGTKITD FGEPRIQQEE GQNQSFSNGL ACLDMVLRIA DVKEEDLLLQ  300
YDCLALNLHG LRRHTVRLSR KNPIDHHSIY CIIAVCSVFL MLINVLVIIL KMFWIEATLL  360
WRDIAKPYKT RNDGKLYDAY VVYPRNYKSS TDGASRVEHF VHQILPDVLE NKCGYTLCIY  420
GRDMLPGEDV VTAVETNIRK SRRHIFILTP QITHNKEFAY EQEVALHCAL IQNDAKVILI  480
EMEALSELDM LQAEALQDSL QHLMKVQGTI KWREDHIANK RSLNSKFWKH VRYQMPVPSK  540
IPRKASSLTP LAAQKQ                                                   556

SEQ ID NO: 353          moltype = AA   length = 570
FEATURE                 Location/Qualifiers
REGION                  1..570
                        note = Human IL-1RAcP (See GenBank accession number Q9NPH3)
source                  1..570
                        mol_type = protein
                        organism = synthetic construct
SEQUENCE: 353
MTLLWCVVSL YFYGILQSDA SERCDDWGLD TMRQIQVFED EPARIKCPLF EHFLKFNYST  60
AHSAGLTLIW YWTRQDRDLE EPINFRLPEN RISKEKDVLW FRPTLLNDTG NYTCMLRNTT  120
YCSKVAFPLE VVQKDSCFNS PMKLPVHKLY IEYGIQRITC PNVDGYFPSS VKPTITWYMG  180
CYKIQNFNNV IPEGMNLSFL IALISNNGNY TCVVTYPENG RTFHLTRTLT VKVVGSPKNA  240
VPPVIHSPND HVVYEKEPGE ELLIPCTVYF SFLMDSRNEV WWTIDGKKPD DITIDVTINE  300
SISHSRTEDE TRTQILSIKK VTSEDLKRSY VCHARSAKGE VAKAAKVKQK VPAPRYTVEL  360
ACGFGATVLL VVILIVVYHV YWLEMVLFYR AHFGTDETIL DGKEYDIYVS YARNAEEEEF  420
VLLTLRGVLE NEFGYKLCIF DRDSLPGGIV TDETLSFIQK SRRLLVVLSP NYVLQGTQAL  480
LELKAGLENM ASRGNINVIL VQYKAVKETK VKELKRAKTV LTVIKWKGEK SKYPQGRFWK  540
QLQVAMPVKK SPRRSSSDEQ GLSYSSLKNV                                    570

SEQ ID NO: 354          moltype = AA   length = 449
FEATURE                 Location/Qualifiers
```

-continued

```
REGION                    1..449
                          note = HC OF H4H9675P
source                    1..449
                          mol_type = protein
                          organism = synthetic construct
SEQUENCE: 354
EVQLVESGGN LEQPGGSLRL SCTASGFTFS RSAMNWVRRA PGKGLEWVSG ISGSGGRTYY   60
ADSVKGRFTI SRDNSKNTLY LQMNSLSAED TAAYYCAKDS YTTSWYGGMD VWGHGTTVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                    449

SEQ ID NO: 355            moltype = AA  length = 214
FEATURE                   Location/Qualifiers
REGION                    1..214
                          note = LC OF H4H9675P
source                    1..214
                          mol_type = protein
                          organism = synthetic construct
SEQUENCE: 355
DIQMTQSPSS VSASVGDRVT ITCRASQGIF SWLAWYQQKP GKAPKLLIYA ASSLQSGVPS   60
RFSGSGSGTD FTLTISSLQP EDFAIYYCQQ ANSVPITFGQ GTRLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 356            moltype = AA  length = 166
FEATURE                   Location/Qualifiers
REGION                    1..166
                          note = HUMAN IL-33 WITH HEXA-HIS TAG (AMINO ACIDS 112-270
                           OF GENBANK ACCESSION NO. O95760)
source                    1..166
                          mol_type = protein
                          organism = synthetic construct
SEQUENCE: 356
MSITGISPIT EYLASLSTYN DQSITFALED ESYEIYVEDL KKDEKKDKVL LSYYESQHPS   60
NESGDGVDGK MLMVTLSPTK DFWLHANNKE HSVELHKCEK PLPDQAFFVL HNMHSNCVSF  120
ECKTDPGVFI GVKDNHLALI KVDSSENLCT ENILFKLSET HHHHHH                166
```

METHOD OF REDUCING SERUM AMYLOID A (SAA) PROTEIN LEVELS IN A PATIENT BY ADMINISTERING AN INTERLEUKIN-33 (IL-33) ANTIBODY

CROSS-REFERENCE TO RELATED APPLICATIONS

This application is a continuation of U.S. application Ser. No. 17/028,011, filed Sep. 22, 2020, now U.S. Pat. No. 11,866,503, which is a continuation of U.S. application Ser. No. 15/827,357, filed Nov. 30, 2017, now U.S. Pat. No. 10,815,305, which claims the benefit under 35 USC § 119 (e) of U.S. Provisional Application Nos. 62/428,634, filed Dec. 1, 2016, 62/473,738, filed Mar. 30, 2017, and 62/567, 318, filed Oct. 3, 2017, all of which are herein specifically incorporated by reference in their entireties.

REFERENCE TO A SEQUENCE LISTING

This application incorporates by reference the sequence listing submitted in computer readable form as XML file 10142US03_Sequence, created on Nov. 29, 2023 and containing 429,198 bytes.

FIELD OF THE INVENTION

The present invention relates to methods for treating an inflammatory condition comprising administering to a subject in need thereof a therapeutically effective amount of an interleukin-33 (IL-33) antagonist alone or in combination with an interleukin-4 (IL-4) antagonist. More specifically, the present invention relates to treating inflammatory or obstructive lung diseases or disorders by administering a therapeutically effective amount of an interleukin-33 (IL-33) antibody alone or in combination with an interleukin-4R (IL-4R) antibody.

BACKGROUND

Inflammation is initiated as a protective response by the host, but it can often result in systemic pathologies. Inflammatory lung diseases such as asthma, allergy and chronic obstructive pulmonary disease (COPD) are increasing in developed countries, resulting in great consequences to healthcare costs. Several inflammatory cells and their mediators participate in the development and progression of these diseases. In certain cases, these diseases reflect the outcome of type 2 immunity, which is characterized by the infiltration of tissues with eosinophils, basophils, mast cells, CD4+ T helper 2 (Th2) cells, group 2 innate lymphoid cells (ILC2s), interleukin-4 (IL-4) and/or IL-13 induced macrophages, as well as by an elevation in serum IgE and by an increase in the cytokines IL-4, IL-5, IL-9 and IL-13.

One cytokine believed to play a role in inflammatory lung diseases is interleukin-33 (IL-33), a proinflammatory cytokine released by damaged epithelial tissue in response to insults such as allergens, viruses, or smoke. IL-33 is a member of the interleukin-1 (IL-1) family that potently drives production of T helper-2 (Th2)-associated cytokines (e.g., IL-4). IL-33 is expressed by a wide variety of cell types, including fibroblasts, mast cells, dendritic cells, macrophages, osteoblasts, endothelial cells, and epithelial cells. Interleukin-33 (IL-33) is a ligand for ST2 (sometimes referred to as "suppression of tumorigenicity 2"), a toll-like/ interleukin-1 receptor super-family member, which associates with an accessory protein, IL-1RAcP ("Interleukin-1 receptor accessory protein", for reviews, see, e.g., Kakkar and Lee, Nature Reviews—Drug Discovery 7(10):827-840 (2008), Schmitz et al., Immunity 23:479-490 (2005); Liew et al., Nature Reviews—Immunology 10:103-110 (2010); US 2010/0260770; US 2009/0041718). Upon activation of ST2/ IL-1RAcP by IL-33, a signaling cascade is triggered through downstream molecules such as MyD88 (myeloid differentiation factor 88) and TRAF6 (TNF receptor associated factor 6), leading to activation of NFκB (nuclear factor-κB), among others. IL-33 signaling has been implicated as a factor in a variety of diseases and disorders, including the inflammatory lung diseases disclosed herein. (Liew et al., Nature Reviews—Immunology 10:103-110 (2010)). Inhibitors of IL-33 signaling have been described in, for example, U.S. Pat. Nos. 9,453,072; 8,187,596; US2013/17373761; US2014/0212412; US2014/0271658; US2014/0271642; US2014/0004107; WO2015/099175; WO2015/106080; WO2011/031600; WO2014/164959; WO2014/152195; WO2013/165894; WO2013/173761; EP1725261; EP10815921A1; and EP2850103A2.

Interleukin-4 (IL-4, also known as B cell stimulating factor or BSF-1) has also been implicated as a key cytokine that drives allergic and T helper cell type 2 (Th2) polarized inflammatory processes. IL-4 has been shown to possess a broad spectrum of biological activities, including growth stimulation of T cells, mast cells, granulocytes, megakaryocytes and erythrocytes. IL-4 induces the expression of class II major histocompatibility complex molecules in resting B cells, and enhances the secretion of IgE and IgG1 isotypes by stimulated B cells. The biological activities of IL-4 are mediated by specific cell surface receptors for IL-4. Human IL-4 receptor alpha (hIL-4R) (SEQ ID NO: 347) is described in, for example, U.S. Pat. Nos. 5,599,905, 5,767,065, and 5,840,869. Antibodies to hIL-4R are described in U.S. Pat. Nos. 5,717,072, 7,186,809 and 7,605,237. Methods for using antibodies to hIL-4R are described in U.S. Pat. Nos. 5,714,146; 5,985,280; 6,716,587 and 9,290,574.

Current therapies for treating inflammatory diseases of the lung leave significant room for improvement of safety and efficacy in patients suffering from, for example, asthma and chronic obstructive pulmonary disease (COPD), particularly in reducing exacerbations. Despite the availability of numerous inhaled combinations of anti-inflammatory and bronchodilator drugs, many patients continue to experience exacerbations. Exacerbations may require the use of systemic corticosteroids, which are efficacious due to their broad immune neutralizing capacity, but laden with undesirable side effects, including bone loss and infection. Several biologic therapies, most of which target single immune mediators, are in late stage development for asthma and COPD. However, due to the complexity of the inflammatory milieu, these agents will likely be limited in their use.

Accordingly, an unmet need exists in the art for novel combinations of therapies for the treatment and/or prevention of inflammatory lung diseases, such as those described herein.

BRIEF SUMMARY OF THE INVENTION

According to certain aspects of the present invention, methods are provided for treating an inflammatory disease or disorder, or at least one symptom associated with the inflammatory disease or disorder, the method comprising administering to a subject in need thereof one or more doses of a therapeutically effective amount of an interleukin-33 (IL-33) antagonist alone, or in combination with one or more doses of a therapeutically effective amount of an interleukin-4 (IL-4) antagonist, or a pharmaceutical composition comprising an IL-33 antagonist and an IL-4α antagonist, to a patient in need thereof. In one embodiment, the administration of the IL-33 antagonist in combination with the IL-4 antagonist results in enhanced therapeutic efficacy as compared to that observed with administration of the IL-33 antagonist alone or the IL-4 antagonist alone.

In certain embodiments, the IL-33 antagonist is any agent that is capable of blocking, attenuating, or otherwise interfering with IL-33 signaling and/or the interaction between IL-33 and a cell receptor (e.g. ST2) or a co-receptor (e.g. IL-1RAcP) or a complex thereof. Any of the above may block or inhibit at least one biological activity of IL-33.

In certain embodiments, the IL-33 antagonist is an antibody that binds to or interacts with IL-33 and blocks the interaction of IL-33 with its receptor, ST2 and prevents or inhibits the interaction of ST2 with the co-receptor, IL1-RAcP, or prevents the formation of the signaling complex. In one embodiment, the IL-33 antagonist is a monoclonal antibody that binds to, or interacts specifically with human IL-33. In one embodiment, the IL-33 antagonist is a receptor-based trap that binds to, or interacts specifically with human IL-33.

In one embodiment, the IL-4 antagonist is an interleukin-4 receptor (IL-4R) antagonist.

In one embodiment, the IL-4R antagonist is any agent, which binds to or interacts with IL-4Rα or an IL-4R ligand, and inhibits or attenuates the normal biological signaling function of a type 1 and/or a type 2 IL-4 receptor. In one embodiment, the IL-4R antagonist is a monoclonal antibody that binds specifically to human IL-4Rα. In one embodiment, the IL-4R antagonist is a monoclonal antibody that binds IL-4Rα and blocks both IL-4 and IL-13 mediated signaling through either the type I or type II receptor. In one embodiment, the monoclonal antibody that binds specifically to human IL-4Rα and blocks both IL-4 and IL-13 mediated signaling is dupilumab, or a bioequivalent thereof. In one embodiment, the method of treating an inflammatory disorder or condition is accomplished through use of a combination of REGN3500 having a heavy chain variable region/light chain variable region (HCVR/LCVR) amino acid sequence pair of SEQ ID NOs: 274/282 and dupilumab having an HCVR/LCVR amino acid sequence pair of SEQ ID NOs: 337/338.

In one embodiment, the inflammatory disease or disorder treatable by the methods of the invention is selected from the group consisting of asthma, chronic obstructive pulmonary disease (COPD), asthma and COPD overlap syndrome (ACOS), atopic dermatitis, nasal polyps, an allergic response, chronic bronchitis, emphysema, chronic rhinosinusitis with or without nasal polyps, inflammatory bowel disease, Crohn's disease, ulcerative colitis, hypersensitivity pneumonitis, multiple sclerosis, arthritis (including osteoarthritis, rheumatoid arthritis, or psoriatic arthritis), allergic rhinitis, fibrosis, eosinophilic esophagitis, vasculitis, urticaria, Churg Strauss syndrome, inflammatory pain and psoriasis.

In one embodiment, the asthma is eosinophilic asthma.

In one embodiment, the asthma is non-eosinophilic asthma.

In one embodiment, the asthma is allergic asthma.

In one embodiment, the asthma is non-allergic asthma.

In one embodiment, the asthma is severe refractory asthma.

In one embodiment, the asthma is steroid resistant asthma.

In one embodiment, the asthma is steroid sensitive asthma.

In one embodiment, the asthma is steroid refractory asthma.

In one embodiment, the asthma is an asthma exacerbation.

In one embodiment, the inflammatory disease or disorder is alleviated, or reduced in severity, duration or frequency of occurrence, or at least one symptom associated with the inflammatory disease or disorder is alleviated, or reduced in severity, duration, or frequency of occurrence.

In one embodiment, the administering of a therapeutically effective amount of one or more doses of an IL-33 antagonist to a subject in need thereof alone, or in combination with one or more doses of a therapeutically effective amount of an IL-4R antagonist results in enhanced therapeutic efficacy as measured by any one or more of the following parameters:

a) a reduction in the frequency of one or more of the following: eosinophils, activated B cells, activated CD8 T cells, or CD4/CD8 T cell ratio in a tissue sample;

b) a reduction in one or more of the following: interleukin-1 beta (IL-1β), interleukin-4 (IL-4), interleukin-5 (IL-5), interleukin-6 (IL-6), interleukin-13 (IL-13), monocyte chemoattractant protein-1 (MCP-1), or tumor necrosis factor alpha (TNFα) levels in a tissue sample; or c) a reduction in the gene expression level of one or more of the following: Il4, Il5, Il6, Il9, Il13, Il1rl1, Il13ra2, tnf, Tgfb1, Ccl2, Ccl11, Ccl24, Col15a1 or Col24a1 in a tissue sample.

In one embodiment, the administering of a therapeutically effective amount of one or more doses of an IL-33 antagonist to a subject in need thereof alone, or in combination with one or more doses of a therapeutically effective amount of an IL-4R antagonist results in enhanced therapeutic efficacy as further measured by one or more of the following:

d) a reduction in serum IgE levels e) a reduction in goblet cell metaplasia in the lung;

f) an improvement in lung consolidation; or g) a decrease in sub-epithelial fibrosis in the lung.

In one embodiment, the tissue sample is obtained from the lung.

In one embodiment, the tissue sample is selected from the group consisting of liver, kidney, heart or whole blood. In certain embodiments, blood cells, serum or plasma may be used for measuring one or more of the parameters described above.

In one embodiment, the chronic obstructive pulmonary disease that is treatable by the methods of the invention is exacerbated by one or more of the following: asthma, a viral disease, a bacterial infection, an exposure to an allergen, an exposure to a chemical or chemical fumes, or an exposure to an environmental irritant or air pollution.

In a related embodiment, the asthma that is treatable by the methods of the invention is exacerbated by one or more of the following: a viral disease, a bacterial infection, an exposure to an allergen, an exposure to a chemical or chemical fumes, or an exposure to an environmental irritant or air pollution.

In a certain embodiment, the asthma that is treatable by the methods of the invention is selected from the group consisting of eosinophilic asthma, non-eosinophilic asthma, steroid resistant asthma and steroid sensitive asthma.

In one embodiment, the chronic obstructive pulmonary disease that is treatable by the methods of the invention results from, or is exacerbated in part by cigarette smoke.

In one embodiment, the patients suffering from chronic obstructive pulmonary disease that is treatable by the methods of the invention may or may not exhibit an increase in the number of eosinophils.

In one embodiment, the patients suffering from asthma and COPD overlap syndrome (ACOS) that is treatable by the methods of the invention may or may not exhibit an increase in the number of eosinophils.

A second aspect of the invention provides for treating an inflammatory disease or disorder, or at least one symptom associated with the inflammatory disease or disorder, by administering an effective amount of one or more additional therapeutic agents useful for alleviating the inflammatory disease or disorder, or at least one symptom of the inflammatory disease or disorder in combination with a therapeutically effective amount of an interleukin-33 (IL-33) antagonist, e.g. an IL-33 antibody or an IL-33 trap, and a therapeutically effective amount of an interleukin-4 (IL-4) antagonist, e.g. an IL-4R antibody such as dupilumab, or a therapeutic equivalent thereof.

In one embodiment, the one or more additional therapeutic agents are selected from the group consisting of a non-steroidal anti-inflammatory (NSAID), a corticosteroid (e.g. an inhaled corticosteroid or ICS), a long acting β2 adrenergic agonist (LABA), a long acting muscarinic antagonist (LAMA), a bronchial dilator, an antihistamine, epinephrine, a decongestant, a thymic stromal lymphopoietin (TSLP) antagonist, an IL-1 antagonist, an IL-8 antagonist, an IL-13 antagonist, a different IL-4 antagonist, an IL-4/IL-13 dual antagonist, an IL-33/IL-13 dual antagonist, an IL-5 antagonist, an IL-6 antagonist, an IL-12/23 antagonist, an IL-22 antagonist, an IL-25 antagonist, an IL-17 antagonist, an IL-31 antagonist, a TNF inhibitor, an IgE inhibitor, a leukotriene inhibitor, an oral PDE4 inhibitor, a methylxanthine, nedocromil sodium, cromolyn sodium, a long-acting beta 2 agonist and another IL-33 antagonist (e.g. a different antibody to IL-33, a different IL-33 receptor based trap, an ST2 antagonist, including an antibody to ST2, or a soluble ST2 receptor, or an antagonist to another IL-33 receptor other than ST2, or an IL-1RAcP antagonist, including an antibody to IL-1RAcP, or an antibody that interacts with an IL-33/ST2 complex).

In some embodiments, the present invention provides methods for treating moderate-to-severe chronic obstructive pulmonary disease (COPD) comprising concomitant administration of an IL-4R antagonist (e.g. dupilumab) and an IL-33 antagonist (e.g. REGN3500), in addition to background therapy, including for example, an inhaled corticosteroid (ICS) and/or a long acting β2 adrenergic agonist (LABA) and/or a long acting muscarinic antagonist (LAMA).

In certain embodiments, the present invention provides methods for reducing the incidence of "loss of asthma control" (LOAC) events comprising treating patients suffering from asthma with an IL-4R antagonist (e.g. dupilumab) in combination with an IL-33 antagonist (e.g. REGN3500). In certain embodiments, the combined use of an IL-4R antagonist in combination with an IL-33 antagonist provides a more effective outcome than administration with either the IL-4R antagonist alone or the IL-33 antagonist alone.

In a related embodiment, the administration of the IL-33 antagonist in combination with the IL-4R antagonist results in an increase in a type 1 immune response, and/or a reduction in a type 2 immune response elicited by the disease, or by the causative agent of the disease or allergy.

A third aspect of the invention provides a method for treating a fibrotic disease or disorder, or at least one symptom associated with the fibrotic disease or disorder, the method comprising administering a combination of an IL-33 antagonist (an IL-33 antibody or IL-33 trap) that binds specifically to IL-33, and an antibody that binds specifically to IL-4Rα or an antigen-binding fragment thereof, or a pharmaceutical composition comprising an IL-33 antagonist and an IL-4α antagonist, to a patient in need thereof, wherein the fibrotic disease or disorder is alleviated, or reduced in severity, or duration, or at least one symptom associated with the fibrotic disease or disorder is alleviated, or reduced in severity, duration, or frequency of occurrence. In one embodiment, treatment of the fibrotic disease with an IL-33 antagonist in combination with an IL-4R antagonist may result in restoring the fibrotic tissue to its normal state.

In one embodiment, the fibrotic diseases or disorders that are treatable by administering the anti-IL-33 and IL-4R antagonists of the invention, such as the IL-33 antibodies or IL-33 traps in combination with the IL-4Rα antibodies described herein, include pulmonary fibrosis (e.g., idiopathic pulmonary fibrosis, bleomycin-induced pulmonary fibrosis, asbestos-induced pulmonary fibrosis, and bronchiolitis obliterans syndrome), chronic asthma, fibrosis associated with acute lung injury and acute respiratory distress (e.g., bacterial pneumonia induced fibrosis, trauma induced fibrosis, viral pneumonia induced fibrosis, ventilator induced fibrosis, non-pulmonary sepsis induced fibrosis and aspiration induced fibrosis), silicosis, radiation-induced fibrosis, chronic obstructive pulmonary disease (COPD, which may or may not be related to, caused in part by, or resulting from, exposure to first or second hand cigarette smoke), scleroderma, ocular fibrosis, skin fibrosis (e.g., scleroderma), hepatic fibrosis (e.g., cirrhosis, alcohol-induced liver fibrosis, non-alcoholic steatohepatitis (NASH), biliary duct injury, primary biliary cirrhosis, infection- or viral-induced liver fibrosis, autoimmune hepatitis, kidney (renal) fibrosis, cardiac fibrosis, atherosclerosis, stent restenosis, and myelofibrosis.

A fourth aspect of the invention provides a method for preventing or reducing the severity of an allergic response, the method comprising administering one or more doses of a therapeutically effective amount of an IL-33 antagonist in combination with one or more doses of a therapeutically effective amount of an IL-4R antagonist to a subject in need thereof, wherein the administration of the combination results in enhanced therapeutic efficacy for preventing or reducing the severity of an allergic response as compared to that observed with administration of the IL-33 antagonist alone or the IL-4R antagonist alone. The subject treated with the IL-33 antagonist in combination with the IL-4R antagonist may demonstrate a reduced sensitivity to, or a diminished allergic reaction against the allergen, or may not experience any sensitivity or allergic reaction to, or anaphylactic response to the allergen following administration of the combination of the IL-33 antagonist and the IL-4R antagonist or a composition comprising the antagonists.

In one embodiment, the IL-33 antagonist for use in the methods of the invention is a monoclonal antibody, or an antigen-binding fragment thereof that binds to, or interacts specifically with, human IL-33. The IL-33 antibody or antigen-binding fragment thereof may block the interaction of IL-33 and ST2, or it may allow for low affinity binding of IL-33 to the ST2 receptor. In so doing, ST2 may be prohibited from interacting with IL-1RAcP. As such, the IL-33 antibodies of the invention are useful, inter alia, for inhibiting IL-33-mediated signaling and for treating diseases and disorders caused by or related to IL-33 activity and/or signaling.

In one embodiment, the IL-33 antibody or antigen-binding fragment thereof reduces the frequency of one or more of the following: eosinophils, CD4+ T cells, B cells, ST2+/CD4+ cells in the T cell population or reduces the CD4/CD8 T cell ratio in the lungs when administered to a mammal having allergen-induced lung inflammation.

In one embodiment, the IL-33 antibody or antigen-binding fragment thereof reduces the expression level of one or more of the following: IL-4, IL-5, IL-6, IL-9, IL-13, Ccl2, Ccl11, Ccl24 or MCP-1 in the lungs when administered to a mammal having allergen-induced lung inflammation.

In one embodiment, the IL-33 antibody or antigen-binding fragment thereof reduces serum IgE levels, goblet cell metaplasia, or epithelial collagen thickness in the lungs when administered to a mammal having allergen-induced lung inflammation.

In certain embodiments, the IL-33 antibodies that bind specifically to human IL-33, or antigen-binding fragments thereof that may be used in the methods of the invention comprise three heavy chain CDRs (HCDR1, HCDR2 and HCDR3) contained within a heavy chain variable region (HCVR) amino acid sequence selected from the group consisting of SEQ ID NO: 2, 18, 34, 50, 66, 82, 98, 114, 130, 146, 162, 178, 194, 210, 226, 242, 258, 274, 290, and 308; and comprises three light chain CDRs (LCDR1, LCDR2 and LCDR3) contained within a light chain variable region (LCVR) amino acid sequence selected from the group consisting of SEQ ID NOs: 10, 26, 42, 58, 74, 90, 106, 122, 138, 154, 170, 186, 202, 218, 234, 250, 266, 282, 298, and 316.

In certain embodiments, the IL-33 antibodies that bind specifically to human IL-33, or antigen-binding fragments thereof that may be used in the methods of the invention comprise a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274, 290, and 308, or a substantially similar sequence thereof having at least 90%, at least 95%, at least 98% or at least 99% sequence identity.

According to certain embodiments, the anti-IL-33 antibodies, or antigen-binding fragments thereof for use in the methods of the invention comprise a light chain variable region (LCVR) having an amino acid sequence selected from the group consisting of SEQ ID NO: 10, 26, 42, 58, 74, 90, 106, 122, 138, 154, 170, 186, 202, 218, 234, 250, 266, 282, 298, and 316, or a substantially similar sequence thereof having at least 90%, at least 95%, at least 98% or at least 99% sequence identity.

According to certain embodiments, the anti-IL-33 antibodies, or antigen-binding fragments thereof for use in the methods of the invention comprise a HCVR and LCVR (HCVR/LCVR) sequence pair selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, and 308/316.

According to certain embodiments, the anti-IL-33 antibodies, or antigen-binding fragments thereof for use in the methods of the invention comprise a heavy chain CDR3 (HCDR3) domain having an amino acid sequence selected from the group consisting of SEQ ID NO: 8, 24, 40, 56, 72, 88, 104, 120, 136, 152, 168, 184, 200, 216, 232, 248, 264, 280, 296, and 314, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 16, 32, 48, 64, 80, 96, 112, 128, 144, 160, 176, 192, 208, 224, 240, 256, 272, 288, 304, and 322, or a substantially similar sequence thereof having at least 90%, at least 95%, at least 98% or at least 99% sequence identity.

According to certain embodiments, the anti-IL-33 antibodies, or antigen-binding fragments thereof for use in the methods of the invention comprise a HCDR3/LCDR3 amino acid sequence pair selected from the group consisting of SEQ ID NO: 8/16, 24/32, 40/48, 56/64, 72/80, 88/96, 104/112, 120/128, 136/144, 152/160, 168/176, 184/192, 200/208, 216/224, 232/240, 248/256, 264/272, 280/288, 296/304 and 314/322.

According to certain embodiments, the anti-IL-33 antibodies, or antigen-binding fragments thereof for use in the methods of the invention further comprise a heavy chain CDR1 (HCDR1) domain having an amino acid sequence selected from the group consisting of SEQ ID NO: 4, 20, 36, 52, 68, 84, 100, 116, 132, 148, 164, 180, 196, 212, 228, 244, 260, 276, 292, and 310, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54, 70, 86, 102, 118, 134, 150, 166, 182, 198, 214, 230, 246, 262, 278, 294, and 312, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60, 76, 92, 108, 124, 140, 156, 172, 188, 204, 220, 236, 252, 268, 284, 300, and 318, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62, 78, 94, 110, 126, 142, 158, 174, 190, 206, 222, 238, 254, 270, 286, 302, and 320, or a substantially similar sequence thereof having at least 90%, at least 95%, at least 98% or at least 99% sequence identity.

Certain non-limiting, exemplary anti-IL-33 antibodies and antigen-binding fragments that may be used in the methods of the invention comprise HCDR1-HCDR2-HCDR3-LCDR1-LCDR2-LCDR3 domains, respectively, having the amino acid sequences selected from the group consisting of: SEQ ID NOs: 4-6-8-12-14-16 (e.g. H1M9559N); 20-22-24-28-30-32 (e.g. H1M9566N); 36-38-40-44-46-48 (e.g. H1M9568N); 52-54-56-60-62-64 (e.g. H4H9629P); 68-70-72-76-78-80 (e.g. H4H9633P); 84-86-88-92-94-96 (e.g. H4H9640P); 100-102-104-108-110-112 (e.g. H4H9659P); 116-118-120-124-126-128 (e.g. H4H9660P); 132-134-136-140-142-144 (e.g. H4H9662P); 148-150-152-156-158-160 (e.g., H4H9663P); 164-166-168-172-174-176 (e.g. H4H9664P); 180-182-184-188-190-192 (e.g., H4H9665P); 196-198-200-204-206-208 (e.g. H4H9666P); 212-214-216-220-222-224 (e.g. H4H9667P); 228-230-232-236-238-240 (e.g. H4H9670P); 244-246-248-252-254-256 (e.g. H4H9671P); 260-262-264-268-270-272 (e.g. H4H9672P); 276-278-280-284-286-288 (e.g. H4H9675P); 292-294-296-300-302-304 (e.g. H4H9676P); and 310-312-314-318-320-322 (H1M9565N).

According to certain embodiments, the anti-IL-33 antibodies, or antigen-binding fragments thereof for use in the methods of the invention, e.g. for treating inflammatory conditions, comprise the heavy and light chain CDR domains contained within heavy and light chain variable region (HCVR/LCVR) sequences selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, and 308/316. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., Proc. Natl. Acad. Sci. USA 86:9268-9272 (1989). Public databases are also available for identifying CDR sequences within an antibody.

In one embodiment, the IL-33 antibody or antigen-binding fragment for use in the methods of the invention comprises the heavy and light chain CDRs of a HCVR/LCVR amino acid sequence pair of SEQ ID NOs: 274/282.

In a related embodiment, the IL-33 antibody or antigen-binding fragment for use in the methods of the invention comprises HCDR1-HCDR2-HCDR3-LCDR1-LCDR2-LCDR3 domains, respectively, of SEQ ID NOs: 276-278-280-284-286-288.

In one embodiment, the antibody that specifically binds human interleukin-33 (IL-33), or an antigen-binding fragment for use in the methods of the invention comprises: (a) a heavy chain variable region (HCVR) having the amino acid sequence of SEQ ID NO: 274; and (b) a light chain variable region (LCVR) having the amino acid sequence of SEQ ID NO:282.

In one embodiment, the IL-33 antibody or antigen-binding fragment for use in the methods of the invention comprises the HCVR/LCVR amino acid sequence pair of: SEQ ID NOs: 274/282.

In one embodiment, the IL-33 antibody or antigen-binding fragment thereof for use in the methods of the invention interacts with an amino acid sequence ranging from about position 1 to about position 12 of SEQ ID NO: 349, and/or with an amino acid sequence ranging from about position 50 to about position 94 of SEQ ID NO: 349 as determined by hydrogen/deuterium exchange.

In one embodiment, the IL-33 antibody or antigen-binding fragment thereof for use in the methods of the invention interacts with an amino acid sequence ranging from about position 112 to about position 123 of SEQ ID NO: 348, and/or with an amino acid sequence ranging from about position 161 to about position 205 of SEQ ID NO: 348 as determined by hydrogen/deuterium exchange.

In one embodiment, the IL-33 antibody or antigen-binding fragment thereof for use in the methods of the invention interacts with either the amino acid sequence of SEQ ID NO: 350, or with the amino acid sequence of SEQ ID NO: 351, or interacts with both SEQ ID NOs: 350 and 351 as determined by hydrogen/deuterium exchange.

In one embodiment, the IL-33 antibody or antigen-binding fragment thereof for use in the methods of the invention competes for binding to IL-33 with a reference antibody comprising the HCVR/LCVR amino acid sequence pair of SEQ ID NOs: 274/282.

In one embodiment, the IL-33 antibody or antigen-binding fragment thereof for use in the methods of the invention binds to the same epitope on IL-33 as a reference antibody comprising the HCVR/LCVR amino acid sequence pair of SEQ ID NOs: 274/282.

In a fifth aspect, the invention provides nucleic acid molecules encoding the anti-IL-33 antibodies or antigen-binding fragments thereof to be used in the methods of the invention. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides methods of using an antibody or fragment thereof that binds specifically to human IL-33 comprising a HCVR encoded by a nucleic acid sequence selected from the group consisting of SEQ ID NO: 1, 17, 33, 49, 65, 81, 97, 113, 129, 145, 161, 177, 193, 209, 225, 241, 257, 273, 289, and 307, or a substantially identical sequence having at least 90%, at least 95%, at least 98%, or at least 99% homology thereof.

The present invention also provides methods of using an antibody or fragment thereof that binds specifically to human IL-33 comprising a LCVR encoded by a nucleic acid sequence selected from the group consisting of SEQ ID NO: 9, 25, 41, 57, 73, 89, 105, 121, 137, 153, 169, 185, 201, 217, 233, 249, 265, 281, 297, and 315, or a substantially identical sequence having at least 90%, at least 95%, at least 98%, or at least 99% homology thereof.

The present invention also provides methods for using an antibody or antigen-binding fragment of an antibody that binds specifically to human IL-33 comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, 279, 295, and 313, or a substantially identical sequence having at least 90%, at least 95%, at least 98%, or at least 99% homology thereof; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, 287, 303, and 321, or a substantially identical sequence having at least 90%, at least 95%, at least 98%, or at least 99% homology thereof.

The present invention also provides methods of using an antibody or fragment thereof that binds specifically to human IL-33, which further comprises a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, 275, 291, and 309, or a substantially identical sequence having at least 90%, at least 95%, at least 98%, or at least 99% homology thereof; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, 277, 293, and 311, or a substantially identical sequence having at least 90%, at least 95%, at least 98%, or at least 99% homology thereof; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, 283, 299, and 317, or a substantially identical sequence having at least 90%, at least 95%, at least 98%, or at least 99% homology thereof; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, 285, 301, and 319, or a substantially identical sequence having at least 90%, at least 95%, at least 98%, or at least 99% homology thereof.

According to certain embodiments, the methods of the invention provide for use of an antibody or fragment thereof that binds specifically to human IL-33, which comprises the heavy and light chain CDR sequences encoded by the nucleic acid sequences of SEQ ID NOs: 1 and 9 (e.g. H1M9559N), 17 and 25 (e.g. H1M9566N), 33 and 41 (e.g. H1M9568N), 49 and 57 (e.g. H4H9629P), 65 and 73 (e.g. H4H9633P), 81 and 89 (e.g. H4H9640P), 97 and 105 (e.g. H4H9659P), 113 and 121 (e.g. H4H9660P), 129 and 137 (e.g. H4H9662P), 145 and 153 (e.g. H4H9663P), 161 and 169 (e.g. H4H9664P), 177 and 185 (e.g. H4H9665P), 193 and 201 (e.g. H4H9666P), 209 and 217 (e.g. H4H9667P), 225 and 233 (e.g. H4H9670P), 241 and 249 (e.g. H4H9671P), 257 and 265 (e.g. H4H9672P), 273 and 281 (e.g. H4H9675P), 289 and 297 (e.g. H4H9676P), or 307 and 315 (H1M9565N).

In one embodiment, the IL-33 antagonist for use in the methods of the invention is an IL-33 receptor based trap, such as those described herein (See FIG. 1).

In one embodiment, the IL-33 receptor based trap comprises a first IL-33 binding domain (D1) attached to a multimerizing domain (M), wherein D1 comprises an IL-33-binding portion of an ST2 protein.

In one embodiment, the IL-33 trap for use in the methods of the invention further comprises a second IL-33 binding domain (D2) attached to D1 and/or M, wherein D2 comprises an extracellular portion of an IL-1RAcP protein. In one embodiment, D1 is attached to the N-terminus of M. In one embodiment, D1 is attached to the C-terminus of M. In one embodiment, D2 is attached to the N-terminus of M. In one embodiment, D2 is attached to the C-terminus of M. In one embodiment, D1 is attached to the N-terminus of D2, and wherein D2 is attached to the N-terminus of M.

In one embodiment, D1 comprises the amino acid sequence of SEQ ID NO: 328 or 329, or an amino acid sequence having at least 90% identity thereto. In one embodiment, D2 comprises the amino acid sequence of SEQ ID NO: 330 or 331, or an amino acid sequence having at least 90% identity thereto.

In one embodiment, the IL-33 antagonist for use in the methods of the invention comprises a first IL-33 binding domain (D1) attached to a first multimerizing domain (M1), and a second IL-33 binding domain (D2) attached to a second multimerizing domain (M2), wherein the D1 and/or D2 domains comprise an IL-33-binding portion of a receptor selected from the group consisting of ST2 and IL-1RAcP.

In one embodiment, the IL-33 antagonist for use in the methods of the invention comprises a third IL-33 binding domain (D3) that is attached to either D1 or M1, and wherein D3 comprises an IL-33-binding portion of a receptor selected from the group consisting of ST2 and IL-1RAcP.

In one embodiment, the IL-33 antagonist for use in the methods of the invention comprises a fourth IL-33 binding domain (D4) that is attached to either D2 or M2, and wherein D4 comprises an IL-33-binding portion of a receptor selected from the group consisting of ST2 and IL-1RAcP.

In one embodiment, D1 is attached to the N-terminus of M1, and D2 is attached to the N-terminus of M2.

In one embodiment, D3 is attached to the N-terminus of D1.

In one embodiment, D3 is attached to the C-terminus of M1.

In one embodiment, D4 is attached to the N-terminus of D2.

In one embodiment, D4 is attached to the C-terminus of M2.

In one embodiment, D3 is attached to the N-terminus of D1, and D1 is attached to the N-terminus of M1; and wherein D4 is attached to the N-terminus of D2, and D2 is attached to the N-terminus of M2.

In one embodiment, D3 is identical or substantially identical to D4 and wherein D1 is identical or substantially identical to D2.

In one embodiment, D3 and D4 each comprise an IL-33-binding portion of an ST2 protein; and wherein D1 and D2 each comprise an extracellular portion of an IL-1RAcP protein.

In one embodiment, the IL-33 trap for use in the methods of the invention comprises an amino acid sequence selected from the group consisting of SEQ ID NOs: 323, 324, 325, 326 and 327.

In one embodiment, the IL-4 antagonist for use in the methods of the invention is an interleukin-4 receptor (IL-4R) antagonist.

In one embodiment, the IL-4R antagonist for use in the methods of the invention is an antibody or antigen-binding fragment thereof that binds IL-4Rα and prevents the interaction of IL-4 and/or IL-13 with a type 1 or a type 2 IL-4 receptor.

In a related embodiment, the IL-4R antibody or antigen-binding fragment thereof for use in the methods of the invention prevents the interaction of IL-4 and/or IL-13 with both type 1 and type 2 IL-4 receptors.

In one embodiment, the IL-4R antagonist for use in the methods of the invention is a monoclonal antibody that binds specifically to human IL-4Rα.

In one embodiment, the monoclonal antibody that binds specifically to human IL-4Rα for use in the methods of the invention is dupilumab, or a bioequivalent thereof.

In a certain embodiment, the IL-4R antibody or antigen-binding fragment thereof for use in the methods of the invention comprises the heavy chain complementarity determining regions (HCDRs) of a heavy chain variable region (HCVR) comprising the amino acid sequence of SEQ ID NO:335 or SEQ ID NO: 337 and the light chain complementarity determining regions (LCDRs) of a light chain variable region (LCVR) comprising the amino acid sequence of SEQ ID NO:336 or SEQ ID NO: 338.

In a related embodiment, the IL-4R antibody or antigen-binding fragment thereof for use in the methods of the invention comprises three HCDRs (HCDR1, HCDR2 and HCDR3) and three LCDRs (LCDR1, LCDR2 and LCDR3), wherein the HCDR1 comprises the amino acid sequence of SEQ ID NO: 339, the HCDR2 comprises the amino acid sequence of SEQ ID NO:340; the HCDR3 comprises the amino acid sequence of SEQ ID NO:341; the LCDR1 comprises the amino acid sequence of SEQ ID NO:342; the LCDR2 comprises the amino acid sequence of SEQ ID NO:343; and the LCDR3 comprises the amino acid sequence of SEQ ID NO:344.

In one embodiment, the IL-4R antibody or antigen-binding fragment thereof for use in the methods of the invention comprises an HCVR comprising the amino acid sequence of SEQ ID NO: 335 or SEQ ID NO: 337 and an LCVR comprising the amino acid sequence of SEQ ID NO: 336 or SEQ ID NO: 338.

In one embodiment, the IL-4R antibody or antigen-binding fragment thereof for use in the methods of the invention comprises an HCVR/LCVR amino acid sequence pair of SEQ ID NOs: 335/336 or SEQ ID NOs: 337/338.

In a related embodiment, the IL-4R antagonist for use in the methods of the invention is dupilumab (SEQ ID NOs: 337/338), or a bioequivalent thereof.

In certain embodiments, the IL-33 antagonist and the IL-4R antagonist are administered in separate formulations.

In certain embodiments, the IL-33 antagonist and the IL-4R antagonist are co-formulated for administration to a patient in need thereof.

In certain embodiments, the IL-33 antagonist and the IL-4R antagonist are administered to the subject subcutaneously, intravenously, intramuscularly, or intranasally.

The IL-33 and IL-4R antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

In one embodiment, the antibodies that bind specifically to human interleukin-33, or human IL-4R are isolated fully human monoclonal antibodies.

In a sixth aspect, the invention provides a pharmaceutical composition comprising a recombinant human antibody or fragment thereof, or a trap, which specifically binds IL-33, or an antibody that specifically binds IL-4R and a pharmaceutically acceptable carrier. In a related aspect, the invention features a composition, which is a combination of an anti-IL-33 antibody or an IL-33 trap, or an antibody that specifically binds IL-4R and one or more additional therapeutic agents. In one embodiment, the one or more additional therapeutic agents is any agent that is advantageously combined with either, or both, the IL-33 antagonist and/or the IL-4R antagonist. Exemplary agents that may be advantageously combined with an IL-33 antagonist and/or an IL-4R antagonist include, without limitation, other agents that inhibit IL-33 activity and/or IL-4 activity (including other antibodies or antigen-binding fragments thereof, peptide inhibitors, small molecule antagonists, etc.) and/or agents, which do not directly bind IL-33, or IL-4 or IL-4R, but nonetheless interfere with, block or attenuate IL-33 or IL-4 mediated signaling. In one embodiment the one or more additional therapeutic agents may be selected from the group consisting of a non-steroidal anti-inflammatory (NSAID), a corticosteroid (e.g. an inhaled corticosteroid), a bronchial dilator, an antihistamine, epinephrine, a decongestant, a thymic stromal lymphopoietin (TSLP) antagonist, an IL-1 antagonist, an IL-8 antagonist, an IL-13 antagonist, a different IL-4 antagonist, an IL-4/IL-13 dual antagonist, an IL-33/IL-13 dual antagonist, an IL-5 antagonist, an IL-6 antagonist, an IL-12/23 antagonist, an IL-22 antagonist, an IL-25 antagonist, an IL-17 antagonist, an IL-31 antagonist, a TNF inhibitor, an IgE inhibitor, a leukotriene inhibitor, an oral PDE4 inhibitor, a methylxanthine, nedocromil sodium, cromolyn sodium, a long-acting beta 2 agonist (LABA), a long acting muscarinic antagonist (LAMA), an inhaled corticosteroid (ICS) and another IL-33 or IL-4 antagonist or a different antibody to IL-33 or IL-4 or IL-4R, and another IL-33 antagonist.

In certain embodiments, the cytokine antagonist may be a small molecule inhibitor (synthetic or naturally derived), or a protein (e.g. an antibody) that interacts with either the cytokine itself, or to a receptor for the cytokine, or to a complex comprising both the cytokine and its receptor(s). Additional combination therapies and co-formulations involving the anti-IL-33 antibodies of the present invention and/or the IL-4R antibodies are disclosed elsewhere herein.

In yet another aspect, the invention provides therapeutic methods for inhibiting IL-33, and/or IL-4 signaling activity using an anti-IL-33 antagonist (such as an IL-33 antibody or an IL-33 trap), and an IL-4R antibody or antigen-binding portion of one or more antibodies of the invention, wherein the therapeutic methods comprise administering a therapeutically effective amount of a pharmaceutical composition comprising an IL-33 antibody or an IL-33 trap, either alone, or in combination with an IL-4R antibody or antigen-binding fragment of one or more antibodies of the invention. The disorder treated is any disease or condition which is improved, ameliorated, inhibited or prevented by removal, inhibition or reduction of IL-33 and/or IL-4 signaling. The anti-IL-33 and/or IL-4R antagonists of the invention, when used together, may function to block the interaction between IL-33 and an IL-33 binding partner, and IL-4 and an IL-4 binding partner or otherwise inhibit the signaling activity of both IL-33 and IL-4. In one embodiment, the IL-4R antagonist is an antibody that binds to IL-4Rα and in so doing prevents both IL-4 and IL-13 signaling through either the type I or type II receptors. In one embodiment, the IL-4Rα antagonist is dupilumab or a bioequivalent thereof. Given the dual blocking activity of dupilumab for both IL-4 and IL-13, it is believed that when used in combination with the IL-33 antagonists of the invention, the combined treatment regimen will result in enhanced inhibition of unwanted inflammatory activity resulting in part from signaling through the IL-4, IL-13 and IL-33 signaling pathways, which may occur during inflammation.

In one embodiment, the IL-33 antagonist is an antibody or antigen-binding fragment thereof that binds specifically to IL-33 and blocks the interaction of IL-33 and its receptor ST2 (also known as IL1RL1).

In one embodiment, the antibody or antigen-binding fragment thereof that binds specifically to IL-33 comprises three heavy chain CDRs (HCDR1, HCDR2 and HCDR3) contained within a heavy chain variable region (HCVR) amino acid sequence selected from the group consisting of SEQ ID NO: 2, 18, 34, 50, 66, 82, 98, 114, 130, 146, 162, 178, 194, 210, 226, 242, 258, 274, 290, and 308; and comprises three light chain CDRs (LCDR1, LCDR2 and LCDR3) contained within a light chain variable region (LCVR) amino acid sequence selected from the group consisting of SEQ ID NOs: 10, 26, 42, 58, 74, 90, 106, 122, 138, 154, 170, 186, 202, 218, 234, 250, 266, 282, 298, and 316.

In one embodiment, the antibody or antigen-binding fragment thereof that binds specifically to IL-33 comprises a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274, 290 and 308.

In one embodiment, the antibody or antigen-binding fragment thereof that binds specifically to IL-33 comprises a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298 and 316.

In one embodiment, the antibody or antigen-binding fragment thereof that binds specifically to IL-33, comprises:

(a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292 and 310;

(b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294 and 312;

(c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296 and 314;

(d) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284 and 318;

(e) a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286 and 320;

(f) a LCDR3 domain having an amino acid sequence selected from the group consisting of SEQ ID NOs: 16, 32, 48, 64, 80, 96, 112, 128, 144, 160, 176, 192, 208, 224, 240, 256, 272, 288 and 322.

In one embodiment, the antibody or antigen-binding fragment thereof that binds specifically to IL-33 comprises a HCVR/LCVR amino acid sequence pair selected from the group consisting of SEQ ID NOs: SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298 and 308/316.

The present invention also includes the use of an IL-33 antagonist alone, or in combination with an IL-4R antagonist in the manufacture of a medicament for the treatment of a disease or disorder related to or caused by IL-33 and/or IL-4 activity or signaling in a patient. In one embodiment, the disease or disorder related to, or caused by IL-33 activity and/or IL-4 activity in a patient is an inflammatory disease or disorder, wherein the inflammatory disease or disorder is selected from the group consisting of asthma (eosinophilic or non-eosinophilic), chronic obstructive pulmonary disease (COPD), asthma and COPD overlap syndrome (ACOS), atopic dermatitis, nasal polyps, an allergic response, chronic bronchitis, emphysema, chronic rhinosinusitis with or without nasal polyps, inflammatory bowel disease, Crohn's disease, ulcerative colitis, hypersensitivity pneumonitis, multiple sclerosis, arthritis (including osteoarthritis, rheumatoid arthritis and psoriatic arthritis), allergic rhinitis, fibrosis, eosinophilic esophagitis, vasculitis, urticaria, Churg Strauss syndrome, inflammatory pain, and psoriasis. The present invention also includes a therapeutically effective amount of an IL-33 antagonist combined with a therapeutically effective amount of an IL-4R antagonist for use in treating an inflammatory disease or disorder, or at least one symptom of an inflammatory disease or disorder, wherein the administration of the IL-33 antagonist in combination with the IL-4R antagonist results in enhanced therapeutic efficacy as compared to that observed with administration of the IL-33 antagonist alone or the IL-4R antagonist alone. Any of the methods discussed herein also encompass use of the IL-33 and/or IL-4R antagonists (e.g., antibodies) to treat, or for treating, the diseases, disorders and/or symptoms discussed in connection with the methods.

Other embodiments will become apparent from a review of the ensuing detailed description.

DETAILED DESCRIPTION

Figure 1:
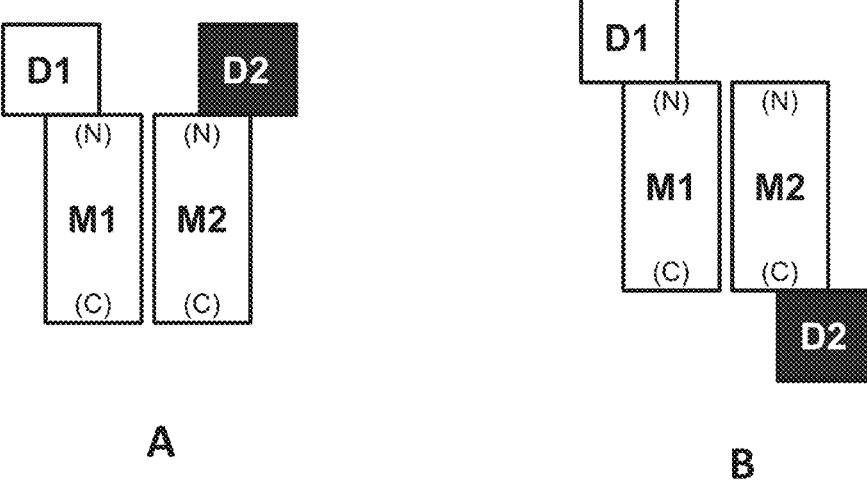
FIG. 1 shows four exemplary arrangements of the individual components of the IL-33 antagonists relative to one another. Panel A shows an arrangement in which a first IL-33-binding domain (D1) is attached to the N-terminus of a first multimerizing domain (M1), and a second IL-33-binding domain (D2) is attached to the N-terminus of a second multimerizing domain (M2). D1 is shown as a white box and D2 is shown as a black box to indicate that D1 and D2 are derived from different IL-33 binding proteins. Panel B shows an arrangement in which a first IL-33-binding domain (D1) is attached to the N-terminus of a first multimerizing domain (M1), and a second IL-33-binding domain (D2) is attached to the C-terminus of a second multimerizing domain (M2). D1 is shown as a white box and D2 is shown as a black box to indicate that D1 and D2 are derived from different IL-33 binding proteins. Panels C and D show arrangements comprising four IL-33-binding domains, D1, D2, D3 and D4. In these arrangements, D3-D1-M1 and D4-D2-M2 are attached in tandem, wherein D3 is attached to the N-terminus of D1, and D1 is attached to the N-terminus of M1; and D4 is attached to the N-terminus of D2, and D2 is attached to the N-terminus of M2. In Panel C, D3 and D4 are identical or substantially identical to one another, and D1 and D2 are identical or substantially identical to one another. In Panel D, D1 and D4 are identical or substantially identical to one another, and D3 and D2 are identical or substantially identical to one another.
Figure 1:
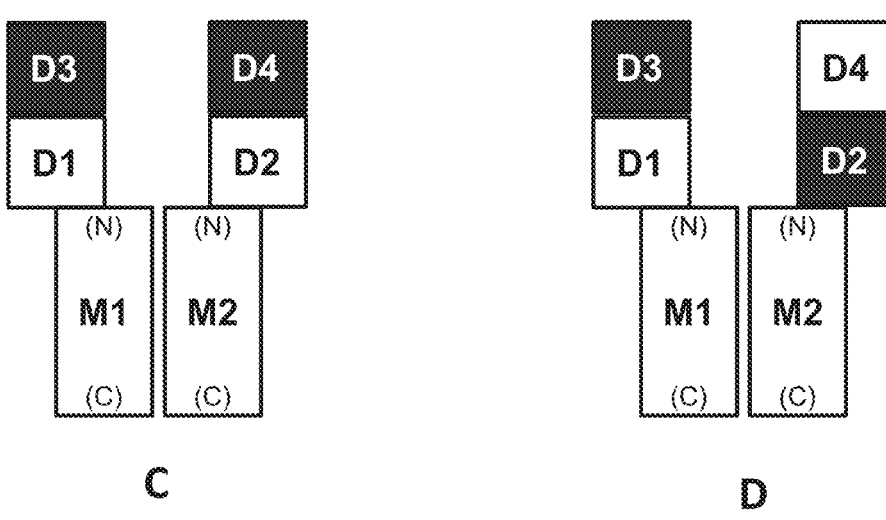

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The terms "interleukin-33," "IL-33," and the like, as used herein, refer to a human IL-33 protein and encompasses the 270 amino acid, full-length, unprocessed IL-33 (See, for example, SEQ ID NO: 348, or UniProtKB accession number O95760), as well as any form of IL-33 that results from processing in the cell (See, for example, SEQ ID NO: 349, which contains amino acid residues 112-270 of the full length protein). Other processed forms of IL-33 are described in Lefrançais, et. al. (Lefrançais, et al., (2012), Proc. Natl. Acad. Sci. 109(5):1693-1678). The term also encompasses naturally occurring variants of IL-33, for example, splice variants (See for example, Hong, et. al., (2011), J. Biol. Chem. 286(22):20078-20086, or), or allelic variants, or any other isoform of IL-33, such as that described in WO2016/156440. All references to proteins, polypeptides and protein fragments herein are intended to refer to the human version of the respective protein, polypeptide or protein fragment unless explicitly specified as being from a non-human species.

As used herein, the expression "IL-33 antagonist" means any agent that is capable of blocking, attenuating or otherwise interfering with IL-33 signaling and/or the interaction between IL-33 and a cell surface receptor (e.g., ST2, also known as IL1RL1) or a co-receptor (e.g. IL1-RAcP), or a complex thereof. For example, an "IL-33 antagonist", also referred to as an "IL-33 inhibitor", or an "IL-33 blocker" includes any of the following: (1) an agent that binds to, or interacts with IL-33; or (2) an agent that binds to, or interacts with the IL-33 receptor (sometimes referred to as "suppression of tumorigenicity" or "ST2"; also known as "IL1RL1"); or (3) an agent that binds to or interacts with the IL-33 co-receptor (interleukin-1 receptor accessory protein, or IL1-RAcP); or (4) an agent that binds to a complex of IL-33/ST2; or (5) an agent that binds to or interacts with ST2/IL-1RAcP. Any of the above may result in inhibition, or attenuation of at least one biological activity of IL-33, such as, but not limited to, the biological signaling function that occurs upon binding of IL-33 to its receptor/co-receptor complex.

In one embodiment, an "IL-33 antagonist" is an antibody that specifically binds to or interacts with IL-33 and prevents IL-33 binding to ST2 and in so doing prevents the interaction of ST2 with the co-receptor IL-1RAcP. In one embodiment, an "IL-33 antagonist" is an antibody that specifically binds to either ST2, or to the ST2/IL-1RAcP complex and prevents binding of IL-33 to ST2, or to the ST2/IL1-RAcP receptor complex. In one embodiment, an "IL-33 antagonist" is an antibody that binds to the IL-33/ST2 complex and then prevents interaction of ST2 with the IL-1RAcP co-receptor. In one embodiment, an "IL-33 antagonist" is an antibody that binds to IL-33 and may allow for low affinity binding to ST2, but at the same time, such low affinity binding may prevent subsequent interaction of ST2 with the co-receptor IL-1RAcP.

An "IL-33 antagonist" may also be an agent such as a soluble ST2 receptor, or an IL-33 receptor based trap, such as those described herein and disclosed in US2014/0271642. Any agent that blocks IL-33-mediated signaling is considered an "IL-33 antagonist". The "IL-33 antagonist" may be a small organic molecule, a protein, such as an antibody or fragment thereof, or a soluble IL-33 receptor based trap (as described herein), or a nucleic acid, such as an antisense molecule or an siRNA. As used herein, "an antibody that binds IL-33" or an "anti-IL-33 antibody" includes antibodies, and antigen-binding fragments thereof, that bind a human IL-33 protein or a biologically active fragment thereof, (e.g., See SEQ ID NOs: 348, 349, 350 and 351).

The expression "interleukin-4 receptor", or "IL-4R" as used herein, refers to a human IL-4Rα receptor having an amino acid sequence of SEQ ID NO: 347.

As used herein, an "IL-4R antagonist" (also referred to herein as an "IL-4R inhibitor," an "IL-4Rα antagonist," an "IL-4R blocker," an "IL-4Rα blocker," etc.) is any agent, which binds to or interacts with IL-4Rα or an IL-4R ligand, and inhibits or attenuates the normal biological signaling function of a type 1 and/or a type 2 IL-4 receptor. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R antagonists that can be used in the methods of the present invention may function by blocking IL-4-mediated signaling, IL-13-mediated signaling, or both IL-4- and IL-13-mediated signaling. The IL-4R antagonists of the present invention may thus prevent the interaction of IL-4 and/or IL-13 with a type 1 or type 2 receptor. Non-limiting examples of categories of IL-4R antagonists include small molecule IL-4R inhibitors, anti-IL-4R aptamers, peptide-based IL-4R inhibitors (e.g., "peptibody" molecules), "receptor-bodies" (e.g., engineered molecules comprising the ligand-binding domain of an IL-4R component), and antibodies or antigen-binding fragments of antibodies that specifically bind human IL-4Rα. As used herein, IL-4R antagonists also include antigen-binding proteins that specifically bind IL-4 and/or IL-13.

The term "antibody", as used herein, means any antigen-binding molecule or molecular complex comprising at least one complementarity determining region (CDR) that specifically binds to or interacts with a particular antigen (e.g., IL-33 or IL-4R). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-33 antibody (or antigen-binding portion thereof), or the anti-IL-4R antibody may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art. For example, the present invention includes methods comprising the use of bispecific antibodies wherein one arm of an immunoglobulin is specific for IL-4Rα or a fragment thereof, or an immunoglobulin specific for IL-33 or a fragment thereof and the other arm of the immunoglobulin is specific for a second therapeutic target or is conjugated to a therapeutic moiety. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [*Epub: Dec.* 4, 2012]).

In certain embodiments of the invention, the anti-IL-33 and the IL-4R antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences. The term includes antibodies recombinantly produced in a non-human mammal, or in cells of a non-human mammal. The term is not intended to include antibodies isolated from or generated in a human subject.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention includes neutralizing and/or blocking anti-IL-33 antibodies and IL-4R antibodies. A "neutralizing" or "blocking" antibody, as used herein, is intended to refer to an antibody whose binding to the target molecule, e.g. either IL-33 or IL-4R: (i) interferes with the interaction between the target molecule and either its receptor (in the case of IL-33 antibodies), or its ligand (in the case of IL-4R antibodies); and/or (ii) results in inhibition of at least one biological function of the target molecule, e.g. signaling. The inhibition caused by an IL-33 or IL-4R neutralizing or blocking antibody need not be complete so long as it is detectable using an appropriate assay.

The antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes antibodies comprising variants of any of the HCVR, LCVR, and/or CDR amino acid sequences disclosed herein having one or more conservative substitutions. For example, the present invention includes antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likeli-hood matrix disclosed in Gonnet et al. (1992) Science 256: 1443-1445, herein incorporated by reference. A "moderately conservative" replacement is any change having a nonnega-tive value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modi-fications, including conservative amino acid substitutions. For instance, GCG software contains programs such as Gap and Bestfit which can be used with default parameters to determine sequence homology or sequence identity between closely related polypeptides, such as homologous polypep-tides from different species of organisms or between a wild type protein and a mutein thereof. See, e.g., GCG Version 6.1. Polypeptide sequences also can be compared using FASTA using default or recommended parameters, a pro-gram in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, espe-cially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

A "disease or disorder", as used herein, is any condition that is treatable with the IL-33 and IL-4 antagonists of the invention. An "inflammatory disease or disorder", as used herein, refers to a disease, disorder or pathological condition where the pathology results, in whole or in part, from, e.g., a change in number, change in rate of migration, or change in activation, of cells of the immune system. Cells of the immune system include, e.g., T cells, B cells, monocytes or macrophages, innate lymphoid cells, antigen presenting cells (APCs), dendritic cells, microglia, NK cells, neutro-phils, eosinophils, mast cells, or any other cell specifically associated with the immunology, for example, cytokine-producing endothelial or epithelial cells. As used herein, in one embodiment, the "inflammatory disease or disorder" is an immune disorder or condition selected from the group consisting of asthma, (including steroid resistant asthma, steroid sensitive asthma, eosinophilic asthma or non-eosino-philic asthma), allergy, anaphylaxis, multiple sclerosis, inflammatory bowel disorder (e.g. Crohn's disease or ulcer-ative colitis), chronic obstructive pulmonary disease (COPD, which may or may not be related to, caused in part by, or resulting from, exposure to first or second hand cigarette smoke), asthma and COPD overlap syndrome (ACOS), eosinophilic esophagitis, chronic bronchitis, emphysema, chronic rhinosinusitis with or without nasal polyps, lupus, atopic dermatitis, psoriasis, scleroderma and other fibrotic diseases, sjogren's syndrome, vasculitis (behcet's disease, Giant cell arteritis, Henoch-Schonlein purpura and Churg Strauss syndrome), inflammatory pain and arthritis. In one embodiment, the arthritis is selected from the group consisting of rheumatoid arthritis, osteoar-thritis, and psoriatic arthritis.

In one embodiment, the "inflammatory disease or disor-der" is an immune disorder or condition that comprises a Type 1 response and/or a Type 2 response.

A "type 1 immune response" is defined by T helper 1 (T$_H$1) cells and T$_H$17 cells, cytotoxic T cells, group 1 and group 3 innate lymphoid cells (ILCs) and immunoglobulin M (IgM), IgA and specific IgG antibody classes and the cytokines including, for example, TNF, IL-1β and IL-6. This effector response mediates immunity to many microorgan-isms including bacteria, viruses, fungi, and protozoa. Ele-ments of Type 1 immunity also help to maintain tumor immune surveillance.

A "type 2 immune response" is characterized by CD4+ T helper 2 (T$_H$2) cells, group 2 innate lymphoid cells (ILCs), eosinophils, basophils, mast cells, IL-4 and/or IL-13 acti-vated macrophages, the IgE antibody subclass, and the cytokines including, for example, IL-4, IL-5, IL-9, IL-13, thymic stromal lymphopoietin, IL-25 and IL-33. Type 2 immunity provides protection against large extracellular parasites by boosting barrier defenses. Elements of the type 2 immune response also help to maintain metabolic homeo-stasis and to promote tissue remodeling following injury. This type of response can also be initiated in response to allergens.

The phrase "inhibits or attenuates IL-33-mediated signal-ing", as used herein, refers to the degree to which IL-33 stimulates signal transduction through its receptor, ST2 and the co-receptor, IL-1RAcP, which is diminished in the presence of an antagonist, such as an IL-33 antibody, or an IL-33 trap, as described herein, relative to the degree to which IL-33 stimulates signal transduction through ST2 and IL-1RAcP in the absence of the antagonist such as an IL-33 antibody, or IL-33 trap as described herein. The phrase "Inhibits or attenuates IL-4R-mediated signaling", as used herein, refers to the degree to which IL-4 stimulates signal transduction through a type 1 and/or a type 2 IL-4 receptor, which is diminished in the presence of an antagonist, such as an IL-4 or IL-4R antibody, as described herein, relative to the degree to which IL-4 stimulates signal transduction through a type 1 and/or type 2 IL-4 receptor in the absence of the antagonist such as an IL-4 or IL-4R antibody, as described herein. To examine the extent of inhibition, a sample is treated with a potential inhibitor/antagonist and is compared to a control sample without the inhibitor/antago-nist. Control samples, i.e., not treated with antagonist, are assigned a relative activity value of 100%. Inhibition is achieved when the activity value relative to the control is about 90%, 85%, 80%, 75%, 70%, 65%, 60%, 55%, 50%, 45%, 40%, 35%, 30%, 25%, or 20% or less. An endpoint in inhibition may comprise a predetermined quantity or per-centage of, e.g., an indicator of inflammation, or cell degranulation, secretion or activation, such as the release of a cytokine. Inhibition of IL-33 signal transduction through ST2 and IL-1RAcP can be determined by assaying for IL-33 signal transduction in an in vitro assay, such as those known to one skilled in the art. In addition, in vivo assays can be used to determine whether a molecule is an antagonist of IL-33. For example, an in vivo assay may be used to assess the effect of an antibody to IL-33 on lung inflammation in allergen-sensitized animals that are homozygous for expression of human IL-33. Following sensitization of the animals with allergen, a subset of the animals is treated with either an anti-IL-33 antibody of the invention or a negative isotype control antibody. Afterwards, the animals are sacrificed and the lungs are harvested for assessment of cellular infiltrates, as well as cytokine measurements (IL-4 and IL-5). An IL-33 antibody that is effective as an antagonist should demonstrate a trend towards reduction in inflammatory cells in the lung, as well as a trend towards reduction in cytokines such as IL-4 and IL-5. Similar assays may be done to assess the ability of an IL-4R antagonist to block signal transduction following binding of IL-4 to a type 1 and/or a type 2 receptor in vitro or in vivo. Moreover, any of the above-noted assays may be modified in order to compare the effects of using either an IL-33 antagonist alone, an IL-4 or IL-4R antagonist alone, or the effect of using a combination of both the IL-33 antagonist and the IL-4 or IL-4R antagonist together.

In another aspect, the invention provides methods for reducing the incidence or recurrence of asthma or COPD, or an asthma or COPD exacerbation, in a subject in need thereof comprising administering a pharmaceutical composition comprising an interleukin-4 receptor (IL-4R) antagonist to the subject in combination with a pharmaceutical composition comprising an IL-33 antagonist. As used herein, the expression "asthma or COPD exacerbation" means an increase in the severity and/or frequency and/or duration of one or more symptoms or indicia of asthma or COPD. An "asthma or COPD exacerbation" also includes any deterioration in the respiratory health of a subject that requires and or is treatable by a therapeutic intervention for asthma or COPD (such as, e.g., steroid treatment, inhaled corticosteroid treatment, hospitalization, etc.).

A "reduction in the incidence or recurrence" of an asthma or COPD exacerbation means that a subject who has received the pharmaceutical compositions of the present invention experiences fewer asthma or COPD exacerbations (i.e., at least one fewer exacerbation) after treatment than before treatment, or experiences no asthma or COPD exacerbations for at least 4 weeks (e.g., 4, 6, 8, 12, 14, or more weeks) following initiation of treatment with a pharmaceutical composition of the present invention. A "reduction in the incidence or recurrence" of an asthma or COPD exacerbation alternatively means that, following administration of a pharmaceutical composition of the present invention, the likelihood that a subject experiences an asthma or COPD exacerbation is decreased by at least 10% (e.g., 10%, 15%, 20%, 25%, 30%, 35%, 40%, 45%, 50%, or more) as compared to a subject who has not received a pharmaceutical composition of the present invention.

A "fibrotic disease or disorder" as used herein refers to conditions that involve an excess of fibrous connective tissue in a tissue or organ. "Fibrosis" refers to a pathologic process, which includes scar formation and overproduction of extracellular matrix by the connective tissue as a response to tissue damage. As used herein, exemplary "fibrotic diseases or disorders" that are treatable by administering the anti-IL-33 and IL-4R antagonists of the invention include pulmonary fibrosis (e.g., idiopathic pulmonary fibrosis, bleomycin-induced pulmonary fibrosis, asbestos-induced pulmonary fibrosis, and bronchiolitis obliterans syndrome), chronic asthma, fibrosis associated with acute lung injury and acute respiratory distress (e.g., bacterial pneumonia induced fibrosis, trauma induced fibrosis, viral pneumonia induced fibrosis, ventilator induced fibrosis, non-pulmonary sepsis induced fibrosis and aspiration induced fibrosis), silicosis, radiation-induced fibrosis, chronic obstructive pulmonary disease (COPD, which may or may not be related to, caused in part by, or resulting from, exposure to first or second hand cigarette smoke), scleroderma, ocular fibrosis, skin fibrosis (e.g., scleroderma), hepatic fibrosis (e.g., cirrhosis, alcohol-induced liver fibrosis, non-alcoholic steato-hepatitis (NASH), biliary duct injury, primary biliary cirrhosis, infection- or viral-induced liver fibrosis, autoimmune hepatitis, kidney (renal) fibrosis, cardiac fibrosis, atherosclerosis, stent restenosis, and myelofibrosis. While asthma and COPD are generally considered to be inflammatory conditions, each is also known to exhibit properties of fibrotic disorders.

A "response" of a patient or a patient's "responsiveness" to treatment or therapy, for example treatment comprising an IL-33 antagonist (e.g., an IL-33 or ST2 binding antagonist), or an IL-4 antagonist, refers to the clinical or therapeutic benefit imparted to a patient at risk for or having an IL-33-mediated disorder (e.g., asthma, COPD, ACOS, nasal polyps, or pulmonary fibrosis, e.g., idiopathic pulmonary fibrosis) from or as a result of the treatment. Such benefit may include cellular or biological responses, a complete response, a partial response, a stable disease (without progression or relapse), or a response with a later relapse of the patient from or as a result of the treatment with the antagonist. A skilled person will readily be in position to determine whether a patient is responsive. For example, a patient suffering from asthma who is responsive to treatment comprising an IL-33 antagonist and/or an IL-4 antagonist may show observable and/or measurable reduction in or absence of one or more of the following exemplary symptoms: recurrent wheezing, coughing, trouble breathing, chest tightness, symptoms that occur or worsen at night, symptoms that are triggered by cold air, exercise or exposure to allergens.

Furthermore, "enhanced therapeutic efficacy" may be determined by assessing whether treating with the combination of an IL-33 antagonist plus an IL-4R antagonist results in marked improvement in at least one symptom of the disease or disorder, or an improvement in at least one of the biological parameters, as measured herein (e.g. lung inflammation, cytokine release, etc.) when compared to the results achieved when the IL-33 antagonist or the IL-4R antagonist is used alone. Any of the biological measures of efficacy, as described in the present application, may be used to determine therapeutic efficacy, or enhancement thereof.

IL-33 Antagonists and IL-4R Antagonists

The methods of the present invention comprise administering to a patient suffering from an inflammatory disease or disorder a therapeutically effective amount of an IL-33 antagonist in combination with a therapeutically effective amount of an IL-4R antagonist.

IL-33 Antagonists

The term "human interleukin-33" or "human IL-33" or "hIL-33", or "IL-33" refers to the 270 amino acid, full-length, unprocessed IL-33 (See, for example, SEQ ID NO: 348, or UniProtKB accession number O95760), or a biologically active fragment thereof, as well as any form of IL-33 that results from processing in the cell (See, for example, SEQ ID NO: 349, which contains amino acid residues 112-270 of the full length protein). The term also encompasses naturally occurring variants of IL-33, for example, splice variants (See for example, Hong, et. al., (2011), J. Biol. Chem. 286(22):20078-20086), or allelic variants, or any other isoform of IL-33, such as the oxidized or reduced forms of IL-33 described in WO2016/156440. The activity of IL-33 that can be neutralized, inhibited, blocked, abrogated, attenuated, reduced or interfered with, by an antibody or antigen-binding fragment thereof of the invention, or by an IL-33 trap of the invention, includes, but is not limited to, inhibition of IL-33 receptor-mediated signaling, or inhibition of IL-33-mediated inflammation.

As used herein, an "IL-33 antagonist" (also referred to herein as an "IL-33 inhibitor," or an "IL-33 blocker," etc.) is any agent, which inhibits the interaction of IL-33 with one or more of its binding partners and in so doing may inhibit IL-33-mediated signaling. For example, an "IL-33 antagonist" may bind to and/or interact with IL-33, or with the IL-33 receptor referred to as "suppression of tumorigenicity" ("ST2"), or with the IL-33 co-receptor referred to as "Interleukin-1 Receptor Accessory Protein ("IL-1RAcP"), or with a complex of any of the following: IL-33/ST2, or ST2/IL-1RAcP and in so doing, may inhibit IL-33-mediated signaling.

Non-limiting examples of categories of IL-33 antagonists include small molecule IL-33 inhibitors, or receptor antagonists, or nucleic acids that hybridize under stringent conditions to nucleic acid sequences encoding either IL-33, or an IL-33 receptor or co-receptor (e.g., short interfering RNAs (siRNA) or clustered regularly interspaced short palindromic repeat RNAs (CRISPR-RNA or crRNA), including single guide RNAs (sgRNAs) having a crRNA and tracrRNA sequence as described in Mali et al. (Science. 339: 823-26, 2013), which is incorporated herein by reference in its entirety). Other IL-33 antagonists include proteins comprising a ligand-binding portion of an IL-33 receptor (e.g. ST2), IL-33-binding scaffold molecules (e.g., DARPins, HEAT repeat proteins, ARM repeat proteins, tetratricopeptide repeat proteins, fibronectin-based scaffold constructs, and other scaffolds based on naturally occurring repeat proteins, etc., [see, e.g., Boersma and Pluckthun, 2011, Curr. Opin. Biotechnol. 22:849-857, and references cited therein]), and anti-IL-33 aptamers or portions thereof.

IL-33 Antibodies

According to certain embodiments, IL-33 antagonists or inhibitors that can be used in the context of the present invention are anti-IL-33 antibodies or antigen-binding fragments of antibodies that specifically bind human IL-33. The amino acid sequence identifiers for exemplary anti-IL-33 antibodies for use in the methods described herein are shown in Table 1 and the nucleic acid sequence identifiers encoding these IL-33 antibodies are shown in Table 2.

In one embodiment, the anti-IL-33 antibodies described herein for use in the methods of the invention are disclosed in U.S. Pat. No. 9,453,072, which is incorporated by reference in its entirety.

According to certain embodiments, the anti-IL-33 antibodies used in the methods of the present invention specifically bind to IL-33. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-33 as used in the context of the present invention, includes antibodies that bind to IL-33 or a biologically active portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-33 may, however, have cross-reactivity to other antigens, such as IL-IL-33 molecules from other (non-human) species.

According to certain exemplary embodiments of the present invention, the IL-33 antagonist is an anti-IL-33 antibody, or antigen-binding fragment thereof comprising a heavy chain variable region (HCVR), light chain variable region (LCVR), and/or complementarity determining regions (CDRs) comprising any of the amino acid sequences of the anti-IL-33 antibodies as set forth in U.S. Pat. No. 9,453,072 and in Table 1 disclosed herein. In certain embodiments, the IL-33 antagonist is an anti-IL-33 antibody having the binding characteristics of the reference antibody described in U.S. Pat. No. 9,453,072. In certain exemplary embodiments, the anti-IL-33 antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO: 274 and the light chain complementarity determining regions (LCDRs) of a light chain variable region (LCVR) comprising the amino acid sequence of SEQ ID NO: 282. According to certain embodiments, the anti-IL-33 antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 276; the HCDR2 comprises the amino acid sequence of SEQ ID NO: 278; the HCDR3 comprises the amino acid sequence of SEQ ID NO: 280; the LCDR1 comprises the amino acid sequence of SEQ ID NO: 284; the LCDR2 comprises the amino acid sequence of SEQ ID NO: 286; and the LCDR3 comprises the amino acid sequence of SEQ ID NO: 288. In yet other embodiments, the anti-IL-33 antibody or antigen-binding fragment thereof comprises an HCVR comprising SEQ ID NO: 274 and an LCVR comprising SEQ ID NO: 282.

In one embodiment, the IL-33 antagonist is an IL-33 antibody referred to as REGN3500, which comprises a HCVR having the amino acid sequence of SEQ ID NO: 274 and a LCVR having the amino acid sequence of SEQ ID NO: 282 and heavy chain complementarity determining regions (HCDR1-HCDR2-HCDR3) having the amino acid sequences of SEQ ID NOS: 276-278-280, respectively, and light chain complementarity determining regions (LCDR1-LCDR2-LCDR3) having the amino acid sequences of SEQ ID NOS: 284-286-288, respectively.

Other anti-IL-33 antibodies and antigen-binding fragments thereof that may be used in the methods described herein are disclosed in EP1725261, U.S. Pat. No. 8,187,596, WO2011031600, WO2015099175, WO2015106080 (ANB020), US2016/0168242, WO2016/077381, WO2016/077366, or WO2016/156440, which are each incorporated herein by reference in their entirety.

IL-33 Traps

According to certain embodiments, IL-33 antagonists or inhibitors that can be used in the context of the present invention are receptor based IL-33 traps, such as those described herein.

The IL-33 traps described herein comprise at least one IL-33 binding domain, which comprises an IL-33 binding portion of an IL-33 receptor protein, designated ST2. In certain embodiments an IL-33 trap further comprises an extracellular portion of an IL-33 co-receptor, designated IL-1 receptor accessory protein, or IL-1RAcP. The IL-33 trap may also contain at least one multimerizing component, which functions to connect the various components of the trap with one another. The various components of the IL-33 traps are described below and shown in FIG. 1.

In one embodiment, the IL-33 traps described herein for use in the methods of the invention are disclosed in US2014/0271642 and WO2014/152195, incorporated herein by reference in their entirety.

Briefly, the IL-33 traps comprise a first IL-33 binding domain (D1) attached to a multimerizing domain (M). In certain embodiments, the IL-33 antagonists of the invention comprise a second IL-33 binding domain (D2) attached to D1 and/or M. According to certain embodiments, D1 comprises an IL-33-binding portion of an ST2 protein. According to certain embodiments, D2 comprises an extracellular portion of an IL-1RAcP protein.

The individual components of the IL-33 traps may be arranged relative to one another in a variety of ways that result in functional antagonist molecules capable of binding IL-33. For example, D1 and/or D2 may be attached to the N-terminus of M. In other embodiments D1 and/or D2 is attached to the C-terminus of M. In yet other embodiments, D1 is attached to the N-terminus of D2, and D2 is attached to the N-terminus of M, resulting in an in-line fusion, from N- to C-terminus, of an antagonist molecule represented by the formula D1-D2-M. Other orientations of the individual components are disclosed elsewhere herein in FIG. 1.

Non-limiting examples of IL-33 traps for use in the methods of the invention are shown in Tables 3a and 3b, and include the IL-33 traps designated "hST2-hFc," "hST2-mFc," "hST2-hIL1RAcP-mFc," "hST2-hIL1RAcP-hFc" and "mST2-mIL1RAcP-mFc". These correspond to SEQ ID NOs: 323, 324, 325, 326 and 327, respectively. The present invention includes IL-33 receptor based traps having an amino acid sequence that is at least 80%, 85%, 90%, 91%, 92%, 93%, 94%, 95%, 96%, 97%, 98% or 99% identical to any of the exemplary IL-33 receptor based traps set forth herein (e.g. SEQ ID NOs: 323, 324, 325, 326 and 327).

Standard molecular biological techniques (e.g., recombinant DNA technology) may be used to construct any of the IL-33 traps of the invention or variants thereof.

The IL-33 traps for use in the methods of the invention comprise at least one IL-33 binding domain (sometimes referred to herein by the designation "D," or "D1," "D2," etc.). In certain embodiments, the IL-33 binding domain comprises an IL-33-binding portion of an ST2 protein. An IL-33-binding portion of an ST2 protein can comprise or consist of all or part of the extracellular domain of an ST2 protein. In certain embodiments, an ST2 protein is a human ST2 protein. A "human ST2 protein," as used herein, refers to an ST2 protein as shown in amino acids 1-556 of accession number NP_057316.3, shown also as SEQ ID NO: 352. In certain embodiments, the ST2 protein is an ST2 protein from a non-human species (e.g., mouse ST2, monkey ST2, etc). An exemplary IL-33-binding portion of an ST2 protein is set forth herein as the amino acid sequence of SEQ ID NO: 328 (corresponding to the extracellular domain of human ST2 [K19-S328 of NCBI Accession No. NP_057316.3]). Other examples of an IL-33-binding portion of an ST2 protein is set forth herein as the amino acid sequence of SEQ ID NO:329 (corresponding to the extracellular domain of mouse ST2 [S27-R332 of NCBI Accession No. P14719]).

In certain embodiments, the IL-33 binding domain comprises an extracellular portion of an IL-1RAcP protein. In certain embodiments, an IL-1RAcP protein is a human IL-1RAcP protein. A "human IL-1RAcP protein," as used herein, refers to an IL-1RAcP protein having the amino acid sequence of SEQ ID NO:353. In certain embodiments, the IL-1RAcP protein is an IL-1RAcP protein from a non-human species (e.g., mouse IL-1RAcP, monkey IL-1RAcP, etc). An exemplary extracellular portion of an IL-1RAcP protein is set forth herein as the amino acid sequence of SEQ ID NO:330 (corresponding to the extracellular domain of human IL-1RAcP [S21-E359 of NCBI Accession No. Q9NPH3]). Another example of an extracellular portion of an IL-1RAcP protein is set forth herein as the amino acid sequence of SEQ ID NO:331 (corresponding to the extracellular domain of mouse IL-1RAcP [S21-E359 of NCBI Accession No. Q61730]).

The present invention includes IL-33 traps comprising D1 and/or D2 components having an amino acid sequence that is at least 80%, 85%, 90%, 91%, 92%, 93%, 94%, 95%, 96%, 97%, 98% or 99% identical to any of the exemplary IL-33 binding domain component amino acid sequences set forth herein (e.g., SEQ ID NOs: 328, 329, 330 and 331).

The IL-33 antagonists of the present invention also comprise at least one multimerizing domain (sometimes referred to herein by the abbreviation "M," "M1", "M2", etc.). In general terms, the multimerizing domain(s) of the present invention function to connect the various components of the IL-33 antagonists (e.g., the IL-33-binding domain(s)) with one another. As used herein, a "multimerizing domain" is any macromolecule that has the ability to associate (covalently or non-covalently) with a second macromolecule of the same or similar structure or constitution. For example, a multimerizing domain may be a polypeptide comprising an immunoglobulin $C_H3$ domain. A non-limiting example of a multimerizing domain is an Fc portion of an immunoglobulin, e.g., an Fc domain of an IgG selected from the isotypes IgG1, IgG2, IgG3, and IgG4, as well as any allotype within each isotype group.

Non-limiting exemplary multimerizing domains that can be used in the IL-33 antagonists of the present invention include human IgG1 Fc (SEQ ID NO:332) or mouse IgG2a Fc (SEQ ID NO:333). The present invention includes IL-33 antagonists comprising M components having an amino acid sequence that is at least 80%, 85%, 90%, 91%, 92%, 93%, 94%, 95%, 96%, 97%, 98% or 99% identical to any of the exemplary M component amino acid sequences set forth herein (e.g., SEQ ID NOs:332 or 333).

In certain embodiments, the IL-33 antagonists of the present invention comprise two multimerizing domains, M1 and M2, wherein M1 and M2 are identical to one another. For example, M1 can be an Fc domain having a particular amino acid sequence, and M2 is an Fc domain with the same amino acid sequence as M1.

The individual components of the IL-33 antagonists of the present invention (e.g., D1, D2, M, etc.) can be arranged relative to one another in a variety of ways. Non-limiting examples of all of the above noted arrangements are illustrated schematically in FIG. 1.

Non-limiting illustrative examples of IL-33 traps for use in the methods of the invention comprising two multimerizing domains (M1 and M2) and four IL-33 binding domains (D1, D2, D3 and D4) are also shown in FIG. 1, arrangements C and D).

The individual components of the IL-33 traps of the present invention (e.g., D1, D2, M1, M2, etc.) may be attached to one another directly (e.g., D1 and/or D2 may be directly attached to M, etc.); alternatively, the individual components may be attached to one another via a linker component (e.g., D1 and/or D2 may be attached to M via a linker oriented between the individual components; D1 may be attached to D2 via a linker; etc.). In any of the arrangements disclosed herein, wherein one component is described as being "attached" to another component, the attachment may be through a linker (even if not specifically designated as such). As used herein, a "linker" is any molecule that joins two polypeptide components together.

The biological characteristics of the IL-33 traps for use in the methods of the invention are described in US2014/0271642 and in WO2014/152195, incorporated by reference herein in their entirety.

Other IL-33 Antagonists

Polypeptides that bind IL-33 and/or its receptor (ST2 and/or IL-1 RAcP) and block ligand-receptor interaction are considered as IL-33 antagonists and are disclosed in WO2014/152195, which is incorporated by reference in its entirety. Other agents that may act as IL-33 antagonists and which may be used in the methods of the invention include immunoadhesins, peptibodies, and soluble ST2, or derivatives thereof; anti-IL-33 receptor antibodies (e.g., anti-ST2 antibodies, for example, AMG-282 (Amgen) or STLM15 (Janssen) or any of the anti-ST2 antibodies described in WO2012/113813, WO 2013/173761, WO 2013/165894, U.S. Pat. No. 8,444,987, or U.S. Pat. No. 7,452,980, which are each incorporated herein by reference in their entirety. Other IL-33 antagonists for use in the methods of the invention include ST2-Fc proteins, such as those described in WO2013/173761, or WO 2013/165894, which are each incorporated herein by reference in their entirety.

IL-4R Antagonists

As used herein, an "IL-4R antagonist" (also referred to herein as an "IL-4R inhibitor," an "IL-4Rα antagonist," an "IL-4R blocker," an "IL-4Rα blocker," etc.) is any agent, which binds to or interacts with IL-4Rα or an IL-4R ligand, and inhibits or attenuates the normal biological signaling function of a type 1 and/or a type 2 IL-4 receptor. The term "human IL-4R" or "hIL-4R", as used herein, refers to IL-4R having the amino acid sequence of SEQ ID NO: 347, or a biologically active fragment thereof. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R antagonists that can be used in the methods of the present invention may function by blocking IL-4-mediated signaling, IL-13-mediated signaling, or both IL-4- and IL-13-mediated signaling. The IL-4R antagonists of the present invention may thus prevent the interaction of IL-4 and/or IL-13 with a type 1 or type 2 receptor.

Non-limiting examples of categories of IL-4R antagonists include small molecule IL-4R antagonists, nucleic acid-based inhibitors of IL-4R expression or activity (e.g., siRNA or antisense), peptide-based molecules that specifically interact with IL-4R (e.g., peptibodies), "receptor-bodies" (e.g., engineered molecules comprising the ligand-binding domain of an IL-4R component), IL-4R-binding scaffold molecules (e.g., DARPins, HEAT repeat proteins, ARM repeat proteins, tetratricopeptide repeat proteins, fibronectin-based scaffold constructs, and other scaffolds based on naturally occurring repeat proteins, etc., [see, e.g., Boersma and Pluckthun, 2011, Curr. Opin. Biotechnol. 22:849-857, and references cited therein]), and anti-IL-4R aptamers or portions thereof. According to certain embodiments, IL-4R antagonists that can be used in the context of the present invention are anti-IL-4R antibodies or antigen-binding fragments of antibodies that specifically bind human IL-4R.

In one embodiment, the anti-IL-4R antibody that is disclosed herein for use in the methods of the invention is dupilumab (See also U.S. Pat. Nos. 7,605,237; 7,608,693 and 9,290,574).

Anti-IL-4R Antibodies

According to certain exemplary embodiments of the present invention, the IL-4R antagonist is an anti-IL-4Rα antibody or an antigen-binding fragment thereof, which specifically binds to IL-4Rα. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4Rα as used in the context of the present invention, includes antibodies that bind IL-4Rα or a biologically active portion thereof, with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-4Rα may, however, have cross-reactivity to other antigens, such as IL-4Rα molecules from other (non-human) species.

According to certain exemplary embodiments of the present invention, the IL-4R antagonist is an anti-IL-4Rα antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. Nos. 7,605,237 and 7,608,693. In certain embodiments, the IL-4R antagonist is an anti-IL-4R antibody having the binding characteristics of the reference antibody referred to herein as dupilumab (See U.S. Pat. Nos. 7,605,237 and 7,608,693). In certain exemplary embodiments, the anti-IL-4Rα antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO: 337 and the light chain complementarity determining regions (LCDRs) of a light chain variable region (LCVR) comprising the amino acid sequence of SEQ ID NO: 338. According to certain embodiments, the anti-IL-4Rα antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 339; the HCDR2 comprises the amino acid sequence of SEQ ID NO: 340; the HCDR3 comprises the amino acid sequence of SEQ ID NO: 341; the LCDR1 comprises the amino acid sequence of SEQ ID NO: 342; the LCDR2 comprises the amino acid sequence of SEQ ID NO: 343; and the LCDR3 comprises the amino acid sequence of SEQ ID NO: 344. In yet other embodiments, the anti-IL-4R antibody or antigen-binding fragment thereof comprises an HCVR comprising SEQ ID NO: 337 and an LCVR comprising SEQ ID NO: 338. In yet other embodiments, the anti-IL-4R antibody or antigen-binding fragment thereof comprises an HCVR comprising SEQ ID NO: 335 and an LCVR comprising SEQ ID NO: 336. In yet other embodiments, the anti-IL-4R antibody or antigen-binding fragment thereof comprises a heavy chain (HC) amino acid sequence as set forth in SEQ ID NO: 345 and a light chain (LC) amino acid sequence as set forth in SEQ ID NO: 346. According to certain exemplary embodiments, the methods of the present invention comprise the use of the anti-IL-4Rα antibody referred to and known in the art as dupilumab, or a bioequivalent thereof. Dupilumab comprises a HCVR having the amino acid sequence of SEQ ID NO: 337 and a LCVR having the amino acid sequence of SEQ ID NO: 338 and heavy chain complementarity determining regions (HCDR1-HCDR2-HCDR3) having the amino acid sequences of SEQ ID NOS: 339-340-341, respectively and light chain complementarity determining regions (LCDR1-LCDR2-LCDR3) having the amino acid sequences of SEQ ID NOS: 342-343-344, respectively.

Other anti-IL-4Rα antibodies that can be used in the context of the methods of the present invention include, e.g., the antibody referred to and known in the art as AMG317 (Corren et al., 2010, *Am J Respir Crit Care Med.*, 181(8): 788-796), or MEDI 9314, or any of the anti-IL-4Rα antibodies as set forth in U.S. Pat. Nos. 7,186,809, 7,605,237, 7,638,606, 8,092,804, 8,679,487, or U.S. Pat. No. 8,877, 189.

pH Dependent Characteristics of the Anti-IL-4 and/or Anti-IL-33 Antibodies

The anti-IL-4Rα and the IL-33 antibodies used in the context of the methods of the present invention may have pH-dependent binding characteristics. For example, an anti-IL-4Rα antibody or an anti-IL-33 antibody for use in the methods of the present invention may exhibit reduced binding to IL-4Rα, or to IL-33 respectively, at acidic pH as compared to neutral pH. Alternatively, an anti-IL-4Rα antibody of the invention, or an anti-IL-33 antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH", or "reduced binding to IL-33 at acidic pH as compared to neutral pH" is expressed in terms of a ratio of the $K_D$ value of the antibody binding to IL-4Rα, or IL-33, respectively at acidic pH to the $K_D$ value of the antibody binding to IL-4Rα, or IL-33, respectively at neutral pH (or vice versa). For example, an antibody or antigen-binding fragment thereof may be regarded as exhibiting "reduced binding to IL-4Rα at acidic pH as compared to neutral pH", or "reduced binding to IL-33 at acidic pH as compared to neutral pH", for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Biological Effects of the IL-33 and IL-4R Antagonists Used in Combination Therapy The present invention includes the use of an IL-33 antagonist in combination with an IL-4R antagonist for treating an inflammatory condition. In one embodiment, the use of an anti-IL-33 antibody in combination with an anti-IL4R antibody in an animal model of fibrosis and lung inflammation, demonstrates enhanced efficacy, as compared to the results obtained when each antibody is used alone as monotherapy.

For example, in the animal model described herein (referred to as a House Dust Mite (HDM) model of lung inflammation and fibrosis), the level of certain cytokines in the lungs is significantly elevated. This includes an elevation of IL-4, IL-5, IL-6, IL-1β, and MCP-1. There was also a trend for increased levels of IL-13 and TNFα in the lungs of mice following administration of house dust mite allergen. However, when tested in this model, the combined use of the IL-33 antibody and the IL-4R antibody resulted in reduced levels of the cytokines IL-4, IL-5, IL-6, IL-13, IL-1β, MCP-1 and TNFα in the lungs of treated mice. The effect on lung cytokine levels observed with the combination of anti-IL-33 and anti-IL-4R antibodies was greater than treatment with either individual antibody when used alone, as shown in Example 4.

In addition, the levels of cytokine genes, chemokine genes and collagen genes, including Il4, Il13, Il6, Ccl2, Tgfb1, Il13ra2 and Col24a1, were elevated in mice receiving a house dust mice allergen. There was a trend towards increased levels of Il5, Il9, Ccl11, Ccl24, Tnf, Il1rl1, and Col15a1 in this model. Upon treatment with the combination of the anti-IL-33 antibody and the anti-IL-4R antibody, there was significant reduction in expression of Il6, Ccl2, Ccl11 and Ccl24, as compared to the levels observed with treatment with either antibody alone. There was also a trend towards reduced Il4, Il5, Il13, Il9, Tnf, Tgfb1, Il1rl1, Il13ra2, Col15a1 and Col24a1 when the mice were treated with the anti-IL-33 antibody plus the anti-IL-4R antibody, compared to treatment with either antibody alone.

Another biological effect associated with combined use of the anti-IL-33 plus the anti-IL-4R antibodies was observed when an analysis was done on pulmonary cell infiltrates in the house dust mite model. As shown in Example 4, the frequency of eosinophils, activated B cells, activated CD8 cells, ST2+CD4+ T cells and CD4/CD8 T cell ratios were significantly higher in mice receiving house dust mite allergen. There was also a trend towards an increased frequency of activated CD4+ T cells in the lungs of mice given the house dust mite allergen. There was a trend towards reduced frequency of eosinophils, activated B cells, activated CD8 cells, ST2+CD4+ T cells and CD4/CD8 T cell ratios in mice treated with both the anti-IL-33 antibody plus the anti-IL-4R antibody as compared to that observed when either antibody was used alone.

Furthermore, mice receiving house dust mite allergen also show an increase in goblet cell metaplasia in their lungs. Similarly, there was also an increase in lung consolidation (the accumulation of solid or liquid material in the alveolar space), and sub-epithelial fibrosis (an excess of interstitial collagen deposition beneath the pulmonary epithelium) in this mouse model. Treatment of these mice with an anti-IL- 33 antibody in combination with an anti-IL-4R antibody resulted in a reduction in goblet cell metaplasia and sub-epithelial collagen thickness and a significant reduction in lung consolidation, as compared to the results observed when either of the two antibodies was used alone.

The mice receiving house dust mite allergen also demonstrated an increase in circulating levels of IgE, as well as a trend towards an increase in house dust mite (HDM) specific IgG1. Administration of both an anti-IL-33 antibody and an IL-4R antibody resulted in a significant decrease in serum IgE levels and a trend towards a decrease in HDM specific IgG1 as compared to the levels of IgE and HDM-specific IgG1 observed when either of the antibodies was used alone.

An IL-33 antagonist and an IL-4R antagonist, such as the antibodies described herein for use as combination therapy to treat inflammatory lung disorders or conditions, may inhibit or attenuate IL-33-mediated signaling and IL-4R-mediated signaling and they may exhibit one or more of the biological properties observed in the HDM model described herein, for example, (1) a reduction in cytokine levels that are elevated in a mammal as a result of exposure to an allergen, e.g. IL-4 or IL-5; (2) inhibition of lung inflammation resulting from acute or chronic exposure to an allergen (e.g. house dust mites (HDM)); (3) a decrease in cellular lung infiltration resulting from acute or chronic exposure to an allergen (e.g. house dust mites (HDM)); (4) an improvement in composite lung gross pathology.

Inhibition of IL-33-mediated signaling or IL-4R-mediated signaling may be measured in a cell-based bioassay and means that an anti-IL-33 antibody or antigen-binding fragment thereof, or an anti-IL-4R antibody or antigen-binding fragment thereof inhibits or reduces the signal produced in cells that express an IL-33 receptor or an IL-4 receptor and a reporter element that produces a detectable signal in response to IL-33 binding, or IL-4 binding. For example, the present invention includes antibodies and antigen-binding fragments thereof that block IL-33-mediated signaling, or IL-4 mediated signaling in cells expressing human ST2, or in cells expressing an IL-4 receptor, respectively, with an $IC_{50}$ of less than about 2 nM, less than about 1 nM, less than about 900 pM, less than about 800 pM, less than about 700 pM, less than about 600 pM, less than about 500 pM, less than about 400 pM, less than about 350 pM, less than about 300 pM, less than about 250 pM, less than about 200 pM, less than about 150 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM, as measured in a cell-based blocking bioassay.

The antibodies of the present invention may demonstrate one or more of the aforementioned biological effects, or any combination thereof. Other biological effects of the antibodies of the present invention will be evident to a person of ordinary skill in the art from a review of the present disclosure including the working Examples herein. The use of other IL-33 antagonists in combination with an IL-4 antagonist may demonstrate similar effects.

Pharmaceutical Compositions and Administration

The invention provides pharmaceutical compositions comprising the IL-33 antagonists, and/or the IL-4R antagonists of the present invention. The IL-33 antagonists and the IL-4R antagonists may be formulated in separate compositions, or they may be co-formulated in one composition. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFEC-TIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present invention is used for treating a condition or disease associated with IL-33 activity and/or IL-4 in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-IL-33 antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or muco-cutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMA-LOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in about delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antagonists contained is generally about 5 to about 500 mg per dosage form in a unit dose; especially in the form of injection, it is preferred that the aforesaid antagonists are contained in about 5 to about 100 mg and in about 10 to about 250 mg for the other dosage forms.

Dosage

The amount of IL-33 and IL-4R antagonist administered to a subject according to the methods of the present invention is, generally, a therapeutically effective amount. As used herein, the phrase "therapeutically effective amount" means an amount of IL-33 antagonist and IL-4R antagonist that, when used in combination, results in a significant change in one or more of the following: (a) prevention of inflammation; (b) treatment of or reduction in the severity of inflammation; (c) a reduction in the frequency of one or more of the following: eosinophils, activated B cells, activated CD8 T cells, or CD4/CD8 T cell ratio in the lungs; (d) a reduction in one or more of the following: interleukin-1 beta (IL-1β), interleukin-4 (IL-4), interleukin-5 (IL-5), interleukin-6 (IL-6), interleukin-13 (IL-13), monocyte chemoattractant protein-1 (MCP-1) or tumor necrosis factor alpha (TNFα) levels in the lung; (e) a reduction in the gene expression level of one or more of the following: Il4, Il5, Il6, Il9, Il13, Il1rl1, Il13ra2, tnf, Tgfb1, Ccl2, Ccl11, Ccl24, Col15a1 or Col24a1 in the lung; (f) a reduction in serum IgE levels; (g) a reduction in goblet cell metaplasia in the lung; or (h) a reduction in lung consolidation, as described herein. While the administration of either the IL-33 antagonist alone, or the IL-4R antagonist alone may result in a positive therapeutic effect as measured using one or more of the above-noted parameters, the use of the IL-33 and the IL-4R antagonists in combination will show a significant improvement (e.g. an additive or a synergistic effect) in any one or more of the parameters compared to that observed using monotherapy with either the IL-33 antagonist alone or the IL-4R antagonist alone.

In the case of an IL-33 antagonist, or an IL-4R antagonist, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg. In certain embodiments, 75 mg, 150 mg, 200 mg, or 300 mg of an IL-4R antagonist is administered to a subject in combination with an IL-33 antagonist. In certain embodiments, 75 mg, 150 mg, 200 mg, or 300 mg of an IL-33 antagonist is administered to a subject in combination with an IL-4R antagonist.

The amount of IL-33 antagonist or IL-4R antagonist contained within the individual doses may be expressed in terms of milligrams of antibody per kilogram of patient body weight (i.e., mg/kg). For example, the IL-33 antagonist or the IL-4R antagonist may be administered to a patient at a dose of about 0.0001 mg/kg to about 25 mg/kg of patient body weight. In certain embodiments, each of the IL-4R and the IL-33 antagonists may be administered at doses of about 0.1 mg/kg, 0.3 mg/kg, 1.0 mg/kg, 3.0 mg/kg, or 10 mg/kg.

The combination of the IL-33 antagonist and the IL-4R antagonist may be administered to the subject subcutaneously, intravenously, intramuscularly, or intranasally. They may be administered concurrently or sequentially.

Therapeutic Uses of the Antibodies

Experiments using a mouse model system, conducted by the present inventors, have contributed to the identification of various diseases and conditions that can be treated, prevented and/or ameliorated by combined IL-33 and IL-4R antagonism. For example, in a house dust mite model of lung inflammation and fibrosis, treatment with a combination of an IL-33 antibody and an IL-4R antibody resulted in a reduction of cytokine levels in the lungs, a reduction in pulmonary cell infiltrates in the lungs (eosinophils, activated B cells, activated CD8 positive cells, ST2+CD4+ T cells and CD4/CD8 T cell ratio), as well as an improvement in lung consolidation and sub-epithelial fibrosis, as compared to the results obtained when each antibody was used alone as monotherapy.

The antibodies of the invention are useful, inter alia, for the treatment, prevention and/or amelioration of any disease or disorder associated with, or mediated by IL-33 expression and IL-4 expression, signaling, or activity, or treatable by blocking the interaction between IL-33 and an IL-33 receptor (e.g., ST2), or blocking the interaction between IL-4 and an IL-4 receptor, or otherwise inhibiting IL-33 and IL-4 activity and/or signaling. In certain embodiments, the IL-4R antagonist is an antibody that binds to, or interacts with IL-4Rα and in so doing, blocks both the IL-4 and IL-13 signaling pathways through the IL-4R type 1 and type 2 receptors. As such, the use of this dual IL-4 and IL-13 antagonist in combination with an IL-33 antagonist may provide for additional clinical benefits when administered to patients having an inflammatory condition mediated in part by all three signaling pathways. For example, the present invention provides methods for treating asthma (allergic asthma, non-allergic asthma, severe refractory asthma, asthma exacerbations, steroid resistant or steroid refractory asthma, steroid sensitive asthma, eosinophilic asthma or non-eosinophilic asthma, etc.), chronic obstructive pulmonary disease (COPD) and COPD exacerbations, asthma and COPD overlap syndrome (ACOS), chronic bronchitis, emphysema, hypersensitivity pneumonitis, atopic dermatitis, urticaria, psoriasis, allergy, allergic rhinitis, chronic rhinosinusitis with or without nasal polyps, eosinophilic esophagitis, anaphylaxis, cardiovascular disease, central nervous system disease, pain (including inflammatory pain), arthritis (e.g., rheumatoid arthritis, osteoarthritis, psoriatic arthritis, etc.), giant cell arteritis, vasculitis (behcet's disease and Churg Strauss syndrome), Henoch-Schonlein purpura, multiple sclerosis, inflammatory bowel disorder (e.g. Crohn's disease or ulcerative colitis), lupus, sjogren's syndrome and other inflammatory diseases or disorders mediated in part by IL-33 and/or IL-4 signaling.

The antibodies of the present invention are also useful for the treatment, prevention and/or amelioration of one or more fibrotic diseases or disorders. Exemplary fibrotic diseases or disorders that are treatable by administering the anti-IL-33 and IL-4R antagonists of the invention include pulmonary fibrosis (e.g., idiopathic pulmonary fibrosis, bleomycin-induced pulmonary fibrosis, asbestos-induced pulmonary fibrosis, and bronchiolitis obliterans syndrome), fibrosis associated with acute lung injury and acute respiratory distress (e.g., bacterial pneumonia induced fibrosis, trauma induced fibrosis, viral pneumonia induced fibrosis, ventilator induced fibrosis, non-pulmonary sepsis induced fibrosis and aspiration induced fibrosis), silicosis, radiation-induced fibrosis, scleroderma, ocular fibrosis, skin fibrosis (e.g., scleroderma), hepatic fibrosis (e.g., cirrhosis, alcohol-induced liver fibrosis, non-alcoholic steatohepatitis (NASH), biliary duct injury, primary biliary cirrhosis, infection- or viral-induced liver fibrosis, autoimmune hepatitis, kidney (renal) fibrosis, cardiac fibrosis, atherosclerosis, stent restenosis, and myelofibrosis.

In the context of the methods of treatment described herein, the anti-IL-33 antibody and the IL-4R antibody may be administered together (i.e., as the only therapeutic regimen) or in combination with one or more additional therapeutic agents (examples of which are described elsewhere herein).

Combination Therapies

The present invention includes the use of compositions and therapeutic formulations comprising any of the anti-IL-33 antagonists and IL-4R antagonists described herein in combination with one or more additional therapeutically active components, and methods of treatment comprising administering such combinations to subjects in need thereof. As used herein, the expression "in combination with" means that the additional therapeutic agents are administered before, after, or concurrent with the pharmaceutical composition comprising the IL-33 antagonist and the IL-4R antagonist. The term "in combination with" also includes sequential or concomitant administration of an IL-4R antagonist and an IL-33 antagonist and one or more additional therapeutic agents. The present invention includes pharmaceutical compositions in which an IL-33 antagonist and an IL-4R antagonist of the present invention is co-formulated with one or more of the additional therapeutically active component(s).

For example, when administered "before" the pharmaceutical compositions comprising the IL-33 antagonist and the IL-4R antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical compositions comprising the IL-33 antagonist and the IL-4R antagonist. When administered "after" the pharmaceutical compositions comprising the IL-33 antagonist and the IL-4R antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical compositions comprising the IL-33 antagonist and the IL-4R antagonist. Administration "concurrent" or with the pharmaceutical compositions comprising the IL-33 antagonist and the IL-4R antagonist means that the additional therapeutic agent is administered to the subject in a separate dosage form within less than 5 minutes (before, after, or at the same time) of administration of the pharmaceutical compositions comprising the IL-33 antagonist and the IL-4R antagonist, or administered to the subject as a single combined dosage formulation comprising both the additional therapeutic agent, the IL-33 antagonist and the IL-4R antagonist.

The additional therapeutic agent may be, e.g., another IL-33 antagonist, another IL-4R antagonist, an IL-1 antagonist (including, e.g., an IL-1 antagonist as set forth in U.S. Pat. No. 6,927,044), an IL-6 antagonist, an IL-6R antagonist (including, e.g., an anti-IL-6R antibody as set forth in U.S. Pat. No. 7,582,298), an IL-13 antagonist, a TNF antagonist, an IL-8 antagonist, an IL-9 antagonist, an IL-17 antagonist, an IL-5 antagonist (e.g. mepolizumab, or NUCALA®), an IgE antagonist (e.g. omalizumab or XOLAIR®), a CD48 antagonist, an IL-31 antagonist (including, e.g., as set forth in U.S. Pat. No. 7,531,637), a thymic stromal lymphopoietin (TSLP) antagonist (including, e.g., as set forth in US 2011/027468), interferon-gamma (IFNγ), antibiotics, corticosteroids (including inhaled corticosteroids, or ICS), long acting β2 adrenergic agonists (LABA), long acting muscarinic antagonists (LAMA), tacrolimus, pimecrolimus, cyclosporine, azathioprine, methotrexate, cromolyn sodium, proteinase inhibitors, anti-histamines, or combinations thereof.

Administration Regimens

According to certain embodiments of the present invention, multiple doses of an IL-33 antagonist and an IL-4R antagonist (or a pharmaceutical composition comprising a combination of an IL-33 antagonist, an IL-4R antagonist and any of the additional therapeutically active agents mentioned herein) may be administered to a subject over a defined time course. The methods according to this aspect of the invention comprise sequentially administering to a subject multiple doses of an IL-33 antagonist and an IL-4R antagonist of the invention. As used herein, "sequentially administering" means that each dose of the IL-33 antagonist and the IL-4R antagonist is administered to the subject at a different point in time, e.g., on different days separated by a predetermined interval (e.g., hours, days, weeks or months). The present invention includes methods which comprise sequentially administering to the patient a single initial dose of an IL-33 antagonist and an IL-4R antagonist, followed by one or more secondary doses of the IL-33 antagonist and the IL-4R antagonist, and optionally followed by one or more tertiary doses of the IL-33 antagonist and the IL-4R antagonist.

The terms "initial dose," "secondary doses," and "tertiary doses," refer to the temporal sequence of administration of the IL-33 antagonist and the IL-4R antagonist of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of IL-33 antagonist and IL-4R antagonist, but generally may differ from one another in terms of frequency of administration. In certain embodiments, however, the amount of IL-33 antagonist and IL-4R antagonist contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of IL-33 antagonist and IL-4R antagonist, which is administered to a patient prior to the administration of the very next dose in the sequence with no intervening doses.

The methods according to this aspect of the invention may comprise administering to a patient any number of secondary and/or tertiary doses of an IL-33 antagonist and an IL-4R antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of once a month, then the maintenance doses may be administered to the patient once every six weeks, once every two months, once every three months, etc.).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Human Antibodies to Human IL-33

Human anti-IL-33 antibodies were generated as described in U.S. Pat. No. 9,453,072. Table 1 sets forth the heavy and light chain variable region amino acid sequence pairs, and CDR sequences, of selected anti-IL-33 antibodies and their corresponding antibody identifiers. Table 2 sets forth the nucleic acid sequences encoding the heavy and light chain variable region amino acid sequence pairs, and CDR sequences, of selected anti-IL-33 antibodies and their corresponding antibody identifiers.

can be converted to an antibody with a human IgG4, etc.), but in any event, the variable domains (including the

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1M9559N | 2 | 4 | 6 | 8 | 10 | 12 | 14 | 16 |
| H1M9566N | 18 | 20 | 22 | 24 | 26 | 28 | 30 | 32 |
| H1M9568N | 34 | 36 | 38 | 40 | 42 | 44 | 46 | 48 |
| H4H9629P | 50 | 52 | 54 | 56 | 58 | 60 | 62 | 64 |
| H4H9633P | 66 | 68 | 70 | 72 | 74 | 76 | 78 | 80 |
| H4H9640P | 82 | 84 | 86 | 88 | 90 | 92 | 94 | 96 |
| H4H9659P | 98 | 100 | 102 | 104 | 106 | 108 | 110 | 112 |
| H4H9660P | 114 | 116 | 118 | 120 | 122 | 124 | 126 | 128 |
| H4H9662P | 130 | 132 | 134 | 136 | 138 | 140 | 142 | 144 |
| H4H9663P | 146 | 148 | 150 | 152 | 154 | 156 | 158 | 160 |
| H4H9664P | 162 | 164 | 166 | 168 | 170 | 172 | 174 | 176 |
| H4H9665P | 178 | 180 | 182 | 184 | 186 | 188 | 190 | 192 |
| H4H9666P | 194 | 196 | 198 | 200 | 202 | 204 | 206 | 208 |
| H4H9667P | 210 | 212 | 214 | 216 | 218 | 220 | 222 | 224 |
| H4H9670P | 226 | 228 | 230 | 232 | 234 | 236 | 238 | 240 |
| H4H9671P | 242 | 244 | 246 | 248 | 250 | 252 | 254 | 256 |
| H4H9672P | 258 | 260 | 262 | 264 | 266 | 268 | 270 | 272 |
| H4H9675P | 274 | 276 | 278 | 280 | 282 | 284 | 286 | 288 |
| H4H9676P | 290 | 292 | 294 | 296 | 298 | 300 | 302 | 304 |
| H1M9565N | 308 | 310 | 312 | 314 | 316 | 318 | 320 | 322 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1M9559N | 1 | 3 | 5 | 7 | 9 | 11 | 13 | 15 |
| H1M9566N | 17 | 19 | 21 | 23 | 25 | 27 | 29 | 31 |
| H1M9568N | 33 | 35 | 37 | 39 | 41 | 43 | 45 | 47 |
| H4H9629P | 49 | 51 | 53 | 55 | 57 | 59 | 61 | 63 |
| H4H9633P | 65 | 67 | 69 | 71 | 73 | 75 | 77 | 79 |
| H4H9640P | 81 | 83 | 85 | 87 | 89 | 91 | 93 | 95 |
| H4H9659P | 97 | 99 | 101 | 103 | 105 | 107 | 109 | 111 |
| H4H9660P | 113 | 115 | 117 | 119 | 121 | 123 | 125 | 127 |
| H4H9662P | 129 | 131 | 133 | 135 | 137 | 139 | 141 | 143 |
| H4H9663P | 145 | 147 | 149 | 151 | 153 | 155 | 157 | 159 |
| H4H9664P | 161 | 163 | 165 | 167 | 169 | 171 | 173 | 175 |
| H4H9665P | 177 | 179 | 181 | 183 | 185 | 187 | 189 | 191 |
| H4H9666P | 193 | 195 | 197 | 199 | 201 | 203 | 205 | 207 |
| H4H9667P | 209 | 211 | 213 | 215 | 217 | 219 | 221 | 223 |
| H4H9670P | 225 | 227 | 229 | 231 | 233 | 235 | 237 | 239 |
| H4H9671P | 241 | 243 | 245 | 247 | 249 | 251 | 253 | 255 |
| H4H9672P | 257 | 259 | 261 | 263 | 265 | 267 | 269 | 271 |
| H4H9675P | 273 | 275 | 277 | 279 | 281 | 283 | 285 | 287 |
| H4H9676P | 289 | 291 | 293 | 295 | 297 | 299 | 301 | 303 |
| H1M9565N | 307 | 309 | 311 | 313 | 315 | 317 | 319 | 321 |

Antibodies are typically referred to herein according to the following nomenclature: Fc prefix (e.g. "H1M," or "H4H"), followed by a numerical identifier (e.g. "9559," "9566," or "9629" as shown in Table 1), followed by a "P," or "N" suffix. Thus, according to this nomenclature, an antibody may be referred to herein as, e.g., "H1M9559N," "H1M9566N," "H4H9629P," etc. The H1M and H4H prefixes on the antibody designations used herein indicate the particular Fc region isotype of the antibody. For example, an "H1M" antibody has a mouse IgG1 Fc, whereas an "H4H" antibody has a human IgG4 Fc. As will be appreciated by a person of ordinary skill in the art, an antibody having a particular Fc isotype can be converted to an antibody with a different Fc isotype (e.g., an antibody with a mouse IgG1 Fc CDRs)—which are indicated by the numerical identifiers shown in Table 1—will remain the same, and the binding properties are expected to be identical or substantially similar regardless of the nature of the Fc domain.

Example 2: Construction of IL-33 Antagonists (IL-33 Traps

Human anti-IL-33 traps were generated as described in US Patent Publication Number 2014/0271642. Table 3a sets forth a summary of the amino acid sequence identifiers for the various components of the IL-33 traps and Table 3b sets forth the full length amino acid sequences of the traps.

Five different exemplary IL-33 antagonists of the invention were constructed using standard molecular biological techniques. The first IL-33 antagonist (hST2-hFc, SEQ ID NO:323) consists of the soluble extracellular region of human ST2 (SEQ ID NO:328) fused at its C-terminus to the N-terminus of a human IgG1 Fc region (SEQ ID NO:332). The second IL-33 antagonist (hST2-mFc, SEQ ID NO:324) consists of the soluble extracellular region of human ST2 (SEQ ID NO:328) fused at its C-terminus to the N-terminus of a mouse IgG2a Fc region (SEQ ID NO:333). The third IL-33 antagonist (hST2-hIL1RAcP-mFc, SEQ ID NO: 325) consists of an in-line fusion having human ST2 (SEQ ID NO:328) at its N-terminus, followed by the extracellular region of human IL-1RAcP (SEQ ID NO:330), followed by a mouse IgG2a Fc (SEQ ID NO:333) at its C-terminus. The fourth IL-33 antagonist (mST2-mIL1RAcP-mFc, SEQ ID NO: 326) consists of an in-line fusion having mouse ST2 (SEQ ID NO:329) at its N-terminus, followed by the extracellular region of mouse IL-1RAcP (SEQ ID NO:331), followed by a mouse IgG2a Fc (SEQ ID NO:333) at its C-terminus. The fifth IL-33 antagonist (hST2-hIL1RAcP-hFc, SEQ ID NO:327) consists of an in line fusion having human ST2 of SEQ ID NO: 328 at its N-terminus, followed by the extracellular region of human IL-1RAcP (SEQ ID NO: 330) followed by a human IgG1 Fc (SEQ ID NO: 332) at its C terminus. Table 3a sets forth a summary description of the different IL-33 antagonists and their component parts.

Table 3b sets forth the amino acid sequences of the IL-33 antagonists and their component parts.

TABLE 3a

Summary of IL-33 Antagonists and the Component Parts

| IL-33 Antagonist | Amino Acid Sequence of Full Antagonist Molecule | D1 Component | D2 Component | M Component |
|---|---|---|---|---|
| hST2-hFc | SEQ ID NO: 323 | human ST2 extracellular (SEQ ID NO: 328) | Absent | human IgG1 Fc (SEQ ID NO: 332) |
| hST2-mFc | SEQ ID NO: 324 | human ST2 extracellular (SEQ ID NO: 328) | Absent | mouse IgG2a Fc (SEQ ID NO: 333) |
| hST2-hIL1RAcP-mFc | SEQ ID NO: 325 | human ST2 extracellular (SEQ ID NO: 328) | human IL-1RAcP extracellular (SEQ ID NO: 330) | mouse IgG2a Fc (SEQ ID NO: 333) |
| mST2-mIL1RAcP-mFc | SEQ ID NO: 326 | mouse ST2 extracellular (SEQ ID ) NO: 329) | mouse IL-1RAcP extracellular (SEQ ID NO: 331) | mouse IgG2a Fc (SEQ ID NO: 333) |
| hST2-hIL1RAcP-hFc | SEQ ID NO: 327 | human ST2 extracellular (SEQ ID NO: 328) | human IL-1RAcP extracellular (SEQ ID NO: 330) | human IgG1 Fc (SEQ ID NO: 332) |

TABLE 3b

Amino Acid Sequences

| Identifier | Sequence |
|---|---|
| SEQ ID NO: 323 (hST2-hFc) | KFSKQSWGLENEALIVRCPRQGKPSYTVDWYYSQTNKSIPTQERNRVFASGQL LKFLPAAVADSGIYTCIVRSPTFNRTGYANVTIYKKQSDCNVPDYLMYSTVSGSE KNSKIYCPTIDLYNVVTAPLEWFKNCQALQGSRYRAHKSFLVIDNVMTEDAGDYT CKFIHNENGANYSVTATRSFTVKDEQGFSLFPVIGAPAQNEIKEVEIGKNANLTC SACFGKGTQFLAAVLWQLNGTKITDFGEPRIQQEEGQNQSFSNGLACLDMVLRI ADVKEEDLLLQYDCLALNLHGLRRHTVRLSRKNPIDHHSDKTHTCPPCPAPELL GGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPGK |
| SEQ ID NO: 324 (hST2-mFc) | KFSKQSWGLENEALIVRCPRQGKPSYTVDWYYSQTNKSIPTQERNRVFASGQL LKFLPAAVADSGIYTCIVRSPTFNRTGYANVTIYKKQSDCNVPDYLMYSTVSGSE KNSKIYCPTIDLYNWTAPLEWFKNCQALQGSRYRAHKSFLVIDNVMTEDAGDYT CKFIHNENGANYSVTATRSFTVKDEQGFSLFPVIGAPAQNEIKEVEIGKNANLTC SACFGKGTQFLAAVLWQLNGTKITDFGEPRIQQEEGQNQSFSNGLACLDMVLRI ADVKEEDLLLQYDCLALNLHGLRRHTVRLSRKNPIDHHSEPRGPTIKPCPPCKCP APNLLGGPSVFIFPPKIKDVLMISLSPIVTCVVVDVSEDDPDVQISWFVNNVEVHT AQTQTHREDYNSTLRVVSALPIQHQDWMSGKEFKCKVNNKDLPAPIERTISKPK GSVRAPQVYVLPPPEEEMTKKQVTLTCMVTDFMPEDIYVEWTNNGKTELNYKN TEPVLDSDGSYFMYSKLRVEKKNWVERNSYSCSVVHEGLHNHHTTKSFSRTPG K |
| SEQ ID NO: 325 (hST2-hIL1RAcP-mFc) | KFSKQSWGLENEALIVRCPRQGKPSYTVDWYYSQTNKSIPTQERNRVFASGQL LKFLPAAVADSGIYTCIVRSPTFNRTGYANVTIYKKQSDCNVPDYLMYSTVSGSE KNSKIYCPTIDLYNWTAPLEWFKNCQALQGSRYRAHKSFLVIDNVMTEDAGDYT CKFIHNENGANYSVTATRSFTVKDEQGFSLFPVIGAPAQNEIKEVEIGKNANLTC SACFGKGTQFLAAVLWQLNGTKITDFGEPRIQQEEGQNQSFSNGLACLDMVLRI ADVKEEDLLLQYDCLALNLHGLRRHTVRLSRKNPIDHHSSERCDDWGLDTMRQI QVFEDEPARIKCPLFEHFLKFNYSTAHSAGLTLIWYWTRQDRDLEEPINFRLPEN RISKEKDVLWFRPTLLNDTGNYTCMLRNTTYCSKVAFPLEVVQKDSCFNSPMKL PVHKLYIEYGIQRITCPNVDGYFPSSVKPTITWYMGCYKIQNFNNVIPEGMNLSFL IALISNNGNYTCVVTYPENGRTFHLTRTLTVKVVGSPKNAVPPVIHSPNDHVVYE KEPGEELLIPCTVYFSFLMDSRNEVWWTIDGKKPDDITIDVTINESISHSRTEDET RTQILSIKKVTSEDLKRSYVCHARSAKGEVAKAAKVKQKVPAPRYTVESGEPRG |

TABLE 3b-continued

Amino Acid Sequences

| Identifier | Sequence |
|---|---|
| | PTIKPCPPCKCPAPNLLGGPSVFIFPPPKIKDVLMISLSPIVTCVVVDVSEDDPDVQI SWFVNNVEVHTAQTQTHREDYNSTLRVVSALPIQHQDWMSGKEFKCKVNNKD LPAPIERTISKPKGSVRAPQVYVLPPPEEEMTKKQVTLTCMVTDFMPEDIYVEWT NNGKTELNYKNTEPVLDSDGSYFMYSKLRVEKKNWVERNSYSCSVVHEGLHN HHTTKSFSRTPGK |
| SEQ ID NO: 326 (mST2- mIL1RAcP- mFc) | SKSSWGLENEALIVRCPQRGRSTYPVEWYYSDTNESIPTQKRNRIFVSRDRLKF LPARVEDSGIYACVIRSPNLNKTGYLNVTIHKKPPSCNIPDYLMYSTVRGSDKNF KITCPTIDLYNWTAPVQWFKNCKALQEPRFRAHRSYLIDNVTHDDEGDYTCQF THAENGTNYIVTATRSFTVEEKGFSMFPVITNPPYNHTMEVEIGKPASIACSACF GKGSHFLADVLWQINKTVVGNFGEARIQEEEGRNESSSNDMDCLTSVLRITGVT EKDLSLEYDCLALNLHGMIRHTIRLRRKQPIDHRSERCDDWGLDTMRQIQVFED EPARIKCPLFEHFLKYNYSTAHSSGLTLIWYWTRQDRDLEEPINFRLPENRISKEK DVLWFRPTLLNDTGNYTCMLRNTTYCSKVAFPLEWQKDSCFNSAMRFPVHKM YIEHGIHKITCPNVDGYFPSSVKPSVTWYKGCTEIVDFHNVLPEGMNLSFFIPLVS NNGNYTCVVTYPENGRLFHLTRTVTVKVVGSPKDALPPQIYSPNDRVVYEKEPG EELVIPCKVYFSFIMDSHNEVWWTIDGKKPDDVTVDITINESVSYSSTEDETRTQI LSIKKVTPEDLRRNYVCHARNTKGEAEQAAKVKQKVIPPRYTVESGEPRGPTIKP CPPCKCPAPNLLGGPSVFIFPPPKIKDVLMISLSPIVTCVVVDVSEDDPDVQISWFV NNVEVHTAQTQTHREDYNSTLRVVSALPIQHQDWMSGKEFKCKVNNKDLPAPI ERTISKPKGSVRAPQVYVLPPPEEEMTKKQVTLTCMVTDFMPEDIYVEWTNNGK TELNYKNTEPVLDSDGSYFMYSKLRVEKKNWVERNSYSCSVVHEGLHNHHTTK SFSRTPGK |
| SEQ ID NO: 327 (hST2- hIL1RAcP- hFc) | KFSKQSWGLENEALIVRCPRQGKPSYTVDWYYSQTNKSIPTQERNRVFASGQL LKFLPAAVADSGIYTCIVRSPTFNRTGYANVTIYKKQSDCNVPDYLMYSTVSGSE KNSKIYCPTIDLYNWTAPLEWFKNCQALQGSRYRAHKSFLVIDNVMTEDAGDYT CKFIHNENGANYSVTATRSFTVKDEQGFSLFPVIGAPAQNEIKEVEIGKNANLTC SACFGKGTQFLAAVLWQLNGTKITDFGEPRIQQEEGQNQSFSNGLACLDMVLRI ADVKEEDLLLQYDCLALNLHGLRRHTVRLSRKNPIDHHSSERCDDWGLDTMRQI QVFEDEPARIKCPLFEHFLKFNYSTAHSAGLTLIWYWTRQDRDLEEPINFRLPEN RISKEKDVLWFRPTLLNDTGNYTCMLRNTTYCSKVAFPLEVVQKDSCFNSPMKL PVHKLYIEYGIQRITCPNVDGYFPSSVKPTITWYMGCYKIQNFNNVIPEGMNLSFL IALISNNGNYTCVVTYPENGRTFHLTRTLTVKVVGSPKNAVPPVIHSPNDHVVYE KEPGEELLIPCTVYFSFLMDSRNEVWWTIDGKKPDDITIDVTINESISHSRTEDET RTQILSIKKVTSEDLKRSYVCHARSAKGEVAKAAKVKQKVPAPRYTVEDKTHTCP PCPAPELLGGPSVFLFPPPKPKDTLMISRTPEVTCVVVDVSHEDPEVKFNWYVDG VEVHNAKTKPREEQYNSTYRVVSVLTVLHQDWLNGKEYKCKVSNKALPAPIEKT ISKAKGQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQKSLS LSPGK |
| SEQ ID NO: 328 (human ST2 extracellular domain) | KFSKQSWGLENEALIVRCPRQGKPSYTVDWYYSQTNKSIPTQERNRVFASGQL LKFLPAAVADSGIYTCIVRSPTFNRTGYANVTIYKKQSDCNVPDYLMYSTVSGSE KNSKIYCPTIDLYNWTAPLEWFKNCQALQGSRYRAHKSFLVIDNVMTEDAGDYT CKFIHNENGANYSVTATRSFTVKDEQGFSLFPVIGAPAQNEIKEVEIGKNANLTC SACFGKGTQFLAAVLWQLNGTKITDFGEPRIQQEEGQNQSFSNGLACLDMVLRI ADVKEEDLLLQYDCLALNLHGLRRHTVRLSRKNPIDHHS |
| SEQ ID NO: 329 (mouse ST2 extracellular domain) | SKSSWGLENEALIVRCPQRGRSTYPVEWYYSDTNESIPTQKRNRIFVSRDRLKF LPARVEDSGIYACVIRSPNLNKTGYLNVTIHKKPPSCNIPDYLMYSTVRGSDKNF KITCPTIDLYNWTAPVQWFKNCKALQEPRFRAHRSYLFIDNVTHDDEGDYTCQF THAENGTNYIVTATRSFTVEEKGFSMFPVITNPPYNHTMEVEIGKPASIACSACF GKGSHFLADVLWQINKTVVGNFGEARIQEEEGRNESSSNDMDCLTSVLRITGVT EKDLSLEYDCLALNLHGMIRHTIRLRRKQPIDHR |
| SEQ ID NO: 330 (human 1L1RAcP extracellular domain) | SERCDDWGLDTMRQIQVFEDEPARIKCPLFEHFLKFNYSTAHSAGLTLIWYWTR QDRDLEEPINFRLPENRISKEKDVLWFRPTLLNDTGNYTCMLRNTTYCSKVAFPL EVVQKDSCFNSPMKLPVHKLYIEYGIQRITCPNVDGYFPSSVKPTITWYMGCYKI QNFNNVIPEGMNLSFLIALISNNGNYTCVVTYPENGRTFHLTRTLTVKVVGSPKN AVPPVIHSPNDHVVYEKEPGEELLIPCTVYFSFLMDSRNEVWWTIDGKKPDDITI DVTINESISHSRTEDETRTQILSIKKVTSEDLKRSYVCHARSAKGEVAKAAKVKQK VPAPRYTVE |
| SEQ ID NO: 331 (mouse I1RAcP extracellular domain) | SERCDDWGLDTMRQIQVFEDEPARIKCPLFEHFLKYNYSTAHSSGLTLIWYWTR QDRDLEEPINFRLPENRISKEKDVLWFRPTLLNDTGNYTCMLRNTTYCSKVAFPL EVVQKDSCFNSAMRFPVHKMYIEHGIHKITCPNVDGYFPSSVKPSVTWYKGCTE IVDFHNVLPEGMNLSFFIPLVSNNGNYTCVVTYPENGRLFHLTRTVTVKVVGSPK DALPPQIYSPNDRVVYEKEPGEELVIPCKVYFSFIMDSHNEVWWTIDGKKPDDV TVDITINESVSYSSTEDETRTQILSIKKVTPEDLRRNYVCHARNTKGEAEQAAKV QKVIPPRYTVE |

TABLE 3b-continued

Amino Acid Sequences

| Identifier | Sequence |
|---|---|
| SEQ ID<br>NO: 332<br>(human IgG1<br>Fc) | DKTHTCPPCPAPELLGGPSVFLFPPKPKDTLMISRTPEVTCVVVDVSHEDPEVK<br>FNWYVDGVEVHNAKTKPREEQYNSTYRVVSVLTVLHQDWLNGKEYKCKVSNK<br>ALPAPIEKTISKAKGQPREPQVYTLPPSRDELTKNQVSLTCLVKGFYPSDIAVEW<br>ESNGQPENNYKTTPPVLDSDGSFFLYSKLTVDKSRWQQGNVFSCSVMHEALH<br>NHYTQKSLSLSPGK |
| SEQ ID<br>NO: 333<br>(mouse IgG2a<br>Fc) | EPRGPTIKPCPPCKCPAPNLLGGPSVFIFPPKIKDVLMISLSPIVTCVVVDVSEDD<br>PDVQISWFVNNVEVHTAQTQTHREDYNSTLRVVSALPIQHQDVVMSGKEFKCKV<br>NNKDLPAPIERTISKPKGSVRAPQVYVLPPPEEEMTKKQVTLTCMVTDFMPEDIY<br>VEWTNNGKTELNYKNTEPVLDSDGSYFMYSKLRVEKKNWVERNSYSCSVVHE<br>GLHNHHTTKSFSRTPGK |
| SEQ ID<br>NO: 334<br>(*M. fascicularis*<br>IL-33-6His) | SITGISPITESLASLSTYNDQSITFALEDESYEIYVEDLKKDKKKDKVLLSYYESQH<br>PSSESGDGVDGKMLMVTLSPTKDFWLQANNKEHSVELHKCEKPLPDQAFFVLH<br>NRSFNCVSFECKTDPGVFIGVKDNHLALIKVDYSENLGSENILFKLSEILEHHHHH<br>H |

Example 3: IL-4R Antagonistic Antibodies

Human anti-IL-4R antibodies were generated as described in U.S. Pat. No. 7,608,693. The exemplary IL-4R antibody used in the following example is a mouse antibody specific for mouse IL-4R and has the following amino acid sequences: a heavy chain variable region (HCVR) comprising SEQ ID NO: 335 and a light chain variable domain (LCVR) comprising SEQ ID NO: 336. The human anti-IL-4R antibody, referred to as dupilumab, specifically binds to human IL-4Rα and comprises a heavy chain variable region (HCVR) comprising SEQ ID NO: 337 and a light chain variable region (LCVR) comprising SEQ ID NO: 338, a heavy chain complementarity determining region 1 (HCDR1) comprising SEQ ID NO: 339, a HCDR2 comprising SEQ ID NO: 340, a HCDR3 comprising SEQ ID NO: 341, a light chain complementarity determining region 1 (LCDR1) comprising SEQ ID NO: 342, a LCDR2 comprising SEQ ID NO: 343 and a LCDR3 comprising SEQ ID NO: 344. The full-length heavy chain of dupilumab is shown as SEQ ID NO: 345 and the full length light chain is shown as SEQ ID NO: 346.

Example 4: A Chronic House Dust Mite (HDM)-Induced Fibrosis and Severe Lung Inflammation Model to Study the Role of IL-33 in Lung Inflammation-Comparison of Efficacy of an Anti-IL-33 Antibody, an IL-4R Antibody, or a Combination of Both Chronic inflammatory airway diseases are a consequence of recurrent episodes of airway inflammation predominantly due to repeated exposure to allergens or other pathogens. In humans, such chronic insults induce a vast array of pathologies that include pulmonary infiltration by immune cells, increased cytokine production, mucus production and collagen deposition (Hirota, (2013) Chest. September; 144(3): 1026-32; Postma, (2015), N Engl J Med., September 24; 373(13):1241-9). This increase in inflammatory cytokines and immune cell infiltrates, accompanied by intense airway remodeling leads to airway narrowing, hyperresponsiveness to inhaled triggers such as allergens or pathogens, airway obstruction and loss of lung function.

To determine the effect of anti-IL-33 inhibition in a relevant in vivo model, a chronic house dust mite extract (HDM)-induced fibrosis and severe lung inflammation and remodeling study was conducted in mice that were homozygous for the expression of human IL-33 in place of mouse IL-33 (IL-33 HumIn mice; See US Patent Publication Nos. 2015/0320021 and 2015/0320022). Chronic HDM extract exposure induces severe lung inflammation, resulting in significant cellular infiltrate, cytokine expression, and remodeling. Efficacy of an anti-IL-33 antibody, an anti-mouse IL-4Rα antibody or a combination of both was compared in this model. The anti-mouse IL-4Rα antibody used in this study is designated M1M1875N and comprises the HCVR/LCVR amino acid sequence pair of SEQ ID NOs: 335/336. The anti-IL-33 antibody used in this study is designated H4H9675P and comprises the HCVR/LCVR amino acid sequence pair of SEQ ID NOs: 274/282.

IL-33 HumIn mice were intranasally administered either 50 µg house dust mite extract (HDM; Greer, #XPB70D3A2.5) diluted in 20 µL of 1× phosphate buffered saline (PBS), or 20 µL of 1×PBS for 3 days per week for 15 weeks. A second control group of IL-33 HumIn mice were administered 50 µg HDM extract diluted in 20 µL of 1×PBS for 3 days per week for 11 weeks, to assess the severity of the disease at the onset of antibody treatment. Four groups of HDM challenged mice were injected subcutaneously with 25 mg/kg of either the anti-IL-33 antibody H4H9675P, the anti-mouse IL-4Rα antibody M1M1875N, a combination of both antibodies, or an isotype control antibody starting after 11 weeks of HDM challenge and then twice per week until the end of the HDM challenge (4 weeks of antibody treatment). On day 108 of the study, all mice were sacrificed and their lungs were harvested. Experimental dosing and treatment protocol for groups of mice are shown in Table 4.

TABLE 4

Experimental dosing and treatment protocol for groups of mice

| Group | Mice | Intranasal challenge | Length of intranasal challenge | Antibody |
|---|---|---|---|---|
| 1 | IL-33 HumIn mice | 1X PBS | 15 weeks | None |
| 2 | IL-33 HumIn mice | 50 µg HDM in 20 µL 1X PBS | 11 weeks | None |
| 3 | IL-33 HumIn mice | 50 µg HDM in 20 µL 1X PBS | 15 weeks | None |
| 4 | IL-33 HumIn mice | 50 µg HDM in 20 µL 1X PBS | 15 weeks | Isotype control antibody |

TABLE 4-continued

Experimental dosing and treatment protocol for groups of mice

| Group | Mice | Intranasal challenge | Length of intranasal challenge | Antibody |
|---|---|---|---|---|
| 5 | IL-33 HumIn mice | 50 µg HDM in 20 µL 1X PBS | 15 weeks | Anti-IL-33 antibody (H4H9675P) |
| 6 | IL-33 HumIn mice | 50 µg HDM in 20 µL 1X PBS | 15 weeks | Anti-IL-4Ra antibody (M1M1875N) |
| 7 | IL-33 HumIn mice | 50 µg HDM in 20 µL 1X PBS | 15 weeks | Anti-IL-33 (H4H9675P) antibody + Anti-IL-4Ra (M1M1875N) antibody |

Lung Harvest for Cytokine Analysis:

Elevated lung levels of key mediators such as the prototypic type 2 cytokines IL-4, IL-5, and IL-13, as well as cytokines more characteristic of type 1 immune responses, such as IL-1β or TNFα have been involved in human the development of lung diseases (Gandhi, (2016) Nat Rev Drug Discov January; 15(1):35-50; Barnes, (2008), Nat Rev Immunol, March; 8(3):183-92. Lung levels of these inflammatory cytokines were measured in the present study.

After exsanguination, the cranial and middle lobes of the right lung from each mouse were removed and placed into tubes containing a solution of tissue protein extraction reagent (1× T-PER reagent; Pierce, #78510) supplemented with 1× Halt Protease inhibitor cocktail (Thermo Scientific, #87786). All further steps were performed on ice. The volume of T-PER Reagent (containing the protease inhibitor cocktail) was adjusted for each sample to match a 1:7 (w/v) tissue to T-PER ratio. Lung samples were mechanically disrupted using the TissueLyser II (Qiagen #85300). The resulting lysates were centrifuged to pellet debris. The supernatants containing the soluble protein extracts were transferred to fresh tubes and stored at 4° C. until further analysis.

Total protein content in the lung protein extracts was measured using a Bradford assay. For the assay, 10 µL of diluted extract samples were plated into 96 well plates in duplicates and mixed with 200 µL of 1× Dye Reagent (Biorad, #500-0006). Serial dilutions of bovine serum albumin (BSA; Sigma, #A7979), starting at 700 µg/mL in 1× T-Per reagent were used as a standard to determine the protein concentration of the extracts. After a 5-minute incubation at room temperature, absorbance at 595 nm was measured on a Molecular Devices SpectraMax M5 plate reader. Data analysis to determine total lung extract protein content based on the BSA standard was performed using GraphPad Prism™ software.

Cytokine concentrations in the lung protein extracts were measured using a Proinflammatory Panel 1 (mouse) multiplex immunoassay kit (MesoScale Discovery, #K15048G-2) and a custom mouse 6plex Multi-Spot® immunoassay kit (MesoScale Discovery, #K152A41-4), according to the manufacturer's instructions. Briefly, 50 µL/well of calibrators and samples (diluted in Diluent 41) were added to plates pre-coated with capture antibodies and incubated at room temperature while shaking at 700 rpm for 2 hours. The plates were then washed 3 times with 1×PBS containing 0.05% (w/v) Tween-20, followed by the addition of 25 µL of Detection Antibody Solution diluted in Diluent 45. After a 2 hour incubation at room temperature while shaking, the plate was washed 3 times, and 150 µL of 2× Read Buffer was added to each well. Electrochemiluminescence was immediately read on a MSD Spector® instrument. Data analysis was performed using GraphPad Prism software.

Each cytokine concentration in lung total protein extracts from all mice in each group was normalized to the total protein content of the extracts measured by the Bradford assay, and expressed for each group as average pg of cytokine per mg of total lung proteins (pg/mg lung protein, ±SD) as shown in Table 5.

Lung Cytokines Analysis:

As shown in table 5, the level of the cytokines and chemokines IL-4, IL-5, IL-6, IL-1β and MCP-1 released in the lungs of IL-33 HumIn mice receiving HDM for 15 weeks, with or without treatment with an isotype control antibody were significantly higher than in IL-33 HumIn mice challenged with 1×PBS alone. Similarly, there was a trend towards an increased release of the cytokines IL-13 and TNFα in the lungs of IL-33 HumIn mice receiving HDM for 15 weeks. In contrast, there was a significant reduction in the levels of IL-6, IL-13 and MCP-1 in the lungs of IL-33 HumIn mice treated with a combination of anti-IL-33 and anti-mouse IL-4Rα antibodies during the last four weeks of the chronic HDM challenge as compared to IL-33 HumIn mice administered HDM with an isotype control antibody during this time period. There was a trend towards reduced IL-4, IL-5, IL-1β and TNFα lung levels in IL-33 HumIn mice treated with a combination of anti-IL-33 and anti-mouse IL-4Rα antibodies during the last four weeks of the chronic HDM challenge as compared to IL-33 HumIn mice administered HDM with an isotype control antibody during this time period. The effects on lung cytokines observed with the combination anti-IL-33 and anti-mouse IL-4Rα antibodies was greater than treatment with either individual antibodies alone.

TABLE 5

| Experimental group | Mean [IL-4] in lung protein extracts (pg/mg lung protein) (±SD) | Mean [IL-5] in lung protein extracts (pg/mg lung protein) (±SD) | Mean [IL-13] in lung protein extracts (pg/mg lung protein) (±SD) | Mean [IL-6] in lung protein extracts (pg/mg lung protein) (±SD) | Mean [IL-1β] in lung protein extracts (pg/mg lung protein) (±SD) | Mean [TNFα] in lung protein extracts (pg/mg lung protein) (±SD) | Mean [MCP-1] in lung protein extracts (pg/mg lung protein) (±SD) |
|---|---|---|---|---|---|---|---|
| Cytokine concentration in lung protein extracts | | | | | | | |
| 1. 1X PBS challenge (n = 5) | 0.13 (±0.17) | 0.80 (±1.41) | ND | 4.75 (±3.39) | 1.97 (±1.67) | 2.86 (±1.01) | 4.12 (±1.12) |

TABLE 5-continued

| | Cytokine concentration in lung protein extracts | | | | | | |
|---|---|---|---|---|---|---|---|
| Experi-mental group | Mean [IL-4] in lung protein extracts (pg/mg lung protein) (±SD) | Mean [IL-5] in lung protein extracts (pg/mg lung protein) (±SD) | Mean [IL-13] in lung protein extracts (pg/mg lung protein) (±SD) | Mean [IL-6] in lung protein extracts (pg/mg lung protein) (±SD) | Mean [IL-1β] in lung protein extracts (pg/mg lung protein) (±SD) | Mean [TNFα] in lung protein extracts (pg/mg lung protein) (±SD) | Mean [MCP-1] in lung protein extracts (pg/mg lung protein) (±SD) |
| 2. HDM challenge 11 weeks (n = 4) | 5.71 (±3.76)* | 7.31 (±3.67) | 0.20 (±0.03) | 293.1 (±139.3)* | 181.8 (±131.0)* | 17.39 (±8.90) | 43.06 (±24.21) |
| 3. HDM challenge 15 weeks (n = 4) | 2.70 (±1.71) | 5.13 (±3.20) | 0.19 (±0.03) | 308.3 (±390.1) | 51.79 (±16.97) | 15.38 (±8.11) | 105.6 (±106.5)* |
| 4. HDM challenge 15 weeks + isotype control antibody (n = 4) | 5.46 (±3.38)** | 7.00 (±4.50)* | 0.22 (±0.02) | 395.0 (±270.1)** | 162.3 (±166.5)** | 19.57 (±14.81) | 141.7 (±126.3)** |
| 5. HDM challenge 15 weeks + anti-IL-33 antibody (n = 5) | 1.15 (±1.38) | 1.93 (±1.90) | 0.20 (±0.02) | 136.8 (±164.1) | 122.9 (±194.1) | 17.05 (±4.48)* | 16.64 (±6.40) |
| 6. HDM challenge 15 weeks + anti-mouse IL-4Rα antibody (n = 5) | 2.88 (±2.43) | 13.13 (±12.81) | 0.16 (±0.03) | 18.24 (±12.43) | 26.73 (±20.94) | 7.85 (±4.89) | 11.63 (±8.69) |
| 7. HDM challenge 15 weeks + anti-IL-33 + anti-mouse IL-4Rα antibodies (n = 5) | 0.47 (±0.13) | 0.73 (±0.37) | 0.10 (±0.05)†† | 7.46 (±2.52) † | 3.722 (±1.59) | 3.07 (±1.34) | 4.62 (±1.27)†† |

Note:
Statistical significance determined by Kruskal-Wallis One-way ANOVA with Dunn's multiple comparison post-hoc test is indicated (*= p < 0.05, **= p < 0.01, compared to groups 1: IL33 HumIn mice, Saline challenge;
† p < 0.05, ††p < 0.01, compared to group 4: IL33 Humin mice, HDM challenge 15 weeks + Isotype control antibody).
ND: Not determined.

Lung Harvest for Gene Expression Analysis

After exsanguination, the accessory lobe of the right lung from each mouse was removed, placed into tubes containing 400 □L of RNA Later (Ambion, #AM7020) and stored at −20° C. until processing. Tissues were homogenized in TRIzol and chloroform was used for phase separation. The aqueous phase, containing total RNA, was purified using MagMAX™-96 for Microarrays Total RNA Isolation Kit (Ambion by Life Technologies, #AM1839) according to manufacturer's specifications. Genomic DNA was removed using MagMAX™ Turbo™ MDNase Buffer and TURBO DNase from the MagMAX kit listed above. mRNA (up to 2.5 g) was reverse-transcribed into cDNA using Super-Script® VILO™ Master Mix (Invitrogen by Life Technologies, #11755500). cDNA was diluted to 2 ng/□L and 10 ng cDNA was amplified with the TaqMan® Gene Expression Master Mix (Applied Biosystems by Life Technologies, #4369542) and the relevant probes (Life Technologies; mouse B2m; Mm00437762_m1; mouse Il4; Mm00445259_m1; mouse Il5; Mm00439646_m1; mouse Il13; Mm00434204_m1; mouse Il9; Mm00434305_m1; mouse Il16; Mm00446190_m1; mouse Ccl2; Mm00441242_m1; mouse Ccl11; Mm00441238_m1; mouse Ccl24; Mm00444701_m1; mouse Tnf; Mm00443258_m1; mouse Tgfb1; Mm01178820_m1; mouse Il1rl1; Mm00516117_m1; mouse Il13ra2; Mm00515166_m1; mouse Col15a1; Mm00456584_m1; mouse Col24a1; Mm01323744_m1) using the ABI 7900HT Sequence Detection System (Applied Biosystems). B2m was used as the internal control genes to normalize any cDNA input differences. The reference group used for normalization of all samples was the average of Group 1 samples ('1×PBS Challenge'). Expression of each gene was normalized to B2m expression within the same sample and expressed relative to its normalized expression in the reference group (mean±SD), as shown in table 6.

Lung Gene Expression Analysis

As shown in table 6, the level of expression of the cytokines, chemokines and collagen genes Il4, Il13, Il6, Ccl2, Tgfb1, Il13ra2 and Col24a1 in the lungs of IL-33 HumIn mice receiving HDM for 15 weeks, with or without treatment with an isotype control antibody were significantly increased compared to IL-33 HumIn mice challenged with 1×PBS alone. Similarly, there was a trend towards an increase in expression of the genes Il5, Il9, Ccl11, Ccl24, Tnf, Il1rl1 and Col15a1 in the lungs of IL-33 HumIn mice receiving HDM for 15 weeks.

In contrast, there was a significant reduction in the expression levels of Il6, Ccl2, Ccl11 and Ccl24 in the lungs of IL-33 HumIn mice treated with a combination of anti-IL-33 and anti-mouse IL-4Rα antibodies during the last four weeks of the chronic HDM challenge as compared to IL-33 HumIn mice administered HDM with an isotype control antibody during this time period. There was a trend towards reduced Il4, Il5, Il13, Il9, Tnf, Tgfb1, Il1rl1, Il13ra2, Col15a1 and Col24a1 expression levels in mice treated with a combination of anti-IL-33 and anti-mouse IL-4Rα antibodies during the last four weeks of the chronic HDM challenge as compared to IL-33 HumIn mice administered HDM with an isotype control antibody during this time period. The effects on gene expression observed with the combination anti-IL-33 and anti-mouse IL-4Rα antibodies was greater than treatment with either individual antibodies alone.

TABLE 6

| | Gene expression (TaqMan) in mouse lungs. | | | | | | | |
|---|---|---|---|---|---|---|---|---|
| Experimental group | Mean Relative Il4 expression in lung (±SD) | Mean Relative Il5 expression in lung (±SD) | Mean Relative Il13 expression in lung (±SD) | Mean Relative Il9 expression in lung (±SD) | Mean Relative Il6 expression in lung (±SD) | Mean Relative Ccl2 expression in lung (±SD) | Mean Relative Ccl11 expression in lung (±SD) | Mean Relative Ccl24 expression in lung (±SD) |
| 1. 1X PBS challenge (n = 5) | 1.03 (±0.28) | 1.54 (±1.61) | 4.51 (±7.59) | 15.91 (±34.81) | 1.25 (±1.09) | 1.20 (±0.93) | 1.24 (±1.07) | 1.05 (±0.33) |
| 2. HDM challenge 11 weeks (n = 4) | 12.78 (±8.45)* | 7.13 (±3.49) | 114.1 (±68.3)* | 38.66 (±30.04) | 9.12 (±1.65) | 18.86 (±8.40) | 13.36 (±5.05) | 15.44 (±12.02) |
| 3. HDM challenge 15 weeks (n = 4) | 6.27 (±3.39) | 4.20 (±1.51) | 58.05 (±31.61) | 30.63 (±20.54) | 8.92 (±4.55) | 22.61 (±13.37) | 8.65 (±3.20) | 4.58 (±1.91) |
| 4. HDM challenge 15 weeks + isotype control antibody (n = 4) | 10.98 (±5.46)* | 5.50 (±3.16) | 92.51 (±75.96) | 19.51 (±10.29) | 13.80 (±6.98)** | 24.53 (±9.13)** | 12.14 (±7.82) | 12.41 (±8.73) |
| 5. HDM challenge 15 weeks + anti-IL-33 antibody (n = 5) | 2.80 (±3.11) | 1.74 (±1.11) | 12.91 (±12.93) | 0.00 (±0.00) | 3.87 (±3.00) | 5.20 (±2.44) | 6.21 (±3.55) | 1.45 (±2.09) |
| 6. HDM challenge 15 weeks + anti-mouse IL-4Rα antibody (n = 5) | 1.87 (±1.03) | 7.98 (±6.52) | 69.56 (±66.86)* | 63.50 (±92.04) | 2.77 (±1.39) | 2.97 (±1.86) | 1.00 (±0.18) | 0.44 (±0.34) |
| 7. HDM challenge 15 weeks + anti-IL-33 + anti-mouse IL-4Ra antibodies (n = 5) | 1.37 (±0.35) | 1.56 (±0.97) | 9.34 (±3.10) | 0.57 (±1.27) | 1.04 (±0.31)†† | 1.08 (±0.28)††§ | 0.72 (±0.28)† | 0.15 (±0.10)†† |

TABLE 6-continued

| | Gene expression (TaqMan) in mouse lungs. | | | | | |
|---|---|---|---|---|---|---|
| Experimental group | Mean Relative Tnf expression in lung (±SD) | Mean Relative Tgfb1 expression in lung (±SD) | Mean Relative Il1rl1 expression in lung (±SD) | Mean Relative Il13ra2 expression in lung (±SD) | Mean Relative Col15a1 expression in lung (±SD) | Mean Relative Col24a1 expression in lung (±SD) |
| 1. 1X PBS challenge (n = 5) | 1.02 (±0.24) | 1.00 (±0.11) | 1.11 (±0.58) | 1.59 (±1.96) | 1.00 (±0.10) | 1.02 (±0.16) |
| 2. HDM challenge 11 weeks (n = 4) | 1.45 (±0.41) | 1.40 (±0.27) | 3.03 (±0.88)* | 48.43 (±34.21) | 2.75 (±0.96) | 24.55 (±7.97)** |
| 3. HDM challenge 15 weeks (n = 4) | 1.58 (±0.43) | 1.32 (±0.33) | 2.53 (±0.79)* | 32.07 (±13.45) | 3.00 (±1.22) | 17.25 (±5.29)* |
| 4. HDM challenge 15 weeks + isotype control antibody (n = 4) | 1.59 (±0.78) | 1.37 (±0.12)* | 3.45 (±1.48)* | 52.02 (±40.63) | 3.80 (±0.96)* | 23.58 (±6.18)*** |
| 5. HDM challenge 15 weeks + anti-IL-33 antibody (n = 5) | 1.38 (±0.27) | 1.22 (±0.24) | 0.99 (±0.47) | 13.54 (±12.25) | 1.64 (±0.30) | 10.58 (±5.42) |
| 6. HDM challenge 15 weeks + anti-mouse IL-4Rα antibody (n = 5) | 1.00 (±0.25) | 1.13 (±0.20) | 3.38 (±1.97) | 1.89 (±0.59) | 1.24 (±0.28) | 7.08 (±4.56) |
| 7. HDM challenge 15 weeks + anti-IL-33 + anti-mouse IL-4Rα antibodies (n = 5) | 0.68 (±0.08)$^{§}$ | 1.09 (±0.12) | 1.12 (±0.57) | 1.89 (±0.27) | 0.74 (±0.21)$^{††§}$ | 1.76 (±0.15)$^{†}$ |

Note:
Statistical significance determined by Kruskal-Wallis One-way ANOVA with Dunn's multiple comparison post-hoc test is indicated (*= $p < 0.05$, = $p < 0.01$, *= $p < 0.01$ compared to groups 1: IL33 HumIn mice, Saline challenge; $^{§}p < 0.05$, $^{§§}p < 0.01$, compared to group 3: IL33 Humin mice, HDM challenge 15 weeks; $^{†}p < 0.05$, $^{††}p < 0.01$, compared to group 4: IL33 Humin mice, HDM challenge 15 weeks + Isotype control antibody;).

Lung Harvest for Pulmonary Cell Infiltrate Analysis

Pulmonary infiltration by immune cells is observed in multiple airway inflammatory diseases, including asthma and COPD. Neutrophilic lung inflammation has been associated with lower lung function and severe tissue remodeling in asthma patients (Wenzel et. al., (2012), Nat Med 18(5): 716-725) and with increased pulmonary damage in COPD patients (Meijer, et. al., (2013), Expert Rev. Clin. Immunol. 9(11): 1055-1068). Eosinophilic lung inflammation is a hallmark of type 2 inflammation usually seen in atopic diseases (Jacobsen, et. al., (2014), Clin. Exp., Allergy, 44(9):1119-1136). In humans, high CD4/CD8 ratios are observed in patients with granulomatous lung diseases and other chronic inflammatory conditions (Costabel, et. al., (1997), Eur. Respir. J. 10(12):2699-2700; Guo, et. al., (2011), Ann. Clin. Biochem, 48(Pt4):344-351). Flow cytom-etry was used in the present study to determine the level of cellular infiltration in the lungs of HDM-exposed mice.

After exsanguination, the caudal lobe of the right lung from each mouse was removed, chopped into cubes that were approximately 2 to 3 mm in size, and then placed into a tube containing a solution of 20 µg/mL DNAse (Roche, #10104159001) and 0.7 U/mL Liberase TH (Roche, #05401151001) diluted in Hank's Balanced Salt Solution (HBSS) (Gibco, #14025), which was incubated in a 37° C. water bath for 20 minutes and vortexed every 5 minutes. The reaction was stopped by adding ethylenediaminetetraacetic acid (EDTA, Gibco, #15575) at a final concentration of 10 mM. Each lung was subsequently dissociated using a gentleMACS Dissociator® (Miltenyi Biotec, #130-095-937), then filtered through a 70 µm filter and centrifuged. The resulting lung pellet was resuspended in 1 mL of 1× red blood cell lysing buffer (Sigma, #R7757) to remove red blood cells. After incubation for 3 minutes at room temperature, 3 mL of 1×DMEM was added to deactivate the red blood cell lysing buffer. The cell suspensions were then centrifuged, and the resulting cell pellets were resuspended in 5 mL of MACS buffer (autoMACS Running Buffer; Miltenyi Biotec, #130-091-221). The resuspended samples were filtered through a 70 μm filter and $1 \times 10^6$ cells per well were plated in a 96-well V-bottom plate. Cells were then centrifuged and the pellets were washed in 1×PBS. After a second centrifugation, the cell pellets were resuspended in 100 μL of LIVE/DEAD® Fixable Blue Dead Cell Stain (Life Technologies, #L23105) diluted at 1:500 in 1×PBS to determine cell viability and incubated for 20 minutes at room temperature while protected from light. After one wash in 1×PBS, cells were incubated in a solution of MACS buffer containing 10 μg/mL of purified rat anti-mouse CD16/CD32 Fc Block, (Clone: 2.4G2; BD Biosciences, #553142) for 10 minutes at 4° C. The cells were then incubated in the appropriate 2× antibody mixture (described in Table 7) diluted in MACS buffer for 30 minutes at 4° C. while protected from light. After antibody incubation, the cells were washed twice in MACS buffer, resuspended in BD CytoFix (BD Biosciences, #554655) and then incubated for 15 minutes at 4° C. while protected from light. The cells were subsequently washed, resuspended in MACS buffer, and then transferred to BD FACS tubes (BD Biosciences, #352235) for analysis of cellular infiltrates by flow cytometry.

CD4 and CD8 T cells were defined as cells that were live, $CD45^+$, $SSC^{Lo}$, $FSC^{Lo}$, $CD3^+$, $CD19^-$, $CD4^+$, $CD8^-$ and live, $CD45^+$, $SSC^{Lo}$, $FSC^{Lo}$, $CD3^+$, $CD19^-$, $CD4^-$, $CD8^+$ respectively. Activated CD4 T cells were defined as cells that were live, $CD45^+$, $SSC^{Lo}$, $FSC^{Lo}$, $CD3^+$, $CD19^-$, $CD4^+$, $CD8^-$, and $CD69^+$. Activated CD8 T cells were defined as cells that were live, $CD45^+$, $SSC^{Lo}$, $FSC^{Lo}$, $CD3^+$, $CD19^-$, $CD4^-$, $CD8^+$, and $CD69^+$. Activated B cells were defined as cells that were live, $CD45^+$, $SSC^{Lo}$, $FSC^{Lo}$, $CD3^-$, $CD19^+$, and $CD69^+$. ST2+ CD4+ T cells were defined as cells that were live, $CD45^+$, $SSC^{Lo}$, $FSC^{Lo}$, CD3+, CD19−, ST2+ and CD4+. Eosinophils were defined as live, $CD45^+$, $GR1^-$, $CD11c^{lo}$, $SiglecF^{hi}$. Alveolar macrophages were defined as live, $CD45^+$, $GR1^-$, $CD11c^{Hi}$, $SiglecF^{hi}$. Data for activated cells is expressed as frequency of activated cells ($CD69^+$) within the parent population (CD4, ±SD). Data for ST2+ CD4+ T cells is expressed as frequency of T cells (defined as cells that were live, $CD45^+$, $SSC^{Lo}$, $FSC^{Lo}$, CD3+ and CD19−). Data for Eosinophils and Alveolar macrophages is expressed as frequency of live cells. CD4/CD8 T cells ratio is calculated as the ratio of the frequency of CD4 T to the frequency of CD8 T cells within the live population. All data is shown in Table 8.

TABLE 7

| | Antibodies Used for Flow Cytometry Analysis | | | |
|---|---|---|---|---|
| Anti-body | Fluoro-chrome | Manu-facturer | Catalogue Number | Final dilution |
| CD45.2 | PerCP-Cy5.5 | eBioscience | 45-0454 | 1/800 |
| Siglec-F | BV 421 | BD | 562681 | 1/200 |
| F4/80 | APC | eBioscience | 17-4801-82 | 1/200 |
| Ly6G | BUV395 | BD | 563978 | 1/200 |
| Ly6C | PE-Cy7 | BD | 560593 | 1/100 |
| CD11c | PE | eBioscience | 12-0114-82 | 1/200 |
| CD11b | FITC | eBioscience | 53-0112-82 | 1/200 |
| CD19 | BV650 | BD | 562701 | 1/400 |
| CD3 | PE-Cy7 | BD | 552774 | 1/200 |
| CD4 | BV421 | BioLegend | 100438 | 1/200 |
| CD8 | BUV 395 | BD | 563786 | 1/400 |
| NKp46 (CD335) | FITC | eBioscience | 11-3351 | 1/800 |
| CD69 | PE | eBioscience | 12-0691 | 1/200 |
| CD25 | BV510 | BioLegend | 102042 | 1/200 |
| ST2 | APC | BioLegend | 145306 | 1/200 |

Pulmonary Cell Infiltrate Analysis:

As shown in table 8, the frequency of eosinophils, activated B cells, activated CD8 cells, ST2+ Cd4+ T cells and CD4/CD8 T cells ratio in the lungs of IL-33 HumIn mice receiving HDM for 15 weeks, with or without treatment with an isotype control antibody were significantly higher than in IL-33 HumIn mice challenged with 1×PBS alone. Similarly, there was a trend towards an increased frequency of activated CD4 T cells in the lungs of IL-33 HumIn mice receiving HDM for 15 weeks. There was a trend towards a decreased frequency of alveolar macrophages detected by flow cytometry in the lungs of IL-33 HumIn mice receiving HDM for 15 weeks, in the absence or presence of an isotype control antibody treatment. The frequency of alveolar macrophages was significantly increased in the lungs of IL-33 HumIn mice treated with a combination of anti-IL-33 and anti-mouse IL-4Rα antibodies during the last four weeks of the chronic HDM challenge as compared to IL-33 HumIn mice administered HDM with an isotype control antibody during this time period. Similarly, there was a trend towards reduced frequency of eosinophils, activated CD4 and CD8 T cells, activated B cells, ST2+CD4+ T cells as well as CD4/CD8 T cells ratio in the lungs of mice treated with a combination of anti-IL-33 and anti-mouse IL-4Rα antibodies during the last four weeks of the chronic HDM challenge as compared to IL-33 HumIn mice administered HDM with an isotype control antibody during this time period. The effects on frequency of eosinophils, alveolar macrophages, activated CD8 T cells, ST2+ CD4+ T cells and CD4/CD8 ratio in the lung observed for the combination anti-IL-33 and anti-mouse IL-4Rα antibodies shows a trend towards greater efficacy than treatment with either individual antibodies alone.

TABLE 8

| Experimental group | Mean Frequency of Eosinophils in the live population (±SD) | Mean Frequency of Alveolar Macrophages in the live population (±SD) | Mean CD4/CD8 T cells ratio (±SD) | Mean Frequency of Activated cells in CD4 T cells population (±SD) | Mean Frequency of Activated cells in CD8 T cells population (±SD) | Mean Frequency of Activated cells in B cells population (±SD) | Mean Frequency of ST2+ CD4+ cells in T cells population (±SD) |
|---|---|---|---|---|---|---|---|
| 1. 1X PBS challenge (n = 5) | 1.45 (±0.92) | 5.05 (±1.64) | 3.00 (±1.48) | 13.12 (±9.89) | 3.26 (±1.64) | 0.39 (±1.17) | 3.25 (±4.15) |

TABLE 8-continued

Frequency of pulmonary cell infiltrate as determined by flow cytometry

| Experimental group | Mean Frequency of Eosinophils in the live population (±SD) | Mean Frequency of Alveolar Macrophages in the live population (±SD) | Mean CD4/CD8 T cells ratio (±SD) | Mean Frequency of Activated cells in CD4 T cells population (±SD) | Mean Frequency of Activated cells in CD8 T cells population (±SD) | Mean Frequency of Activated cells in B cells population (±SD) | Mean Frequency of ST2+ CD4+ cells in T cells population (±SD) |
|---|---|---|---|---|---|---|---|
| 2. HDM challenge 11 weeks (n = 4) | 17.08 (±3.94)* | 2.34 (±0.93) | 6.42 (±2.71) | 49.95 (±8.76) | 9.58 (±7.44) | 4.67 (±1.47)** | 32.60 (±12.23) |
| 3. HDM challenge 15 weeks (n = 4) | 15.40 (±3.99)* | 4.92 (±1.55) | 6.95 (±0.71)** | 58.53 (±5.76) | 15.68 (±3.03)* | 3.70 (±1.44)* | 37.33 (±8.98)* |
| 4. HDM challenge 15 weeks + isotype control antibody (n = 4) | 15.00 (±3.35)* | 2.33 (±1.60) | 7.49 (±1.28)* | 57.75 (±7.64) | 14.59 (±3.82) | 3.90 (±1.48)* | 37.96 (±16.71)* |
| 5. HDM challenge 15 weeks + anti-IL-33 antibody (n = 5) | 8.51 (±7.52) | 7.44 (±4.18) | 4.03 (±1.28) | 48.22 (±5.66) | 13.86 (±5.21) | 1.72 (±0.72) | 19.24 (±5.72) |
| 6. HDM challenge 15 weeks + anti-mouse IL-4Rα antibody (n = 5) | 12.30 (±7.83) | 9.93 (±5.18) | 5.56 (±2.22) | 53.42 (±6.52) | 13.11 (±6.26) | 2.14 (±1.23) | 35.01 (±9.83)* |
| 7. HDM challenge 15 weeks + anti-IL-33 + anti-mouse IL-4Rα antibodies (n = 5) | 3.78 (±1.60) | 14.64 (±3.86) † | 2.96 (±0.93) | 42.52 (±9.79) | 7.90 (±1.30) | 1.74 (±0.91) | 11.78 (±3.73) |

Note:
Statistical significance determined by Kruskal-Wallis One-way ANOVA with Dunn's multiple comparison post-hoc test is indicated (*= $p < 0.05$, **= $p < 0.01$, compared to groups 1: IL33 HumIn mice, Saline challenge;
† $p < 0.05$, compared to group 4: IL33 Humin mice, HDM challenge 15 weeks + Isotype control antibody).

Lung Harvest for Quantification of Histopathology:

The inflammatory pattern observed in this model is accompanied by widespread and severe structural changes in HDM-exposed lungs, with evidence of goblet cell metaplasia, increases in sub-epithelial collagen deposition and significant pulmonary consolidation. These pathologies are known features of human inflammatory respiratory diseases that contribute to decline of lung function and airway hyperreactivity (James, (2007) Eur Respir J., July; 30(1): 134-55; Jeong, (2007) Radiographics May-June; 27(3):617-37).

After exsanguination, the left lungs were removed and placed into plates containing a 3 mL solution of 4% (w/v) paraformaldehyde (Boston Bioproducts, #BM-155) in 1× phosphate buffered saline and stored at room temperature for 3 days. Lung samples were then blotted dry and transferred to tubes containing 70% ethanol for histological analysis.

The samples were sent to Histoserv, Inc (Germantown, MD) for paraffin embedding, sectioning and periodic acid Schiff (PAS) or Hematoxylin and Eosin (H&E) staining.

Quantification of Goblet Cell Metaplasia:

Goblet cell metaplasia and mucus hyper-secretion are hallmarks of many pulmonary diseases including asthma, chronic obstructive pulmonary disease, and cystic fibrosis (Boucherat, (2013) Exp Lung Res. 2013 May-June; 39(4-5):207-16). Excessive mucus production leads to airway obstruction and affects several important outcomes such as lung function, health-related quality of life, exacerbations, hospitalizations, and mortality in humans (Ramos, F L, et. al., (2014), Int J Chron Obstruct Pulmon Dis, January 24; 9:139-150). PAS-positive goblet cells and total epithelial cells were counted in a millimeter length of the primary bronchus. Goblet cell metaplasia is expressed as the frequency of PAS-positive cells in a millimeter of bronchial epithelium (%, +SD) as shown in Table 9.

Quantification of Lung Consolidation:

"Lung consolidation" is defined as the accumulation of solid or liquid material in the alveolar space. Lung consolidation is a compound endpoint likely reflecting the combination of cellular infiltrate, hyperplasia, and mucus production, used here as a measurement of gross pathology. The fraction of lung area occupied by the crystal bodies was quantified on Movat pentachrome stained paraffin-embedded lung sections using ImageJ software (NIH, Bethesda, MD). Using the particle analysis function, total lung area in the section, as well as consolidated area in the section were measured. The fraction of consolidated lung area is given by the ratio of both measurements, as shown in Table 9.

Quantification of Sub-Epithelial Fibrosis

"Sub-epithelial fibrosis" is defined as an excess of interstitial collagen deposition beneath the pulmonary epithelium (Redington, et. al., (1997), Thorax, April; 52(4):310-312). Increased sub-epithelial fibrosis has been reported to be specifically associated with asthma in humans (Boulet, et. al., (1997) Chest, July; 112(1):45-52; James, A L and Wenzel, S., (2007), Eur Respir J, July, 30(1):134-155). In the present model, sub-epithelial fibrosis was measured on Masson's trichrome stained paraffin-embedded lung sections using HaLo software (Indica Labs, NM). Using the 'Layer thickness' tool, the thickness of the collagen layer beneath the bronchial epithelium was recorded multiple times, with about 30 µm intervals, across a millimeter of the primary bronchus. Sub-epithelial fibrosis is expressed as the mean thickness of the collagen layer beneath the epithelium (µm, ±SD) as shown in Table 9.

Analysis of Lung Histopathology:

As shown in table 9, there was a trend towards an increase in goblet cell metaplasia in the lungs of IL-33 HumIn mice receiving HDM for 15 weeks, with or without treatment with an isotype control antibody compared to IL-33 HumIn mice challenged with 1×PBS alone. Similarly, there was a significant increase in lung consolidation, as well as in sub-epithelial collagen thickness, in IL-33 HumIn mice receiving HDM for 15 weeks.

In contrast, there was trend towards a reduction in goblet cell metaplasia and sub-epithelial collagen thickness, and a significant reduction in lung consolidation in IL-33 HumIn mice treated with a combination of anti-IL-33 and anti-mouse IL-4Rα antibodies during the last four weeks of the chronic HDM challenge as compared to IL-33 HumIn mice administered HDM with an isotype control antibody during this time period. The effects on goblet cell metaplasia, lung consolidation and sub-epithelial collagen thickness observed for the combination anti-IL-33 and anti-mouse IL-4Rα antibodies showed a trend towards greater efficacy than treatment with either individual antibodies alone.

TABLE 9

| | Quantification of histopathology in mouse lungs | | |
|---|---|---|---|
| Experi-mental group | Mean Goblet cell metaplasia (% PAS-positive cells) (±SD) | Mean lung consolidation (% ±SD) | Mean sub-epithelial collagen thickness (µm) (±SD) |
| 1. 1X PBS challenge (n = 5) | 32.94 (±43.61) | 6.97 (±3.72) | 25.90 (±4.00) |

TABLE 9-continued

| | Quantification of histopathology in mouse lungs | | |
|---|---|---|---|
| Experi-mental group | Mean Goblet cell metaplasia (% PAS-positive cells) (±SD) | Mean lung consolidation (% ±SD) | Mean sub-epithelial collagen thickness (µm) (±SD) |
| 2. HDM challenge 11 weeks (n = 4) | 59.98 (±39.01) | 70.70 (±12.94) | 81.76 (±25.37) * |
| 3. HDM challenge 15 weeks (n = 4) | 92.15 (±10.16) | 83.21 (±3.65) ** | 82.12 (±23.04) * |
| 4. HDM challenge 15 weeks + isotype control antibody (n = 4) | 81.60 (±17.56) | 84.16 (±5.85) ** | 63.11 (±11.87) |
| 5. HDM challenge 15 weeks + anti-IL-33 antibody (n = 5) | 39.22 (±18.93) | 58.82 (±18.26) | 70.99 (±23.85) |
| 6. HDM challenge 15 weeks + anti-mouse IL-4Rα antibody (n = 5) | 79.82 (±25.02) | 57.79 (±18.72) | 57.62 (±15.34) |
| 7. HDM challenge 15 weeks + anti-IL-33 + anti-mouse IL-4Rα antibodies (n = 5) | 19.69 (±8.80) | 35.01 (±20.68) | 48.19 (±18.58) |

Note:
Statistical significance determined by Kruskal-Wallis One-way ANOVA with Dunn's multiple comparison post-hoc test is indicated (** = p < 0.01, compared to groups 1: IL33 HumIn mice, Saline challenge).

Serum Collection for IgE and HDM-Specific IgG1 Levels Measurement:

To determine the total IgE concentration in the serum samples for each mouse, a sandwich ELISA OPTEIA kit (BD Biosciences, #555248) was used according to the manufacturer's instructions. Serum samples were diluted and incubated with anti-IgE capture antibody coated on 96-well plates. Total IgE was detected by biotinylated anti-mouse IgE secondary antibody. Purified horseradish peroxidase (HRP)-labeled mouse IgE was used as a standard. The chromagen 3,3',5,5'-tetramethylbenzidine (TMB) (BD OPTEIA substrate reagent set, BD, #555214) was used to detect HRP activity. A stop solution of 1 M sulfuric acid was then added, and absorbance at 450 nm was measured on a Molecular Devices SpectraMax M5 plate reader. Data analysis was performed using Prism™ software. The mean amounts of circulating IgE levels in serum for each experimental group are expressed as ng/ml (±SD) as shown in Table 10.

To determine the HDM specific IgG1 levels in the serum samples from each mouse, an ELISA was utilized. HDM (Greer, #XPB70D3A2.5) coated plates were incubated with serially diluted mouse serum samples, followed by incubation with a rat anti-mouse IgG1-HRP conjugated antibody (BD Biosciences, #559626). All samples were developed with a TMB solution and analyzed as described above.

Relative levels of circulating IgG1 in serum were represented as titer units (titer units were calculated by multiplying the measured OD by a dilution factor required to achieve OD450 that was greater than two times background). The mean circulating HDM-specific IgG1 levels in serum for each experimental group are expressed as titer×$10^6$ (±SD) as shown in Table 10.

Analysis of the Circulation Levels of IgE and HDM-Specific IgG1

As shown in table 10, there was a significant increase in circulating levels of IgE in the serum of IL-33 HumIn mice receiving HDM for 15 weeks, with or without treatment with an isotype control antibody in IL-33 HumIn mice challenged with 1×PBS alone. Similarly, there was a trend towards an increased level of circulating HDM-specific IgG1 in the serum of IL-33 HumIn mice receiving HDM for 15 weeks. In contrast, there was a significant decrease in circulating levels of IgE and a trend towards a decrease in circulating levels of HDM-specific IgG1 in the serum of IL-33 HumIn mice treated with a combination of anti-IL-33 and anti-mouse IL-4Rα antibodies during the last four weeks of the chronic HDM challenge as compared to IL-33 HumIn mice administered HDM with an isotype control antibody.

TABLE 10

Circulating levels of IgE and
HDM-specific IgG1 in mouse serum.

| Experimental group | Mean circulating IgE levels (µg/mL) (±SD) | Mean circulating HDM-specific IgG1 levels (Titer × $10^6$) (±SD) |
| --- | --- | --- |
| 1. 1X PBS challenge (n = 5) | 2.16 (±2.02) | ND |
| 2. HDM challenge 11 weeks (n = 4) | 50.16 (±8.35) | 1.18 (±0.15) |
| 3. HDM challenge 15 weeks (n = 4) | 131.38 (±106.84) * | 1.88 (±0.81) |
| 4. HDM challenge 15 weeks + isotype control antibody (n = 4) | 193.07 (±78.96) *** | 1.62 (±0.62) |
| 5. HDM challenge 15 weeks + anti-IL-33 antibody (n = 5) | 45.74 (±45.74) | 1.76 (±0.98) |
| 6. HDM challenge 15 weeks + anti-mouse IL-4Rα antibody (n = 5) | 11.12 (±8.65) | 0.99 (±0.56) |
| 7. HDM challenge 15 weeks + anti-IL-33 + anti-mouse IL-4Rα antibodies (n = 5) | 6.45 (±5.79) † | 0.75 (±0.30) |

Note:
Statistical significance determined by Kruskal-Wallis One-way ANOVA with Dunn's multiple comparison post-hoc test is indicated (* = p < 0.05,  = p < 0.01, * = p < 0.001, compared to groups 1: IL33 HumIn mice, Saline challenge; † p < 0.05, compared to group 4: IL33 HumIn mice, HDM challenge 15 weeks + Isotype control antibody). ND: Not determined.

A combination of H4H9675P and anti-mIL-4Rα treatment initiated in the context of severe, mixed inflammation improves all inflammatory parameters measured, reducing most to baseline levels. Additionally, additive effects are observed on some of the most pernicious endpoints, including composite lung gross pathology, goblet cell metaplasia, lung cellular infiltration, and cytokine levels. Therefore, blocking both pathways simultaneously has the potential to impact multiple inflammatory mediators in the context of severe mixed inflammation and tissue pathology, and normalize multiple parameters to baseline.

Example 5: Epitope Mapping H4H9675P Binding
to IL33 by Hydrogen Deuterium Exchange In order to determine the epitopes of human IL33 recognized by an anti-IL33 antibody, H4H9675P, hydrogen-deuterium (H/D) exchange studies were performed for the antibody co-complexed with human IL33. For the experiments recombinant human IL33 expressed with a C-terminal hexahistidine tag (SEQ ID NO: 356) was used. A general description of the H/D exchange method has been set forth in Ehring et al. (1999) *Analytical Biochemistry* 267(2):252-259 and Engen and Smith (2001) *Anal. Chem.* 73:256A-265A. H/D exchange experiments were performed on an integrated Waters HDX/MS platform, consisting of a Leaptec HDX PAL system for the deuterium labeling, a Waters Acquity M-Class (Auxiliary solvent manager) for the sample digestion and loading, a Waters Acquity M-Class (µBinary solvent manager) for the analytical column gradient, and Synapt G2-Si mass spectrometer for peptic peptide mass measurement.

The labeling solution was prepared in 10 mM PBS buffer in $D_2O$ at pD 7.0 (equivalent to pH 6.6). For deuterium labeling, 3.8 µL of hIL33-MMH (96 pmol/µL) or hIL33-MMH premixed with the antibody in a 1:1 molar ratio was incubated with 56.2 µL $D_2O$ labeling solution for various time-points (2 min, 10 min, and undeuterated control=0 sec). The deuteration was quenched by transferring 50 µL of the sample to 50 µL of pre-chilled 0.2 M TCEP, 6 M guanidine chloride in 100 mM phosphate buffer at pH 2.5 (quench buffer) and the mixed sample was incubated at 1.0° C. for two minutes. The quenched sample was then injected into a Waters HDX Manager for online pepsin/protease XIII digestion. The digested peptides were trapped onto an ACQUITY UPLC BEH C18 1.7-µm, 2.1×5 mm VanGuard pre-column at 0° C. and eluted to an ACQUITY UPLC BEH C18 1.7-µm, 1.0×50 mm column using a 9-minute gradient separation of 5%-40% B (mobile phase A: 0.1% formic acid in water, mobile phase B: 0.1% formic acid in acetonitrile). The mass spectrometer was set at cone voltage of 37 V, scan time of 0.5 s, and mass/charge range of 50-1700 Th.

For the identification of the peptides from hIL33-MMH, LC-MS$^E$ data from undeuterated sample were processed and searched against the database including human IL33, pepsin, and their randomized sequences via Waters ProteinLynx Global Server (PLGS) software. The identified peptides were imported to DynamX software and filtered by two criteria: 1) minimum products per amino acid: 0.3, and 2) replication file threshold: 3. DynamX software then automatically determined deuterium uptake of each peptide based on retention time and high mass accuracy (<10 ppm) across multiple time points with 3 replicates at each time point.

Using the online pepsin/protease XIII column coupled with MSE data acquisition, a total of 68 peptides from hIL33-MMH were identified in the absence or presence of H4H9675P, representing 95% sequence coverage. Eleven peptides had significantly reduced deuteration uptake (centroid delta values >0.4 daltons with p-values <0.05) when bound to H4H9675P and are listed in Table 11. The recorded peptide mass corresponds to the average value of the centroid MH$^+$ mass from three replicates. These peptides, corresponding to amino acids 1-12 and 50-94 of SEQ ID NO: 349), had a slower deuteration rate by the binding of H4H9675P. These identified residues also correspond to residues 112-123 and 161-205 of human IL-33 as defined by Uniprot entry O95760 (IL33_HUMAN; see also SEQ ID NO: 348). These data provide support for amino acid residues 112-123 and 161-205 of SEQ ID NO: 348, or amino acid residues 1-12 and 50-94 of SEQ ID NO: 349 defining at least in part the binding region in IL-33 for antibody H4H9675P.

TABLE 11

| Human IL33 peptides with significant reduced deuteration upon binding to H4H9675P | | | | | | |
|---|---|---|---|---|---|---|
| Residue numbers based on | 2 min Deuteration | | | 10 min Deuteration | | |
| SEQ ID NO: 349 | IL33 Centroid MH⁺ | IL33 + H4H9675P Centroid MH⁺ | Δ | IL33 Centroid MH⁺ | IL33 + H4H9675P Centroid MH⁺ | Δ |
| 1-9 | 893.43 + 0.06 | 891.89 + 0.02 | −1.54 | 893.60 + 0.03 | 892.00 + 0.08 | −1.60 |
| 1-10 | 1023.15 + 0.06 | 1021.53 + 0.05 | −1.62 | 1023.31 + 0.01 | 1021.69 + 0.03 | −1.63 |
| 1-11 | 1186.18 + 0.06 | 1184.39 + 0.13 | −1.80 | 1186.43 + 0.02 | 1184.61 + 0.03 | −1.82 |
| 1-12 | 1300.27 + 0.07 | 1297.88 + 0.04 | −2.39 | 1300.60 + 0.03 | 1298.65 + 0.01 | −1.95 |
| 50-61 | 1458.12 + 0.06 | 1456.36 + 0.00 | −1.75 | 1458.27 + 0.08 | 1456.34 + 0.01 | −1.93 |
| 52-67 | 1791.16 + 0.12 | 1789.89 + 0.25 | −1.27 | 1791.20 + 0.02 | 1790.27 + 0.02 | −0.93 |
| 52-72 | 2353.80 + 0.12 | 2351.27 + 0.05 | −2.53 | 2353.89 + 0.03 | 2351.95 + 0.10 | −1.94 |
| 53-70 | 1945.19 + 0.10 | 1944.26 + 0.07 | −0.93 | 1945.25 + 0.02 | 1944.84 + 0.03 | −0.41 |
| 53-72 | 2189.95 + 0.13 | 2188.03 + 0.03 | −1.92 | 2190.02 + 0.02 | 2188.58 + 0.04 | −1.44 |
| 71-81 | 1253.89 + 0.07 | 1253.08 + 0.18 | −0.81 | 1254.07 + 0.02 | 1253.52 + 0.16 | −0.55 |
| 71-94 | 2815.35 + 0.05 | 2814.48 + 0.00 | −0.87 | 2816.06 + 0.12 | 2815.10 + 0.12 | −0.96 |

Example 6: Effect of an IL-33 Antibody (REGN3500) and an IL-4R Antibody (Dupilumab), Alone or in Combination, in a 19-Week Model of Allergen Induced Lung Inflammation Using IL-33-, IL-4-, and IL-4Ralpha-Humanized Mice The effect of an IL-33 antibody alone, an IL-4R antibody alone, or a combination of both antibodies was first tested in Example 4 above, using mice that were homozygous for the expression of human IL-33 in place of mouse IL-33 (IL-33 HumIn mice; See US Patent Publication Nos. 2015/0320021 and 2015/0320022). A fully human anti-IL-33 antibody (REGN3500), and an anti-mouse IL-4Rα antibody or a combination of both was compared in this model and the results described in Example 4.

Since neither the human anti-IL-33 antibody (REGN3500), nor the human anti-IL-4R antibody (dupilumab) bind their respective murine target proteins, genetically modified mice, in which mouse IL-33, IL-4, and the ectodomain of IL-4Rα were replaced with the corresponding human sequences (Il4ra$^{hu/hu}$ Il4$^{hu/hu}$ Il33$^{hu/hu}$), were generated. The Il4ra$^{hu/hu}$ Il4$^{hu/hu}$ Il33$^{hu/hu}$ mouse strain was validated as a tool to study the effect of REGN3500 and dupilumab administration using a 4-week model of HDM exposure-induced lung inflammation. In this model, HDM-exposed Il14ra$^{hu/hu}$ Il4$^{hu/hu}$ Il33$^{hu/hu}$ mice demonstrated immune responses similar to wild-type mice as assessed by evaluation of eosinophilic lung infiltration.

The study described below was conducted to determine if simultaneous blockade of the IL-33 and IL-4/IL-13 pathways could have a greater impact on lung inflammation than blocking either pathway alone. In this study, Il4ra$^{hu/hu}$ Il4$^{hu/hu}$ Il33$^{hu/hu}$ mice were intranasally (IN) exposed to HDM or saline for 19 weeks. A control group of Il4ra$^{hu/hu}$ Il4$^{hu/hu}$ Il33$^{hu/hu}$ mice was sacrificed after 11 weeks of HDM exposure to assess disease severity at the onset of antibody treatment. Nineteen-week HDM-exposed mice either received no antibody treatment, or received twice-weekly subcutaneous (SC) antibody injections from week 12 to week 19 of HDM exposure for a total of 8 weeks and 16 doses. The following antibodies were administered at a final protein dose of 11 mg/kg: (a) 11 mg/kg isotype control antibody, (b) 1 mg/kg REGN3500+10 mg/kg isotype control antibody (c) 10 mg/kg dupilumab+1 mg/kg isotype control antibody, or (d) 1 mg/kg REGN3500+10 mg/kg dupilumab.

The effect of REGN3500 and dupilumab treatment, alone or in combination, on HDM-exposed mice was assessed for the following pathological markers of airway inflammation:

Gross pathology (relative lung weight)

Lung tissue infiltration by type 1 inflammatory cells (neutrophils, quantified by lung protein levels of the neutrophil marker Myeloperoxidase [MPO]) and type 2 inflammatory cells (total and activated [CD11c$^{Hi}$] eosinophils and ST2$^+$ CD4$^+$ T cells, quantified by flow cytometry)

Inflammatory cytokine lung protein levels (human IL-4 and mouse IL-5, IL-6, IL-1β, TNFα, IFNγ, GROα, and MCP-1, quantified by immunoassay)

Circulating levels of the systemic marker of inflammation, serum amyloid A [SAA] protein (quantified by immunoassay)

Materials and Methods

Test System

IL-33-, IL-4-, and IL-4Rα Ectodomain-Humanized Mice

Neither REGN3500 nor dupilumab bind mouse IL-33 or mouse IL-4Rα respectively. Therefore, in order to test REGN3500 and dupilumab side by side and in combination, genetically modified mice were generated in which mouse IL-33, IL-4, and the ectodomain of IL-4Rα were replaced with the corresponding human sequences (Il4ra$^{hu/hu}$ Il4$^{hu/hu}$ Il33$^{hu/hu}$). This triple-humanized mouse strain was generated using VelociGene® technology at Regeneron Pharmaceuticals (Valenzuela, D M, et al. Nat Biotechnol. (2003), June; 21(6):652-9, Poueymirou, W T, et al. Nat Biotechnol. (2007) January; 25(1):91-9) by crossing the previously characterized IL-4/IL-4Rα ectodomain-humanized mouse strain Il4ra$^{hu/hu}$ Il4$^{hu/hu}$ with the previously characterized IL-33-humanized strain Il33$^{hu/hu}$ Lung Inflammation Mouse Model The mouse lung inflammation model employs repeated intranasal (IN) exposure to HDM extract that serves as the source of house dust mite allergen (Johnson, et al.; American Journal of Respiratory and Critical Care Medicine; (2004) February 1; 169 (3):378-85), a significant cause of indoor allergy in humans (Calderon, et al., (2015), Respiratory allergy caused by house dust mites: What do we really know? J Allergy Clin Immunol. 2015 July; 136 (1):38-48). Chronic exposure to HDM is reported to induce severe lung inflammation resulting in significant pulmonary cellular infiltrate, cytokine expression, and remodeling. In particular, it has been demonstrated that mice chronically exposed to HDM exhibit lung inflammation of mixed type 1/type 2 phenotypes such as tissue infiltration by type 1 and type 2 inflammatory cells (neutrophils and eosinophils, respectively), increased serum IgE, increased serum HDM-specific IgG1, as well as induction of type 2 inflammatory cytokines such as IL-5 and IL-13 (Johnson, et al. (2004), American Journal of Respiratory and Critical Care Medicine; February 1; 169 (3):378-85; Johnson, et al. (2011). PloS ONE. January 20; 6 (1):e16175; Llop-Guevara, et al., (2008), PloS ONE, June 11; 3(6):e2426.

Experimental Design

Four-Week HDM Exposure-Induced Lung Inflammation Model

Female mice of the genotypes indicated in Table 12 were randomized into 2 groups each per genotype. Saline (20 μL) or 50 μg HDM diluted in 20 μL of saline solution were administered IN 3 times per week for 4 weeks. All mouse strains were of a mixed C57BL/6NTac/129S6SvEvTac background. Mice were sacrificed 4 days after the last exposure, lungs were harvested, and eosinophilic lung infiltration was determined.

TABLE 12

Experimental Protocol for 4-week HDM Model

| Group | Genotype | N | Exposure Reagent | Duration of Exposure (weeks) |
|---|---|---|---|---|
| A | Wild type | 3 | 20 μL Saline | 4 |
| B | Wild type | 5 | 50 μg HDM | 4 |
| C | Il33$^{hu/hu}$ | 5 | 20 μL Saline | 4 |
| D | Il33$^{hu/hu}$ | 5 | 50 μg HDM | 4 |
| E | Il4ra$^{hu/hu}$ | 5 | 20 μL Saline | 4 |
| F | Il4ra$^{hu/hu}$ | 5 | 50 μg HDM | 4 |
| G | Il4ra$^{hu/hu}$ Il4$^{hu/hu}$ | 5 | 20 μL Saline | 4 |
| H | Il4ra$^{hu/hu}$ Il4$^{hu/hu}$ | 5 | 50 μg HDM | 4 |
| I | Il4ra$^{hu/hu}$ Il4$^{hu/hu}$ Il33$^{hu/hu}$ | 4 | 20 μL Saline | 4 |
| J | Il4ra$^{hu/hu}$ Il4$^{hu/hu}$ Il33$^{hu/hu}$ | 5 | 50 μg HDM | 4 |

Wild type = C57BL/6NTac/129S6SvEvTac

Nineteen-Week HDM Exposure-Induced Lung Inflammation Model

Il4ra$^{hu/hu}$ Il4$^{hu/hu}$ Il3$^{hu/hu}$ mice used in this study were of a mixed background C57BL/6NTac (72%)/129S6SvEvTac (28%); female mice were randomized into 7 separate groups. The HDM exposure and treatment or control dosing protocol for each group of mice is shown in Table 13. Saline (20 μL) or 50 μg HDM diluted in 20 μL of saline solution were administered IN 3 times per week for 19 weeks. A control group of Il4ra$^{hu/hu}$ Il4$^{hu/hu}$ Il33$^{hu/hu}$ mice were sacrificed after 11 weeks of HDM exposure to assess disease severity at the onset of antibody treatment. Nineteen-week HDM-exposed mice either received no antibody treatment, or received twice-weekly subcutaneous (SC) injections from week 12 to week 19 of HDM exposure for a total of 16 antibody doses as indicated in Table 13. In brief, the following antibodies were administered at a final protein dose of 11 mg/kg: 11 mg/kg isotype control antibody (group D), 1 mg/kg REGN3500+10 mg/kg isotype control antibody (group E), 10 mg/kg dupilumab+1 mg/kg isotype control antibody (group F), or 1 mg/kg REGN3500+10 mg/kg dupilumab (group G). For the purpose of this document, the dual antibody treatment groups (D-G) will only be identified by the therapeutic antibody (REGN3500 and/or dupilumab). On day 134 of the study, 4 days after the last IN exposure and antibody injection, all mice were sacrificed, blood was collected via cardiac puncture, and lungs were harvested for analysis.

TABLE 13

Experimental Protocol for 19-week HDM Model

| Group | N | Exposure Reagent | Duration of Exposure (weeks) | Antibody Administration | Antibody Dose (mg/kg) |
|---|---|---|---|---|---|
| A | 5 | 20 μL Saline | 19 | None | None |
| B | 9 | 50 μg HDM | 11 | None | None |
| C | 9 | 50 μg HDM | 19 | None | None |
| D | 9 | 50 μg HDM | 19 | IgG4$^P$ Control | 11 |
| E | 7 | 50 μg HDM | 19 | REGN3500 + IgG4$^P$ Control | 1 + 10 |
| F | 8 | 50 μg HDM | 19 | dupilumab + IgG4$^P$ Control | 10 + 1 |
| G | 8 | 50 μg HDM | 19 | REGN3500 + dupilumab | 1 + 10 |

IgG4$^P$ Control = isotype-matched control antibody, REGN1945.

Mouse Husbandry

For the entire duration of each experiment, animals remained housed in the Regeneron animal facility under standard conditions, and were allowed to acclimate for at least 7 days prior to being placed on study. All animal experiments were performed in accordance with the guidelines for the Institutional Animal Care and Use Committee at Regeneron.

Specific Procedures

Relative Lung Weight Measurement

A terminal body weight measurement was recorded before sacrifice. After exsanguination, the left lung from each mouse was removed and placed into a tube containing a solution of 4% paraformaldehyde. Wet weight of the left lung for each mouse was recorded on a Mettler Toledo New Classic MS scale. To determine relative lung weights, the ratio of lung wet weight (in mg) to body weight (in g) was calculated by dividing the lung wet weight by the body weight.

Analysis of Cellular Pulmonary Infiltrates

After exsanguination, the caudal lobe of the right lung from each mouse was removed, placed into a tube containing a solution of 20 μg/mL DNase I and 0.7 U/mL Liberase TH diluted in Hank's Balanced Salt Solution (HBSS), and cut into pieces that were approximately 2 to 3 mm in size. The tubes containing diced lung lobes were then incubated in a 37° C. water bath for 20 minutes. The reaction was stopped by adding ethylenediaminetetraacetic acid (EDTA) at a final concentration of 10 mM. The samples were then transferred to gentleMACS C Tubes. Then, 2 mL of autoMACS buffer was added and the samples were subsequently dissociated to form single cell suspensions using a gentleMACS™ dissociator (Miltenyi Biotec). The tubes were then centrifuged and the resulting pellet was resuspended in 4 mL of 1× Red Blood Cell Lysing Buffer to lyse red blood cells. After incubation for 3 minutes at room temperature, 2.5 times volume of 1×DPBS was added to deactivate the red blood cell lysing buffer. The cell suspensions were then centrifuged, and the resulting cell pellets were resuspended in 1 mL of DPBS. The resuspended samples were each filtered through a 50 μm cup-type filcon and transferred to a 2 mL deep well plate. The plate was centrifuged for 4 min at 400×g and each sample resuspended in 1 mL DPBS. Approximately $1.5 \times 10^6$ cells per well were plated in a 96-well U-bottom plate. Cells were then centrifuged and the cell pellets resuspended in 100 µL of LIVE/DEAD Fixable Dead Cell Stain diluted at 1:500 in 1× DPBS to determine cell viability. Cells were incubated with the viability dye for 15 minutes at room temperature while protected from light. After one wash in 1×DPBS, cells were incubated with purified rat anti-mouse CD16/CD32 Fc Block diluted 1:50 in 50 µL of autoMACS buffer for 15 minutes at 4° C. The cells were then incubated in the appropriate 2× antibody mixture diluted in Brilliant Stain Buffer (described in Table 14) for 30 minutes at 4° C. while protected from light. After antibody incubation, the cells were washed twice in autoMACS buffer, resuspended in BD CytoFix that had been diluted 1:4 in 1×DPBS and then incubated for 15 minutes at 4° C. while protected from light. The cells were subsequently washed and resuspended in autoMACS buffer. Cell suspensions were then filtered into a new U-Bottom plate through an AcroPrep Advance 96 Filter Plate 30-40 µm. Sample data were acquired on a LSR Fortessa X-20 cell analyzer using the HTS attachment (BD Biosciences). Data analysis was performed using FlowJo X Software (Tree Star, OR) and statistical analysis was performed using GraphPad Prism™ (GraphPad Software, CA).

Gating Strategy for Eosinophils (Total and Activated)

Eosinophils were defined as intact, single, live cells (low LIVE/DEAD viability dye signal), CD45+, F4/80+, Ly6G−, SiglecF+. Data for eosinophils were expressed as frequency of live cells. Within the eosinophil population, activated eosinophils were defined as intact, single, live, CD45+, F4/80+, Ly6G−, SiglecF+, CD11c$^{Hi}$ and expressed as frequency of total eosinophils.

Gating Strategy for ST2+ CD4+ T Cells

ST2+ CD4+ T cells were defined as intact, single, live, CD45+, CD3+, CD19, CD4+, CD8−, ST2+. Data for ST2+ CD4+ T cells were expressed as frequency of CD4+ T cells (intact, single, live, CD45+, CD3+, CD19−, CD4+, CD8−).

TABLE 14

Antibodies Used for Flow Cytometry Analysis

| Anti-body | Fluoro-chrome | Manu-facturer | Catalog # | Lot # | Final dilution |
|---|---|---|---|---|---|
| Mix 1: Total and Activated Eosinophils | | | | | |
| CD45 | Alexa Fluor 700 | BioLegend | 103128 | B191240/B211311 | 1/200 |
| Siglec-F | BV421 | BD | 562681 | 4234913/6007723 | 1/200 |
| F4/80 | PE | BD | 565410 | 5168713/5257914 | 1/500 |
| Ly6G | BUV395 | BD | 563978 | 5156800/7103737 | 1/200 |
| CD11c | PerCP-Cy5.5 | BD | 560584 | 5148566/7074758 | 1/200 |
| Mix 2: ST2+ CD4+ T Cells | | | | | |
| CD45 | Alexa Fluor 700 | BioLegend | 103128 | B211311 | 1/200 |
| CD19 | BUV737 | BD | 564296 | 6315651 | 1/200 |
| ST2 | PerCP-eFluor710 | eBio-science | H6-9335-82 | E17254-105 | 1/200 |
| CD3 | PE-Cy7 | BD | 552774 | 7074769 | 1/200 |
| CD8 | BUV395 | BD | 563786 | 6245983 | 1/200 |
| CD4 | BV786 | BD | 563331 | 7075503 | 1/200 |

Determination of Lung Protein Levels

After exsanguination, the cranial and middle lobes of the right lung from each mouse were removed, weighed, and placed into tubes containing a solution of tissue protein extraction reagent (T-PER) supplemented with a protease inhibitor cocktail. To achieve a final 1:8 (w/v) lung tissue weight to T-PER volume ratio, 8 µL of T-PER solution (containing the protease inhibitor cocktail) were added per mg of tissue. Lung samples were mechanically homogenized using the TissueLyser II. The resulting lysates were centrifuged to pellet debris. The supernatants containing the soluble protein extracts were transferred to fresh tubes and stored at 4° C. until further analysis. Cytokines and MPO concentrations were expressed as the total amount of protein per lobe examined (ng/lung lobe and µg/lung lobe respectively).

Cytokines Multiplex Immunoassay

Mouse cytokines (IL-5, IL-13, IL-6, IL-1β, IL-12p70, TNFα, IFNγ, GROα and MCP-1) concentrations in the lung protein extracts were measured using a multiplex immunoassay kit (Custom mouse 10-Plex, MSD), according to the manufacturer's instructions. Briefly, lung homogenate samples were diluted and incubated on plates pre-coated with capture antibodies. Calibrator proteins provided by the manufacturer were used as standards. Cytokines in the homogenates was detected by tagged detection antibodies incubated with Read Buffer. Electrochemiluminescence was immediately read on a MSD Spector® instrument. Data analysis was performed using GraphPad Prism software. The lowest concentration of standard within the linear range of each assay was defined as the assay's lower limit of quantification (LLOQ) for the respective cytokine. The LLOQ values for the individual cytokines tested were as follows: IFNγ=0.2 pg/mL, IL-1β=1.6 pg/mL, IL-5=0.2 pg/mL, IL-6=1.4 pg/mL, IL-12p70=125.8 pg/mL, IL-13=24.4 pg/mL, GROα: 0.5 pg/mL, MCP-1=9.8 pg/mL, TNFα=2.4 pg/mL.

Human IL-4 ELISA

Human IL-4 concentrations in the lung protein extracts were measured using a sandwich ELISA kit according to the manufacturer's instructions (Human IL-4 Quantikine ELISA, R&D Systems). Briefly, lung homogenates were diluted and incubated on 96-well plates pre-coated with anti-human IL-4 capture antibody. Purified human IL-4 was used as a standard. Captured human II-4 was detected using HRP-conjugated anti-human IL-4 detection antibody. HRP activity was detected using the chromagen 3,3',5,5'-tetramethylbenzidine (TMB). A stop solution was then added, and the optical density at 450 nm (OD$_{450}$) was measured on a Molecular Devices SpectraMax M5 plate reader. Data analysis was performed using GraphPad Prism software. The lowest concentration of standard within the linear range of the assay was defined as the assay's LLOQ=31.25 pg/mL.

MPO ELISA

MPO concentrations in the lung protein extracts were measured using a sandwich ELISA kit according to the manufacturer's instructions (mouse MPO ELISA kit, Hycult Biotech). Briefly, lung homogenates were diluted and incubated on 96-well plates pre-coated with anti-MPO capture antibody. Purified mouse MPO was used as a standard. Captured MPO was detected using biotinylated anti-mouse MPO detection antibody. Purified HRP-conjugated streptavidin was used to detect biotinylated anti-mouse MPO. HRP activity was detected using the chromagen 3,3',5,5'-tetramethylbenzidine (TMB). A stop solution was then added, and the optical density at 450 nm (OD$_{450}$) was measured on a Molecular Devices SpectraMax M5 plate reader. Data analysis was performed using GraphPad Prism software. The lowest concentration of standard within the linear range of the assay was defined as the assay's LLOQ=156.3 ng/ml.

Serum Collection

Whole blood was collected into Microtainer tubes by cardiac puncture at the end of the study. Blood was allowed to clot by leaving it undisturbed at room temperature for at least 30 minutes. Clotted blood and cells were pelleted by centrifuging at 18,000×g for 10 minutes at 4° C. The resulting supernatant, designated serum, was transferred into clean polypropylene plates and used to determine circulating antibody levels as described below.

Determination of SAA Levels in Serum by ELISA

Total SAA concentrations in the serum samples for each mouse were determined using a commercial immunoassay (Quantikine ELISA, R&D Systems) according to the manufacturer's instructions. Briefly, serum samples were diluted and incubated on 96-well plates previously coated with monoclonal anti-mouse SAA capture antibody. Recombinant mouse SAA was used as a standard. Captured SAA was detected using HRP-conjugated polyclonal anti-mouse SAA detection antibody. HRP activity was detected using the colorimetric HRP substrate TMB. A stop solution of diluted hydrochloric acid was then added, and the $OD_{450}$ was measured on a Molecular Devices SpectraMax M5 plate reader. The concentration of circulating SAA in serum for each sample was determined as ng/ml and graphed as µg/mL. Data analysis was performed using GraphPad Prism software. The lowest concentration of standard within the linear range of the assay was defined as the assay's LLOQ=31.2 ng/ml.

Determination of Serum IgE Levels by ELISA

Total IgE concentrations in the serum samples for each mouse were determined using a colorimetric sandwich ELISA OPTEIA kit according to the manufacturer's instructions. Briefly, serum samples were diluted and incubated on 96-well plates previously coated with anti-IgE capture antibody. Purified mouse IgE was used as a standard. Captured IgE was detected using biotinylated anti-mouse IgE detection antibody. Purified HRP-conjugated streptavidin was used to detect biotinylated anti-mouse IgE. HRP activity was detected using the TMB. A stop solution of 2N sulfuric acid was then added, and the $OD_{450}$ was measured on a Molecular Devices SpectraMax M5 plate reader. The concentration of circulating IgE in serum for each sample was expressed as µg/mL. Data analysis was performed using GraphPad Prism software. The lowest concentration of standard within the linear range of the assay was defined as the assay's LLOQ=78.15 ng/ml.

Determination of Serum HDM-Specific IgG1 Levels by ELISA

A colorimetric ELISA assay was developed to determine the levels of HDM-specific IgG1 in serum samples. Plates were coated with HDM at a concentration of 4 µg/mL in phosphate buffered saline (PBS) overnight at 4° C., washed, blocked with a solution of 0.5% BSA in PBS for 1 hour at room temperature, and incubated with serially diluted mouse serum samples. After 1 hour at room temperature, plates were washed and IgG1 antibodies captured onto the plates were detected by incubation with rat anti-mouse IgG1 HRP-conjugated antibody for 1 hour at room temperature. HRP activity was detected using TMB. A stop solution of 2N sulfuric acid was then added, and $OD_{450}$ was measured on a Molecular Devices SpectraMax M5 plate reader. Relative levels of IgG1 in serum were represented as titer units. Titer units were calculated by multiplying the measured $OD_{450}$ by the dilution factor required to achieve an $OD_{450}$ reading that was greater than 2 times background $OD_{450}$. Data analysis was performed using GraphPad Prism software. The lowest dilution factor used in the assay was defined as the assay's LLOQ=100.

Determination of Human Target-Specific IgG4 Antibody Levels by ELISA

The concentration of human antibody (REGN3500, dupilumab, or IgG4$^P$ isotype control) in the serum samples for each mouse was determined using a colorimetric sandwich ELISA developed to detect human IgG4 antibodies. Microtiter wells were coated with the antigen specific for the human antibody to be measured, i.e. Human IL-33 (REGN3931) to capture REGN3500, Human IL-4Rα (REGN560) to capture REGN668, Natural Fel d 1 to capture REGN1945, at a concentration of 2 µg/mL in PBS overnight at 4° C. Wells were washed four times with 0.05% Tween 20 in DPBS, blocked with a solution of 5% BSA in DPBS for 3 hours at room temperature and incubated with serially diluted mouse serum samples or serially diluted calibration standards. Purified antibodies (REGN3500, REGN668, and IgG4$^P$ control antibody) were used as standards for calibration and quantitation of the respective antibody concentrations in serum. After 1 hour at room temperature, plates were washed 7 times and human IgG4 captured onto the plates was detected using a biotinylated mouse anti-human IgG4-specific monoclonal antibody followed by incubation with Poly HRP, Streptavidin conjugated. HRP activity was detected using a TMB substrate according to manufacturer's instructions. After 10 minutes, absorbance was measured at 450 nm using a Molecular Devices SpectraMax multimode plate reader. The lowest concentration of standard (REGN3500, REGN668, or IgG4$^P$ control antibody) used for calibration (0.002 µg/mL) was defined as this assay's LLOQ. Data analysis was performed using GraphPad Prism™ (GraphPad Software, CA). The concentration of human antibody in serum for each sample was expressed as µg/mL.

Statistical Analyses

Statistical analyses were performed using GraphPad Prism version 7.0 (GraphPad Software, CA).

Statistical Analysis of Data from Characterization of IL-33-, IL-4-, and IL-4Rα-Humanized Mice in the 4-Week HDM Exposure Model Results were interpreted by two-way analysis of variance (ANOVA) followed by the Tukey's post hoc test for multiple comparisons. Differences were considered to be statistically significant when p≤0.05.

Statistical Analysis of Data from REGN3500/Dupilumab Treatment in 19-Week HDM Exposure-Induced Lung Inflammation Model Normality of the data was evaluated using the Shapiro-Wilk test. If data passed the normality test, and standard deviations of the different groups were not statistically different from each other as assessed by the Brown-Forsythe test, results were interpreted by one-way ANOVA followed by Tukey's post hoc test for multiple comparisons. If data failed to pass the normality test, or standard deviations were significantly different, results were interpreted using the Kruskal-Wallis test followed by Dunn's post hoc test for multiple comparisons. Differences were considered to be statistically significant when p≤0.05.

RESULTS

Characterization of IL-33-, IL-4-, and IL-4Rα Ectodomain-Humanized Mice

Figure 2:
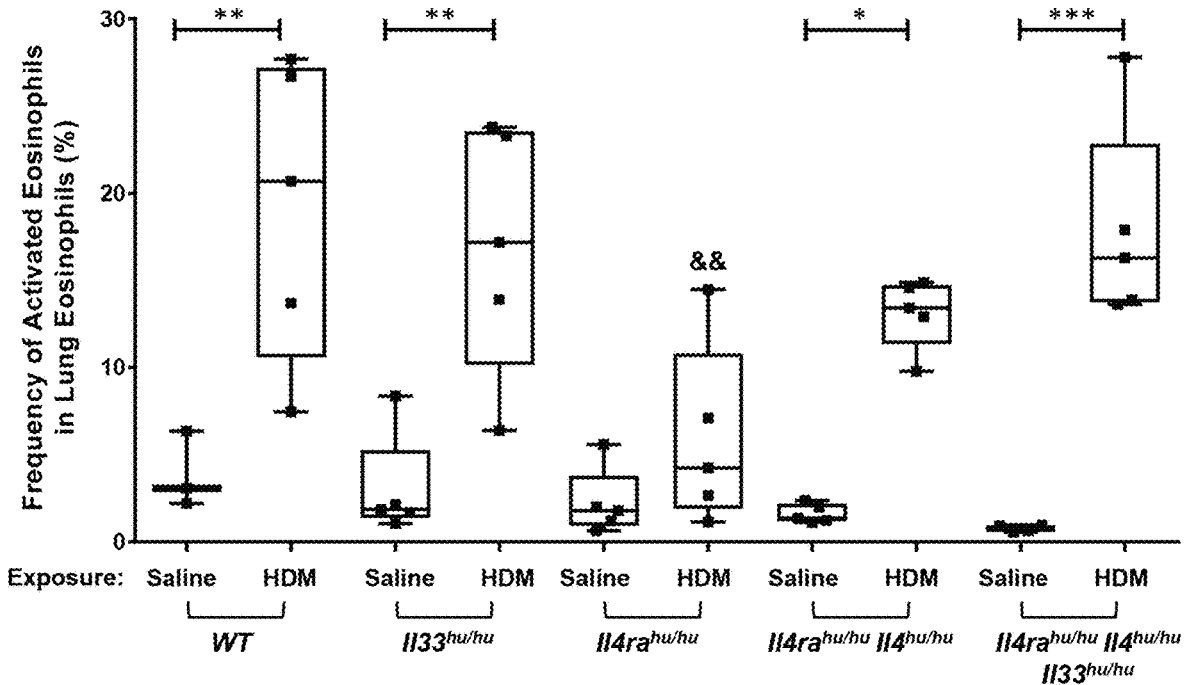
FIG. 2 Shows that HDM exposure induces similar increases in activated eosinophils in lungs of IL-33-, IL-4-, and IL-4Rα-triple humanized and wild-type mice. Statistical significance was determined by two-way ANOVA with Tukey's multiple comparisons test. The following symbols were used to indicate statistically significant differences: "*" asterisks mark comparisons between saline- and HDM-exposed mice of the same genotype; "&" ampersand symbols mark comparisons with the respective saline- or HDM-exposed wildtype group of mice. Increasing numbers of symbols indicate increasing significance: $1x=p\leq0.05$; $2x=p\leq0.01$; $3x=p\leq0.001$; $4x=p\leq0.0001$. Abbreviations: WT=wild type. All mice were of a mixed C57BL/6NTac/129S6SvEvTac background.

Wild type, Il33$^{hu/hu}$- and Il4ra$^{hu/hu}$-single humanized, Il4ra$^{hu/hu}$ Il4$^{hu/hu}$-double humanized, and Il4ra$^{hu/hu}$ Il4$^{hu/hu}$ Il33$^{hu/hu}$-triple humanized mice were exposed IN to saline or HDM 3 times per week for 4 weeks. Mice were sacrificed 4 days after the last exposure and lungs were harvested to assess the lung infiltration by activated eosinophils identified by high CD11c expression. Individual mouse data and statistical analyses are provided in FIG. 2. Triple-humanized Il4ra$^{hu/hu}$ Il4$^{hu/hu}$ Il33$^{hu/hu}$ mice showed robust response to HDM similar to wild-type mice, as indicated by a significant increase in the frequency of activated eosinophils in lung tissue following 4 weeks of HDM exposure. Il4ra$^{hu/hu}$ Il4$^{hu/hu}$ Il33$^{hu/hu}$ and wild-type mice also showed similar frequencies of activated eosinophils in lung tissue in the absence of HDM exposure (saline-exposed control mice). No statistically significant differences were observed comparing HDM-exposed wild-type mice with HDM-exposed mice from any of the tested humanized mouse strains, with the exception of Il4ra$^{hu/hu}$ single humanized mice. The lack of statistically significant HDM exposure-induced increases in percentage of activated eosinophilic lung infiltration in Il4ra$^{hu/hu}$ mice is likely due to the fact that mouse IL-4 does not signal via the human IL-4Rα receptor. Human IL-33, on the other hand, has been shown to signal via the murine receptor complex (REGN3500-MX-16069). Additionally, no statistically significant differences were observed comparing saline-exposed wild-type mice with saline-exposed mice from any of the tested humanized mouse strains. These findings validate the Il4ra$^{hu/hu}$ Il4$^{hu/hu}$ Il33$^{hu/hu}$ mouse strain for use as a mouse model of HDM-exposure induced lung inflammation.

Effect of REGN3500 and Dupilumab Treatment in 19-Week HDM-Exposed Mice

Il4ra$^{hu/hu}$ Il4$^{hu/hu}$ Il33$^{hu/hu}$ mice were exposed IN to saline or HDM 3 times per week for 11 or 19 weeks. Four groups of 19-week HDM-exposed mice received twice-weekly SC injections of antibodies from week 12 to week 19; all other groups received no treatment (none, light gray boxes). Antibodies were administered alone or in combination at final protein doses of 11 mg/kg as follows: 11 mg/kg isotype control antibody, 1 mg/kg REGN3500+10 mg/kg isotype control antibody, 10 mg/kg dupilumab+1 mg/kg isotype control antibody, or 1 mg/kg REGN3500+10 mg/kg dupilumab. One cohort of mice was sacrificed after 11 weeks of exposure to determine inflammatory profile at the start of antibody treatment (11-week exposure group). The other 4 cohorts were sacrificed on day 134 (19-week exposure groups), four days after the last exposure and antibody injection. Whole blood was collected by cardiac puncture for serum isolation and lungs were harvested for further analysis. All groups comprised mice of the same strain, (Il4ra$^{hu/hu}$ Il4$^{hu/hu}$ Il33$^{hu/hu}$) unless noted otherwise.

Analysis of Gross Lung Pathology

Figure 3:
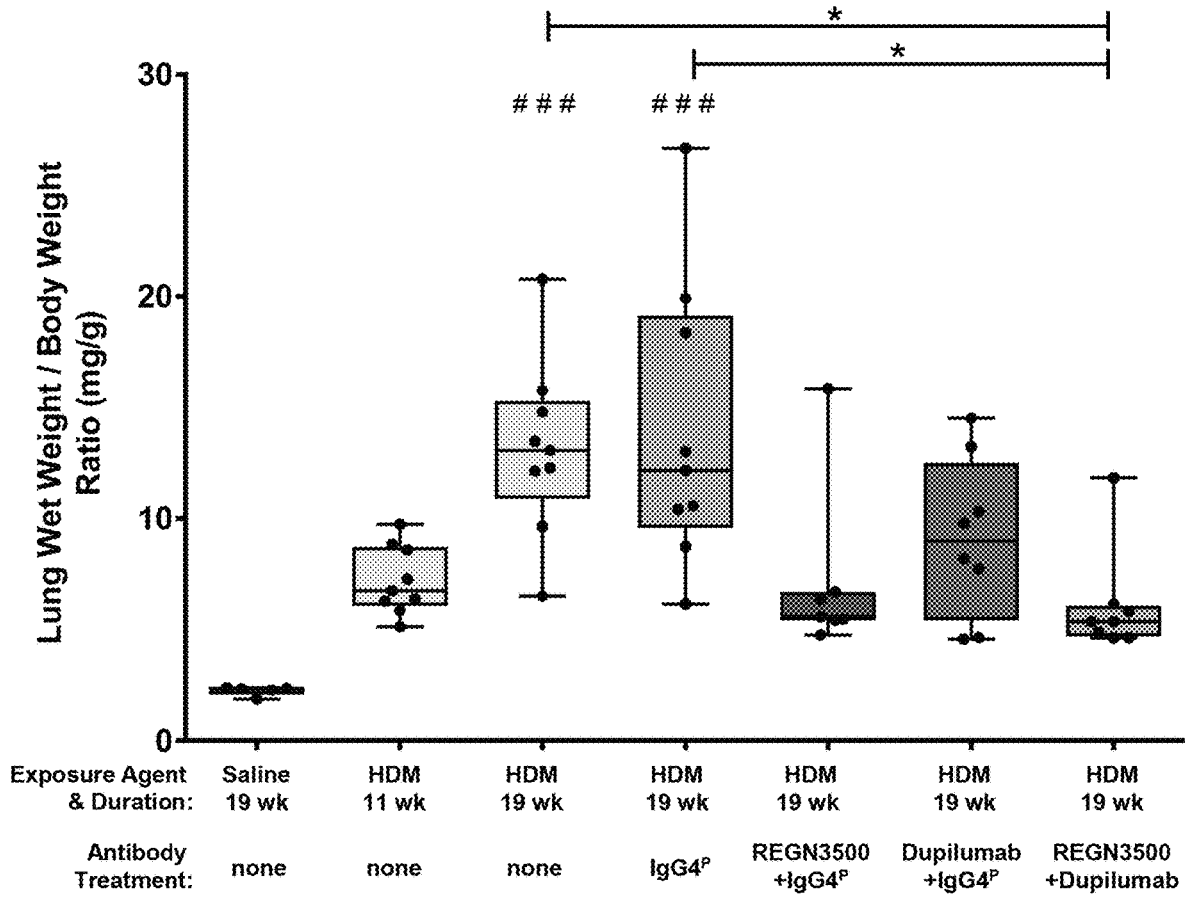
FIG. 3 shows that combined administration of REGN3500 and dupilumab blocks HDM exposure-induced increases in relative lung weight. Relative lung weight is expressed as the ratio of lung wet weight (in mg) to body weight (in g). Statistical significance was determined by Kruskal-Wallis one-way ANOVA with Dunn's multiple comparison post hoc test. The following symbols were used to indicate statistically significant differences: "*" asterisks mark comparisons among all 19-week HDM-exposure groups; and "#" hashtags mark comparison of saline-exposed, untreated animals with all other groups. Increasing numbers of symbols indicate increasing significance: $1x=p\leq0.05$; $2x=p\leq0.01$; $3x=p\leq0.001$. Abbreviations: wk=week; $IgG4^P$=isotype control antibody, REGN1945.

Relative lung weight was significantly increased in 19-week HDM-exposed mice compared with saline-exposed control mice FIG. 3. This is likely due to increased cellular infiltration, collagen deposition, muscle hypertrophy, and mucus production. In HDM-exposed mice, the combined administration of REGN3500 and dupilumab significantly blocked HDM exposure-induced increases in relative lung weight compared with mice administered isotype control antibody (FIG. 3). A trend towards reduced relative lung weight was also observed in HDM-exposed mice dosed with REGN3500 alone.

Analysis of Pulmonary Cell Infiltrates

Figure 4A:
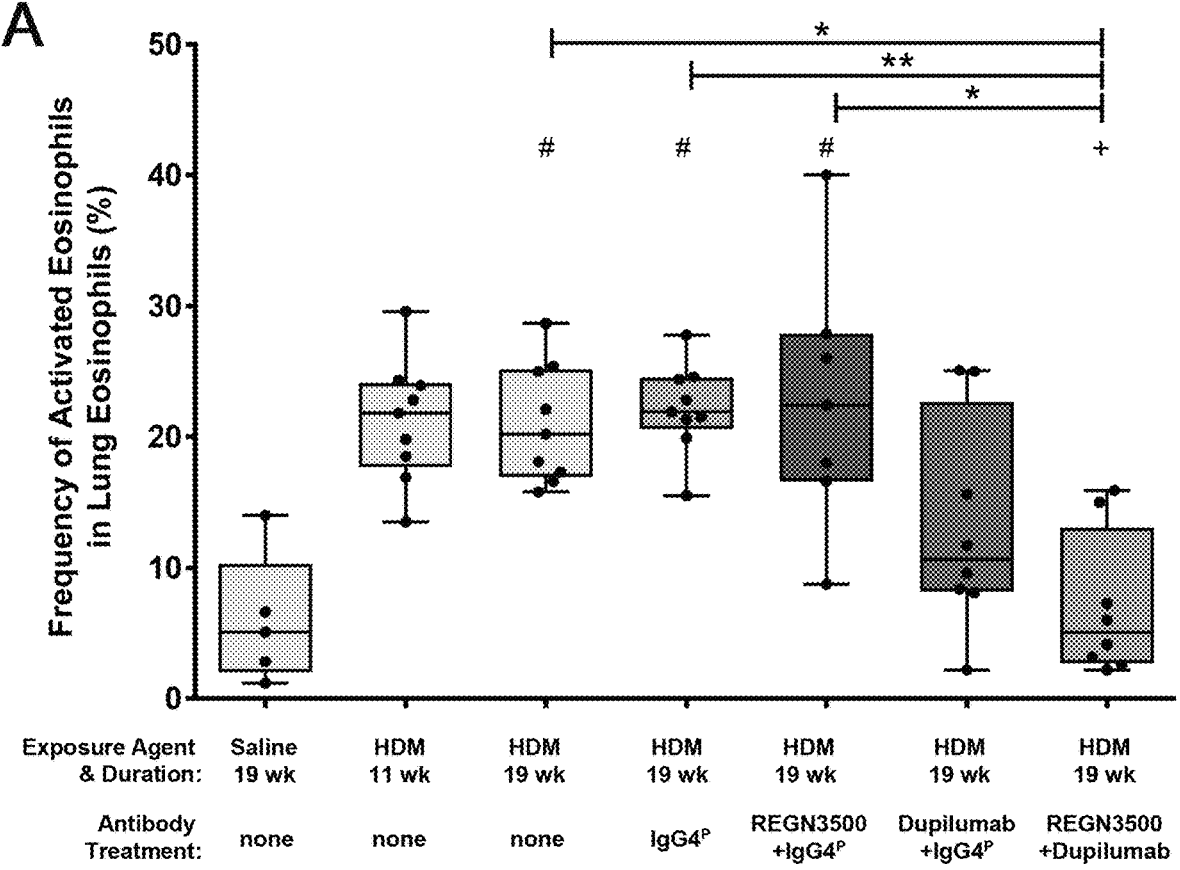
FIGS. 4A and 4B show the effect of REGN3500 and dupilumab, alone and in combination, on HDM exposure-induced pulmonary eosinophilic infiltration. Statistical significance was determined by Kruskal-Wallis one-way ANOVA with Dunn's multiple comparison post hoc test. The following symbols were used to indicate statistically significant differences: "*" asterisks mark comparisons among all 19-week HDM-exposure groups; "#" hashtags mark comparison of saline-exposed, untreated animals with all other groups; and "+" plus signs mark comparison of 11-week HDM-exposed, untreated animals with all other groups. Increasing numbers of symbols indicate increasing significance: $1x=p\leq0.05$; $2x=p\leq0.01$; $3x=p\leq0.001$; $4x=p\leq0.0001$. Abbreviations: wk=week; $IgG4^P$=isotype control antibody, REGN1945.

Four days after the last antibody injection, the mouse lungs were harvested and the caudal lobe of the right lung was dissociated into a single cell suspension for flow cytometric analysis of eosinophils. Eosinophils were defined as intact, single, live, CD45$^+$, F4/80$^+$, Ly6G$^-$, SiglecF$^+$ and activated eosinophils were further defined as CD11c$^{Hi}$. Lung infiltration by activated eosinophils was reported as frequency (%) of total lung eosinophils in (A) and overall lung eosinophilic infiltration was reported as frequency (%) of total lung eosinophils in live (intact, single, live) cells. Compared with saline-exposed control mice, exposure to HDM for 19 weeks significantly increased cellular pulmonary infiltration, as assessed by flow cytometry for detection of total and activated lung eosinophils (FIGS. 4A and 4B) and lung ST2$^+$ CD4$^+$ T cells (ST2$^+$ CD4$^+$ T cells were defined as intact, single, live, CD45$^+$, CD3$^+$, CD19$^-$, CD4$^+$, CD8$^-$, ST2$^+$ and reported as frequency of CD4$^+$ T cells) (FIG. 5), or by immunoassay for detection of lung MPO protein levels as a marker for neutrophils (MPO protein levels were measured by enzyme-linked immunosorbent assay. Lung MPO protein levels are expressed as MPO protein amount (µg) per lung lobe) (FIG. 6).

Figure 4B:
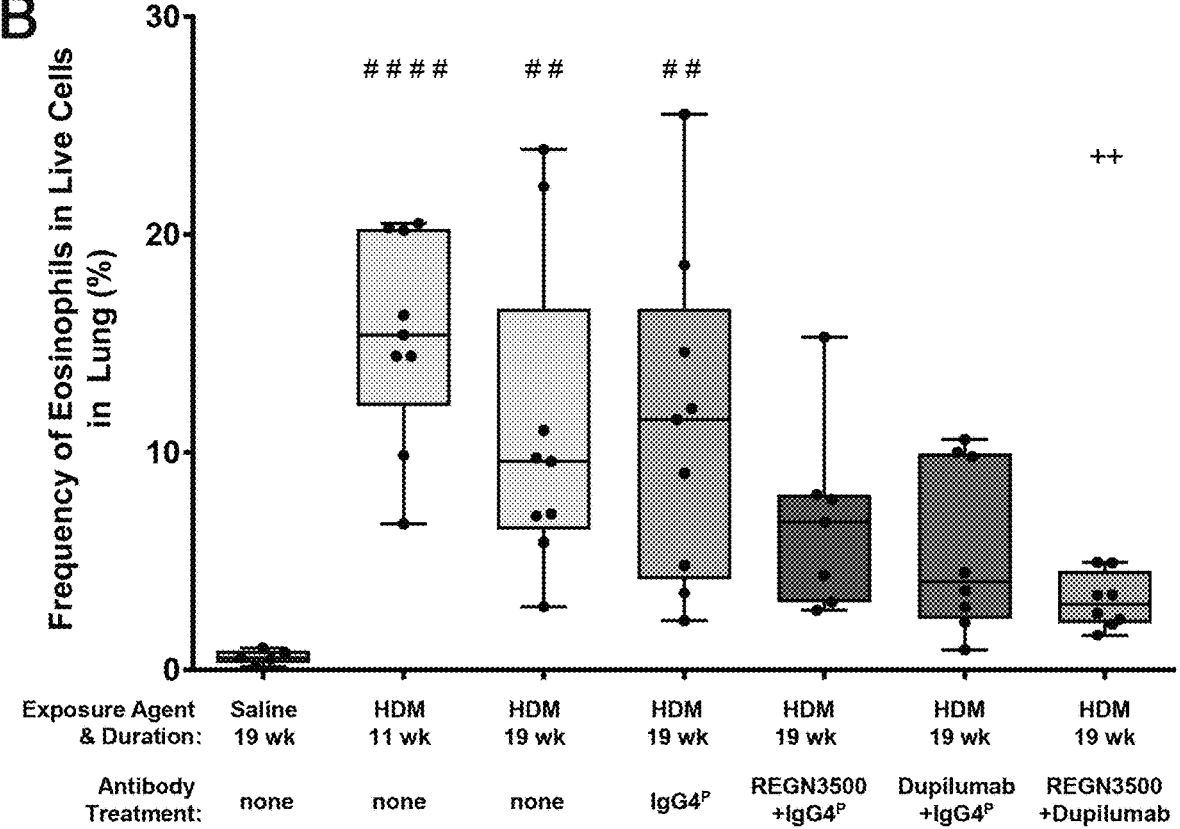

Combined administration of REGN3500 and dupilumab in 19-week HDM-exposed mice, but not of either antibody alone, significantly reduced levels of lung infiltration by activated eosinophils compared with administration of an isotype control antibody. Notably, levels of lung infiltration by activated eosinophils in mice administered REGN3500 and dupilumab in combination were also significantly reduced compared with 11-week HDM exposure-induced levels, which corresponds to the onset of treatment FIG. 4A. While administration of either antibody alone did not result in significant effects, a trend towards reduced pulmonary infiltration by activated eosinophils was observed in dupilumab-administered mice. HDM-exposed mice administered REGN3500 and dupilumab in combination also showed a trend towards a reduction in HDM-induced lung infiltration by total eosinophils (FIG. 4B).

Figure 5:
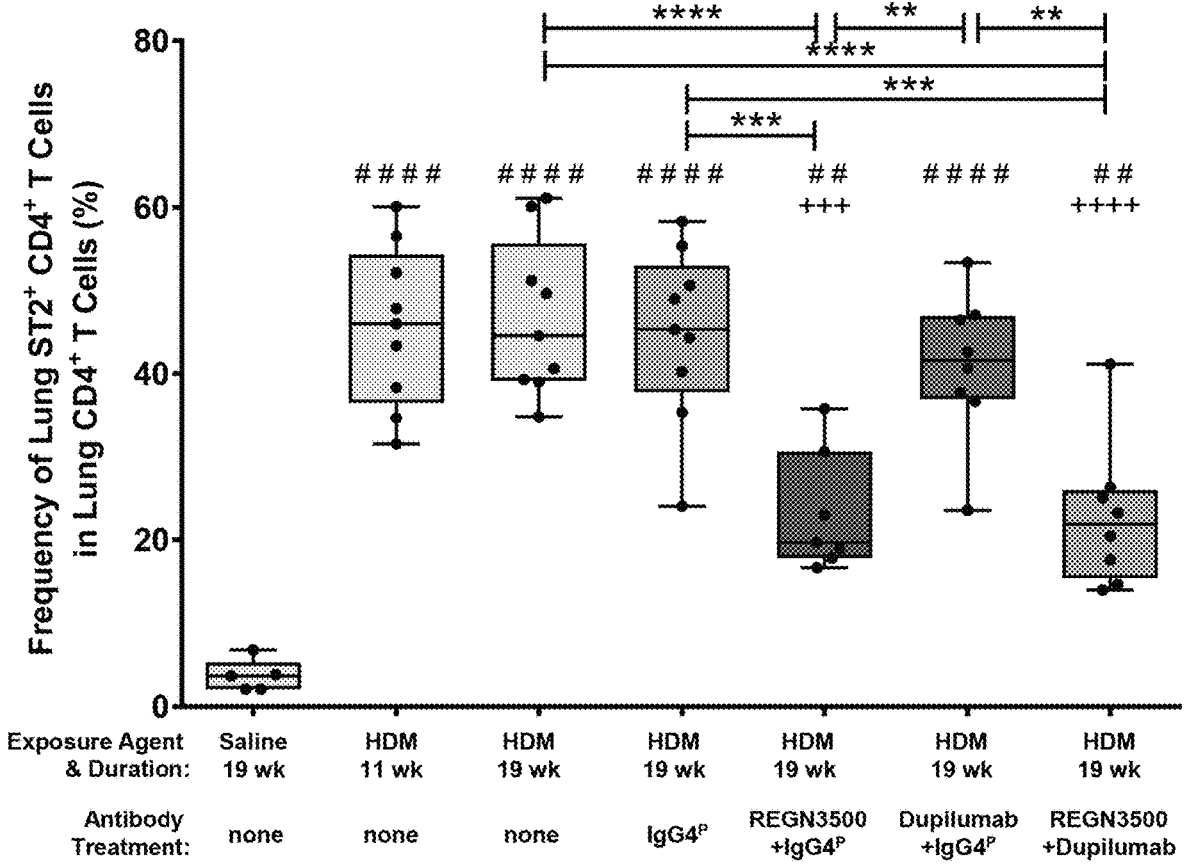
FIG. 5 shows that REGN3500, alone or in combination with dupilumab, blocks HDM exposure-induced lung infiltration by ST2+ CD4+ T cells. Statistical significance was determined by one-way ANOVA with Tukey's multiple comparison post hoc test. The following symbols were used to indicate statistically significant differences: "*" asterisks mark comparisons among all 19-week HDM-exposure groups; "#" hashtags mark comparison of saline-exposed, untreated animals with all other groups; and "+" plus signs mark comparison of 11-week HDM-exposed, untreated animals with all other groups. Increasing numbers of symbols indicate increasing significance: 1x=p≤0.05; 2x=p≤0.01; 3x=p≤0.001; 4x=p≤0.0001. Abbreviations: wk=week; IgG4$^P$=isotype control antibody, REGN1945.
Figure 6:
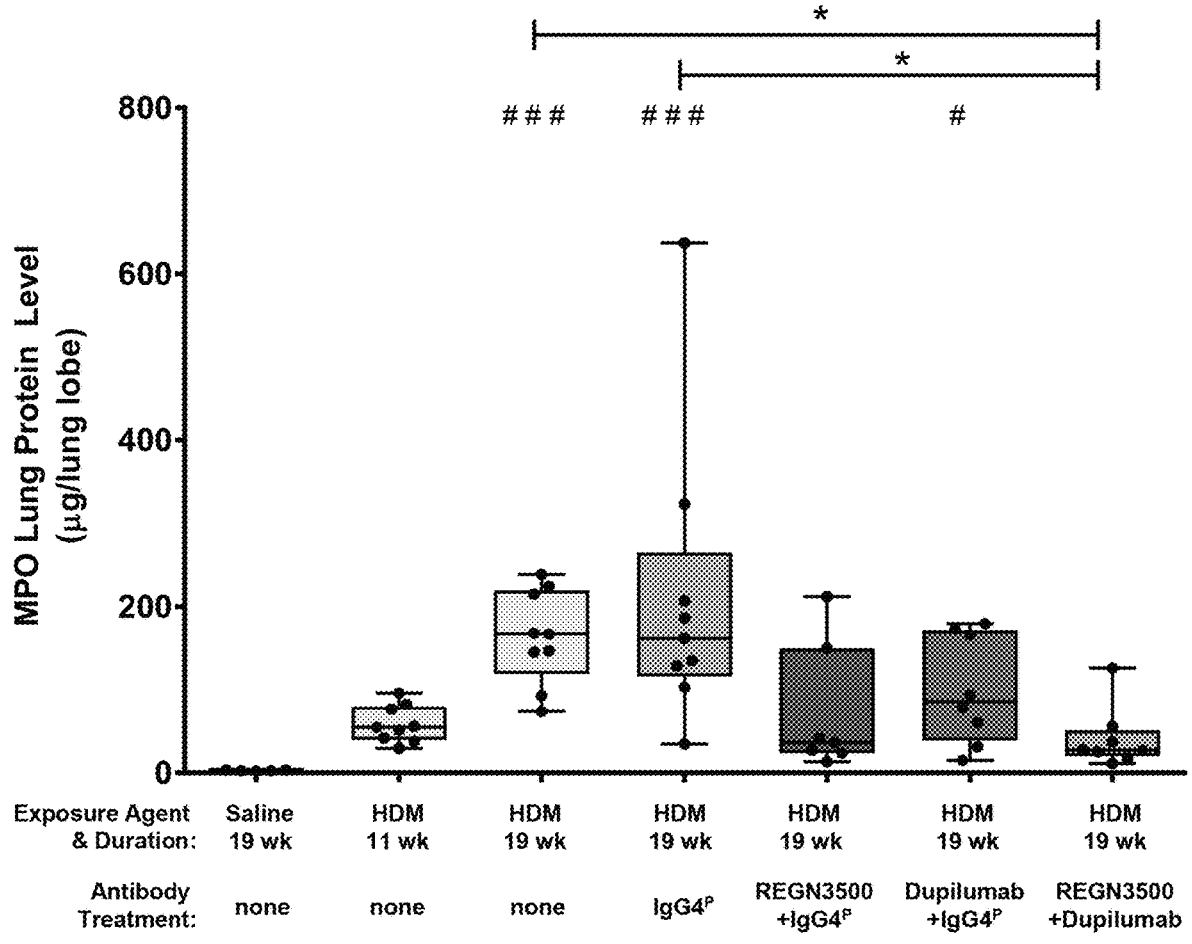
FIG. 6 shows that combined administration of REGN3500 and dupilumab blocks HDM exposure-induced increases in levels of MPO lung protein, a marker of neutrophilic infiltration. Statistical significance was determined by Kruskal-Wallis one-way ANOVA with Dunn's multiple comparison post hoc test. The following symbols were used to indicate statistically significant differences: "*" asterisks mark comparisons among all 19-week HDM-exposure groups; and "#" hashtags mark comparison of saline-exposed, untreated animals with all other groups. Increasing numbers of symbols indicate increasing significance: 1x=p≤0.05; 2x=p≤0.01; 3x=p≤0.001. Abbreviations: wk=week; IgG4$^P$=isotype control antibody, REGN1945.

In 19-week HDM-exposed mice administered REGN3500 alone or in combination with dupilumab, levels of lung infiltration by ST2$^+$ CD4$^+$ T cells were significantly reduced compared with levels in isotype control-administered mice, and compared with 11-week HDM exposure-induced levels at the onset of treatment (FIG. 5). Similar blocking of infiltration (mean frequencies within 1.02-fold) was observed for REGN3500 alone and in combination with dupilumab, indicating that this pathology is mainly driven by IL-33.

Similar to eosinophilic infiltration, combined administration of REGN3500 and dupilumab showed a stronger effect on blocking neutrophilic lung infiltration than either antibody alone. HDM exposure-induced increases in lung protein levels of myeloperoxidase (MPO), a marker of neutrophilic infiltration, were significantly blocked by combined administration of REGN3500 and dupilumab compared with isotype control (FIG. 6). While administration of either antibody alone did not result in significant effects, a trend towards reduced lung MPO protein levels was observed in REGN3500-administered mice.

Lung Tissue Cytokine Level Analysis

The effect of HDM exposure and antibody treatment on lung protein levels (total protein per lobe) was assessed for mouse cytokines IL-5, IL-13, IL-6, IL-1β, IL-12p70, TNFα, IFNγ, GROα, and MCP-1, and for the human cytokine hIL-4.

Lungs (cranial and middle lobes of the right lung) were harvested and protein levels of the indicated mouse cytokines were measured by multiplexed immunoassay. Human IL-4 protein levels (hIL-4) were detected using a commercially available ELISA kit. IL-5 (FIG. 7A) and IL-6 (FIG. 7B) protein levels were measured by multiplexed immunoassay. Lung tissue cytokine protein levels were calculated as protein amount (pg) per lung lobe. A false-colored heat map (not shown here) was generated to denote the relative cytokines ranging from light yellow to dark blue. A scale of relative lung cytokine levels was created by defining the lowest and highest recorded mean lung protein level for each separate cytokine as 0% (light yellow) and 100% (dark blue), respectively. Relative lung cytokine protein levels (%) were indicated by numbers and by color in the heat map. Statistical significance was determined by Kruskal-Wallis one-way ANOVA with Dunn's multiple comparison post hoc test.

The result for IL-12p70 was below the lower limit of quantification for all groups and is therefore not reported here.

Eight cytokines (hIL-4, IL-5, IL-6, IL-13, IL-1β, TNFα, GROα, and MCP-1) showed significant increases in lung protein levels in response to 19-week HDM exposure compared with saline-exposed control mice. Only IFNγ did not show significant increases in lung protein levels in response to 19-week HDM exposure compared with saline-exposed control mice, nor were IFNγ levels affected by therapeutic antibody administration compared with 19-week HDM-exposed mice administered isotype control antibody. HDM exposure-induced increases in lung protein levels of 5 cytokines (hIl-4, IL-6, TNFα, GROα, and MCP-1) were significantly blocked by combined administration of REGN3500 and dupilumab, but not by administration of either antibody alone, compared with isotype control anti-body-administered mice.

Figure 7A:
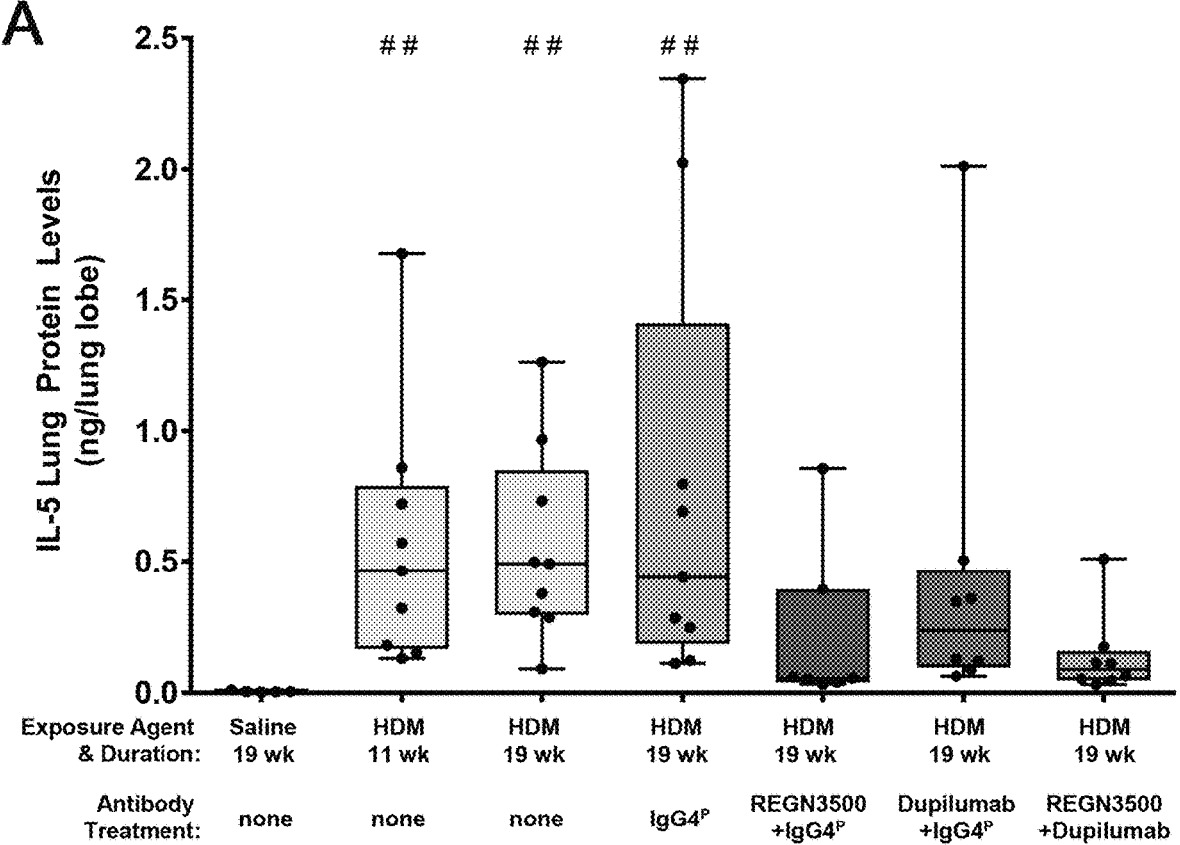
FIGS. 7A and 7B show the effect of REGN3500 and dupilumab, alone or in combination, on HDM exposure-induced increases in lung IL-5 and IL-6 protein levels. Lungs (cranial and middle lobes of the right lung) were harvested and IL-5 (A) and IL-6 (B) protein levels were measured by multiplexed immunoassay. Lung tissue IL-5 and IL-6 protein levels are expressed as protein amount (pg) per lung lobe. Statistical significance was determined by Kruskal-Wallis one-way ANOVA with Dunn's multiple comparison post hoc test. The following symbols were used to indicate statistically significant differences: "*" asterisks mark comparisons among all 19-week HDM-exposure groups; and "#" hashtags mark comparison of saline-exposed, untreated animals with all other groups. Increasing numbers of symbols indicate increasing significance: 1x=p≤0.05; 2x=p≤0.01; 3x=p≤0.001. Abbreviations: wk=week; IgG4$^P$=isotype control antibody, REGN1945.
Figure 7B:
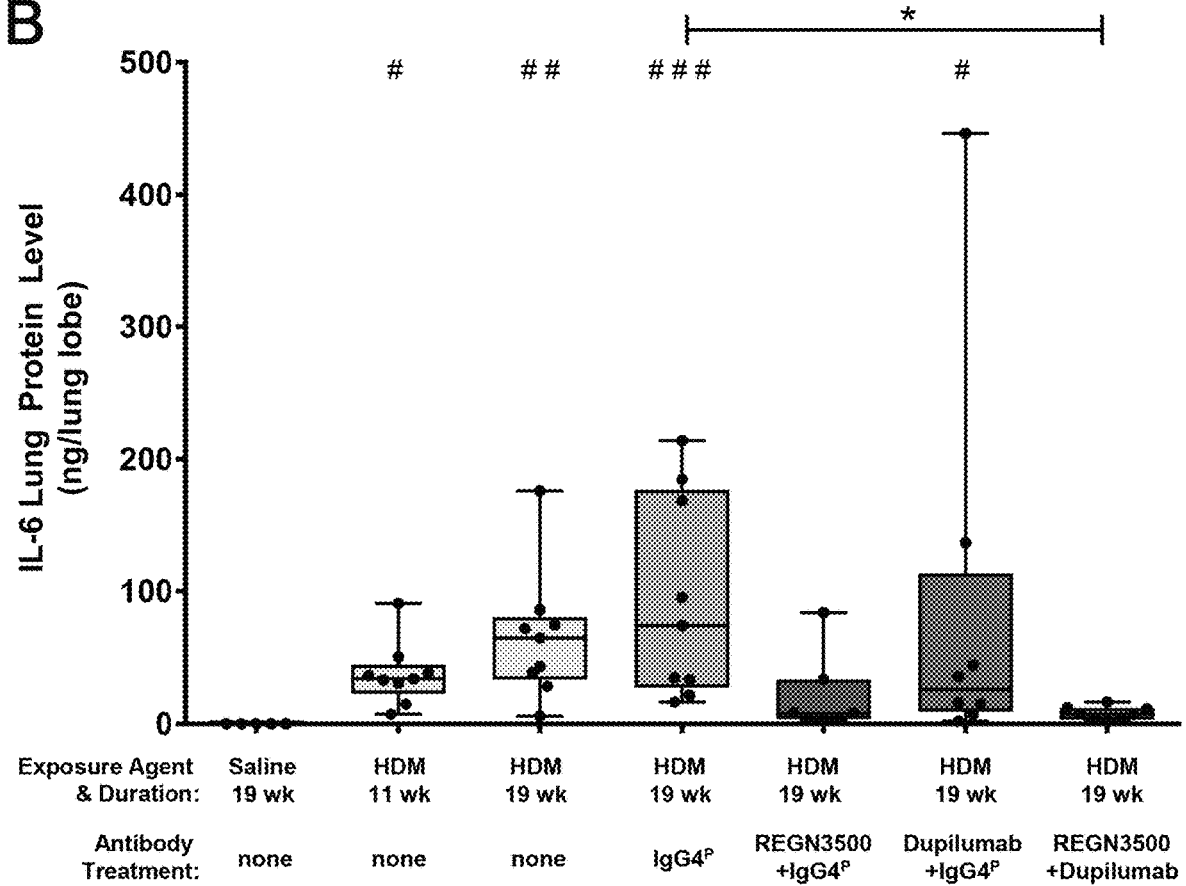

Another 2 HDM exposure-responsive cytokines (IL-5 and IL-1β) showed trends towards blockade by combined REGN3500 and dupilumab treatment, with 83% and 78% reduction of lung protein levels, respectively, compared with isotype control antibody-administered mice (FIGS. 7A and 7B). Administration of individual antibodies resulted in less pronounced trends in reduction of IL-5 and IL-1β levels.

Analysis of SAA, a Systemic Marker of Inflammation

Four days after the last exposure and antibody injection, whole blood was collected by cardiac puncture and serum was isolated. Circulating SAA protein levels were measured Quantification of Humoral Allergic Reponses Following HDM Exposure Four days after the last exposure and antibody injection, whole blood was collected by cardiac puncture and serum was isolated. Circulating IgE protein levels were measured using a commercially available ELISA kit. Circulating IgE protein levels are expressed as IgE protein amount (μg) per mL of serum.

Humoral allergic responses were elicited by HDM-exposure as assessed by levels of circulating IgE (FIG. 9) and HDM-specific IgG1 (Table 15) at the end of the study (day 134).

Figure 9:
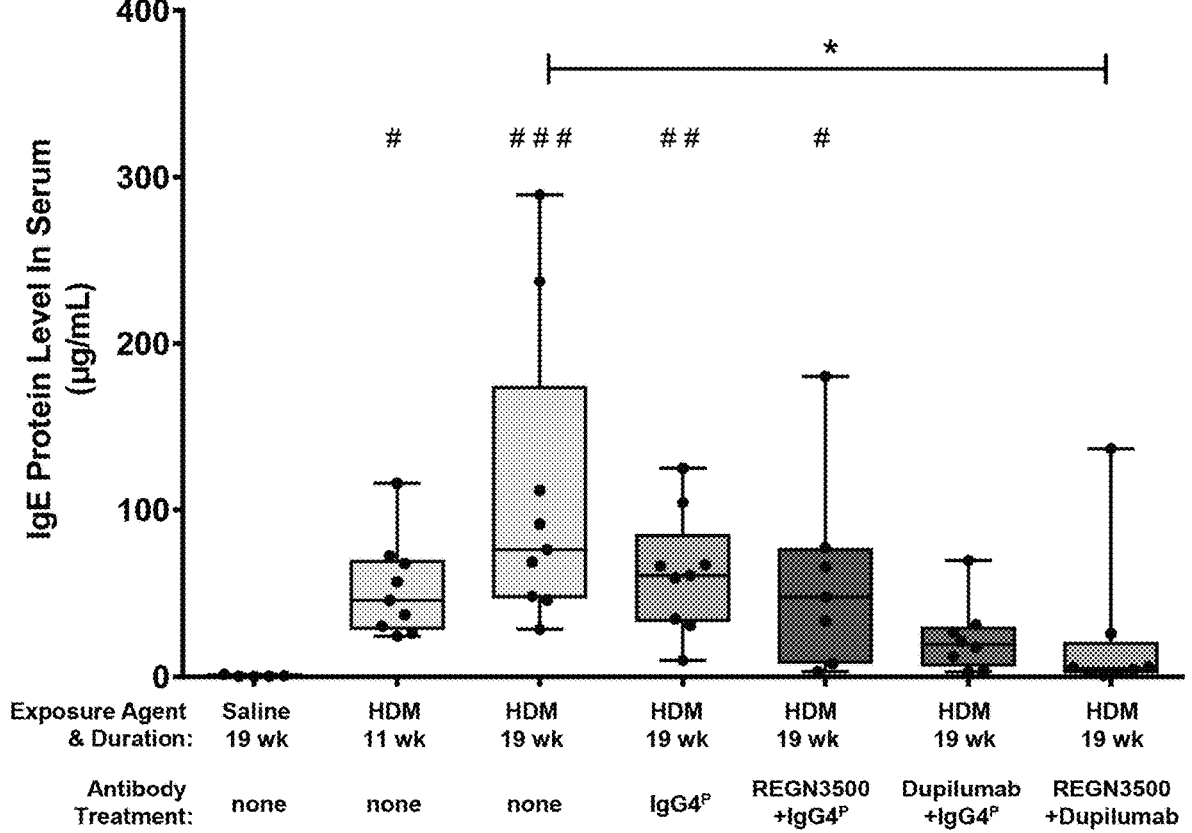
FIG. 9 shows that circulating IgE protein levels are increased in response to HDM exposure. Whole blood was collected by cardiac puncture and serum was isolated. Circulating IgE protein levels were measured using a commercially available ELISA kit. Circulating IgE protein levels are expressed as IgE protein amount (µg) per mL of serum. Statistical significance was determined by Kruskal-Wallis one-way ANOVA with Dunn's multiple comparison post hoc test. The following symbols were used to indicate statistically significant differences: "*" asterisks mark comparisons among all 19-week HDM-exposure groups; and "#" hashtags mark comparison of saline-exposed, untreated animals with all other groups. Increasing numbers of symbols indicate increasing significance: 1x=p≤0.05; 2x=p≤0.01; 3x=p≤0.001. Abbreviations: wk=week; IgG4$^P$=isotype control antibody, REGN1945.

Circulating protein levels of IgE were significantly increased in 19-week HDM-exposed mice compared with saline-exposed control mice (FIG. 9). Average titers for circulating HDM-specific IgG1 increased from 1.14E+02 in saline-exposed control mice to levels ranging from 1.37E+ 06 to 2.43E+06 in mice exposed to HDM for 19 weeks (Table 15). No statistically significant effect of REGN3500, dupilumab, or combination treatment was observed for either of these endpoints, but a trend towards reduced serum IgE levels was observed in mice administered a combination of REGN3500 and dupilumab.

TABLE 15

Summary of Serum Concentrations of HDM-specific IgG1

Figure 8:
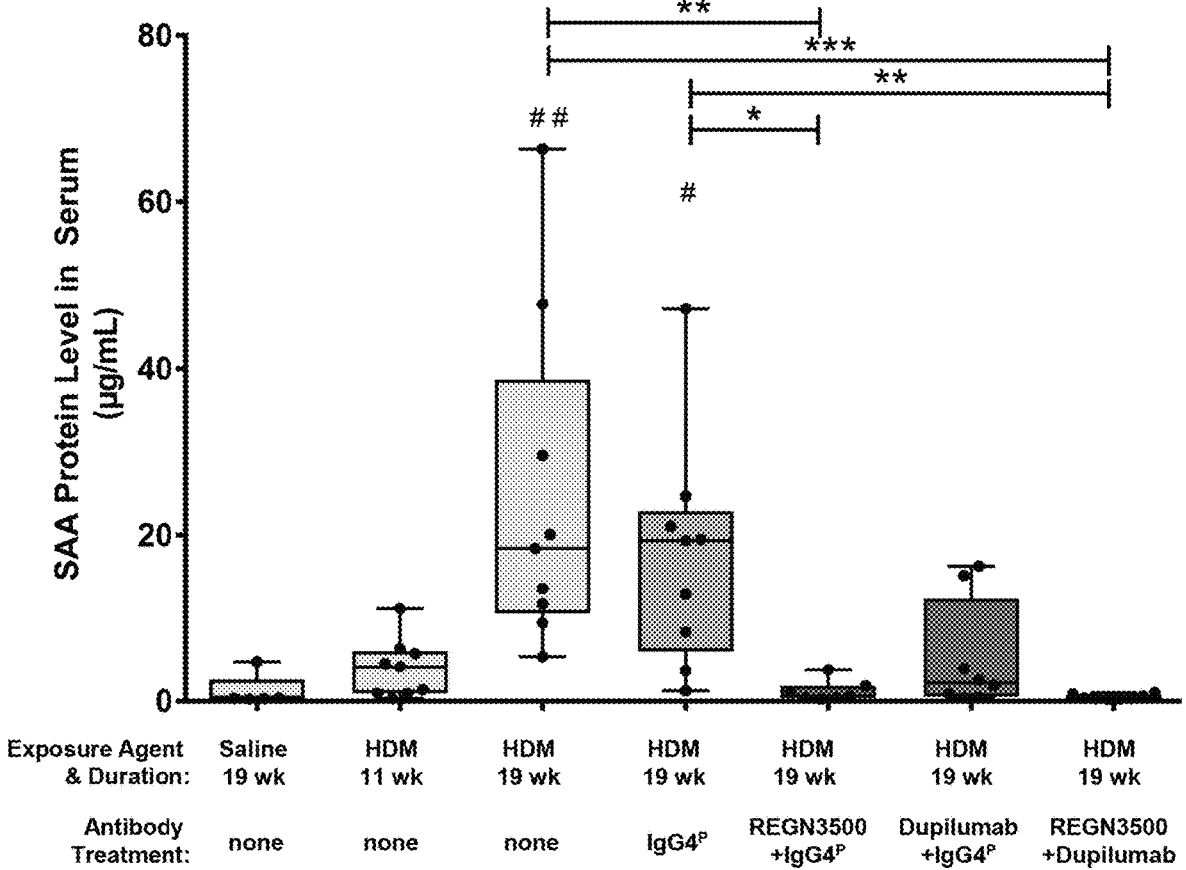
FIG. 8 shows that REGN3500 alone or in combination with dupilumab blocks HDM exposure-induced increases in circulating SAA protein levels. Four days after the last antibody injection whole blood was collected by cardiac puncture and serum was isolated. Circulating SAA protein levels were measured using a commercially available ELISA kit. Circulating SAA protein levels are expressed as SAA protein amount (µg) per mL of serum. Statistical significance was determined by Kruskal-Wallis one-way ANOVA with Dunn's multiple comparison post hoc test. The following symbols were used to indicate statistically significant differences: "*" asterisks mark comparisons among all 19-week HDM-exposure groups; and "#" hashtags mark comparison of saline-exposed, untreated animals with all other groups. Increasing numbers of symbols indicate increasing significance: 1x=p≤0.05; 2x=p≤0.01; 3x=p≤0.001. Abbreviations: wk=week; IgG4$^P$=isotype control antibody, REGN1945.

| HDM-specific IgG1 in Serum (Titer) | Saline 19 weeks | HDM 11 weeks | HDM 19 weeks | | | | |
|---|---|---|---|---|---|---|---|
| | | | No Antibody | IgG4$^P$ | REGN3500 + IgG4$^P$ | Dupilumab + IgG4$^P$ | REGN3500 + Dupilumab |
| Mean | 1.14E+02 | 2.19E+06 | 2.43E+06 | 2.14E+06 | 1.47E+06 | 1.37E+06 | 1.21E+06 |
| SD | 6.15E+01 | 1.07E+06 | 9.81E+05 | 5.60E+05 | 1.17E+06 | 5.79E+05 | 5.29E+05 | using a commercially available ELISA kit. Circulating SAA protein levels are expressed as SAA protein amount (pg) per mL of serum. Circulating protein levels of the systemic marker of inflammation SAA were significantly increased in 19-week HDM-exposed mice compared with saline-exposed control mice (FIG. 8).

Quantification of Serum Concentrations of Human Antibodies

The serum concentration of human IgG4$^P$ antibodies (IgG4$^P$ isotype control, REGN3500 and dupilumab) were determined at the end of the study (day 134), four days after the last antibody administration, by target-specific anti-human IgG4 ELISA. Average concentrations of human IgG4 antibodies are summarized in Table 16.

TABLE 16

Human Antibody Serum Levels at End of Study

| | Serum Antibody Levels, Mean + SD (μg/mL) | | | | | | |
|---|---|---|---|---|---|---|---|
| | 19-wk Saline | 11-wk HDM | 19-wk HDM | 19-wk HDM IgG4$^P$ (11 mg/kg) | 19-wk HDM REGN3500 (1 mg/kg) + IgG4$^P$ (10 mg/kg) | 19-wk HDM Dupilumab (10 mg/kg) + IgG4$^P$ (1 mg/kg) | 19-wk HDM REGN3500 (1 mg/kg) + Dupilumab (10 mg/kg) |
| REGN3500 | <LLOQ | <LLOQ | <LLOQ | n/t | 11.4 ± 10.1 | n/t | 12.7 ± 8.8 |
| Dupilumab | <LLOQ | <LLOQ | <LLOQ | n/t | n/t | 8.0 ± 13.5 | 48.9 ± 27.9 |
| IgG4$^P$ | 0.0 ± 0.0$^a$ | <LLOQ | <LLOQ | 54.5 ± 63.9 | 88.6 ± 76.0 | 0.1 ± 0.1 | n/t |

[a]One mouse in this group had serum IgG4$^P$ levels >LLOQ, therefore a rounded value is reported here.

HDM exposure-induced increases in circulating SAA levels were significantly reduced in mice administered REGN3500 alone or in combination with dupilumab (FIG. 8), while a trend towards reduced circulating SAA levels was observed in mice administered dupilumab alone.

SUMMARY

Compared to control mice exposed to saline only, mice exposed to HDM for 19 weeks demonstrated significant increases in all but one (lung IFNγ levels) of the 14 measured pathological markers of inflammation when left untreated or after administration of an $IgG4^P$ isotype control antibody.

Combined administration of REGN3500 and dupilumab significantly blocked 10/13 of the tested HDM exposure-responsive endpoints compared with isotype control antibody (relative lung weight, pulmonary infiltration by activated eosinophils, neutrophils [MPO levels], and $ST2^+$ $CD4^+$ T cells, lung protein levels of cytokines hIL-4, IL-6, TNFα, GROα, and MCP-1, and serum levels of SAA). Furthermore, levels of lung infiltration by activated eosinophils and $ST2^+$ $CD4^+$ T cells were significantly reduced to levels below those observed in 11-week HDM-exposed mice, which corresponds to the onset of antibody treatment. Administration of dupilumab alone did not significantly block any of the 13 tested HDM exposure-responsive endpoints in this model, while administration of REGN3500 alone significantly blocked 2 tested endpoints: $ST2^+$ $CD4^+$ T cell lung infiltration and circulating SAA levels. For these 2 endpoints, blockade mediated by REGN3500 alone was similar to blockade mediated by REGN3500 in combination with dupilumab, suggesting that these pathological markers are mainly driven by IL-33.

Combined administration of REGN3500 and dupilumab showed a trend towards blocking HDM exposure-induced responses for another 3 HDM exposure-responsive endpoints without reaching statistical significance (pulmonary infiltration by eosinophils [total], lung protein levels of cytokines IL-5 and IL-1β, and serum protein levels of IgE). For these markers, individual antibody treatment with REGN3500 or dupilumab generally resulted in weaker reduction than combined treatment.

All antibody treatment groups were associated with detectable serum levels for target-specific human IgG4 antibodies at the end of the study. In mice dosed twice-weekly for 8 weeks with either therapeutic antibody alone or in combination, average serum concentrations of REGN3500 were 11.4±10.1 and 12.7±8.8 µg/mL, respectively, and average serum concentrations of dupilumab were 8.0±13.5 and 48.9±27.9 µg/mL, respectively at the end of the study.

In conclusion, combined treatment with REGN3500 and dupilumab in a 19-week HDM exposure-induced lung inflammation model using $Il4ra^{hu/hu}$ $Il4^{hu/hu}$ $Il33^{hu/hu}$ mice resulted in a more pronounced improvement of almost all of tested lung pathologies and markers of inflammation compared with treatment with either antibody alone.

CONCLUSION

Combined treatment with REGN3500 and dupilumab in a 19-week HDM exposure-induced lung inflammation model using $Il4ra^{hu/hu}$ $Il4^{hu/hu}$ $Il33^{hu/hu}$ mice resulted in a more pronounced improvement of almost all of tested lung pathologies and markers of inflammation compared with treatment with either antibody alone.

Example 7: Evaluation of SAR440340/REGN3500, or Dupilumab, when Used Alone and when Used as Combination Therapy in Moderate-to-Severe COPD Patients Study Design This study is a randomized, double-blind, placebo-controlled, parallel-group, 24 week proof-of-concept study to assess the efficacy, safety and tolerability of an IL-33 monoclonal antibody (SAR440340/REGN3500), an IL-4R monoclonal antibody (dupilumab, also known as DUPIX- ENT®), when each is used alone, or when used in combination in patients with moderate-to-severe chronic obstructive pulmonary disease (COPD).

Eight hundred and thirty two total subjects will participate in the study. The study will consist of four arms, one arm being patients administered subcutaneously (SC) the anti-IL-33 monoclonal antibody (SAR440340/REGN3500) alone; the second arm being patients administered subcutaneously the anti-IL-4R monoclonal antibody (dupilumab) alone; the third arm being patients coadministered both SAR440340/REGN3500 and dupilumab subcutaneously; and the fourth arm being placebo.

The patients in arm 1 will receive 2 SC injections of SAR440340/REGN3500 every 2 weeks for 24 weeks and coadministered the dupilumab placebo as 1 SC injection every 2 weeks for 24 weeks; the patients in arm 2 will receive 1 SC injection of dupilumab every 2 weeks for 24 weeks and coadministered the SAR440340/REGN3500 placebo as 2 SC injections every 2 weeks for 24 weeks; the patients in arm 3 will receive 2 SC injections of SAR440340/REGN3500 every 2 weeks for 24 weeks and coadministered dupilumab as 1 SC injection every 2 weeks for 24 weeks; the patients in arm 4 will receive matching placebos for SAR440340/REGN3500 and dupilumab administered as 2 and 1 SC injections, respectively, every 2 weeks for 24 weeks.

Study Objectives

The primary objective of this study is to determine and compare the effects of an interleukin-33 antibody (SAR440340/REGN3500), an interleukin-4 receptor monoclonal antibody (dupilumab), and the coadministration of both, compared to placebo, in patients with moderate-to-severe chronic obstructive pulmonary disease (COPD), who have been treated with an inhaled corticosteroid (ICS), and/or a long acting β2 adrenergic agonist (LABA) and/or long acting muscarinic antagonist (LAMA) background therapy (double or triple therapy), on improving respiratory function, as assessed by post bronchodilator forced volume in 1 second (FEV1), over 24 weeks.

The secondary objectives will be to evaluate the effects of SAR440340/REGN3500, dupilumab and the coadministration of both, each compared with placebo, on the incidence of moderate-to-severe acute exacerbations of COPD (AECOPD) over 24 weeks of treatment.

Another secondary objective is to evaluate the effects of SAR440340/REGN3500, dupilumab and the coadministration of both, each compared to placebo on: Pre-bronchodilator FEV1 over 24 weeks; Duration from baseline to first moderate or severe AECOPD event over 24 weeks; Evaluation of clinical symptoms of COPD; Safety and Tolerability.

Inclusion Criteria

Inclusion criteria for the study are as follows: (1) Patients with moderate-to-severe Chronic Obstructive Pulmonary Disease (COPD) (post bronchodilator Forced Expiratory Volume in one second (FEV1) forced vital capacity (FVC) <70% and post bronchodilator FEV1% predicted <80%, but ≥30%); (2) Patients with COPD Assessment Test (CAT) score ≥10 at screening visit 1 and visit 2/Randomization; (3) Patients with reported history of signs and symptoms of chronic bronchitis (chronic productive cough for 3 months in the year up to screening in a patient in whom other causes of chronic cough (eg. gastroesophageal reflux, chronic rhinosinusitis, bronchiectasis) have been excluded; (4) Patients with documented history of ≥2 moderate exacerbations or ≥1 severe exacerbation within the year prior to screening; (5) Patients with Standard of Care background therapy, for 3 months prior to Visit 2/Randomization and at a stable dose for at least 1 month prior to the screening visit 1, including either: Double therapy: Long acting β agonist (LABA)+ Long acting Muscarinic antagonist (LAMA) or Inhaled Corticosteroid (ICS)+LABA or ICS+LAMA; or Triple therapy: ICS+LABA+LAMA; (6) Signed written informed consent; and (7) Current or former smokers with a smoking history of ≥10 packs/year.

Exclusion Criteria

Exclusion criteria for the study are as follows: (1) Age of ≤40 years or >75 years; (2) Patients with body mass index (BMI)<16; (3) Patients with COPD diagnosed within the 6 months prior to randomization; (4) A current diagnosis of asthma according to the Global Initiative for Asthma (GINA) guidelines; (5) Significant pulmonary disease other than COPD (eg, lung fibrosis, sarcoidosis, interstitial lung disease, pulmonary hypertension, bronchiectasis, eosinophilic granulomatosis with polyangiitis, significant sleep apnea on Bilevel Positive Airway Pressure, etc) or another diagnosed pulmonary or systemic disease associated with elevated peripheral eosinophil counts; (6) Diagnosis of $\alpha$-1 anti-trypsin deficiency; (7) Advanced COPD with need for chronic (>15 hours/day) oxygen support; (8) Patient with a moderate or severe Acute Exacerbation of COPD event within 4 weeks prior to screening; (9) A patient who has experienced an upper or lower respiratory tract infection within 4 weeks prior to Screening/Visit 1 or during the screening period; (10) Prior history of or planned pneumonectomy or lung volume reduction surgery; (11) Patients with a history of a systemic hypersensitivity reaction to a biologic drug.

Example 8. Evaluation of SAR440340/REGN3500, or Dupilumab, when Used Alone and when Used as Combination Therapy in Moderate-to-Severe Asthma Patients Study Design This study is a randomized, double-blind, placebo-controlled, parallel-group, 12-week proof-of-concept (PoC) study to assess the efficacy, safety, and tolerability of SAR440340/REGN3500, dupilumab (also known as DUPIXENT®), and the coadministration of SAR440340 and dupilumab in patients with moderate-to-severe asthma who are not well controlled on inhaled corticosteroid (ICS) plus long-acting β2 adrenergic agonist (LABA) therapy.

Eight hundred total subjects will participate in this study. The study will consist of four arms, one arm being patients administered subcutaneously (SC) the anti-IL-33 monoclonal antibody (SAR440340/REGN3500) alone; the second arm being patients administered subcutaneously the anti-IL-4R monoclonal antibody (dupilumab) alone; the third arm being patients coadministered both SAR440340/REGN3500 and dupilumab subcutaneously; and the fourth arm being placebo.

The patients in arm 1 will receive SAR440340/REGN3500 administered as 2 subcutaneous (SC) injections every 2 weeks for 12 weeks and coadministration of dupilumab placebo as 1 SC injection every 2 weeks for 12 weeks; the patients in arm 2 will receive dupilumab administered as 1 SC injection every 2 weeks for 12 weeks and coadministration of SAR440340/REGN3500 placebo as 2 SC injections every 2 weeks for 12 weeks; the patients in arm 3 will receive SAR440340/REGN3500 administered as 2 SC injections every 2 weeks for 12 weeks and coadministration of dupilumab administered as 1 SC injection every 2 weeks for 12 weeks; the patients in arm 4 will receive coadministration of matching placebos for SAR440340/REGN3500 and dupilumab administered as 2 and 1 SC injections, respectively, every 2 weeks for 12 weeks.

Study Objectives

The primary study objective is to evaluate the effects of SAR440340/REGN3500 with or without dupilumab, compared to placebo, on reducing the incidence of "loss of asthma control" (LOAC) events.

The secondary study objectives will be to evaluate the effects of SAR440340/REGN3500 and coadministration of SAR440340/REGN3500 and dupilumab, compared with placebo, on forced expiratory volume in 1 second (FEV1); to evaluate the effects of coadministration of SAR440340/REGN3500 and dupilumab, compared with SAR440340/REGN3500 and compared with dupilumab, on FEV1; to evaluate the effects of the concurrent administration of SAR440340/REGN3500 and dupilumab compared to SAR440340/REGN3500 alone and dupilumab alone on reducing the LOAC; and to assess safety and tolerability of SAR440340/REGN3500 alone and in coadministration with dupilumab.

Inclusion Criteria

Inclusion criteria for the study are as follows: (1) Adult patients (18 years and above) with a physician diagnosis of asthma for at least 12 months based on the Global Initiative for Asthma (GINA) 2016 Guidelines whose asthma is partially controlled or uncontrolled on ICS/LABA combination therapy with the following criteria: Existing treatment with medium to high dose Inhaled Corticosteroids (ICS) (≥250 mcg of fluticasone propionate twice daily (BID) or equipotent ICS daily dosage to a maximum of 2000 mcg/day of fluticasone propionate or clinically comparable) in combination with a Long Acting Beta-Agonist (LABA) as second controller for at least 3 months with a stable dose ≥1 month prior to Visit 1; (2) Pre-bronchodilator Forced Expiratory Volume in One Second (FEV1) ≥50% but ≤85% of predicted normal at Visit 2/Baseline; (3) Reversibility of at least 12% and 200 mL in FEV1 after administration of 2 to 4 puffs (200-400 mcg) of albuterol/salbutamol or levalbuterol/levosalbutamol during screening (up to 3 opportunities during the same visit are allowed with a maximum of 12 puffs of reliever medication if tolerated by the patient); documented history of 20% variability in pre bronchodilator FEV1 when comparing 2 acceptable spirometric assessments within 6 months prior to Visit 1/Screening, or positive airway hyperresponsiveness to methacholine within 12 months prior to Visit 1/Screening is considered acceptable to meet this inclusion criterion; (4) Must have experienced, within 1 year prior to Visit 1, any of the following events at least once: Treatment with a systemic steroid (oral or parenteral) for worsening asthma, or hospitalization or emergency medical care visit for worsening asthma; (5) Signed written informed consent.

Exclusion Criteria

Exclusion criteria for the study are as follows: (1) Patients <18 years or >70 years of age (ie, have reached the age of 71 at the screening visit); (2) Patients with body mass index (BMI) <16; (3) Chronic lung disease (for example, chronic obstructive pulmonary disease [COPD], or idiopathic pulmonary fibrosis [IPF]) which may impair lung function; (4) History of life threatening asthma (ie, severe exacerbation that requires intubation); (5) Co-morbid disease that might interfere with the evaluation of IMP; (6) Patients with any of the following events within the 4 weeks prior to their Screening Visit 1: Treatment with 1 or more systemic (oral and/or parenteral) steroid bursts for worsening asthma, or hospitalization or emergency medical care visit for worsening asthma; (7) Asthma Control Questionnaire 5-question version (ACQ-5) score <1.25 or >3.0 at V2/randomization. During the screening period an ACQ-5 of up to ≤4 is acceptable; (8) Anti-immunoglobulin E (IgE) therapy (eg, omalizumab [Xolair®]) within 130 days prior to Visit 1 or any other biologic therapy (including anti-IL5 mAb) or systemic immunosuppressant (eg, methotrexate) to treat inflammatory disease or autoimmune disease (eg, rheumatoid arthritis, inflammatory bowel disease, primary biliary cirrhosis, systemic lupus erythematosus, multiple sclerosis, etc.) and other diseases, within 2 months or 5 half-lives prior to Visit 1, whichever is longer; (9) Patients with a history of a systemic hypersensitivity reaction to a biologic drug; (10) Patients on or initiation of bronchial thermoplasty within 2 years prior to Visit 1 or plan to begin therapy during the screening period or the randomized treatment period; (11) Current smoker or cessation of smoking within the 6 months prior to Visit 1; (12) Previous smoker with a smoking history >10 pack-years.

We claim:

1. A method for reducing serum amyloid A (SAA) protein levels in a subject in need thereof, the method comprising administering an interleukin-33 (IL-33) antibody or antigen-binding fragment thereof to the subject, wherein the IL-33 antibody or antigen-binding fragment thereof comprises a heavy chain variable region (HCVR) comprising three heavy chain complementarity determining regions, HCDR1, HCDR2, and HCDR3, comprising the amino acid sequences of SEQ ID NOs: 276, 278, and 280, respectively, and a light chain variable region (LCVR) comprising three light chain complementarity determining regions, LCDR1, LCDR2, and LCDR3, comprising the amino acid sequences of SEQ ID NOs: 284, 286, and 288, respectively.

2. The method of claim 1, wherein the subject in need thereof has an inflammatory disease or disorder.

3. The method of claim 1, wherein the HCVR comprises the amino acid sequence of SEQ ID NO: 274.

4. The method of claim 1, wherein the LCVR comprises the amino acid sequence of SEQ ID NO: 282.

5. The method of claim 1, wherein the HCVR comprises the amino acid sequence of SEQ ID NO: 274 and the LCVR comprises the amino acid sequence of SEQ ID NO: 282.

6. The method of claim 1, wherein the IL-33 antibody or antigen-binding fragment thereof is the IL-33 antibody designated REGN3500.

7. The method of claim 1, wherein the IL-33 antibody or antigen-binding fragment thereof is administered to the subject subcutaneously, intravenously, intramuscularly, or intranasally.

8. The method of claim 7, wherein the IL-33 antibody is administered to the subject subcutaneously.

9. The method of claim 7, wherein the IL-33 antibody is administered to the subject intravenously.

10. The method of claim 2, wherein the inflammatory disease or disorder is an inflammatory lung disease or disorder.

11. The method of claim 10, wherein the inflammatory lung disease or disorder is asthma, chronic obstructive pulmonary disease (COPD), or chronic bronchitis.

12. The method of claim 2, wherein the inflammatory disease or disorder is chronic rhinosinusitis with or without nasal polyps.

13. The method of claim 2, wherein the inflammatory disease or disorder is inflammatory bowel disease, Crohn's disease, or ulcerative colitis.

14. The method of claim 1, further comprising administering an effective amount of one or more additional therapeutic agents.

15. The method of claim 11, wherein the inflammatory disease or disorder is chronic obstructive pulmonary disease (COPD).

16. The method of claim 12, wherein the inflammatory disease or disorder is chronic rhinosinusitis with nasal polyps.

17. The method of claim 12, wherein the inflammatory disease or disorder is chronic rhinosinusitis without nasal polyps.

* * * * *